US007811577B2

(12) United States Patent
Bianchi et al.

(10) Patent No.: US 7,811,577 B2
(45) Date of Patent: Oct. 12, 2010

(54) COVALENTLY STABILIZED CHIMERIC COILED-COIL HIV GP41 N-PEPTIDES WITH IMPROVED ANTIVIRAL ACTIVITY

(75) Inventors: Elisabetta Bianchi, Rome (IT); Antonello Pessi, Rome (IT); Romas Geleziunas, Belmont, CA (US); David Bramhill, Westfield, NJ (US)

(73) Assignees: Merck Sharp & Dohme Corp., Rahway, NJ (US); Istituto Di Ricerche Di Biologia Molecolare P. Angeletti S.p.A., Rome (IT)

( * ) Notice: Subject to any disclaimer, the term of this patent is extended or adjusted under 35 U.S.C. 154(b) by 718 days.

(21) Appl. No.: 11/628,483

(22) PCT Filed: May 27, 2005

(86) PCT No.: PCT/US2005/018808

§ 371 (c)(1),
(2), (4) Date: Nov. 30, 2006

(87) PCT Pub. No.: WO2005/118886

PCT Pub. Date: Dec. 15, 2005

(65) Prior Publication Data
US 2007/0224212 A1 Sep. 27, 2007

Related U.S. Application Data

(60) Provisional application No. 60/668,365, filed on Apr. 5, 2005, provisional application No. 60/636,724, filed on Dec. 16, 2004, provisional application No. 60/576,062, filed on Jun. 1, 2004.

(51) Int. Cl.
A61K 39/00 (2006.01)
A61K 39/21 (2006.01)
(52) U.S. Cl. .................. 424/192.1; 424/208.1
(58) Field of Classification Search .................. None
See application file for complete search history.

(56) References Cited

U.S. PATENT DOCUMENTS

| 5,444,044 | A | 8/1995 | Jiang et al. |
| 5,464,933 | A | 11/1995 | Bolognesi et al. |
| 5,656,480 | A | 8/1997 | Wild et al. |
| 6,150,088 | A | 11/2000 | Chan et al. |
| 6,303,317 | B1 | 10/2001 | Alber et al. |
| 6,506,554 | B1 | 1/2003 | Chan et al. |
| 6,596,497 | B1 | 7/2003 | Jiang et al. |
| 6,656,906 | B1 | 12/2003 | Barney et al. |
| 6,716,429 | B1 | 4/2004 | Sodroski et al. |
| 6,747,126 | B1* | 6/2004 | Eckert et al. ............... 530/324 |
| 6,818,740 | B1 | 11/2004 | Eckert et al. |
| 6,841,657 | B2 | 1/2005 | Eckert et al. |
| 6,861,059 | B2 | 3/2005 | Johnson et al. |
| 7,053,179 | B2 | 5/2006 | Root et al. |
| 2003/0219451 | A1 | 11/2003 | Sia et al. |
| 2004/0213801 | A1 | 10/2004 | Wild et al. |

FOREIGN PATENT DOCUMENTS

| WO | WO 94/02505 | 3/1994 |
| WO | WO 94/28920 | 12/1994 |
| WO | WO 96/40191 | 12/1996 |
| WO | WO 98/32848 | 7/1998 |
| WO | WO99/16883 | 4/1999 |
| WO | WO 00/06599 | 2/2000 |
| WO | WO 00/40616 | 7/2000 |
| WO | WO 01/03723 | 1/2001 |
| WO | WO 01/44286 | 6/2001 |
| WO | WO 02/24735 | 3/2002 |
| WO | WO 2003/052122 | 6/2003 |
| WO | WO 2005/058968 | 6/2005 |
| WO | WO 2005/118886 | 12/2005 |

OTHER PUBLICATIONS

Louis, J. M., et al., 2001, Design and Properties of NCCG-gp41, a Chimeric gp41 Molecule with Nanomolar HIV Fusion Inhibitory Activity, J. Biol. Chem. 276(31):29485-29489.*
Annis, Iona, et al., Methods in Enzymology, "Disulfide bond formation in peptides", vol. 289, pp. 198-221, 1997.
Bewley, Carole A., et al., The Journal of Biological Chemistry, "Design of a novel peptide inhibitor of HIV fusion that disrupts the internal trimeric coiled-coil of gp41", vol. 277, No. 16, pp. 14238-14245, 2002.
Blacklow, Stephen C., et al., Biochemistry, "A trimeric subdomain of the simian immunodeficiency virus envelope glycoprotein", vol. 34, No. 46, pp. 14955-14962, 1995.
Borgia, Jeffrey A., et al., Tibtech Reviews, "Chemical synthesis of proteins", vol. 18, pp. 243-251, 2000.
Bullough, Per A., et al., Nature, "Structure of influenza haemagglutinin at the pH of membrane fusion", vol. 371, pp. 37-43, 1994.
Burton, Dennis R., et al., Proc. Natl. Acad. Sci. USA, "A vaccine for HIV type 1: The antibody perspective", vol. 94, pp. 10018-10023, 1997.

(Continued)

Primary Examiner—Jeffrey S. Parkin
(74) Attorney, Agent, or Firm—Henry P. Wu; Sheldon O. Heber

(57) ABSTRACT

Methods of covalently-stabilizing alpha-helical, chimeric peptides constrained within a homotrimeric or heterotrimeric coiled-coil structure are disclosed. The coiled-coil structures made by the methods disclosed within this specification mimic all or a portion of the internal, trimeric coiled-coil motif contained within the fusogenic conformation of an enveloped virus membrane-fusion protein, particularly the internal coiled-coil domain of the HIV gp41 ectodomain. The HIV-derived, chimeric peptides disclosed comprise a non-HIV, soluble, trimeric form of a coiled-coil fused in helical phase to all or a portion of the N-helix of HIV gp41 and are covalently-stabilized in a homotrimeric or heterotrimeric coiled-coil structure through the formation of disulfide or chemoselective bonds between said peptides. The covalently-stabilized, HIV-derived, homotrimeric or heterotrimeric coiled-coil structures made by the methods disclosed herein represent a close mimetic of a HIV gp41 fusion intermediate and are potent inhibitors of HIV infectivity. These HIV-derived chimeric peptides may provide for therapeutic treatment against HIV infection by inhibiting the virus-host cell membrane fusion process.

31 Claims, 20 Drawing Sheets

OTHER PUBLICATIONS

Caffrey, Michael, et al., EMBO J., "Three-dimensional solution structure of the 44 kDa ectodomain of SIV gp41", vol. 17, No. 16, pp. 4572-4584, 1998.

Cao, Jie, et al., J. Virology, "Effects of amino acid changes in the extracellular domain of the human immunodeficiency virus type 1 gp41 envelope glycoprotein", vol. 67, No. 5, pp. 2747-2755, 1993.

Chan, David C., et al., Cell, "Core structure of gp41 from the HIV envelope glycoprotein", vol. 89, pp. 263-273, 1997.

Chan, David C., et al., Proc. Natl. Acad. Sci, "Evidence that a prominent cavity in the coiled coil of HIV type I gp41 is an attractive drug target", vol. 95, pp. 15613-15617, 1998.

Chan, David C., et al., Cell, "HIV entry and its inhibition", vol. 93, pp. 681-684, 1998.

Chen, Chin-Ho, et al., J. Virology, "A molecular clasp in the human immunodeficiency virus (HIV) type 1 TM protein determines the anti-HIV activity of gp41 derivatives: Implication for viral fusion", vol. 69, No. 6, pp. 3771-3777, 1995.

Cole, James L., et al., Biochemistry, "Thermodynamics of peptide inhibitor binding to HIV-1 gp41", vol. 40, pp. 5633-5641, 2001.

Dong, Xiao-Nan, et al., Immunology Letters, "N- and C-domains of HIV-1 gp41: Mutation, structure and functions", vol. 75, pp. 215-220, 2001.

Eckert, Debra M., et al., J. Mol. Biol., "Crystal structure of GCN4-$pI_QI$, a trimeric coiled coil with buried polar residues", vol. 284, pp. 859-865, 1998.

Eckert, Debra M., et al., Cell, "Inhibiting HIV-1 entry: Discovery of D-peptide inhibitors that target the gp41 coiled-coil pocket", vol. 99, pp. 103-115, 1999.

Eckert, Debra M., et al., Annu. Rev. Biochem., "Mechanisms of viral membrane fusion and its inhibition", vol. 70, pp. 777-810, 2001.

Eckert, Debra M., et al., PNAS, "Design of potent inhibitors of HIV-1 entry from the gp41 N-peptide region", vol. 98, No. 20, pp. 11187-11192, 2001.

Eckhart, Leopold, et al., Journal of General Virology, "Immunogenic presentation of a conserved gp41 epitope of human immunodeficiency virus type 1 on recombinant surface antigen of hepatitis B virus", vol. 77, pp. 2001-2008, 1996.

Erlanson, Daniel A., et al., PNAS, "Site-directed ligand discovery", vol. 97, No. 17, pp. 9367-9372, 2000.

Farzan, Michael, et al., Journal of Virology, "Stabilization of human immunodeficiency virus type 1 envelope glycoprotein trimers by disulfide bonds introduced into the gp41 glycoprotein ectodomain", vol. 72, No. 9, pp. 7620-7625, 1998.

Fass, Deborah, et al., Current Biology, "Dissection of a retrovirus envelope protein reveals structural similarity to influenza hemagglutinin", vol. 5, No. 12, pp. 1377-1383, 1995.

Ferrer, Marc, et al., Nature Structural Biology, "Selection of gp41-mediated HIV-1 cell entry inhibitors from biased combinatorial libraries of non-natural binding elements", vol. 6, No. 10, pp. 953-960, 1999.

Furuta, et al., Nature Structural Biology, "Capture of an early fusion-active conformation of HIV-1 gp41", vol. 5, No. 4, pp. 276-279, 1998.

Jiang, Shibo, et al., Nature, "HIV-1 inhibition by a peptide", vol. 365, p. 113, 1993.

Jiang, Shibo, et al, Journal of Virology, "A conformation-specific monoclonal antibody reacting with fusion-active gp41 from the human immunodeficiency virus type 1 envelope glycoprotein", vol. 72, No. 12, pp. 10213-10217, 1998.

Jiang, Shibo, et al., J. Virol. Methods, "A screening assay for antiviral compounds targeted to the HIV-1 gp41 core structure using a conformation-specific monoclonal antibody", vol. 80, pp. 85-96, 1999.

Jiang, Shibo, et al., Biochemical and Biophysical Research Communications, "Development of HIV entry inhibitors targeted to the coiled-coil regions of gp41", vol. 269, pp. 641-646, 2000.

Joshi, Sangeeta Bagai, et al., Virology, "A core trimer of the paramyxovirus fusion protein: Parallels to influenza virus hemagglutinin and HIV-1 gp41", vol. 248, pp. 20-34, 1998.

Judice, J. Kevin, et al., Proc. Natl. Acad. Sci., "Inhibition of HIV type 1 infectivity by constrained α-helical peptides: Implications for the viral fusion mechanism", vol. 94, pp. 13426-13430, 1997.

Kilby, J. Michael, et al., Nature Medicine, "Potent suppression of HIV-1 replication in humans by T-20, a peptide inhibitor of gp41-mediated virus entry", vol. 4, No. 11, pp. 1302-1307, 1998.

Kliger, Yossef, et al., J. Biol. Chem., "Mode of action of an antiviral peptide from HIV-1", vol. 276, No. 2, pp. 1391-1397, 2001.

Lemieux, George A., et al., Tibtech, "Chemoselective ligation reactions with proteins, oligosaccharides and cells", vol. 16, pp. 506-513, 1998.

Louis, John M., et al., The Journal of Biological Chemistry, "Covalent trimers of the internal N-terminal trimeric coiled-coil of gp41 and antibodies directed against them are potent inhibitors of HIV envelope-mediated cell fusion", vol. 278, No. 22, pp. 20278-20285, 2003.

Louis, John M., et al., The Journal of Biological Chemistry, "Design and Properties of $N_{ccg}$-gp41, a chimeric gp41 molecule with nanomolar HIV fusion inhibitory activity", vol. 276, No. 31, pp. 29485-29489, 2001.

Lu, Min, et al., Nature Structural Biology, "A trimeric structural domain of the HIV-1 transmembrane glycoprotein", vol. 2, No. 12, pp. 1-8, 1995.

Lu, Min, et al., J. Bio-mol, Structure & Dynamics, "A trimeric structural subdomain of the HIV-1 transmembrane glycoprotein", vol. 15, No. 3, pp. 465-471, 1997.

Malashkevic, Vladimir N., et al., Proc. Natl. Acad. Sci., "Crystal structure of the simian immunodeficiency virus (SIV) gp41 core: Conserved helical interactions underlie the broad inhibitory activity of gp41 peptides", vol. 95, pp. 9134-9139, 1998.

Muir, Tom W., et al., Biochemistry, "Design and chemical synthesis of a neoprotein structural model for the cytoplasmic domain of a multisubunit cell-surface receptor: Integrin αIIbβ3", vol. 33, pp. 7701-7708, 1994.

Nautiyal, Shivani, et al., Protein Science, "Crystal structure of a designed, thermostable, heterotrimeric coiled coil", vol. 8, pp. 84-90, 1999.

O'Neil, Karyn T., et al., Science, "A thermodynamic scale for the helix-forming tendencies of the commonly occurring amino acids", vol. 250, pp. 646-351, 1990.

Root, Michael J., et al., Science, "Protein design of an HIV-1 entry inhibitor", vol. 291, pp. 884-888, 2001.

Schelte, Philippe, et al., Bioconjugate Chem., "Differential reactivity of maleimide and bromoacetyl functions with thiols: Application to the preparation of liposomal diepitope constructs", vol. 11, pp. 118-123, 2000.

Singh, Mona, et al., J. Mol. Biol., "LearnCoil-VMF: Computational evidence for coiled-coil-like motifs in many viral membrane-fusion proteins", vol. 290, pp. 1031-1041, 1999.

Suzuki, Kazuo, et al., Protein Engineering, "An isoleucine zipper peptide forms a native-like triple stranded coiled coil in solution", vol. 11, No. 11, pp. 1051-1055, 1998.

Tan, Kemin, et al., Proc. Natl. Acad. Sci. USA, "Atomic structure of a themostable subdomain of HIV-1 gp41", vol. 94, pp. 12203-12308, 1997.

Weissenhorn, Winfried, et al., Proc. Natl. Acad. Sci. USA, "Assembly of a rod-shaped chimera of a trimeric GCN4 zipper and the HIV-1 gp41 ectodomain expressed in *Escherichia coli*", vol. 94, pp. 6065-6069, 1997.

Weissenhorn, Winfried, et al., Nature, "Atomic structure of the ectodomain from HIV-1 gp41", vol. 387, pp. 426-429, 1997.

Weng, Yongkai, et al., Journal of Virology, "Mutational analysis of residues in the coiled-coil domain of human immunodeficiency virus type 1 transmembrane protein gp41", vol. 72, No. 12, pp. 9676-9682, 1998.

Wild, Carl T., et al., Proc. Natl. Acad. Sci. USA, "Peptides corresponding to a predictive α-helical domain of human immunodeficiency virus type 1 gp41 are potent inhibitors of virus infection", vol. 97, pp. 9770-9774, 1994.

Wild, Carl T., et al., Proc. Natl. Acad. Sci. USA, "A synthetic peptide inhibitor of human immunodeficiency virus replication: Correlation between solution structure and viral inhibition", vol. 89, pp. 10537-10541, 1992.

Yang, Xinzhen, et al., Journal of Virology, "Characterization of stable, soluble trimers containing complete ectodomains of human immunodeficiency virus type 1 envelope glycoproteins", vol. 74, No. 12, pp. 5716-5725, 2000.

Zeng, Weiguang, et al., Vaccine, "Assembly of synthetic peptide vaccines by chemoselective ligation of epitopes: influence of different chemical linkages and epitope orientations on biological activity", vol. 19, pp. 3843-3852, 2001.

* cited by examiner

A.

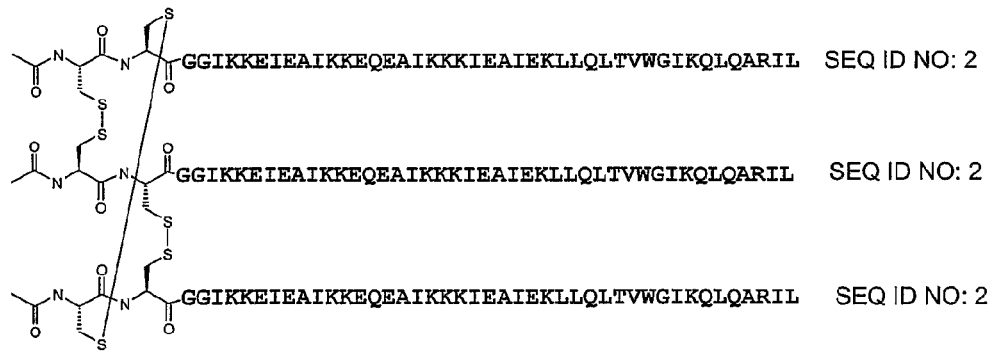

GGIKKEIEAIKKEQEAIKKKIEAIEKLLQLTVWGIKQLQARIL SEQ ID NO: 2
GGIKKEIEAIKKEQEAIKKKIEAIEKLLQLTVWGIKQLQARIL SEQ ID NO: 2
GGIKKEIEAIKKEQEAIKKKIEAIEKLLQLTVWGIKQLQARIL SEQ ID NO: 2

B.

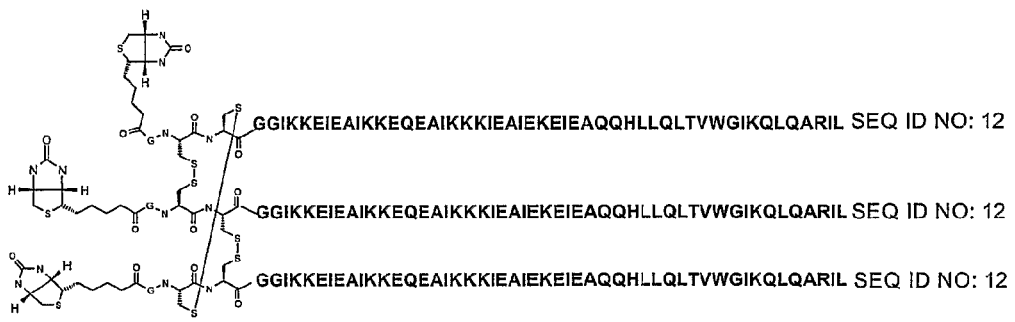

GGIKKEIEAIKKEQEAIKKKIEAIEKEIEAQQHLLQLTVWGIKQLQARIL SEQ ID NO: 12
GGIKKEIEAIKKEQEAIKKKIEAIEKEIEAQQHLLQLTVWGIKQLQARIL SEQ ID NO: 12
GGIKKEIEAIKKEQEAIKKKIEAIEKEIEAQQHLLQLTVWGIKQLQARIL SEQ ID NO: 12

C.

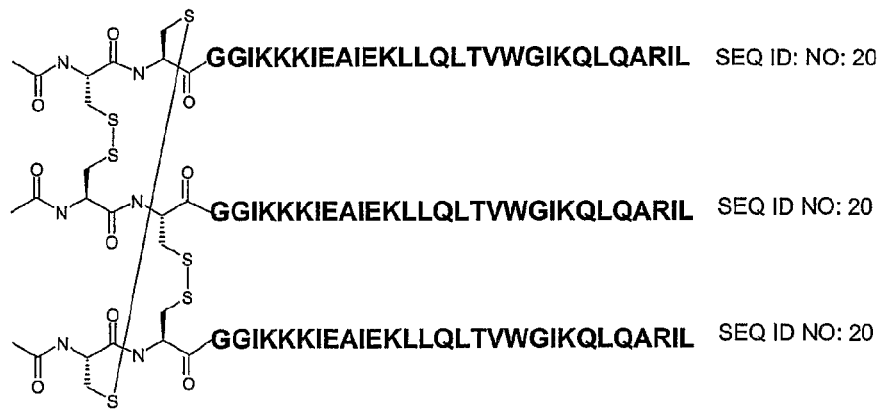

GGIKKKIEAIEKLLQLTVWGIKQLQARIL SEQ ID: NO: 20
GGIKKKIEAIEKLLQLTVWGIKQLQARIL SEQ ID NO: 20
GGIKKKIEAIEKLLQLTVWGIKQLQARIL SEQ ID NO: 20

FIG. 2A-C

A.
B.
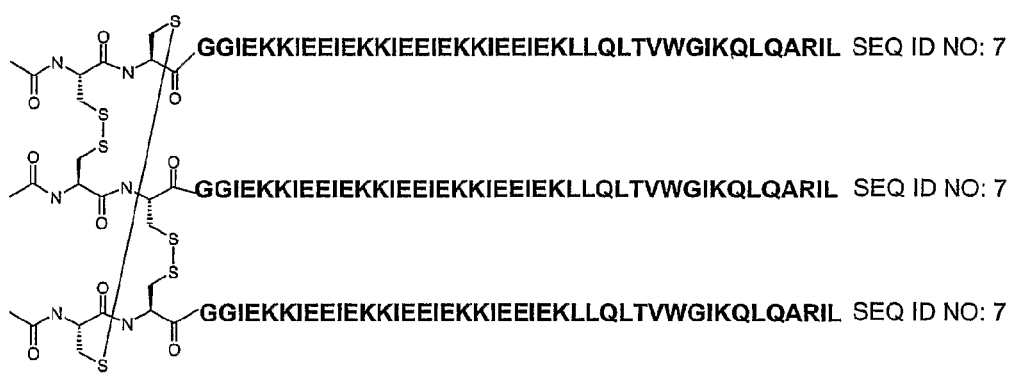
FIG. 3A-B

| Name | Peptide sequence[1] |
|---|---|
| IZN17 | IKKEIEAIKKEQEAIKKKIEAIEKLLQLTVWGIKQLQARIL (SEQ ID NO:1) |
| CCIZN17 | CCGGIKKEIEAIKKEQEAIKKKIEAIEKLLQLTVWGIKQLQARIL (SEQ ID NO:2) |
| (CCIZN17)₃ | (CCGGIKKEIEAIKKEQEAIKKKIEAIEKLLQLTVWGIKQLQARIL)₃ [SEQ ID NO:2] |
| Biotin-IZN17 | Biotin-GKGIKKEIEAIKKEQEAIKKKIEAIEKLLQLTVWGIKQLQARIL (SEQ ID NO:3) |
| IZN17Ala4 | IKKEIEAIKKEQEAIKKKIEAIEKLLQLTVWGIKALAAAIA (SEQ ID NO:4) |
| CCIZN17Ala4 | CCGGIKKEIEAIKKEQEAIKKKIEAIEKLLQLTVWGIKALAAAIA (SEQ ID NO:5) |
| (CCIZN17Ala4)₃ | (CCGGIKKEIEAIKKEQEAIKKKIEAIEKLLQLTVWGIKALAAAIA)₃ [SEQ ID NO:5] |
| EZN17 | IEKKIEEIEKKIEEIEKKIEEIEKLLQLTVWGIKQLQARIL (SEQ ID NO:6) |
| CCEZN17 | CCGGIEKKIEEIEKKIEEIEKKIEEIEKLLQLTVWGIKQLQARIL (SEQ ID NO:7) |
| (CCEZN17)₃ | (CCGGIEKKIEEIEKKIEEIEKKIEEIEKLLQLTVWGIKQLQARIL)₃ [SEQ ID NO:7] |
| EZN17Ala4 | IEKKIEEIEKKIEEIEKKIEEIEKLLQLTVWGIKALAAAIA (SEQ ID NO:8) |
| CCEZN17Ala4 | CCGGIEKKIEEIEKKIEEIEKKIEEIEKLLQLTVWGIKALAAAIA (SEQ ID NO:9) |
| (CCEZN17Ala4)₃ | (CCGGIEKKIEEIEKKIEEIEKKIEEIEKLLQLTVWGIKALAAAIA)₃ [SEQ ID NO:9] |
| IZN23 | IKKEIEAIKKEQEAIKKKIEAIEKEIEAQQHLLQLTVWGIKQLQARIL (SEQ ID NO:10) |
| Biotin-IZN23 | Biotin-GGIKKEIEAIKKEQEAIKKKIEAIEKEIEAQQHLLQLTVWGIKQLQARIL (SEQ ID NO:11) |
| Biotin-CCIZN23 | Biotin-GCCGGIKKEIEAIKKEQEAIKKKIEAIEKEIEAQQHLLQLTVWGIKQLQARIL (SEQ ID NO:12) |
| (Biotin-CCIZN23)₃ | (Biotin-GCCGGIKKEIEAIKKEQEAIKKKIEAIEKEIEAQQHLLQLTVWGIKQLQARIL)₃ [SEQ ID NO:12] |
| CCIZN23 | CCGGIKKEIEAIKKEQEAIKKKIEAIEKEIEAQQHLLQLTVWGIKQLQARIL (SEQ ID NO:13) |
| (CCIZN23)₃ | (CCGGIKKEIEAIKKEQEAIKKKIEAIEKEIEAQQHLLQLTVWGIKQLQARIL)₃ [SEQ ID NO:13] |
| EZN23 | IEKKIEEIEKKIEEIEKKIEEIEEKIEAQQHLLQLTVWGIKQLQARIL (SEQ ID NO:14) |
| CCEZN23 | CCGGIEKKIEEIEKKIEEIEKKIEEIEEKIEAQQHLLQLTVWGIKQLQARIL (SEQ ID NO:15) |

FIG. 4A

| | |
|---|---|
| IZN36 | IKKEIEAIKKEQEAIKKKIEAIEKEISGIVQQQNNLLRAIEAQQHLLQLTVWGIK QLQARIL (SEQ ID NO:16) |
| Biotin-IZN36 | Biotin-GKGIKKEIEAIKKEQEAIKKKIEAIEKEISGIVQQQNNLLRAIEAQQHL LQLTVWGIKQLQARIL (SEQ ID NO:17) |
| CCIZN36 | CCGGIKKEIEAIKKEQEAIKKKIEAIEKEISGIVQQQNNLLRAIEAQQHLLQLTV WGIKQLQARIL (SEQ ID NO:18) |
| (CCIZN36)$_3$ | (CCGGIKKEIEAIKKEQEAIKKKIEAIEKEISGIVQQQNNLLRAIEAQQHLLQLT VWGIKQLQARIL)$_3$ [SEQ ID NO:18] |
| EZN36 | IEKKIEEIEKKIEEIEKKIEEIEEKISGIVQQQNNLLRAIEAQQHLLQLTVWGIK QLQARIL (SEQ ID NO:19) |
| CCI10N17 | CCGGIKKKIEAIEKLLQLTVWGIKQLQARIL (SEQ ID NO:20) |
| (CCI10N17)$_3$ | (CCGGIKKKIEAIEKLLQLTVWGIKQLQARIL)$_3$ [SEQ ID NO:20] |
| SCCIZN17 | SGGCCGGIKKEIEAIKKEQEAIKKKIEAIEKLLQLTVWGIKQLQARIL (SEQ ID NO:21) |
| (SCC-IZN17)$_3$ | (SGGCCGGIKKEIEAIKKEQEAIKKKIEAIEKLLQLTVWGIKQLQARIL)$_3$ [SEQ ID NO:21] |
| IZN17G572D | IKKEIEAIKKEQEAIKKKIEAIEKLLQLTVWDIKQLQARIL (SEQ ID NO:22) |
| IQN17 | RMKQIEDKIEEIESKQKKIENEIARIKKLLQLTVWGIKQLQARIL (SEQ ID NO:23) |
| IQN23 | RMKQIEDKIEEIESKQKKIENEIARIKKLIEAQQHLLQLTVWGIKQLQARIL (SEQ ID NO:24) |
| IQN36 | RMKQIEDKIEEIESKQKKIENEIARIKKLISGIVQQQNNLLRAIEAQQHLLQLT VWGIKQLQARIL (SEQ ID NO:25) |
| CCIQN17 | CCGGRMKQIEDKIEEIESKQKKIENEIARIKKLLQLTVWGIKQLQARIL (SEQ ID NO:26) |
| (CCIQN17)$_3$ | (CCGGRMKQIEDKIEEIESKQKKIENEIARIKKLLQLTVWGIKQLQARIL)$_3$ [SEQ ID NO:26] |
| CCIQN17-Ala4 | CCGGRMKQIEDKIEEIESKQKKIENEIARIKKLLQLTVWGIKALAAAIA (SEQ ID NO:27) |
| IZ17N17 | IKKEIEAIKKEQEAIKKLLQLTVWGIKQLQARIL (SEQ ID NO:41) |
| CCIZ17N17 | CCGGIKKEIEAIKKEQEAIKKLLQLTVWGIKQLQARIL (SEQ ID NO:42) |
| IZ17N17CC | IKKEIEAIKKEQEAIKKLLQLTVWGIKQLQARILGGCC (SEQ ID NO:43) |
| IZN17+7 | IKKEIEAIKKEQEAIKKKIEAIEKLLQTVWGIKQLQARILAVERYLK (SEQ ID NO:54) |
| EZN17+7 | IEKKIEEIEKKIEEIEKKIEEIEEKLLQLTVWGIKQLQARILAVERYLK (SEQ ID NO:55) |
| IQN17+7 | RMKQIEDKIEEIESKQKKIENEIARIKKLLQLTVWGIKQLQARILAVERYLK (SEQ ID NO:56) |

FIG. 4B

| | |
|---|---|
| IZ17N23 | *IKKEIEAIKKEQEAIKKEIEAQQHLLQLTVWGIKQLQARIL* (SEQ ID NO:57) |
| IZ17N36 | *IKKEIEAIKKEQEAIKKEISGIVQQQNNLLRAIEAQQHLLQLTVWGIKQLQARIL* (SEQ ID NO:58) |
| IZ17N17+7 | *IKKEIEAIKKEQEAIKKLLQLTVWGIKQLQARILAVERYLK* (SEQ ID NO:59) |
| CCIZ17-N17Ala4 | *CCGGIKKEIEAIKKEQEAIKKLLQLTVWGIKALAAAIA* (SEQ ID NO:61) |
| Biotin-CCIZN17 | Biotin-*GCCGGIKKEIEAIKKEQEAIKKKIEAIEKLLQLTVWGIKQLQARIL* (SEQ ID NO:68) |
| Biotin-CCEZN17 | Biotin-*GCCGGIEKKIEEIEKKIEEIEKKIEEIEKLLQLTVWGIKQLQARIL* (SEQ ID NO:69) |
| I10N17CC | *IKKKIEAIEKLLQLTVWGIKQLQARILGGCC* (SEQ ID NO:83) |
| I10N17Ile | *IKKKIEAIEKLIQLIVWGIKQIQARIL* (SEQ ID NO:86) |
| CCI10-N17Ile | *CCGGIKKKIEAIEKLIQLIVWGIKQIQARIL* (SEQ ID NO:87) |
| I10-N17IleCC | *IKKKIEAIEKLIQLIVWGIKQIQARILGGCC* (SEQ ID NO:88) |
| IZ17N17Ile | *IKKEIEAIKKEQEAIKKLIQLIVWGIKQIQARIL* (SEQ ID NO:89) |
| CCIZ17-N17Ile | *CCGGIKKEIEAIKKEQEAIKKLIQLIVWGIKQIQARIL* (SEQ ID NO:90) |
| IZ17-N17IleCC | *IKKEIEAIKKEQEAIKKLIQLIVWGIKQIQARILGGCC* (SEQ ID NO:91) |
| I10N17+7 | *IKKKIEAIEKLLQLTVWGIKQLQARILAVERYLK* (SEQ ID NO:92) |
| CCN17IZ | *CCGGLLQLTVWGIKQLQARILAIKKEIEAIKKEQEAIKKKIEAI* (SEQ ID NO:93) |
| N17IZ | *LLQLTVWGIKQLQARILAIKKEIEAIKKEQEAIKKKIEAI* (SEQ ID NO:94) |
| CCIZN13 | *CCGGIKKEIEAIKKEQEAIKKKIEAIEKLLQLTVWGIKQLQ* (SEQ ID NO:95) |
| (CCIZN13)₃ | *(CCGGIKKEIEAIKKEQEAIKKKIEAIEKLLQLTVWGIKQLQ)₃* [SEQ ID NO:95] |
| CCIZN11IZ | *CCGGIKKEIEAIKKEQEAIKKKIEAIEKLLQLTVWGIKQIKKEIEAI* (SEQ ID NO:96) |
| (CCIZN11-IZ)₃ | *(CCGGIKKEIEAIKKEQEAIKKKIEAIEKLLQLTVWGIKQIKKEIEAI)₃* [SEQ ID NO:96] |
| SZN17 | *IEKKIEAIEKKIEAIEKKIEAIEKLLQLTVWGIKQLQARIL* (SEQ ID NO:97) |
| CCSZN17 | *CCGGIEKKIEAIEKKIEAIEKKIEAIEKLLQLTVWGIKQLQARIL* (SEQ ID NO:98) |
| (CCSZ-N17)₃ | *(CCGGIEKKIEAIEKKIEAIEKKIEAIEKLLQLTVWGIKQLQARIL)₃* [SEQ ID NO:98] |
| S17N17 | *IEKKIEAIEKKIEAIEKLLQLTVWGIKQLQARIL* (SEQ ID NO:99) |
| CCS17N17 | *CCGGIEKKIEAIEKKIEAIEKLLQLTVWGIKQLQARIL* (SEQ ID NO:100) |
| (CCS17-N17)₃ | *(CCGGIEKKIEAIEKKIEAIEKLLQLTVWGIKQLQARIL)₃* [SEQ ID NO:100] |

FIG. 4C

| | |
|---|---|
| S10N17 | *IEKKIEAIEKLLQLTVWGIKQLQARIL* (SEQ ID NO:101) |
| CCS10N17 | *CCGGIEKKIEAIEKLLQLTVWGIKQLQARIL* (SEQ ID NO:102) |
| (CCS10-N17)₃ | *(CCGGIEKKIEAIEKLLQLTVWGIKQLQARIL)₃* [SEQ ID NO:102] |
| CCCIZN17 | *CCCGGIKKEIEAIKKEQEAIKKKIEAIEKLLQLTVWGIKQLQARIL* (SEQ ID NO:103) |
| GGGIZN17 | *GGGIKKEIEAIKKEQEAIKKKIEAIEKLLQLTVWGIKQLQARIL* (SEQ ID NO:104) |
| CCCS17N17 | *CCCGGIEKKIEAIEKKIEAIEKLLQLTVWGIKQLQARIL* (SEQ ID NO:105) |
| GGGS17N17 | *GGGIEKKIEAIEKKIEAIEKLLQLTVWGIKQLQARIL* (SEQ ID NO:106) |
| E10N17 | *IEEKIEEIEELLQLTVWGIKQLQARIL* (SEQ ID NO:108) |
| CCE10N17 | *CCGGIEEKIEEIEELLQLTVWGIKQLQARIL* (SEQ ID NO:109) |
| GGGE10N17 | *GGGIEEKIEEIEELLQLTVWGIKQLQARIL* (SEQ ID NO:110) |
| CCCE10N17 | *CCCGGIEEKIEEIEELLQLTVWGIKQLQARIL* (SEQ ID NO:111) |
| CCCEZN17 | *CCCGGIEKKIEEIEKKIEEIEKKIEEIEKLLQLTVWGIKQLQARIL* (SEQ ID NO:122) |
| GGGEZN17 | *GGGIEKKIEEIEKKIEEIEKKIEEIEKLLQLTVWGIKQLQARIL* (SEQ ID NO:121) |
| EZ17N17 | *IEKKIEEIEKKIEEIEKLLQLTVWGIKQLQARIL* (SEQ ID NO:115) |
| EZ17Glu-N17 | *IEKKIEEIEEKIEEIEKLLQLTVWGIKQLQARIL* (SEQ ID NO:118) |
| CCEZ17N17 | *CCGGIEKKIEEIEKKIEEIEKLLQLTVWGIKQLQARIL* (SEQ ID NO:116) |
| CCEZ17Glu N17 | *CCGGIEKKIEEIEEKIEEIEKLLQLTVWGIKQLQARIL* (SEQ ID NO:120) |
| CCCEZ17-N17 | *CCCGGIEKKIEEIEKKIEEIEKLLQLTVWGIKQLQARIL* (SEQ ID NO:126) |
| GGGEZ17-N17 | *GGGIEKKIEEIEKKIEEIEKLLQLTVWGIKQLQARIL* (SEQ ID NO:125) |
| CCC-EZ17GluN17 | *CCCGGIEKKIEEIEEKIEEIEKLLQLTVWGIKQLQARIL* (SEQ ID NO:124) |
| GGG-EZ17GluN17 | *GGGIEKKIEEIEEKIEEIEKLLQLTVWGIKQLQARIL* (SEQ ID NO:123) |

¹ in italics, non-HIV residues; N terminus acetyl (except with biotinylated and SCC-peptides), C terminus amide

A.
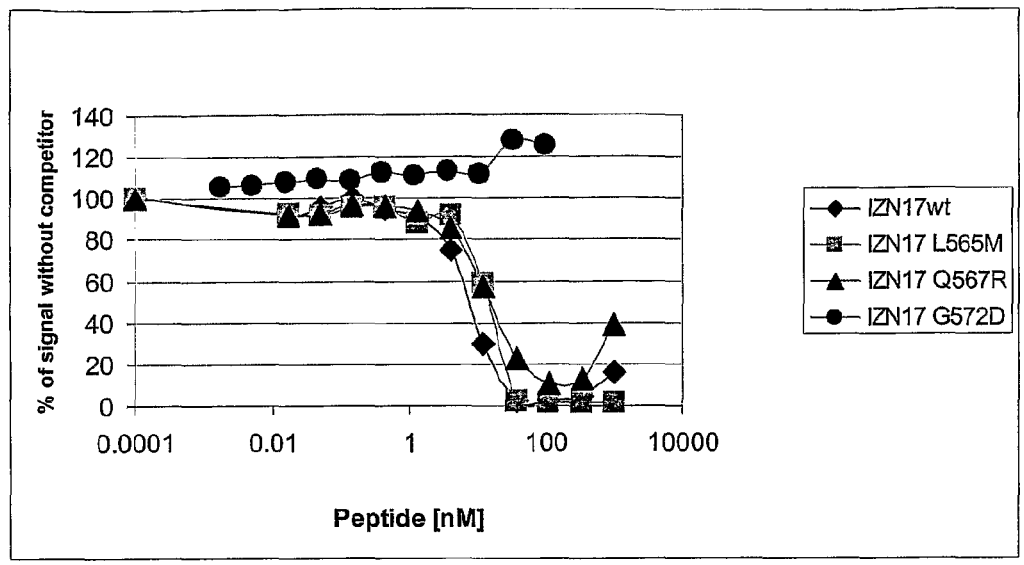
B.
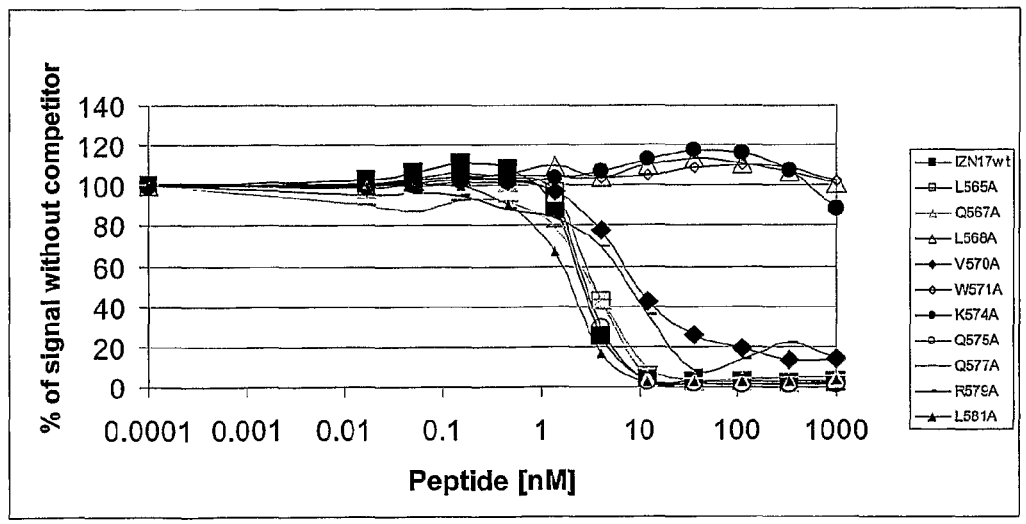
FIG. 9A-B

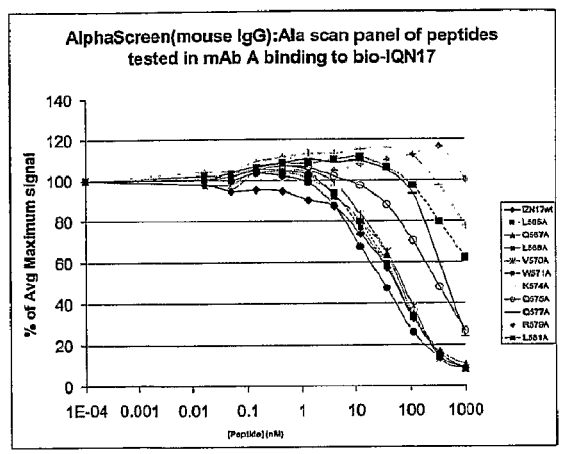
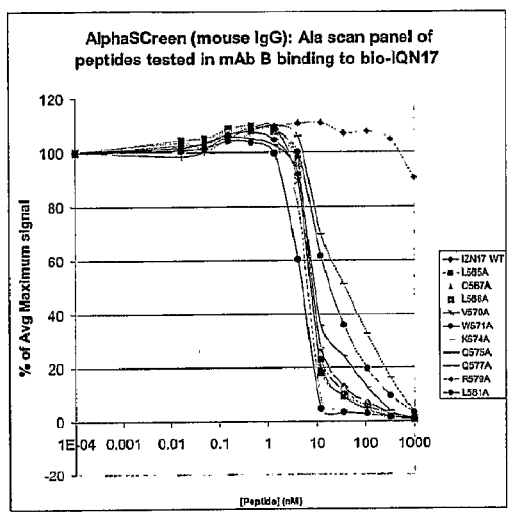
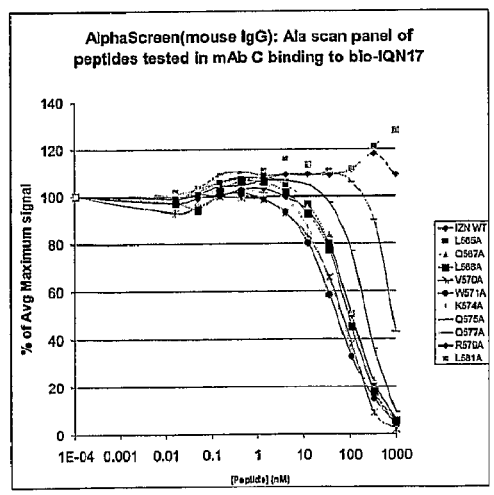
FIG. 10A-C

| IZN17 MUTANT | A1 | L | A3 | A4 | A6 | A7 | D8 | A10 | A11 | L | A13 | A | A15 | I | A17 |
|---|---|---|---|---|---|---|---|---|---|---|---|---|---|---|---|
| Amino acid position | L565A | | Q567A | L568A T | V570A | W571A | G572D | K574A | Q575A | | Q577A | | R579A | | L581A |
| ANTIBODIES | | | | | | | | | | | | | | | |
| D5 IgG | NO | | NO | YES | WEAK | YES | YES | YES | NO | | NO | |

A.

Titration of IZAla4, EZN17 and IZN17 Peptides in VERTICAL Against HIV-Hxb2

| IZAla4 | |
|---|---|
| | Value |
| IC50 Value | 0.025286 uM |
| $R^2$ | 0.94463 |

| EZN17 | |
|---|---|
| | Value |
| IC50 Value | 1.0781 uM |
| $R^2$ | 0.65663 |

| IZN17 | |
|---|---|
| | Value |
| IC50 Value | 0.00017339 uM |
| $R^2$ | 0.94613 |

B.

IZN17 Ala 4 Inhibits D5 IgG binding to IZN17

FIG. 12A-B

| Peptide | Anti-viral activity against HIV-HXB2 IC$_{50}$ (nM) | D5 IgG binding IC$_{50}$ (nM)* | D5 IgG binding IC$_{50}$ (nM)*** |
|---|---|---|---|
| IZN17 (SEQ ID NO:1) | 1.68 | 3.22 | |
| (CCIZN17)$_3$ (SEQ ID NO:2) | 0.04 | 0.86 | 34 |
| EZN17 (SEQ ID NO:6) | Not Active | Binds** | |
| (CCEZN17)$_3$ (SEQ ID NO:7) | Not Active | 8.34 | |
| (CCI10N17)$_3$ (SEQ ID NO:20) | 24 | 0.11 | |
| (I10N17CC)$_3$ (SEQ ID NO:83) | 77.6 | 2.5 | |
| IZN17Ala4 (SEQ ID NO:4) | 25.3 | Binds** | |
| (CCIZN17Ala4)$_3$ (SEQ ID NO:5) | 46.95 | Binds** | |
| (CCIZN13)$_3$ (SEQ ID NO:95) | 85.3 | n.d. | Binds** |
| N17IZ (SEQ ID NO:94) | 800 | 91.5 | |
| (CCIZN11IZ)$_3$ (SEQ ID NO:96) | 0.3 | n.d. | 19 |
| (CCS10N17)$_3$ (SEQ ID NO:102) | 21.3 | n.d. | 262 |
| SZN17 (SEQ ID NO:97) | 1.5 | n.d. | |
| (CCS17N17)$_3$ (SEQ ID NO:100) | 0.33 | n.d. | 44 |
| NH$_2$-C(Fm)(thioIZN17)$_3$ | 1.1 | n.d. | |
| ac-C(Acm)(thioIZN17)$_3$ | 0.24 | n.d. | 28 |
| ac-C(Acm)(thioE10N17)$_3$ | 150 | n.d. | Weak binding |
| ac-C(Acm)(thioS17N17)$_3$ | 0.27 | n.d. | 51 |

\* Peptide competitions in biotinylated-5-Helix/D5 IgG interaction assay
\*\* Indicates that peptide competes interaction but accurate IC$_{50}$ could not be derived
\*\*\* Peptide competitions in biotinylated-5-Helix/D5-FITC IgG interaction assay

FIG. 13

A.
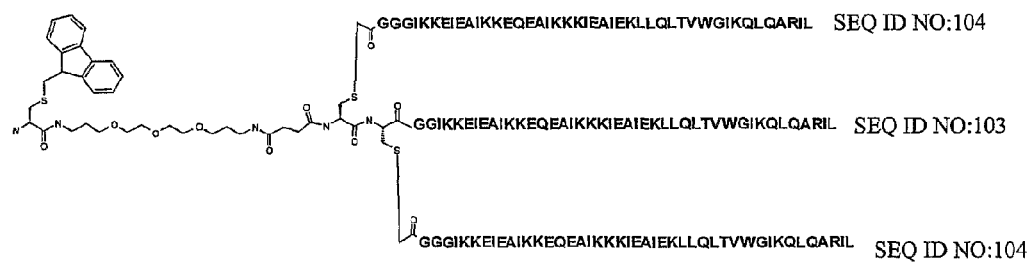
B.
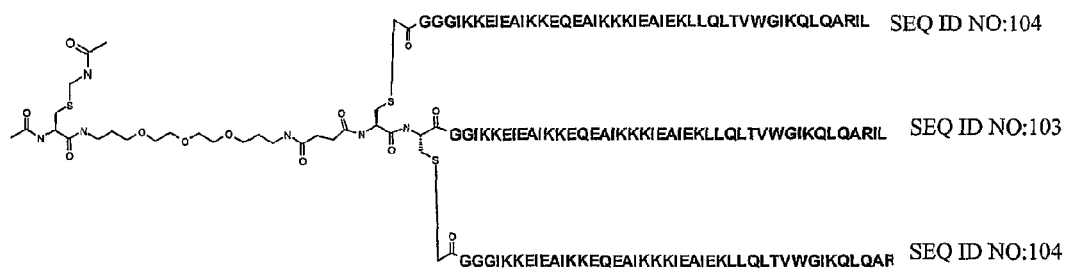
FIG. 14A-B

A.
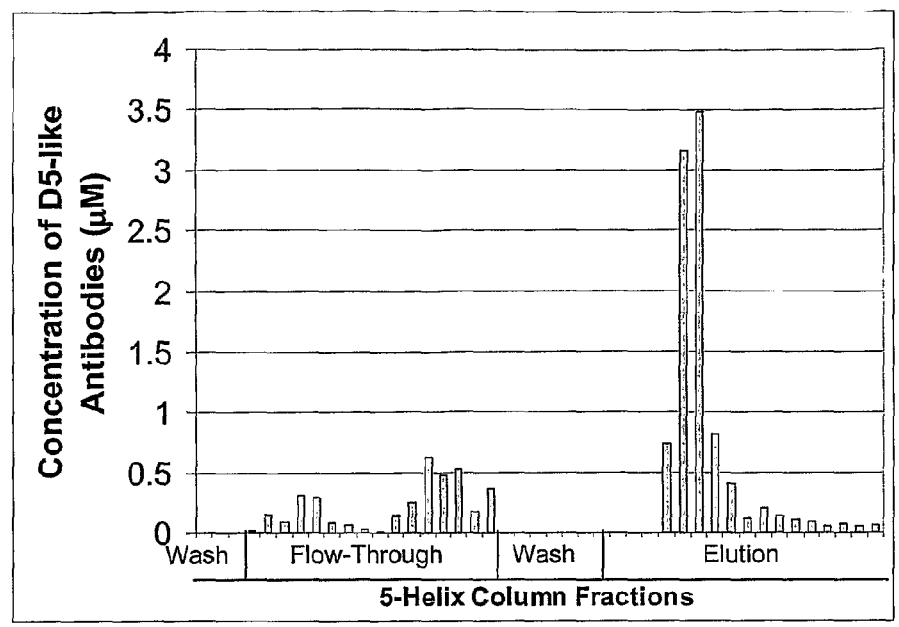
B.
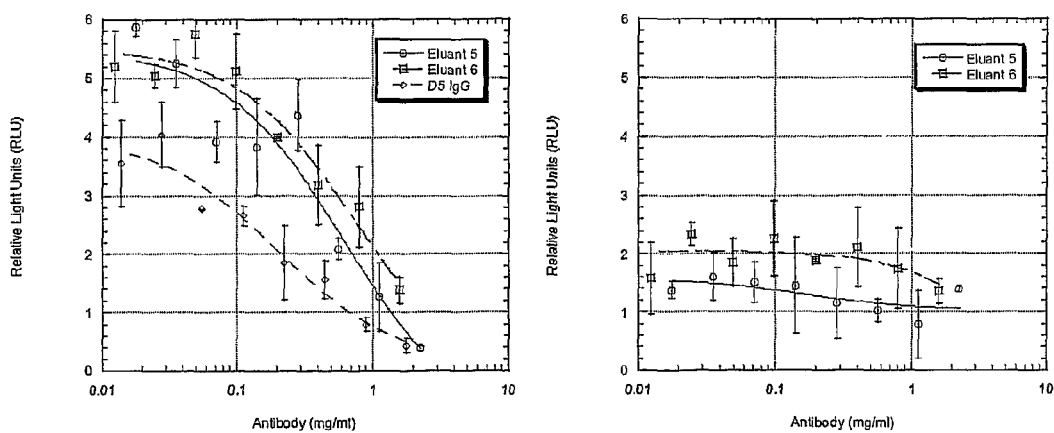
FIG. 15A-B

A.
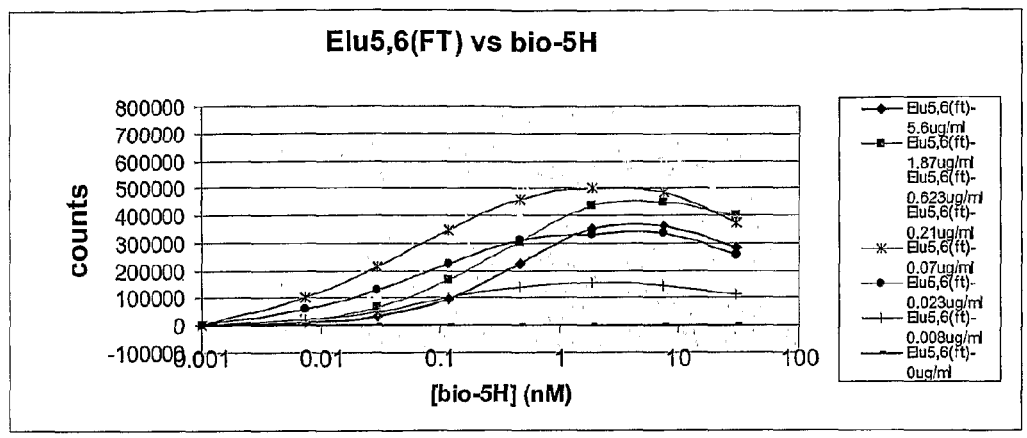
B.
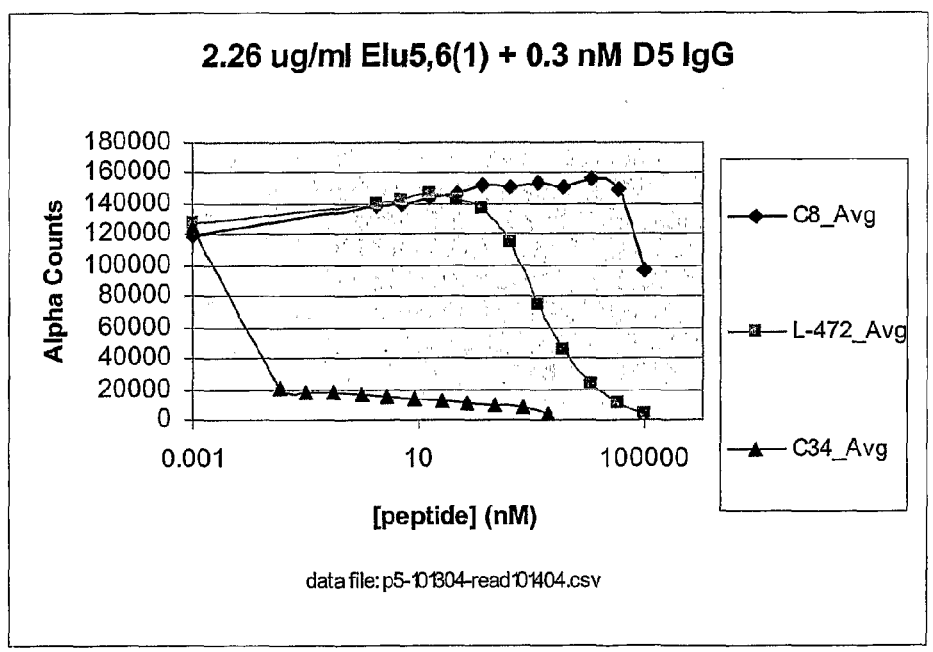
Fig. 16A-B

A.
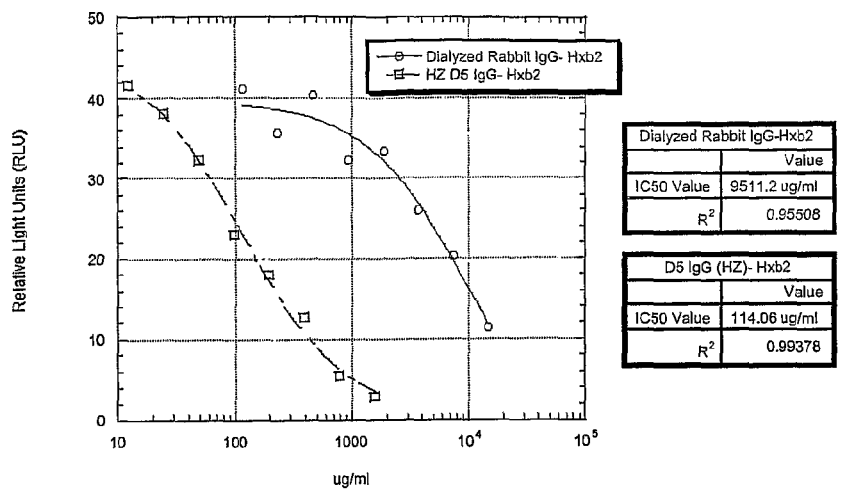
B.
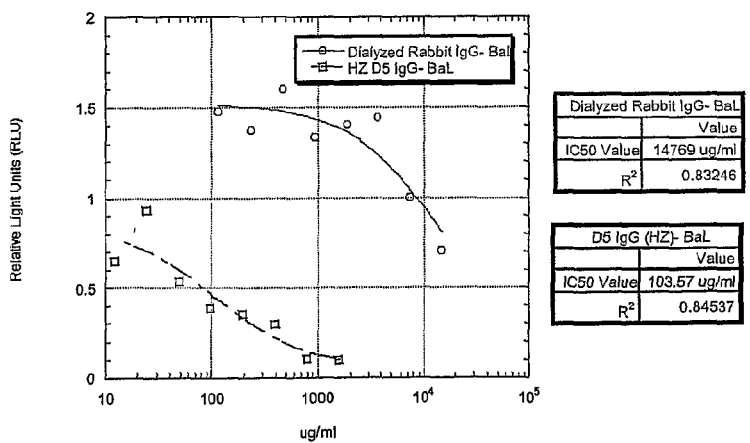
C.
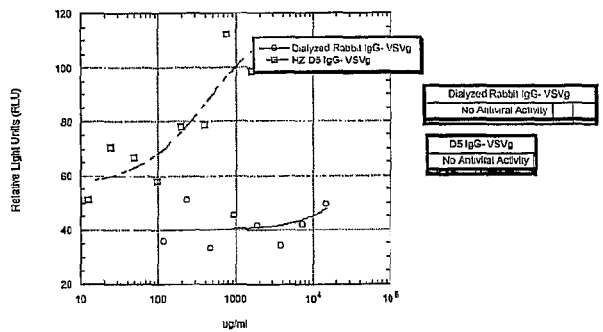
Fig. 17A-C

US 7,811,577 B2

COVALENTLY STABILIZED CHIMERIC COILED-COIL HIV GP41 N-PEPTIDES WITH IMPROVED ANTIVIRAL ACTIVITY

CROSS-REFERENCE TO RELATED APPLICATIONS

The present application is the §371 National Stage application of PCT International Application serial no. PCT/US2005/018808, having an international filing date of May 27, 2005, which claims priority to U.S. Provisional Application Ser. No. 60/576,062, filed Jun. 1, 2004, U.S. Provisional Application Ser. No. 60/636,724, filed Dec. 16, 2004, and U.S. Provisional Application Ser. No. 60/668,365, filed Apr. 5, 2005, now expired.

FIELD OF THE INVENTION

The present invention relates to a method of covalently-stabilizing alpha-helical, chimeric peptides constrained within a homotrimeric or heterotrimeric coiled-coil structure, wherein said coiled-coil structure mimics all or a portion of the internal, trimeric coiled-coil motif contained within the fusogenic conformation of an enveloped virus membrane-fusion protein. In one embodiment, the present invention relates to a method of covalently-stabilizing a homotrimeric coiled-coil structure that mimics all or a portion of the internal coiled-coil domain of the HIV gp41 ectodomain, wherein chimeric peptides comprising a non-HIV, soluble, trimeric form of a coiled-coil fused in helical phase to all or a portion of the N-helix of HIV gp41 are covalently-stabilized in said coiled-coil structure through the formation of disulfide bonds between cysteine residues added to either the $NH_2$- or COOH-terminus of said peptides. Methods whereby trimeric coiled-coil structures that mimic the internal coiled-coil domain of the HIV gp41 ectodomain are stabilized by covalent bonds resulting from chemoselective ligation reactions are also disclosed. The covalently-stabilized, HIV-derived coiled-coil structures made by the methods disclosed herein represent close mimetics of a HIV gp41 fusion intermediate and are potent inhibitors of HIV infectivity.

BACKGROUND OF THE INVENTION

Human Immunodeficiency Virus (HIV) is the etiological agent of acquired human immune deficiency syndrome (AIDS) and related disorders. HIV genes encode at least nine proteins and are divided into three classes: the major structural proteins (Gag, Pol, and Env); the regulatory proteins (Tat and Rev); and the accessory proteins (Vpu, Vpr, Vif and Nef).

The env gene encodes the viral envelope glycoprotein that is translated as a 160-kilodalton (kDa) precursor (gp160) and then cleaved by a cellular protease to yield the external 120-kDa envelope glycoprotein (gp120) and the transmembrane 41-kDa envelope glycoprotein (gp41). Gp120 and gp41 remain linked through a labile non-covalent association. Entry of HIV into host cells is initiated by liberation of gp120 from the envelope complex through its interaction with the CD4 receptor present on the surface of helper T-lymphocytes, macrophages and other target cells. This interaction causes subtle conformational changes in gp120, exposing structural elements of the V3 loop that subsequently interact with a second host cell receptor, either a CCR5 or a CXCR4 chemokine receptor. Once gp120 is completely unmasked, gp41 undergoes a dramatic conformational change that ultimately results in fusion of the viral and cellular membranes and insertion of viral contents into the cytoplasm of the host cell.

Gp41-mediated fusion is a complex process involving three essential components located in the ectodomain of the glycoprotein: an $NH_2$-terminal fusion peptide, an $NH_2$-terminal heptad repeat ("N-helix") and a COOH-terminal heptad repeat ("C-helix"). The two heptad repeat regions ($NH_2$:HR1; COOH:HR2) impart periodic hydrophobicity to the glycoprotein and are predictive of alpha-helical structures that interact with each other to form a fusogenic (i.e., fusion-active) conformation of gp41 called the "trimer-of hairpins," a common structural motif involved in the fusion mechanism of many enveloped viruses. The trimer-of-hairpins structure is a bundle of six α-helices: three α-helices (formed by C-helix regions from three gp41 ectodomains) packed in an anti-parallel manner against a central, three-stranded coiled-coil (formed by N-helix regions from three gp41 ectodomains). The fusion process progresses via the formation of a "pre-hairpin" conformation of gp41 that places the $NH_2$-terminal fusion peptide near/in the target cell membrane, exposing the N-helix coiled-coil. The trimer-of-hairpins forms when three C-helices fold back to associate with the central, N-helix coiled-coil, drawing the viral and host cell membranes into close contact as a prelude to membrane fusion.

Effective treatment regimens are available for HIV infected individuals encompassing combination therapy of anti-retroviral agents targeting either the reverse transcriptase enzyme or the viral protease. This therapy has been effective at temporarily controlling viral load; however, the development of drug resistance over time in most patients, the necessity of sustained adherence to complex regimens and the potential for toxic effects underscores the importance for the development of new therapeutic approaches to battle HIV infection. To meet these needs, investigations into a new class of anti-retroviral agents targeting viral entry, called "fusion inhibitors," are underway. Fusion inhibitors are designed to inhibit the merging of HIV with the target cell membrane, blocking the virus before it enters the immune cell. The FDA recently approved the first of this new class of anti-retroviral agents, Fuzeon™ (enfuvirtide; also known as T-20), for use in combination with other anti-HIV medications. T-20 is one of a number of synthetic peptides, "C-peptides" or "N-peptides," derived from either the C- or N-helix regions of gp41, respectively, that have been shown to inhibit HIV-1 viral infection. C-peptides, including T-20, bind to N-helices of gp41 in a dominant-negative manner, preventing formation of the fusogenic trimer-of-hairpins and inhibiting HIV-1 infectivity. N-peptides also inhibit HIV-1 entry by either targeting an exposed C-helix region of gp41, or alternatively, forming a heterotrimeric coiled-coil and interfering with the coiled-coil formation of gp41. Anti-HIV agents that prevent viral/host cell membrane fusion also include neutralizing antibodies that bind to the pre-hairpin or trimer-of-hairpins complex. As such, a hydrophobic pocket within the heptad repeat 1 (HR1) region of the gp41 ectodomain, formed by the central, N-helix coiled-coil, is thought to be an attractive target for eliciting broadly cross-reactive, neutralizing antibodies to BV.

HV-1 N-peptides are far less potent inhibitors of viral entry than C-peptides, possibly due to the fact that N-peptides aggregate in the absence of C-helix regions. In order to facilitate the formation of a nonaggregated, trimeric, N-peptide coiled-coil, Eckert et al. (1999, *Cell* 99:103-115) constructed a chimeric N-peptide comprising a portion of the N-helix domain fused to a soluble, trimeric coiled-coil acting as a scaffold. This peptide, called IQN17 (also disclosed in PCT International Application PCT/US99/17351; International publication number WO 00/06599), formed a soluble, stable, trimeric coiled-coil. Eckert and Kim (2001, *Proc. Natl. Acad.*

*Sci. USA* 98:11187-11192) tested the inhibitory activity of IQN17 and other similarly constructed chimeric N-peptides fused to alternative coiled-coil scaffolds, e.g. IZN17 (also disclosed in PCT International Application PCT/US01/29637; International publication number WO 02/24735), identifying said peptides as potent inhibitors of HIV-1 entry. These results suggest that the inhibitory activity of N-peptides maybe be correlated to their stability. To further stabilize N-peptides with the goal of generating a closer mimetic of HIV fusion, the present invention discloses soluble, chimeric N-peptides that are covalently-stabilized in a trimeric conformation through the addition of cysteine residues to the ends of the peptide sequence. Upon oxidation at a neutral pH, disulfide bridges are formed between the engineered cysteine residues on adjacent N-peptide molecules. The method of stabilizing chimeric N-peptides of HIV gp41 in a homotrimeric or heterotrimeric coiled-coil conformation via the formation of disulfide bonds between engineered cysteine residues located outside of the α-helical domain of said individual peptides can be applied to other enveloped virus membrane-fusion proteins known to form an internal, coiled-coil motif in preparation of viral-target cell membrane fusion.

Louis, J. M. et al. (2001, *J. Biol. Chem.* 276:29485-29489) discloses a chimeric gp41 molecule comprising a N-helix domain grafted onto the $NH_2$-terminus of a minimal six-helix bundle of gp41 that is stabilized by intermolecular disulfide bridges. The disulfide bonds are generated between cysteine residues that are incorporated into the six-helix bundle by mutating residues 576-578 of the gp41 ectodomain, located within the N-helix region, to cysteine-cysteine-glycine (Cys-Cys-Gly).

Louis, J. M. et al. (2003, *J. Biol. Chem.* 278:20278-20285) and PCT International Application PCT/US02/40684 (International publication number WO 03/052122) disclose two soluble, covalently-linked, trimeric polypeptides comprising the internal, N-helix coiled-coil of the HIV-1 gp41 ectodomain. The HIV sequences are stabilized via engineered intersubunit disulfide bonds as the result of mutating the N-helix at residues 576-578 of the gp41 ectodomain to Cys-Cys-Gly.

SUMMARY OF THE INVENTION

The present invention relates to methods of covalently-stabilizing soluble, chimeric peptides which are capable of forming a homotrimeric or heterotrimeric coiled-coil structure that mimics all or a portion of an internal, trimeric coiled-coil motif of an enveloped virus membrane-fusion protein, wherein said internal, trimeric coiled-coil represents the core domain of the fusogenic (i.e., fusion-active) conformation of said membrane-fusion protein required for viral-host cell membrane fusion. As disclosed herein, stabilization of said soluble, chimeric peptides can occur via the formation of covalent bonds generated between individual peptides including, for example, disulfide bonds or any covalent bond which results from a chemoselective ligation reaction. Therefore, the present invention relates to a method of covalently-stabilizing a trimeric coiled-coil structure that mimics all or a portion of an internal, trimeric coiled-coil motif of an enveloped virus membrane-fusion protein comprising: (a) engineering a soluble chimeric peptide comprising an α-helical domain which comprises a soluble, trimeric form of a coiled-coil fused in helical phase to all or a portion of a $NH_2$-terminal heptad repeat domain, or a modified form thereof, of said enveloped virus membrane-fusion protein; and, (b) stabilizing three chimeric peptides from (a) in a trimeric coiled-coil structure by formation of covalent bonds between said peptides, wherein said covalent bonds are selected from the group consisting of disulfide bonds and bonds resulting from a chemoselective ligation reaction. Said trimeric coiled-coil structures generated by the methods disclosed herein can represent either homotrimeric or heterotrimeric structures.

The present invention relates to a method of covalently-stabilizing a trimeric coiled-coil structure that mimics all or a portion of an internal, trimeric coiled-coil motif of an enveloped virus membrane-fusion protein comprising the formation of covalent, disulfide bonds between cysteine residues on juxtaposed, α-helical peptides contained within the coiled-coil structure, wherein said cysteine residues are incorporated within said peptides outside of the α-helical domain. Therefore, the present invention relates to a method of covalently-stabilizing a homotrimeric or heterotrimeric coiled-coil structure that mimics all or a portion of an internal, trimeric coiled-coil motif of an enveloped virus membrane-fusion protein comprising: (a) engineering a soluble chimeric peptide comprising: (i) an α-helical domain which comprises a soluble, trimeric form of a coiled-coil fused in helical phase to all or a portion of a $NH_2$-terminal heptad repeat domain, or a modified form thereof, of said enveloped virus membrane-fusion protein; and, (ii) at least two cysteine residues located outside of said α-domain; (b) incubating a plurality of said soluble chimeric peptides at a concentration at which a homotrimeric or heterotrimeric coiled-coil structure forms; and, (c) oxidizing said homotrimeric or heterotrimeric coiled-coil structure formed in (b) to covalently-stabilize said coiled-coil via formation of disulfide bonds between cysteine residues on juxtaposed chimeric peptides of said coiled-coil. In one embodiment of the present invention, the soluble chimeric peptide in (a) comprises all or a portion of a N-peptide of HIV gp41.

The present invention further relates to a method of covalently-stabilizing a trimeric coiled-coil structure that mimics all or a portion of an internal, trimeric coiled-coil motif of an enveloped virus membrane-fusion protein comprising the formation of covalent, chemical bonds between juxtaposed, α-helical peptides contained within the coiled-coil structure, wherein said covalent, chemical bonds result from a chemoselective ligation reaction. Therefore, the present invention further relates to a method of covalently-stabilizing a homotrimeric or heterotrimeric coiled-coil structure that mimics all or a portion of an internal, trimeric coiled-coil motif of an enveloped virus membrane-fusion protein comprising: (a) engineering a soluble chimeric peptide comprising an α-helical domain which comprises a soluble, trimeric form of a coiled-coil fused in helical phase to all or a portion of a $NH_2$-terminal heptad repeat domain, or a modified form thereof, of said enveloped virus membrane-fusion protein; (b) incubating a plurality of said soluble chimeric peptides at a concentration at which a trimeric coiled-coil structure forms; and (c) stabilizing the trimeric coiled-coil structure in (b) by formation of covalent, chemical bonds between said chimeric peptides, wherein said chemical bonds are formed by a chemoselective reaction. In one embodiment of the present invention, said covalent, chemical bonds formed by a chemoselective reaction are thioether bonds. In another embodiment of the present invention, the plurality of soluble chimeric peptides in (b) is incubated at a concentration at which the resulting trimeric coiled-coil structure is comprised of: (a) one chimeric peptide which further comprises at least two cysteine residues located outside of the α-helical domain of said peptide; and, (b) two chimeric peptides which are each derivatized to incorporate an electrophilic moiety; wherein a nucleophilic sulfhydryl of each cysteine residue in the chimeric peptide in (a) forms a thioether bond with the electrophilic moiety of the derivatized chimeric peptides in (b). In a further embodiment of the present invention, the chimeric peptides in (b) are derivatized to incorporate an electrophilic moiety selected from the group consisting of an alkyl halide moiety and a Michael acceptor. The soluble chimeric peptides in both (a) and (b) above may comprise all or a portion of a N-peptide of HIV gp41.

The present invention also relates to a method of covalently-stabilizing a homotrimeric or heterotrimeric coiled-coil structure that mimics all or a portion of the internal, trimeric coiled-coil domain of a HIV gp41 ectodomain comprising: (a) engineering a soluble chimeric peptide comprising (i) an α-helical domain which comprises a soluble, trimeric form of a coiled-coil fused in helical phase to all or a portion of a N-peptide of HIV gp41, or a modified form thereof, and (ii) at least two cysteine residues located outside of said α-helical domain; (b) incubating a plurality of said soluble chimeric peptides at a concentration at which a homotrimeric or heterotrimeric coiled-coil structure forms; and, (c) oxidizing said coiled-coil structure formed in (b) to covalently-stabilize said coiled-coil via formation of disulfide bonds between cysteine residues on juxtaposed chimeric peptides of said coiled-coil. In one embodiment, the N-peptide portions of the chimeric peptides that are covalently-stabilized by the method of the present invention are derived from the ectodomain of HIV-1 gp41.

The present invention further relates to a method of covalently-stabilizing a trimeric coiled-coil structure that mimics all or a portion of the internal, trimeric coiled-coil motif of a HIV gp41 ectodomain including but not limited to the ectodomain of HIV-1 gp41, comprising: (a) engineering a soluble chimeric peptide comprising an α-helical domain which comprises a soluble, trimeric form of a coiled-coil fused in helical phase to all or a portion of a N-peptide of HIV gp41, or a modified form thereof; (b) incubating a plurality of said soluble chimeric peptides at a concentration at which a homotrimeric or heterotrimeric coiled-coil structure forms; and (c) stabilizing the trimeric coiled-coil structure in (b) by formation of covalent, chemical bonds between said chimeric peptides, wherein said chemical bonds are formed by a chemoselective reaction. In one embodiment of the present invention, the chemical bonds are thioether bonds. In a further embodiment, the plurality of soluble chimeric peptides is incubated at a concentration at which the resulting trimeric coiled-coil structure is comprised of: (a) one chimeric peptide which further comprises at least two cysteine residues located outside of the α-helical domain of said peptide; and, (b) two chimeric peptides which are each derivatized to incorporate an electrophilic moiety; wherein a nucleophilic sulfhydryl of each cysteine residue in the chimeric peptide in (a) forms a thioether bond with the electrophilic moiety of the derivatized chimeric peptides in (b). In another embodiment of the present invention, the chimeric peptides in (b) are derivatized to incorporate an electrophilic moiety selected from the group consisting of an alkyl halide moiety and a Michael acceptor.

The present invention further relates to a covalently-stabilized coiled-coil that mimics all or a portion of a HIV gp41 N-peptide coiled-coil, including but not limited to a HIV-1 gp41 N-peptide coiled-coil, made by the disclosed methods. Therefore, the present invention also relates to a covalently-stabilized coiled-coil that mimics all or a portion of a HIV gp41 N-peptide coiled-coil comprising three identical (i.e., for generating homotrimeric structures) or substantially similar (i.e., for generating heterotrimeric structures) chimeric peptides, wherein each chimeric peptide comprises the following: (a) an α-helical domain comprising a soluble, trimeric form of a coiled-coil fused in helical phase to all or a portion of a HIV-1 gp41 N-peptide, or a modified form thereof; and, (b) at least two cysteine residues located outside of the α-helical domain of said chimeric peptide; wherein said three, identical or substantially similar chimeric peptides are covalently-stabilized as a coiled-coil via disulfide bonds between said cysteine residues of individual peptides. The present invention further relates to a covalently-stabilized trimeric coiled-coil that mimics all of a portion of a HIV gp41 N-peptide coiled-coil which comprises: (a) one chimeric peptide comprising: (i) an α-helical domain which comprises a soluble, trimeric form of a coiled-coil fused in helical phase to all or a portion of a HIV gp41 N-peptide, or a modified form thereof; and, (ii) at least two cysteine residues located outside of the α-helical domain of said peptide; and, (b) two chimeric peptides comprising an α-helical domain which comprises a soluble, trimeric form of a coiled-coil fused in helical phase to all or a portion of a HIV gp41 N-peptide, or a modified form thereof, that are each derivatized with an electrophilic moiety capable of forming a thioether bond; wherein a nucleophilic sulfhydryl of each cysteine residue in the chimeric peptide in (a) forms a thioether bond with the electrophilic moiety of the derivatized chimeric peptides in (b). In one embodiment of the present invention, thioether bonds are formed between a single chimeric peptide as described in (a) and two chimeric peptides in (b), wherein each chimeric peptide in (b) is derivatized with an electrophilic moiety selected from the group consisting of an alkyl halide-moiety (including, but not limited to, a bromoacetyl or an iodoacetyl moiety) and a Michael acceptor (including, but not limited to, a maleimide moiety).

The present invention also relates to soluble chimeric peptides that can be covalently-stabilized in a homotrimeric or heterotrimeric coiled-coil conformation, wherein said coiled-coil structure represents a stable, faithful mimetic of a HIV gp41 fusion intermediate, including but not limited to a HIV-1 gp41 fusion intermediate. In one embodiment of the present invention, said soluble chimeric peptides can be covalently-stabilized in a trimeric coiled-coil conformation via the formation of covalent, disulfide bonds between said peptides. Said soluble chimeric peptides of this embodiment of the present invention embrace the same general design, each having the following components: (1) an α-helical scaffold protein capable of acquiring a trimeric coiled-coil conformation (the "scaffold portion" of the chimeric peptide); (2) all or a portion of the $NH_2$-terminal heptad repeat domain ("N-helix") of a HIV gp41 (the "N-peptide portion" of the chimeric peptide); and, (3) at least two cysteine residues located at either the $NH_2$- or COOH-terminus of the chimeric peptide sequence (the "cysteine portion" of the chimeric peptide). These chimeric peptides are herein designated as "CC-chimeric N-peptides." The cysteine portion of the CC-chimeric N-peptides of the present invention is optionally separated from the chimeric peptide sequence by a linker/spacer region for increased flexibility. Said peptides of the present invention are capable of forming a soluble, trimeric coiled-coil structure comprising three, chimeric peptide chains physically associated in a parallel orientation, wherein said trimeric structure is then covalently-stabilized via the formation of disulfide bonds between the engineered cysteine amino acid residues on juxtaposed peptide chains. The disulfide linkages ensure that the chimeric peptide monomers do not dissociate, even at very low concentrations. Therefore, a soluble, chimeric peptide of the present invention comprises: (a) a scaffold portion comprising a soluble, trimeric form of a coiled-coil; (b) a N-peptide portion comprising all or a portion of a N-peptide of HIV gp41, or a modified form thereof; and, (c) a cysteine portion comprising at least two cysteine (Cys) residues; wherein said scaffold portion in (a) is fused in helical phase to said N-peptide portion in (b), forming an α-helical domain, and said cysteine portion in (c) is located outside of said α-helical domain, wherein said chimeric peptide can form a covalently-stabilized, homotrimeric or heterotrimeric coiled-coil structure with identical or substantially similar peptides via the formation of disulfide bonds between Cys residues of said peptides.

The present invention further relates to soluble chimeric peptides that can be covalently-stabilized in a trimeric coiled-coil conformation via the formation of covalent, chemical bonds between said peptides, wherein said chemical bonds are formed by a chemoselective ligation reaction. Said soluble chimeric peptides of this embodiment of the present invention embrace a similar general design as those which are stabilized by disulfide bonds, each having the following components: (1) an α-helical scaffold protein capable of acquiring a trimeric coiled-coil conformation (the "scaffold portion" of the chimeric peptide); and, (2) all or a portion of the NH$_2$-terminal heptad repeat domain ("N-helix") of a HIV gp41 (the "N-peptide portion" of the chimeric peptide). However, the chimeric peptides in this embodiment of the present invention are further modified to provide them with the capability of participating in chemoselective ligation reactions which generate covalent, chemical bonds between said peptides and CC-chimeric N-peptides as described above. Said peptides are herein designated as "derivatized-chimeric N-peptides." For example, in one embodiment of the present invention, a trimeric coiled-coil that is covalently-stabilized by thioether bond formation comprises the following peptide components: (i) one, soluble CC-chimeric N-peptide, as described above, comprising a "scaffold portion," a "N-peptide portion," and a "cysteine portion" having at least two cysteine residues located at either the NH$_2$- or COOH-terminus of the chimeric peptide sequence; and, (ii) two, soluble derivatized-chimeric N-peptides comprising the same or substantially similar scaffold and N-peptide portions as the CC-chimeric N-peptide in (i), wherein each peptide is derivatized to incorporate an electrophilic moiety capable of forming a thioether bond (including, but not limited to, an alkyl halide moiety and a Michael acceptor). Therefore, one embodiment of the present invention relates to a soluble chimeric peptide which comprises: (a) a scaffold portion comprising a soluble, trimeric form of a coiled-coil; and, (b) a N-peptide portion comprising all or a portion of a N-peptide of HIV gp41, or a modified form thereof; wherein said chimeric peptide is derivatized to incorporate an electrophilic moiety capable of forming a thioether bond.

The present invention further relates to a chimeric peptide comprising an amino acid sequence selected from the group consisting of:

(a)  CCGGIKKEIEAIKKEQEAIKKKIEAIEKLLQLTVWGIKQLQARIL
     (SEQ ID NO:2; "CCIZN17");

(b)  CCGGIEKKIEEIEKKIEEIEKKIEEIEKLLQLTVWGIKQLQARIL
     (SEQ ID NO:7; "CCEZN17");

(c)  CCGGIKKEIEAIKKEQEAIKKKIEAIEKLLQLTVWGIKALAAAIA
     (SEQ ID NO:5; "CCIZN17Ala4");

(d)  CCGGIEKKIEEIEKKIEEIEKKIEEIEKLLQLTVWGIKALAAAIA
     (SEQ ID NO:9; "CCEZN17Ala4");

(e)  CCGGIKKEIEAIKKEQEAIKKKIEAIEKEIEAQQHLLQLTVWGIK
     QLQARIL
     (SEQ ID NO:13; "CCIZN23");

(f)  CCGGIEKKIEEIEKKIEEIEKKIEEIEEKIEAQQHLLQLTVWGIK
     QLQARIL
     (SEQ ID NO:15; "CCEZN23");

(g)  GCCGGIKKEIEAIKKEQEAIKKKIEAIEKEIEAQQHLLQLTVWGI
     KQLQARIL
     (SEQ ID NO:12; "Biotin-CCIZN23");

(h)  SGGCCGGIKKEIEAIKKEQEAIKKKIEAIEKLLQLTVWGIKQLQA
     RIL
     (SEQ ID NO:21; "SCCIZN17");

(i)  CCGGIEKKIEAIEKKIEAIEKKIEAIEKLLQLTVWGIKQLQARIL
     (SEQ ID NO:98; "CCSZN17")

(j)  CCGGIEKKIEAIEKKIEAIEKLLQLTVWGIKQLQARIL
     (SEQ ID NO:100; "CCS17N17");

(k)  CCGGIEEKIEEIEELLQLTVWGIKQLQARIL
     (SEQ ID NO: 109; "CCE10N17");

(l)  CCGGIEKKIEEIEKKIEEIEKLLQLTVWGIKQLQARIL
     (SEQ ID NO:116; "CCE17N17");
and, (m)  CCGGIEKKIEEIEEKIEEIEKLLQLTVWGIKQLQARIL
     (SEQ ID NO: 120; "CCE17GluN17").

The present invention also relates to a chimeric peptide:
(a) wherein said chimeric peptide consists of an amino acid sequence as set forth in SEQ ID NO:2 ("CCIZN17");
(b) wherein said chimeric peptide consists of an amino acid sequence as set forth in SEQ ID NO:7 ("CCEZN17");
(c) wherein said chimeric peptide consists of an amino acid sequence as set forth in SEQ ID NO:5 ("CCIZN17Ala4");
(d) wherein said chimeric peptide consists of an amino acid sequence as set forth in SEQ ID NO:9 ("CCEZN17Ala4");
(e) wherein said chimeric peptide consists of an amino acid sequence as set forth in SEQ ID NO:13 ("CCIZN23");
(f) wherein said chimeric peptide consists of an amino acid sequence as set forth in SEQ ID NO:15 ("CCEZN23");
(g) wherein said chimeric peptide consists of an amino acid sequence as set forth in SEQ ID NO: 12 ("Biotin-CCIZN23");
(h) wherein said chimeric peptide consists of an amino acid sequence as set forth in SEQ ID NO:21 ("SCCIZN17");
(i) wherein said chimeric peptide consists of an amino acid sequence as set forth in SEQ ID NO:98 ("CCSZN17");
j) wherein said chimeric peptide consists of an amino acid sequence as set forth in SEQ ID NO:100 ("CCS17N17");
(k) wherein said chimeric peptide consists of an amino acid sequence as set forth in SEQ ID NO: 109 ("CCE10N17");
(l) wherein said chimeric peptide consists of an amino acid sequence as set forth in SEQ ID NO:103 ("CCCIZN17");
(m) wherein said chimeric peptide consists of an amino acid sequence as set forth in SEQ ID NO:105 ("CCCS17N17");
(n) wherein said chimeric peptide consists of an amino acid sequence as set forth in SEQ ID NO:106 ("GGGS17N17");
(o) wherein said chimeric peptide consists of an amino acid sequence as set forth in SEQ ID NO:111 ("CCCE10N17");
(p) wherein said chimeric peptide consists of an amino acid sequence as set forth in SEQ ID NO:110 ("GGGE10N17");
(q) wherein said chimeric peptide consists of an amino acid sequence as set forth in SEQ ID NO:121 ("GGGEZN17");
(r) wherein said chimeric peptide consists of an amino acid sequence as set forth in SEQ ID NO: 122 ("CCCEZN17");
(s) wherein said chimeric peptide consists of an amino acid sequence as set forth in SEQ ID NO:125 ("GGGE17N17");

(t) wherein said chimeric peptide consists of an amino acid sequence as set forth in SEQ ID NO: 126 ("CCCE17N17");

(u) wherein said chimeric peptide consists of an amino acid sequence as set forth in SEQ ID NO:123 ("GGGE17GluN17"); and, (v) wherein said chimeric peptide consists of an amino acid sequence as set forth in SEQ ID NO: 124 ("CCCE17GluN17").

The present invention relates to a covalently-stabilized, coiled-coil that mimics all or a portion of a HIV-1 gp41 N-peptide coiled-coil selected from the group consisting of: (a) (CCIZN17)$_3$ ([SEQ ID NO:2]$_3$); (b) (CCEZN17)$_3$ ([SEQ ID NO:7]$_3$); (c) (CCIZN17Ala4)$_3$ ([SEQ ID NO:5]$_3$); (d) (CCEZN17Ala4)$_3$ ([SEQ ID NO:9]$_3$); (e) (CCIZN23)$_3$ ([SEQ ID NO: 13]3); (f) (CCEZN23)$_3$ ([SEQ ID NO: 15]3); (g) (Biotin-CCIZN23)$_3$ ([SEQ ID NO: 12]3); (h) (SC-CIZN17)$_3$ ([SEQ ID NO:21]$_3$); (i) C(thioIZN17)$_3$; (j) C(thioS17N17)$_3$; (k) C(thioE10N17)$_3$; (l) C(thioEZ-N17)$_3$; (m) C(thioE17N17)$_3$; and (n) C(thioE17GluN17)$_3$. The covalently-stabilized coiled-coils exemplified herein predominantly have an NH$_2$-terminus acetyl group and a COOH-terminus amide group; however, in no way is this limiting to the invention as whole.

The present invention further relates to antigenic conjugates of the HIV-derived, chimeric peptides described herein comprising a soluble chimeric peptide of the present invention covalently linked to an immunogenic carrier (e.g., OMPC). The present invention also relates to antigenic conjugates of covalently-stabilized, homotrimeric or heterotrimeric coiled-coil structures described herein that mimic all or a portion of a HIV gp41 N-peptide coiled-coil, wherein said coiled-coil structure is covalently-linked to an immunogenic carrier. A pharmaceutical composition comprising said antigenic conjugates, optionally mixed with a biologically effective adjuvant, protein, or other agent capable of increasing the immune response, can be used as an immunogen capable of eliciting HIV-specific neutralizing antibodies in mammals. The present invention also relates to a therapeutic method of treating a HIV positive subject by eliciting an immune response against HIV in said subject. This method comprises administering to the subject an effective amount of a pharmaceutical composition comprising the covalently-stabilized, homotrimeric coiled-coil described herein, or antigenic conjugates thereof, and optionally one or more carriers, one or more excipients, and/or one or more chemical derivatives.

The present invention relates to a method of inhibiting fusion of HIV to a cell, including but not limited to a human cell, and/or a method of preventing infection of said cells by HIV which comprises contacting HIV with an effective amount of a chimeric peptide composition described herein, such that the chimeric peptide effectively blocks formation of the fusogenic, six-helical conformation of gp41. The chimeric peptide composition interferes with the ability of gp41 to adopt a structural conformation that can mediate fusion of HIV to said cell by binding to an epitope in a gp41 fusion intermediate, thereby inhibiting HIV infection of said cell. In one embodiment, said cell is a human cell present in an individual. In one embodiment, the chimeric peptide composition comprises an effective amount of a covalently-stabilized, homotrimeric or heterotrimeric coiled-coil that mimics all or a portion of a HIV gp41 N-peptide coiled-coil comprising three, identical chimeric peptides, wherein each chimeric peptide comprises: (a) an α-helical domain comprising a soluble, trimeric form of a coiled-coil fused in helical phase to all or a portion of a N-peptide of HIV gp41, or a modified form thereof; and, (b) at least two cysteine residues located outside of the α-helical domain of said chimeric peptide; wherein said three, identical or substantially similar chimeric peptides are covalently-stabilized as a coiled-coil via disulfide bonds between said cysteine residues of individual peptides. In a further embodiment of the present invention, said chimeric peptide composition comprises an effective amount of a trimeric coiled-coil that mimics all or a portion of a HIV gp41 N-peptide coiled-coil that is covalently-stabilized via the formation of chemical, covalent bonds resulting from a chemoselective ligation reaction, as described above. The present invention further relates to methods of identifying HIV fusion inhibitors which include, but are not limited to small molecule inhibitors, using the chimeric peptides disclosed herein.

As used herein, "HIV" is meant to represent either HIV-1, HIV-2, or HIV-1 and/or HIV-2.

As used herein, "neutralizing" is used as in the art, namely to denote the ability of an antibody to prevent viral infection in an ini vitro cell/virus-based assay. Neutralizing activity may be measured quantitatively as the IC$_{50}$ value for that specific antibody. A "neutralizing antibody" or a "HIV neutralizing antibody" is shown in an art accepted infectivity assay to neutralize at least one HIV isolate.

As used herein, the term "epitope" relates to a protein determinant capable of specific binding to an antibody. It is well known that epitopes usually consist of chemically active surface groupings of molecules such as amino acids or sugar side chains and usually have specific three dimensional structural characteristics, as well as specific charge characteristics. Conformational and nonconformational epitopes are distinguished in that the binding of the former but not the latter is lost in the presence of denaturing solvents.

As used herein, the term "Michael acceptor" refers to any chemical moiety that contains a polarized, electrophilic carbon-carbon double bond that is able to react with a nucleophilic species (e.g., O$^-$, C$^-$, or S$^-$).

BRIEF DESCRIPTION OF THE DRAWINGS

FIG. 2A-C shows the chemical, structural representation of the disulfide bonds stabilizing three CC-chimeric N-peptide, trimeric coiled-coils: (CCIZN17)$_3$ ([SEQ ID NO:2]$_3$) (A), (Biotin-CCIZN23)$_3$ ([SEQ ID NO: 12]3) (B), and (CCI10N17)$_3$ ([SEQ ID NO:20]$_3$) (C). Each trimeric coiled-coil has three disulfide bonds located between thiol (—SH) groups of NH$_2$-terminal cysteine residues. The amino acids located at the carboxy terminus of the cysteine residues are in bold with single letter nomenclature.

FIG. 3A-B shows the chemical, structural representation of the disulfide bonds stabilizing two CC-chimeric N-peptide, trimeric coiled-coils: (SCCIZN17)$_3$ ([SEQ ID NO:21]$_3$) (A) and (CCEZN17)$_3$ ([SEQ ID NO:7]$_3$) (B). Each trimeric coiled-coil has three disulfide bonds located between thiol (—SH) groups of NH$_2$-terminal cysteine residues. In (A), the amino acids located both at the COOH- and NH$_2$-terminus of the cysteine residues are in bold with single letter nomenclature. In (B), the amino acids located at the carboxy terminus of the cysteine residues are in bold with single letter nomenclature.

FIG. 4A-D shows a table summarizing the peptide sequences and Sequence Identification Numbers ("SEQ ID NO:") of the chimeric peptides described herein.

FIG. 9A-B shows how mutations within IZN17 affect D5-IgG binding to said mutated chimeric peptide in an AlphaScreen™ study. In (A), IZN17 was mutated at amino acid positions located within the hydrophobic pocket region of gp41 (IZN17 L565M, IZN17 Q567R, IZN17 G572D). Panel (B) shows an IZN17-based alanine scanning experiment wherein individual, solvent exposed amino acids of the N17 segment of HIV-1 gp41 were substituted with alanine residues. The mutant peptides in (A) and (B) were tested for their ability to inhibit the binding of D5-IgG to biotinylated-IQN17. These experiments indicate critical amino acids within the hydrophobic pocket that are necessary for D5-IgG binding.

FIG. 10A-C shows a series of mutant IZN17 peptides of which individual amino acids of the N17 segment of HIV-1 gp41 that are solvent exposed were substituted with alanine residues. These mutant peptides were tested for ability to inhibit the binding of three, non-HIV-neutralizing monoclonal antibodies raised against IQN17 (A, B and C) to biotinylated-IQN17.

FIG. 11 summarizes the results presented in FIGS. 9 and 10, identifying individual amino acids of the N17 segment of the gp41 ectodomain that are involved in binding the HIV-neutralizing human monoclonal antibody D5 and three non-HIV neutralizing mouse monoclonal antibodies (A, B, C) raised against IQN17 (SEQ ID NO:23). "YES" indicates that the amino acid in IZN17 is critical for the binding of the antibody. "WEAK" indicates that the amino acid contributes to antibody binding but is not essential, and "NO" indicates that the amino acid is dispensable for antibody binding.

FIG. 12A-B shows the activity of chimeric N-peptide IZN17Ala4 (SEQ ID NO:4) in an anti-viral assay against HIV-1 HXB2 (A) and the ability of IZN17Ala4 to inhibit binding of D5 IgG to biotinylated-IZN17 in an AlphaScreen™-based assay format (B). Although IZN17Ala4 inhibits HIV-1 HXB2 with an IC$_{50}$ of only 25 nM, an approximately 125-fold reduction in anti-viral activity relative to the parental chimeric N-peptide IZN17 (SEQ ID NO:1), IZN17Ala4 interacts with a neutralizing antibody that recognizes the hydrophobic pocket of the gp41 ectodomain.

FIG. 13 summarizes and compares the activity of various chimeric N-peptides (IZN17, EZN17, IZN17Ala4, N17IZ and SZN17); covalently-stabilized, trimeric CC-chimeric N-peptide coiled-coils stabilized by covalent disulfide bonds ((CCIZN17)$_3$, (CCEZN17)$_3$, (CCI10N17)$_3$, (I10N17CC)$_3$, (CCIZN17Ala4)$_3$, (CCIZN13)$_3$, (CCS17N17)$_3$, (CCS10N17)$_3$ and (CCIZN11IZ)$_3$); and covalently-stabilized, trimeric coiled-coils stabilized by thioether bonds (NH$_2$—C(Fm)(thioIZN17)$_3$, ac-C(Acm)(thioIZN17)$_3$, ac-C(Acm)(thioE10N17)$_3$, ac-C(Acm)(thioS17N17)$_3$). The activity of these peptides is measured in both anti-viral assays against the HIV-1 HXB2 strain and biotinylated-5-Helix/D5 IgG or biotinylated-5-Helix/D5-FITC IgG interactions assays. The term "n.d." signifies that said experimental value has not yet been determined.

FIG. 14A-B shows the chemical, structural representation of two trimeric coiled-coil structures of the present invention which are covalently-stabilized by thioether bonds (see Example 11). (A) Chemical, structural representation of NH$_2$—C(Fm)(thioIZN17)$_3$ formed between one CC-chimeric N-peptide, NH$_2$—C(Fm)Tds-CCIZN17, and two derivatized-chimeric N-peptides, Br-acetyl-GGGIZN17. (B) Chemical, structural representation of ac-C(Acm)(thioIZN17)$_3$ formed between one CC-chimeric N-peptide, ac-C(Acm)Ttds-CCIZN17, and two derivatized-chimeric N-peptides, Br-acetyl-GGGIZN17. Each trimeric coiled-coil is stabilized by two thioether bonds located between a thiol (—SH) group on each of two cysteine residues of the CC-chimeric N-peptide (represented in FIG. 14 by chemical structure) and the electrophilic bromo-moiety of each derivatized-chimeric N-peptide. The amino acids located at the COOH-terminus of the bonded cysteine residues are in single letter nomenclature. While both coiled-coil structures in (A) and (B) have the same peptide sequence composition, the structures differ by the protecting group shielding the thiol of the NH$_2$-terminal cysteine residue of the CC-chimeric N-peptide of each structure—a fluoroenylmethoxy ("Fm") group in (A) versus a acetamidomethyl ("Acm") group in (B). Additionally, the coiled-coil in (A) has a free amino group at the NH$_2$-terminus, while the coiled-coil in (B) has a NH$_2$-terminal acetyl group.

FIG. 15A-B demonstrates that sera from (CCIZN17)-3-immunized rabbits contain D5 IgG-competitive antibodies. In (A), fractions retrieved from a 5-Helix affinity column percolated with pooled serum from rabbits immunized with (CCIZN17)$_3$ were tested in a 5-Helix/D5-FITC interaction assay for presence of D5-competing antibodies. Several flow-through and eluant fractions contain detectable D5-competitive antibodies. FIG. 15B demonstrates that antibodies collected from eluant fractions 5 and 6 possess inhibitory activity, displaying a concentration-dependent inhibitory effect (left panel). Neither fraction produced inhibitory activity when tested against Rhabdovirus VSV-pseudotyped HIV particles (right panel).

FIG. 16A-B shows that polyclonal rabbit antibodies elicited by (CCIZN17)$_3$ immunization bind the hydrophobic pocket formed in the heptad-repeat 1 (HR1) region of HIV gp41. In (A), pooled fractions 5 and 6 (see FIG. 15A) were titrated against biotinylated 5-Helix in the presence of streptavidin coated donor beads and protein-A acceptor beads. Peak signals seen when combining 1-10 nM 5-Helix with 250 µg/ml of antibody demonstrate the presence of antibodies capable of interacting with 5-Helix. In (B), two peptides, C34 and D10-p5-2K, were tested for their ability to prevent interaction of the purified antibodies with the HR1 hydrophobic pocket. C34 binds the entire HR1 groove. D10-p5-2K specifically interacts with the hydrophobic pocket. The C8 peptide was used as a negative control. Incubation of increasing concentrations of C34 and D10-p5-2K with 5-Helix prior to the addition of the rabbit antibodies show inhibition of the attachment of antibody to 5-Helix.

FIG. 17A-C shows that rabbit antibodies generated by (CCIZN17)$_3$ immunization and subsequently purified by protein-A chromatography demonstrate antiviral activity in HIV-1 single-cycle infectivity assays against HIV-1 strains, HXB2 (A) and BaL (B). For both HXB2 and BaL strains, the dialyzed rabbit IgG (circles) is less potent than the antiviral activity demonstrated with the human monoclonal antibody D5 (open squares). No inhibitory activity was observed against VSV-G pseudotyped HIV-1 virus (C).

DETAILED DESCRIPTION OF THE INVENTION

Figure 1:
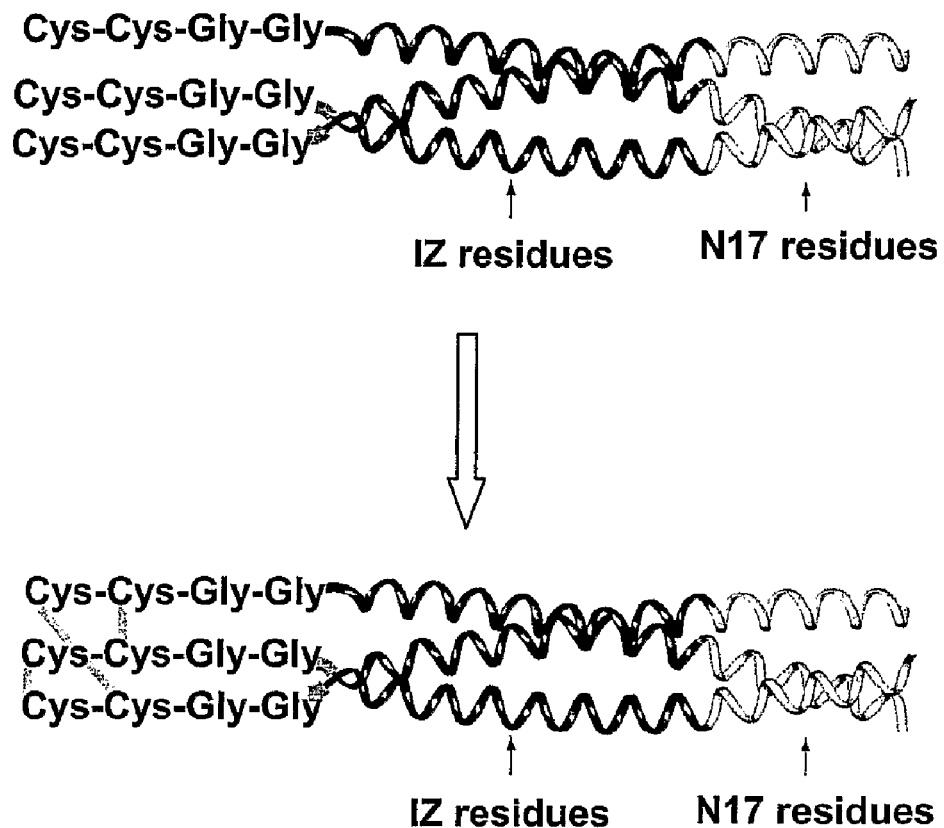
FIG. 1 shows a schematic representation of the oxidation reaction yielding the covalently-stabilized, homotrimeric coiled-coil (CCIZN17)$_3$. There are three disulfide bonds stabilizing the coiled-coil, one bond between each peptide chain.

The present invention relates to methods of covalently-stabilizing soluble, chimeric peptides in a homotrimeric or heterotrimeric coiled-coil conformation that mimics all or a portion of an internal, trimeric coiled-coil motif of an enveloped virus membrane-fusion protein, wherein said internal, trimeric coiled-coil motif represents the core domain of the fusogenic (i.e., fusion-active) conformation of said viral membrane-fusion protein which is necessary to achieve viral-host cell membrane fusion. The chimeric peptides that are covalently-stabilized by the methods of the present invention comprise an alpha("α")-helical domain comprising an α-helical scaffold protein capable of forming a trimeric coiled-coil (the "scaffold portion") fused in helical phase to all or a portion of a NH$_2$-terminal heptad repeat domain of an enveloped virus membrane-fusion protein (the "N-peptide" portion). The enveloped virus is known to achieve viral-host cell membrane fusion via a fusion-active conformation of its membrane-fusion protein that comprises a core, trimeric coiled-cold motif. Three identical or substantially similar chimeric peptides, as described above, are capable of forming a homotrimeric or heterotrimeric, respectively, coiled-coil structure that mimics said core, trimeric coiled-coil motif of the viral membrane-fusion protein; however, at low concentrations, the individual chimeric peptide chains dissociate. Thus, one embodiment of the present invention relates to a method of covalently-stabilizing said homotrimeric or heterotrimeric coiled-coil structures comprising adding at least two cysteine residues to the NH$_2$- or COOH-terminus of the α-helical domain of the individual chimeric peptides. In this embodiment of the present invention, three, identical or substantially similar cysteine-containing chimeric peptides are then covalently-stabilized in a homotrimeric or heterotrimeric molecule via intermolecular disulfide bonds formed under oxidizing conditions between juxtaposed cysteine residues on closely associated chimeric peptide chains. The covalently-stabilized, homotrimeric or heterotrimeric coiled-coil is formed either by exposing a pre-formed, trimeric coiled-coil to an oxidizing environment or by promoting the association of individual peptide chains into a coiled-coil conformation under oxidizing conditions. The added cysteine residues are located outside of the α-helical domain of the chimeric peptide, ensuring high conformational freedom, and optionally separated from the core, chimeric peptide sequence by a linker or spacer region.

In another embodiment of the present invention, a method of covalently-stabilizing a trimeric coiled-coil structure (e.g., homotrimeric or heterotrimeric) that mimics a core, trimeric coiled-coil motif of a viral membrane-fusion protein includes stabilizing alpha("α")-helical chimeric peptides comprising a "scaffold" domain and a "N-peptide" domain, as described above, via covalent, chemical bonds resulting from a chemoselective ligation reaction. Said chemoselective ligation reaction generates stabilizing thioether bonds between said peptides, forming a mimetic of the internal portion of the fusogenic conformation of an enveloped virus membrane-fusion protein, including but not limited to HIV gp41. For example, in one embodiment of the present invention, three chimeric peptides each having an α-helical domain comprising a soluble, trimeric form of a coiled-coil fused in helical phase to all or a portion of an internal, trimeric coiled-coil of an enveloped virus membrane-fusion protein, as described above, are stabilized via thioether bond formation between said peptides, resulting in the formation of a trimeric coiled-coil having the following peptide composition: (i) one chimeric peptide which further comprises at least two cysteine residues located outside of the α-helical domain of said peptide; and, (ii) two chimeric peptides which are each derivatized to incorporate an electrophilic moiety; wherein a nucleophilic sulfhydryl of each cysteine residue in the chimeric peptide in (a) forms a thioether bond with the electrophilic moiety (e.g., alkyl halide moiety, Michael acceptor) of the derivatized chimeric peptides in (b).

During HIV gp41-mediated fusion of viral and host cell membranes, two heptad repeat regions within the gp41 ectodomain (the N-helix:HR1 and C-helix:HR2 regions), predictive of α-helical regions, interact with each other to form a fusogenic conformation of the gp41 glycoprotein called the trimer-of hairpins. The trimer-of-hairpins structure is a bundle of six α-helices: three α-helices (formed by C-helix regions from three gp41 ectodomains) packed in an antiparallel manner against a central, three-stranded coiled-coil (formed by N-helix regions from three gp41 ectodomains). Prior to formation of the trimer-of-hairpins structure, a "pre-hairpin" conformation is generated that places the NH$_2$-terminal fusion peptide near/in the target cell membrane, exposing the coiled-coil structure formed by three N-helices. The trimer-of-hairpins forms when the three C-helices of the pre-hairpin structure fold back to associate with the N-helix coiled-coil, drawing the viral and host cell membranes into close contact as a prelude to fusion.

A hairpin-like structure is a common feature of many enveloped viral membrane-fusion proteins (Singh et al., 1999, *J. Mol. Biol.* 290:1031-1041). For example, advanced structural studies of the membrane-fusion proteins of influenza virus (hemagglutinin HA2), simian immunodeficiency virus (SIV gp41) and Ebola virus (Ebola GP2) have revealed hairpin-like structures containing a core, parallel, homotrimeric coiled-coil located adjacent to the NH$_2$-terminal fusion-peptide regions. Fusogenic, hairpin-like structures are formed when three extended helices pack on the exterior of said core (or internal) homotrimeric structure, supporting this internal coiled-coil. In addition to those enveloped viruses mentioned, many other members of the retrovirus, paramyxovirus, and filovirus families are predicted to contain a similar structural motif (Singh et al., 1999, supra; Joshi et al., 1998, *Virology* 248:20-34). The methods of covalently-stabilizing soluble chimeric peptides of the present invention are exemplified herein, both in the Detailed Description and in the Examples, using HIV gp41-specific chimeric peptides; however, this exemplification is not intended to limit the scope of the present invention solely to the stabilization of HIV-specific chimeric peptides and/or use of said covalently-stabilized peptides to, for example, inhibit viral infectivity. It will be known to one of skill in the art that the basic strategy described herein, a method of covalently-stabilizing a homotrimeric coiled-coil structure that mimics all or a portion of the internal, trimeric coiled-coil motif of an enveloped virus membrane-fusion protein can be applied to many enveloped virus systems in order to generate structures that will inhibit viral-target cell membrane fusion.

One embodiment of the present invention relates to a method of covalently-stabilizing a trimeric coiled-coil structure that mimics all or a portion of an internal, trimeric coiled-coil motif of an enveloped virus membrane-fusion protein comprising stabilizing said trimeric coiled-coil via the formation of covalent, disulfide bonds between cysteine residues on juxtaposed, α-helical peptides contained within the coiled-coil structure, wherein said cysteine residues are incorporated within said peptides outside of the α-helical domain of said peptides. Therefore, the present invention relates to a method of covalently-stabilizing a homotrimeric or heterotrimeric coiled-coil structure that mimics all or a portion of an internal, trimeric coiled-coil motif of an enveloped virus membrane-fusion protein comprising: (a) engineering a soluble chimeric peptide comprising: (i) an α-helical domain which comprises a soluble, trimeric form of a coiled-coil fused in helical phase to all or a portion of a $NH_2$-terminal heptad repeat domain, or a modified form thereof, of said enveloped virus membrane-fusion protein; and, (ii) at least two cysteine residues located outside of said α-helical domain; (b) incubating a plurality of said soluble chimeric peptides at a concentration at which a homotrimeric or heterotrimeric coiled-coil structure forms; and, (c) oxidizing said homotrimeric or heterotrimeric coiled-coil structure formed in (b) to covalently-stabilize said coiled-coil via formation of disulfide bonds between cysteine residues on juxtaposed chimeric peptides of said coiled-coil. In one embodiment of the present invention, the method of covalently-stabilizing a homotrimeric or heterotrimeric coiled-coil that mimics all or a portion of an internal, trimeric coiled-coil motif of an enveloped virus membrane-fusion protein via disulfide bond formation is applied to HIV gp41, including but not limited to HIV-1 gp41. In this embodiment, said resulting homotrimeric or heterotrimeric coiled-coil structure comprises three chimeric peptides, each containing all or a portion of a N-peptide of HIV gp41, or a modified form thereof, that is covalently stabilized via the formation of disulfide bonds between engineered cysteine residues within individual, chimeric peptide chains. The covalently-stabilized chimeric peptides described herein are members of a new class of anti-retroviral agents targeting viral entry.

The present invention further relates to a method of covalently-stabilizing a homotrimeric or heterotrimeric coiled-coil structure that mimics all or a portion of an internal, trimeric coiled-coil motif of an enveloped virus membrane-fusion protein comprising stabilizing said trimeric coiled-coil structure via the formation of covalent, chemical bonds between juxtaposed, α-helical peptides contained within the coiled-coil, wherein said covalent, chemical bonds result from chemoselective ligation reactions. Therefore, the present invention further relates to a method of covalently-stabilizing a homotrimeric or heterotrimeric coiled-coil structure that mimics all or a portion of an internal, trimeric coiled-coil motif of an enveloped virus membrane-fusion protein comprising: (a) engineering a soluble chimeric peptide comprising an α-helical domain which comprises a soluble, trimeric form of a coiled-coil fused in helical phase to all or a portion of a $NH_2$-terminal heptad repeat domain, or a modified form thereof, of said enveloped virus membrane-fusion protein; (b) incubating a plurality of said soluble chimeric peptides at a concentration at which a trimeric coiled-coil structure forms; and (c) stabilizing the trimeric coiled-coil structure in (b) by formation of covalent, chemical bonds between said chimeric peptides, wherein said chemical bonds are formed by a chemoselective reaction. Chemoselective ligation reactions that may be used to stabilize chimeric peptides as described herein include, but are not limited to, reactions between the following chemical species, wherein said chemical species are incorporated within the chimeric peptides contained within the resulting trimeric coiled-coil: (i) an aldehydge/ketone and a hydrazide to form a hydrazone; (ii) a ketone and a aminoxy group to form an oxime; (iii) a ketone and a thiosemicarbazide to form a thiosemicarbazone; (iv) an aldehyde and a β-amino thiol to form a thiazolidine; (v) a thiocarboxylate and a α-halo carbonyl to form a thioester; (vi) a thioester and a N-terminal peptide cysteine to form an amide; (vii) a alkyl halide and a thiol to form a thioether; and, (viii) a maleimide and a thiol to form a thioether. In one method described as part of the present invention, covalently-stabilizing, chemical bonds between chimeric peptides described herein are formed by a chemoselective reaction which generates thioether bonds. In one embodiment of the present invention, the soluble chimeric peptides in (b) above are incubated at a concentration at which the resulting trimeric coiled-coil structure is comprised of the following peptide chains: (a) one chimeric peptide which further comprises at least two cysteine residues located outside of the α-helical domain of said peptide (i.e., a CC-chimeric N-peptide); and, (b) two chimeric peptides which are each derivatized to incorporate an electrophilic moiety (i.e., derivatized-chimeric N-peptides); wherein a nucleophilic sulfhydryl of each cysteine residue in the chimeric peptide in (a) forms a thioether bond with the electrophilic moiety of the derivatized chimeric peptides in (b). This can be achieved by incubating said chimeric peptides at approximately a 1:2 concentration ratio, peptide (a): peptide (b). In another embodiment of the present invention, the chimeric peptides in (b) are derivatized to incorporate an electrophilic moiety selected from the group consisting of an alkyl halide moiety (including, but not limited to, a bromoacetyl moiety or a iodoacetyl moiety) and a Michael acceptor (e.g., a maleimide moiety). The soluble chimeric peptides in both (a) and (b) above may comprise all or a portion of a N-peptide of HIV gp41.

The present invention relates to soluble, chimeric peptides which fold into covalently-stabilized, trimeric coiled-coil structures and inhibit HIV infection of mammalian cells, including human cells. Soluble, chimeric peptides referred to herein as "CC-chimeric N-peptides" comprise the following components: (1) an α-helical scaffold protein capable of acquiring a trimeric coiled-coil conformation ("scaffold portion"); (2) all of a portion of the $NH_2$-terminal heptad repeat domain ("N-helix") of the HIV glycoprotein gp41 ("N-peptide portion"), including but not limited to all or a portion of the N-helix region of HIV-1 gp41; and, (3) at least two cysteine residues located at either the $NH_2$- or COOH-terminus of the chimeric peptide sequence ("cysteine portion"), optionally separated from the core chimeric peptide sequence by a linker/spacer region for increased flexibility. Said peptides are capable of forming a soluble, trimeric coiled-coil structure wherein three, identical (i.e., to form a homotrimeric coiled-coil) or substantially similar (i.e., to form a heterotrimeric coiled-coil) chimeric peptide chains physically associate in a parallel orientation. In one embodiment of the present invention, this homotrimeric or heterotrimeric coiled-coil structure is covalently-stabilized through the formation of at least three disulfide bonds generated between the engineered cysteine amino acid residues. The disulfide bond linkages between the chimeric peptides of the present invention ensure that the CC-chimeric N-peptide monomers (i.e., single helical subunits of the homotrimeric or heterotrimeric coiled-coil structure) do not dissociate, even at very low concentrations. In another embodiment of the present invention, a single CC-chimeric N-peptide monomer is comprised within a homotrimeric or heterotrimeric coiled-coil structure which is stabilized via covalent bonds formed as a result of a chemoselective ligation reaction. For example, in one embodiment, and as described further infra, a single CC-chimeric N-peptide is covalently-stabilized in a complex with two derivatized-chimeric N-peptides each having an incorporated electrophilic moiety, wherein each of the at least two cysteine residues incorporated within the CC-chimeric N-peptide forms a stable thioether bond with the electrophilic moiety of each derivatized-chimeric N-peptide.

Thus, a covalently-stabilized, trimeric coiled-coil structure of the present invention is intended to encompass trimeric coiled-coil structures comprised of one or more CC-chimeric N-peptides, whereby said coiled-coil structures are stabilized via either disulfide bonds or covalent, chemical bonds resulting from chemoselective ligation reactions, including but not limited to thioether bonds. Thus, a "covalently-stabilized CC-chimeric N-peptide" is defined as encompassing those trimeric coiled-coil structures having at least one CC-chimeric N-peptide. The covalent-stabilization of the CC-chimeric N-peptides or CC- and derivatized-chimeric N-peptides described herein present stable, exposed portions of the central, trimeric, N-helix coiled-coil of HIV gp41. Said covalently-stabilized CC-chimeric N-peptides can be used as anti-HIV therapeutic molecules in humans wherein the mechanism of action of said therapeutic molecule is to inhibit the membrane fusion process of HIV. Since these covalently-stabilized CC-chimeric N-peptides represent stable, faithful mimetics of the central, N-helix coiled-coil of gp41, they also can be used as immunogens to elicit a neutralizing response targeting HIV fusion intermediates. And finally, said described peptides can be used in screening protocols for the identification of inhibitors (e.g., small molecules, scFvs) that bind to and inhibit the fusion intermediates of HIV.

"Chimeric N-peptides," defined as chimeric peptides which comprise all or a portion of the $NH_2$-terminal heptad repeat domain (N-helix) of gp41 fused to an α-helical scaffold protein capable of acquiring a trimeric coiled-coil conformation, are known in the art. In one embodiment of the present invention, a chimeric N-peptide, "IZN17," disclosed in Eckert and Kim, 2001, supra, is modified by adding the sequence Cys-Cys-Gly-Gly (SEQ ID NO:28) to the $NH_2$-terminus of the chimeric N-peptide, forming a CC-chimeric N-peptide designated herein as "CCIZN17" and having the following amino acid sequence: CCG-GIKKEIEAIKKEQEAIKKKIEAIEK-LLQLTVWGIKQLQARIL (SEQ ID NO:2). The added cysteine residues impart the ability of the CCIZN17 peptide to form covalently-stabilized, trimeric coiled-coils (see FIGS. 1 and 2A for disulfide bond-stabilized, CCIZN17-derived coiled-coils; see FIG. 14 for thioether bond-stabilized, CCIZN17-derived coiled-coils). The added glycine residues represent a spacer region separating the cysteines from the α-helical portion of the chimeric peptide, giving said cysteines greater conformational freedom to participate in disulfide or chemoselective (e.g., thioether) bond formation. In another embodiment of the present invention, chimeric N-peptides as described herein (e.g., IZN17) are derivatized to incorporate an electrophilic moiety capable of participating in chemoselective reactions, "derivatized-chimeric N-peptides." The electrophilic moiety may be separated from the α-helical portion of the chimeric N-peptide by a flexible linker region (e.g., two or more consecutive glycine residues) to help minimize interference between coiled-coil formation of the chimeric peptides and covalent bond formation to stabilize the resulting coiled-coil.

The original IZN17 chimeric N-peptide (<u>IKKEIEAIKKE-OEAIKKKIEAIEK</u>LLQLTVWGIKQLQARIL (SEQ ID NO: 1)) was designed with the capability of forming a non-aggregating, trimeric coiled-coil of a portion of the N-helix domain of HIV-1 gp41. IZN17 is a chimeric peptide consisting of a soluble α-helical domain capable of forming a trimeric coiled-coil, the "IZ" domain (underlined above), fused in helical phase to the $NH_2$-terminus of a portion of the N-helix (the "N17" domain) of gp41, creating a continuous coiled-coil that is 41 amino acids in length. The IZ domain is a modified isoleucine zipper based on a design described by Suzuki et al. (1998, Protein Eng. 11: 1051-1055) that is helical and trimeric in solution. The N17 domain is a truncated portion of a 36 amino acid peptide ("N36") derived from the N-helix region of gp41 identified by protein dissection of the gp41 ectodomain. IZN17 was determined to be helical by circular dichroism spectroscopy ("CD") and capable of forming discrete trimers (see Eckert and Kim, 2001, supra). Additionally, IZN17 was found to be an order of magnitude more potent than a similarly constructed chimeric peptide, IQN17 (SEQ ID NO:23), comprised of the N17 peptide domain, fused to an alternative, trimeric coiled-coil motif derived from the yeast transcription activator, GCN4 (the "IQ" domain). As described in the present invention, individual CCIZN17 peptides also associate as a trimeric helical structure arranged in parallel orientation, causing the juxtaposition of the engineered cysteine residues. Said cysteine residues, located outside of the α-helical domain of the CC-chimeric N-peptide, are free to spontaneously oxidize at a neutral pH to form disulfide bridges between the three CC-chimeric N-peptide chains. Alternatively, added cysteine residues on a single CC-chimeric N-peptide are free to participate in covalent thioether bond formation with electrophilic moieties incorporated within two juxtaposed derivatized-chimeric N-peptides. The presence of covalent, disulfide bond linkages among three CCIZN17 peptides makes the resulting, covalently-stabilized, trimeric coiled-coil, $(CCIZN17)_3$ (see FIG. 2A), more stable than the original IZN17 trimeric coiled-coil, especially since the subsistence of the trimer is no longer dependent on the concentration of the monomeric chains. When comparing the ability of $(CCIZN17)_3$ versus IZN17 to inhibit both primary and laboratory isolates of HIV in a single-cycle infectivity assay using VSV-G-HIV (HIV pseudotyped with G protein of Vesicular Stomatitis Virus) as a negative control, $(CCIZN17)_3$ displays at least one order of magnitude greater potency than IZN17 (see Example 3). $(CCIZN17)_3$ shows anti-viral activity in the picomolar or low nanomolar range against various HIV strains with potencies higher than any other fusion inhibitor known to date. Furthermore, thioether bond formation between a single CC-chimeric N-peptide-derived peptide (ac-C(Acm)CCIZN17) and two derivatized, IZN17 peptides (bromoacetyl-derived IZN17), generating the trimeric coiled-coil ac-C(Acm)(thioIZN17)$_3$ (see Example 11), shows comparable antiviral activity to $(CCIZN17)_3$ against HIV and similar binding activities to mAbD5 (see FIG. 13).

One embodiment of the present invention relates to a chimeric peptide sequence comprising a "N-peptide," defined herein as all or a portion of the N-helix heptad region of the HIV gp41 ectodomain, fused in helical phase to a soluble, α-helical domain capable of forming a trimeric coiled-coil (referred to herein as the "scaffold domain" or the "scaffold portion" of the chimeric peptide), wherein the chimeric peptide sequence optionally further comprises at least two cysteine residues located at either the NH$_2$- or COOH-terminus and outside of the core helical region of the chimeric peptide. The scaffold domain or scaffold portion of the CC- and derivatized-chimeric N-peptides of the present invention comprises non-HIV amino acid residues. In one embodiment of the present invention, the scaffold domain is fused to the NH$_2$-terminus of the N-peptide region. In another embodiment, the scaffold domain is fused to the COOH-terminus of the N-peptide region. In a still further embodiment, the scaffold domain can be divided such that portions of said domain are located at both the NH$_2$- and COOH-termini of the N-peptide region. A coiled-coil is a protein structural motif consisting of two or more α-helices wrapped around each other with a superhelical twist. A simple pattern of amino acid residues determines the fold of a coiled-coil, consisting of a characteristic heptad repeat of amino acids designated by the letters "a" through "g". It has been determined that the first and fourth positions of the heptad repeat, the "a" and "d" positions, respectively, form the interior of the interacting strands of the coiled-coil and are generally hydrophobic. The scaffold domain contained within the covalently-stabilized CC-chimeric N-peptides of the present invention predominantly forms trimeric coiled-coil structures so as to mimic the internal, trimeric coiled-coil present in the pre-hairpin and trimer-of-hairpins structures formed by N-helices of three gp41 ectodomains. Coiled-coil motifs can be isolated from a variety of sources. The scaffold domains which comprise the covalently-stabilized, CC- and derivatized-chimeric N-peptides of the present invention particularly include the isoleucine zipper motif disclosed in Suzuki et al. (1998, supra; hereinafter "Suzuki-IZ") and the GCN4-pI$_Q$I coiled-coil motif disclosed in Eckert et al. (1998, *J. Mol. Biol.* 284:859-865 and PCT/US01/29637, supra), and truncated and/or modified versions thereof. The Suzuki-IZ coiled-coil motif has the following amino acid sequence: YGG IEKKIEAIEKKIEAIEKKIEAIEKKIEA (SEQ ID NO:29). The "a" positions of the heptad repeat that comprise the Suzuki-IZ motif ([IEKKIEA (SEQ ID NO:33)]$_n$) are underlined. The GCN4-pI$_Q$I coiled-coil motif has the following amino acid sequence: RMKQIEDKIEEILSKQYHIENE IARIKKLIGER (SEQ ID NO:30). The "a" positions of this helical motif are also underlined.

It is contemplated that the covalently-stabilized coiled-coil structures generated by the methods described herein encompass both homotrimeric coiled-coil structures (i.e., comprised of three identical chimeric peptides) or heterotrimeric coiled-coil structures (i.e., comprised of three chimeric peptides which are not identical, although substantially similar). In one embodiment, the heterogeneity of the heterotrimeric coiled-coil structures of the present invention may result from amino acid differences residing in the stabilizing region of the individual chimeric peptides comprising the coiled-coil structure. This is demonstrated herein by the formation of trimeric coiled-coil structures that mimic the HIV N-peptide coiled-coil domain of gp41 that are covalently-stabilized via thioether bonds between individual chimeric peptides. As described in detail herein, and especially within Example 11, the exemplified heterotrimeric coiled-coil structures stabilized via thioether bond formation are comprised of one C-chimeric N-peptide and two derivatized N-peptides. While the amino acid sequence of the core chimeric-N-peptide region of each of the two species can be identical, the stabilizing mechanism can impart heterogeneity to the resulting coiled-coil. For example, the C-chimeric N-peptide contains a stabilizing unit of at least two cysteine residues and a spacer/linker domain located outside the α-helical domain of the core chimeric N-peptide region, while the each derivatized-chimeric N-peptide has an amino acid linker region between the incorporated electrophilic moiety and the core chimeric N-peptide region (i.e., no added cysteine residues). Alternatively, the heterogeneity of the heterotrimeric coiled-coil structures of the present invention may result from amino acid differences residing within the core chimeric N-peptide of the individual peptides comprised within the coiled-coil. For example, and in no way limiting to the scope of the present invention, a heterotrimeric coiled-coil structure of the present invention may be comprised of three chimeric peptides wherein the "a" and "d" amino acid positions of the heptad repeat of each individual peptide, important for the trimerization ability of the peptides, are identical while the amino acid positions external to the hydrophobic region (e.g., position "f") are different among the individual peptides of the trimeric coiled-coil. Importantly, such heterotrimeric structures could still be identified as faithful mimetics of a HIV gp41 fusion intermediate because the function of the coiled-coil is similar to that of the wildtype structure (e.g., antiviral activity and/or generation of a faithful conformation epitope).

The stabilizing scaffold domain that comprises a portion of the CC- and derivatized-chimeric N-peptides of the present invention, as described herein, can be all or a portion of the Suzuki-IZ (SEQ ID NO:29) or GCN4-pI$_Q$I (SEQ ID NO:30) coiled-coil motifs, or modified forms thereof. As such, the Suzuki-IZ or GCN4-pI$_Q$I stabilizing scaffold domains can be changed by the addition, substitution, modification and/or deletion of one or more amino acid residues. "Suzuki-IZ-like" and "GCN4-pI$_Q$I-like" scaffold domains are defined herein as coiled-coil motifs that comprise either a portion of the "Suzuki-IZ" or "GCN4-pI$_Q$I" coiled-coils, respectively, or a modified version of all or a portion of said respective coiled-coils. The Suzuki-IZ-like and GCN4-pI$_Q$I-like scaffold domains must consist of a sufficient portion (i.e., a sufficient length) of the Suzuki-IZ and GCN4-pI$_Q$I trimeric coiled-coil domains, respectively, or modified versions thereof, such that they form soluble, trimeric (helical) coiled-coils. The tolerance for changes in the amino acid sequence of the scaffold protein will depend on whether the changed amino acids serve structural and/or functional roles. Thus, mutated or modified scaffold proteins used herein must retain the ability to form trimeric coiled-coils. Additionally, a covalently-stabilized, homotrimeric or heterotrimeric coiled-coil comprised of at least one CC-chimeric N-peptide of the present invention generated with a mutated/modified scaffold domain must retain either the ability to inhibit HIV infectivity with potencies in at least the low nanomolar concentration range or the capacity to bind gp41-specific antibodies that recognize conformational epitopes located in the N-helix coiled-coil (described further infra). Modification of the scaffold protein may provide several advantages. For example, the outside surface of the chimeric peptides of the present invention can be varied to enhance bioavailability (e.g., increase solubility of the peptide), decrease toxicity and avoid immune clearance. If the covalently-stabilized chimeric peptides described herein are to be used as either anti-HIV vaccine immunogens or anti-HIV therapeutic molecules requiring multiple administrations, individuals may develop antibodies to the scaffold domain which will likely increase peptide clearance from the body. The availability of multiple versions of the chimeric peptides of the present invention encompassing alternative scaffolds would help to circumvent this problem by evading preexisting antibodies. The scaffold protein may also be modified in an attempt to make the scaffold domain of the chimeric peptide less immunogenic, for example, by introducing glycosylation sites on its external surface. Furthermore, the scaffold domain may be modified to facilitate the conjugation of said chimeric peptide to an immunogenic carrier or an affinity resin.

In certain embodiments of the present invention, the CC- and derivatized-chimeric N-peptides described herein, possessing the capability of forming covalently-stabilized, trimeric coiled-coil structures, comprise all or a portion of a Suzuki-IZ scaffold domain, or a modified version thereof, fused in helical phase to all or a portion of the N-helix region of the HIV gp41 ectodomain, wherein the non-HIV scaffold is fused to either the NH$_2$-terminus or the COOH-terminus of the HIV sequence. The Suzuki-IZ domain is disclosed as SEQ ID NO:29. As described above, this scaffold domain (i.e., coiled-coil motif) can be shortened, modified or both; however, it is important that the resulting CC- or derivatized-chimeric N-peptide, comprising a truncated and/or modified Suzuki-IZ scaffold domain, retains the ability to properly present the N-peptide coiled-coil structure (i.e., retains the ability to generate a stable, faithful mimetic of the N-helix trimeric coiled-coil). The ability of said CC- or derivatized-chimeric N-peptide to retain this structural conformation can be determined by testing whether the resulting covalently-stabilized, homotrimeric or heterotrimeric coiled-coil comprised of said chimeric peptides inhibits HIV infectivity and/or is able to bind to antibodies that recognize conformational epitopes in the N-peptide domain. For example, in one embodiment of the present invention, CCIZN17 (SEQ ID NO:2) comprises the stabilizing unit Cys-Cys-Gly-Gly (SEQ ID NO:28) fused to the chimeric N-peptide IZN17 (SEQ ID NO:1). IZN17 comprises 17 contiguous amino acids from the N-helix region of gp41 (representing the COOH-terminal 17 residues of the N36 peptide, described infra) fused to the COOH-terminus of a modified Suzuki-IZ scaffold domain designated as "IZ". The IZ scaffold motif represents a portion of the Suzuki-IZ coiled-coil motif that has been significantly altered in the "e" and "g" positions and possesses an isoleucine to glutamine (I→Q) substitution at an "a" position (see PCT/US01/29637, supra). The amino acid sequence of the "IZ" scaffold domain is IKKE<u>I</u>EAIKKE<u>Q</u>EAIKKK<u>I</u>EAIEK (SEQ ID NO:31; "a" positions are underlined), wherein the NH$_2$-terminus is acetylated and the COOH-terminus amidated. IZN17, a chimeric N-peptide disclosed in Eckert and Kim, 2001 (supra), is a fusion of this IZ scaffold with the N17 peptide having the following amino acid sequence: IKKE<u>I</u>EAIKKE<u>Q</u>EAIKKK<u>I</u>EAIEKL<u>L</u>QLTVWG<u>I</u>KQLQAR<u>I</u>L (SEQ ID NO:1). The scaffold domain of IZN17 is in italics, and the "a" positions of the α-helix generated by this chimeric N-peptide are underlined. In order to maintain proper helical structure when generating alternative chimeric N-peptides having longer HIV sequence segments, as well as covalently-stabilized versions thereof (CCIZN-peptides or derivatized-IZN-peptides), this "IZ" scaffold may need to be extended by from one to a few amino acids, generating "IZ-like" scaffold domains. For example, IZN23 and IZN36 are chimeric N-peptides also disclosed in Eckert and Kim, 2001 (supra) which can be been stabilized via the method described in the instant specification. The amino acid sequences of IZN23 and IZN36 are as follows: IKKE<u>I</u>EAIKKE<u>Q</u>EAIKKK<u>I</u>EAIEKE<u>I</u>EAQQHL<u>L</u>QLTVWG<u>I</u>KQLQAR<u>I</u>L (SEQ ID NO:10) and IKKE<u>I</u>EAIKKE<u>Q</u>EAIKKK<u>I</u>EAIEKE<u>I</u>SGIVQQQNNLLRA<u>I</u>EAQQHL<u>L</u>QLTVWG<u>I</u>KQLQAR<u>I</u>L (SEQ ID NO:16), respectively. The scaffold domains of IZN23 and IZN36 are in italics, and the "a" positions of the peptides are underlined. In comparison to the IZ scaffold used to make IZN17 and CCIZN17, the IZ-like scaffold domains of IZN23 and CCIZN17 are extended by one (IZN23) or two (IZN36) amino acids. This is required to maintain proper "a" through "g" spacing and, thus, facilitates generation of an α-helical conformation.

The amino acids chosen to extend the scaffold domain in this manner should enable electrostatic interaction between adjacent helices (see Suzuki et al., 1998, supra). When generating CC- or derivatized-chimeric N-peptides to be stabilized by a method as described herein, one of skill in the art will appreciate that the scaffold domain may need to be minimally altered, as seen with IZN23 and IZN36, in order to maintain the helical conformation of the resulting peptide.

Shortened versions of the IZ scaffold domain can also be generated for incorporation into CCIZN-peptides or derivatized-chimeric IZN-peptides of the present invention. A specific example of a shortened IZ-like domain represents 17 amino acids of the IZ scaffold: IKKE<u>I</u>EAIKKE<u>Q</u>EAIKK (SEQ ID NO:40; designated as "IZ17"; "a" positions are underlined). For example, a chimeric N-peptide comprising IZ17 fused in helical phase to N17 can be generated having the following amino acid sequence: IKKE<u>I</u>EAIKKE<u>Q</u>EAIKKL<u>L</u>QLTVWG<u>I</u>KQLQAR<u>I</u>L (SEQ ID NO:41; designated as "IZ17N17"; scaffold domain is underlined). A CC-chimeric N-peptide can be generated comprising IZ17N17 with the addition of the stabilizing unit Cys-Cys-Gly-Gly (SEQ ID NO:28) to the NH$_2$-terminus of the peptide, generating CCIZ17N17 (CCGGIKKEIEAIKK-EQEAIKKLLQLTVWGIKQLQARIL (SEQ ID NO:42)). Alternatively, the mirror image of the Cys-Cys-Gly-Gly (SEQ ID NO:28) sequence, Gly-Gly-Cys-Cys (SEQ ID NO:82), can be engineered to reside at the COOH-terminus of the chimeric N-peptide, generating the following CC-chimeric N-peptide:
IKKEIEAIKKEQEAIKKLLQLTVWGIKQLQARILGGCC (SEQ ID NO:43; designated "IZ17N17CC"). As described earlier, in order to maintain proper helical structure when generating alternative chimeric peptides having longer HIV sequence segments, the "IZ17" scaffold may need to be extended by from one to a few amino acids, generating "IZ17-like" scaffold domains. For example, IZ17N23 and IZ17N36 are chimeric N-peptides which can be been stabilized via a method described in the instant specification. The amino acid sequences of IZ17N23 and IZ17N36 are as follows: IKKE<u>I</u>EAIKKE<u>Q</u>EAIKKE<u>I</u>EAQQHL<u>L</u>QLTVWG<u>I</u>KQLQAR<u>I</u>L (SEQ ID NO:57) and IKKE<u>I</u>EAIKKE<u>Q</u>EAIKKE<u>I</u>SGIVQQQNNLLRA<u>I</u>EAQQHL<u>L</u>QLTVWG<u>I</u>KQLQAR<u>I</u>L (SEQ ID NO:58), respectively. The scaffold domains of IZ17N23 and IZ17N36 are in italics, and the "a" positions of the peptides are underlined. In comparison to the IZ17 scaffold used to make IZ17N17, the IZ17-like scaffold domains of IZ17N23 and IZ17N36 are extended by one (IZ17N23) or two (IZ17N36) amino acids. This is required to maintain proper "a" through "g" spacing and, thus, facilitates generation of an α-helical conformation. Therefore, when generating chimeric peptides to be stabilized as described herein, one of skill in the art will appreciate that the scaffold domain may need to be minimally altered, as seen with IZN23 and IZN36, in order to maintain the helical conformation of the resulting peptide.

In another embodiment, a CC-chimeric N-peptide or derivatized-chimeric N-peptide of the present invention that is capable of becoming covalently-stabilized in a homotrimeric or heterotrimeric conformation through the formation of either disulfide or chemoselective bonds between engineered cysteine residues comprises a modified Suzuki-IZ-like domain, designated as the "EZ" scaffold, having the following amino acid sequence: IKK<u>I</u>EEIEKK<u>I</u>EEIEKK<u>I</u>EEIEK (SEQ ID NO:32; "a" positions are underlined). The EZ scaffold was designed to facilitate conjugation of CCEZN-peptides (i.e., CC-chimeric N-peptides comprising the EZ scaffold fused to all or a portion of the N-helix domain of gp41) to Neisseria meninigitidis Outer Membrane Proteosome Complex ("OMPC") particles, an immunogenic carrier. OMPC has shown to be a very effective immunogenic carrier, even in cases of poorly immunogenic antigens (e.g., polysaccharides) and vaccines with weak immune responsiveness (e.g., as in infants under the age of two years). However, the covalent addition of a peptide to a carrier (i.e., to prepare a carrier-peptide conjugate) frequently results in irreversible precipitation of the conjugate, as is the case with OMPC-peptide conjugates. To prevent this, the maximum number of peptide moles that can be incorporated on a mole of OMPC (usually referred to as peptide "load") has to be carefully controlled. For many peptide sequences, even after optimization, it is not possible to achieve a good load of peptide onto OMPC. A strategy was recently developed that enables the straightforward conjugation of a peptide of any sequence to OMPC and ensures that the peptide load will be above a certain threshold, critical to obtaining a satisfactory immune response against the peptide epitope (see Bianchi et al., U.S. Provisional Patent Application Ser. No. 60/530,867, "A Method to Make a Peptide-Carrier Conjugate with a High Immunogenicity," filed on Dec. 18, 2003). The method entails manipulation of the pI (isoelectric point) of the peptide sequence, adjusting its value to, optimally, between approximately 3.5-5.0. In order to achieve a pI within this range, the peptide can be modified outside of its active, immunogenic domain, ensuring maintenance of the peptide's immunological properties. For example, IZN17 (SEQ ID NO:1) has a very high pI, not within the optimal range of ~3.5-5.0 for conjugation to OMPC (see Table 1).

TABLE 1

| Name | Peptide Sequence[1] | pI |
|---|---|---|
| IZN17 | *IKKEIEAIKKEQEAIKKKIEAIEK*LLQLTVWGIKQLQARIL (SEQ ID NO:1) | 10.7 |
| EZN17 | *IEKKIEEIEKKIEEIEKKIEEIEK*LLQLTVWGIKQLQARIL (SEQ ID NO:6) | 5.2 |

[1]in italics, scaffold residues; N-terminus acetyl; C-terminus amide

Because the high pI value is mostly determined by the large number of basic amino acid residues present on IZ, a new scaffold was designed, designated as the "EZ" scaffold, with a more acidic character. The Suzuki-IZ scaffold which was used to generated the "IZ" scaffold of the IZN17 peptide has a heptad repeat sequence of $(IEKKIEA)_n$ (SEQ ID NO:33), as designed by Suzuki et al., 1998, supra, (see FIG. 7). To generate the EZ scaffold, this heptad repeat sequence was modified to a $(IEKKIEE)_n$ (SEQ ID NO:34) heptad repeat by mutating the alanine residue at position "c" of the Suzuki-IZ heptad repeat to glutamic acid (see FIG. 7). The resulting chimeric N-peptide, EZN17 (SEQ ID NO:6), has a pI of 5.2. Analysis of EZN17 by circular dichroism spectroscopy shows that this peptide is still able to adopt a fully helical conformation with a typical coiled-coil signature (see Example 6). However, when tested for its ability to inhibit HIV infectivity of single cells, the anti-viral activity of EZN17 is several orders of magnitude less potent than IZN17. Despite this observation, EZN17 still binds to D5-IgG, a newly identified, neutralizing antibody that recognizes a conformational epitope located within the hydrophobic pocket of the N-helix coiled-coil region of gp41 (described further infra), having an affinity comparable IZN17 (see FIG. 6). These observations indicate that the acidic EZ scaffold interferes with the resulting peptide's ability to inhibit HIV infectivity, probably due to the charge of the scaffold or possible steric hindrance with the HIV fusion machinery; however, since the resulting peptide properly presents the conformational epitope recognized by D5, it still folds accurately to form a faithful mimetic of the gp41 fusion intermediate. This validates CCEZN-derived peptides, and covalently-stabilized homotrimeric or heterotrimeric forms thereof (e.g., $(CCEZN17)_3$, see Example 6), as putative immunogens to elicit HIV-specific antibodies that target the fusion intermediate of gp41.

Longer CCEZN-peptides or derivatized-chimeric N-peptides having an EZ scaffold domain can also be generating, specifically by extending the HIV N-peptide domain. For example, the following chimeric N-peptide containing 23 contiguous amino acids of the N-helix domain of gp41, EZN23, can be generated to which a stabilizing unit, as described herein, can be added to either terminus of said peptide: IEKK<u>I</u>EEIEKK<u>I</u>EEIEKK<u>I</u>EEIEEK<u>I</u>EAQQHL<u>L</u>QLTVWG<u>I</u>KQLQAR<u>I</u>L (SEQ ID NO:14). The scaffold domain of EZN23 is in italics, and the "a" positions of the α-helix are underlined. As seen with the IZN- and IZ17N-peptides, when lengthening the N-peptide domain of the EZN- or CCEZN-chimeric peptides described herein, it may be necessary to extend the EZ scaffold domain by one or a few amino acid residues in order to maintain proper "a" through "g" spacing of the resulting α-helix. For example, the chimeric N-peptide "EZN36" would consist of the following amino acid sequence: IEKK<u>I</u>EEIEKK<u>I</u>EEIEKK<u>I</u>EEIEEK<u>I</u>SGIVQQQNNLLRA<u>I</u>EAQQHL<u>L</u>QLTV<u>W</u>GIKQ<u>L</u>QAR<u>I</u>L (SEQ ID NO:19). The scaffold domain of EZN36 is in italics, and the "a" positions of the peptide are underlined. In comparison to the EZ scaffold used to make EZN17 and EZN23, the EZ-like scaffold domain of EZN36 is extended by one amino acid. As described supra, the amino acids used to extend the EZ scaffold domain is designated in order to enable electrostatic interaction between adjacent helices (see Suzuki et al., 1998, supra).

Shortened versions of the EZ scaffold can also be generated for incorporation into chimeric peptides of the present invention. A specific example of a shortened EZ-like domain represents 17 amino acids of the EZ scaffold: IEKKIEEIEKKIEEIEK (SEQ ID NO:114; designated "E17"). For example, a chimeric N-peptide comprising E17 fused in helical phase to N17 can be generated having the following amino acid sequence: <u>IEKKIEEIEKKIEEIEK</u>-LLQLTVWGIKQLQARIL (SEQ ID NO:115; designated "E17N17"; scaffold domain is underlined). A CC-chimeric N-peptide can be generated comprising E17N17 with the addition of the stabilizing unit Cys-Cys-Gly-Gly (SEQ ID NO:28) to the $NH_2$-terminus of the peptide, generating "CCE17N17" (CCGGIEKKEEIEKKIEEIEK-LLQLTVWGIKQLQARIL; SEQ ID NO:116). Alternatively, the mirror image of the Cys-Cys-Gly-Gly (SEQ ID NO:28) sequence, Gly-Gly-Cys-Cys (SEQ ID NO: 82), can be engineered to reside at the COOH-terminus of the chimeric N-peptide, generating the following CC-chimeric N-peptide: IEKKIEIEKKIEEIEKLLQLTVWGIKQLQARILGGCC (SEQ ID NO:117; designated "E17N17CC"). The E17 scaffold can be further mutated in order to further decrease the pI of the chimeric peptide of which it is a component. For example, one or more lysine residue of the E17 scaffold can be mutated to a glutamic acid residue (e.g., IEKKIEEIE<u>E</u>KIEEIEK (SEQ ID NO:119; designated "E17Glu") wherein the underlined amino acid has been mutated from Lys to Glu). This scaffold can be used to produce either a CC- or derivatized-chimeric N-peptide for covalent stabilization within a trimeric structure via either disulfide bond or thioether bond formation (e.g., see FIG. 4). As described earlier, in order to maintain proper helical structure when generating alternative chimeric peptides having longer HIV sequence segments, the "E17" and "E17Glu" scaffolds may need to be extended by from one to a few amino acids, generating "E17-like" and "E17Glu-like" scaffolds, respectively.

CCIQN-peptides of the present invention comprise a stabilizing unit (e.g., Cys-Cys-Gly-Gly (SEQ ID NO:28)) fused to an IQN-peptide. Alternatively, a derivatized-IQN-peptide of the present invention represents an IQN-peptide derivatized to incorporate a chemical species, including but not limited to an electrophilic moiety, which can participate in a chemoselective reaction. IQN-peptides comprise all or a portion of the N-helix region of the HIV-1 gp41 ectodomain fused in helical phase to all or a portion of the GCN4-pI$_Q$I coiled-coil motif (i.e., the scaffold domain), or a modified version thereof. The GCN4-pI$_Q$I coiled-coil motif is disclosed as SEQ ID NO:30. As described above, this scaffold domain can be shortened and/or modified to generate CCIQN-peptides or derivatized-IQN-peptides that are still capable of forming a stable, faithful mimetic of the N-helix trimeric coiled-coil. The ability of said IQN-like peptides to retain the ability to form said structural conformation can be determined by testing whether a covalently-stabilized, homotrimeric or heterotrimeric coiled-coil comprised of said chimeric peptides inhibits HIV infectivity and/or is able to bind to antibodies that recognize conformational epitopes in the N-peptide domain (described further infra). For example, in one embodiment of the present invention, CCIQN17 (SEQ ID NO:26) comprises the stabilizing unit Cys-Cys-Gly-Gly (SEQ ID NO:28) fused to IQN17. IQN17 comprises 17 amino acids from the N-helix region of gp41 fused to a GCN4-pI$_Q$I-like coiled-coil motif designated as "IQ," said IQ scaffold having the amino acid sequence R<u>M</u>KQIED<u>K</u>IEEIESK<u>Q</u>KKIENE<u>I</u>ARIKKL (SEQ ID NO:35; "a" positions are underlined). The IQ scaffold comprises consecutive amino acid residues from the GCN4-pI$_Q$I coiled-coil motif that have been modified by three substitutions to increase solubility, in addition to being shortened by five amino acids at the COOH-terminus. Thus, CCIQN17 comprises 29 amino acid residues of a modified GCN4-pI$_Q$I coiled-coil motif, 17 residues of the COOH-terminal portion of the N36 peptide of gp41 (described further infra), and Cys-Cys-Gly-Gly (SEQ ID NO:28) located at the NH$_2$-terminus of the chimeric N-peptide. There is one residue overlap between the HIV and non-HIV amino acid sequences in CCIQN17, making the total length of said CC-chimeric N-peptide 49 amino acids. IQN17 (SEQ ID NO:23), the core chimeric sequence of CCIQN17, has been shown to inhibit HIV infection of human cells (see Eckert and Kim, 2001, supra; and PCT/US01/29637, supra). CCIQN-peptides can be generating having longer HIV N-peptide sequences. For example, IQN23 and IQN36 are chimeric N-peptides disclosed in Eckert and Kim, 2001 (supra) which can be been stabilized via the method described in the instant specification. IQN23 has the following amino acid sequence: R<u>M</u>KQIED<u>K</u>IEEIESK<u>Q</u>KKIENE<u>I</u>ARIKKL *IEAQQHL<u>L</u>QLTVWG<u>I</u>KQLQAR<u>I</u>L* (SEQ ID NO:24). The scaffold domain is in italics, and the "a" positions of the α-helix are underlined. As seen with the IZN-, IZ17N- and EZN-derived chimeric peptides described above, and covalently-stabilized forms thereof, in order to maintain proper helical structure when generating alternative chimeric peptides with longer HIV N-peptide sequences, the "IQ" scaffold sequence as used to generate the IQN17/IQN23 may need to be extended by from one to a few amino acids. For example, IQN36, as disclosed in Eckert and Kim, 2001 (supra), has the following amino acid sequence: R<u>M</u>KQIEDK *IEEIESKQ<u>K</u>KIENE<u>I</u>ARIKKL<u>I</u>SGIVQ<u>Q</u>QNNLLRA IEAQQHL<u>L</u>QLTVWG<u>I</u>KQLQAR<u>I</u>L* (SEQ ID NO:25). The scaffold domain is in italics, and the "a" positions of the α-helix are underlined. In comparison to the IQ scaffold used to make IQN17 and IQN23, the IQ-like scaffold domain of IQN36 is extended by one amino acid. As described previously, this is to maintain proper "a" through "g" spacing and, thus, facilitates generation of α-helical conformation.

Shortened versions of the IQ scaffold domain can also be generated for incorporation into CCIQN-peptides or derivatized-IQN-peptides of the present invention. Specific examples of shortened IQ-like domains are as follows: 15 amino acid residues of IQ consisting of KQKKIENE-IAAIKKL (SEQ ID NO:36); 15 amino acid residues of IQ with a Q→I mutation consisting of KIKKIENEIARIKKL (SEQ ID NO:37); 21 amino-acid residues of IQ consisting of KIEEIESKQKKIENEIAEJKKL (SEQ ID NO:38); and 21 amino acid residues of IQ with a Q→I mutation consisting of KIEEIESKIKKIENEIARIKK (SEQ ID NO:39).

As described above, the amino acid sequence of the scaffold domain of the CC-chimeric N-peptides or derivatized-chimeric N-peptides of the present invention can be modified and/or shortened; however, in doing so, the resulting chimeric peptides must retain the ability to form a trimeric coiled-coil representing a stable, faithful mimetic of the internal, N-helix coiled-coil of gp41. A number of different experimental methods can be used to determine whether or not a CC- or derivatized-chimeric N-peptide comprised of a modified/truncated scaffold domain can form a stable, faithful mimetic of said internal coiled-coil. For example, an assay designed to measure the ability of the covalently-stabilized, homotrimeric or heterotrimeric CC-chimeric N-peptides (including both disulfide bond-stabilized and thioether bond-stabilized homotrimeric coiled-coils) to inhibit infectivity of HIV particles can be performed. In one such assay, described further in Example 3, HeLa cells stably expressing human CD4 and CCR5 receptors and harboring a β-galactosidase reporter gene driven by a tat-responsive fragment of HIV-2 LTR are infected with HIV-1 of various strains in the presence of covalently-stabilized, homotrimeric CC-chimeric N-peptides at varying concentrations. After incubating said cells for a specific period of time, the cells are lysed and β-galactosidase activity is quantified. If a covalently-stabilized, homotrimeric or heterotrimeric coiled-coil comprised of either three CC-chimeric N-peptides or a combination of CC- and derivatized-chimeric N-peptides containing a modified/shorter scaffold domain retains the ability to inhibit HIV infectivity by interfering with the gp41 fusion intermediate, a low β-galactosidase activity is recorded. The potency of the chimeric peptides tested can be compared. Clearly, as described herein, one embodiment of the present invention focuses on generating covalently-stabilized CC-chimeric N-peptides with anti-viral potencies in the low nanomolar concentration range, thus representing more potent inhibitors than those already known in the art. However, another embodiment of the present invention relates to covalently-stabilized chimeric peptides, as described herein, that, when covalently-stabilized in a homotrimeric coiled-coil, may display weak anti-viral activity but still represent stable mimetics of the gp41 fusion intermediate. For example, although the N-peptide portion of a covalently-stabilized, homotrimeric or heterotrimeric coiled-coil may represent a faithful mimetic of the internal, N-helix coiled-coil, the stabilizing scaffold protein may ultimately interfere with the association of the covalently-stabilized coiled-coil with the gp41 fusion machinery (e.g., due to steric hindrance or charge effects).

This scenario can be identified if the homotrimeric or heterotrimeric coiled-coil shows a weak ability to inhibit HIV infectivity but, alternatively, strongly binds to an antibody which recognizes a conformational epitope in the N-helix domain of gp41 (e.g., D5 antibody, see Example 4).

It is important to recognize, however, that there will be a point at which the scaffold domain is mutated/truncated to such an extent that the resulting CC-chimeric N-peptide-containing, homotrimeric or heterotrimeric coiled-coil no longer displays a faithful mimetic of the gp41 fusion intermediate. This is demonstrated with the CC-chimeric N-peptide designated as "CCI10N17" (SEQ ID NO:20). CCI10N17 comprises a shortened IZ scaffold domain, designated "110" (IKKKEAIEK (SEQ ID NO:45)), fused in helical phase to the $NH_2$-terminus of N17 (SEQ ID NO:44), and further comprising the stabilizing unit Cys-Cys-Gly-Gly (SEQ ID NO:28) at the $NH_2$-terminus of the chimeric peptide: CCGGIKKK IEAIEKLLQLTVWGIKQLQARIL (SEQ ID NO:20; "a" positions are underlined). The 110 scaffold consists of ten amino acids of the IZ scaffold. CCI10N17 was designed for the purpose of reducing the number of non-HIV residues, thus attempting to focus immunogenic responses to the HIV portions of the chimeric peptide (see Example 5 for further detail). However, the resulting covalently-stabilized, trimeric CC-chimeric N-peptide, $(CCI10N17)_3$ (see FIG. 2C), was shown to be less potent in anti-viral activity assays when compared to covalently-stabilized CC-chimeric N-peptides with longer scaffolds. Additionally, the covalently-stabilized $(CCI10N17)_3$ trimer displayed weak binding to a neutralizing antibody known to bind a conformational epitope located within the hydrophobic pocket of the internal N-helix coiled-coil, D5 IgG (described further infra). This shows that there is a point at which the scaffold domain is too short to faithfully display and/or stabilize the N-peptide domain of the chimeric peptide. One of skill in the art can easily determine whether a resulting CC- or derivatized-chimeric N-peptide faithfully displays the N-peptide domain when in its trimeric, covalently-stabilized conformation, e.g. testing either its ability to inhibit HIV infectivity with high potency or its capacity to bind an antibody that recognizes a conformational epitope located in the N-helix region of gp41. It is important to note, however, that an alternative method of stabilizing a CC-chimeric N-peptide described herein is to add the cysteine residues to the opposite terminus of the peptide. Thus, initially, if a trimeric coiled-coil formed with CC-chimeric N-peptides stabilized via disulfide bonds between cysteine residues residing at one terminus of said peptides does not display either an ability to inhibit HwV infectivity with a high potency or the capacity to bind an antibody that recognizes a conformational epitope located in the N-helix domain, one of skill in the art may generate a similar covalently-stabilized trimeric coiled-coil having the stabilizing cysteine residues located at the opposite terminus of the CC-chimeric N-peptides. When stabilizing a trimeric coiled-coil of the present invention via thioether bond formation using a CC-chimeric N-peptide with stabilizing cysteine residues located at, for example, the COOH-terminus of the peptide, it is important that the electrophilic moiety incorporated within the two, derivatized-chimeric N-peptides is located at the same terminus (in this case, the COOH-terminus) of said peptides. It can then be determined if the location of the stabilizing mechanism (i.e., the covalent bond mechanism as demonstrated herein by disulfide or thioether bond formation) affects the functionality of the covalently-stabilized chimeric peptides. Moving the stabilizing mechanism to the opposite terminus may have a further stabilizing affect if the end to which the unit is added is less stable than the opposite end of the peptide. Often, the N-peptide portion of the chimeric N-peptides described herein is less stable than the scaffold portion of the peptide. Thus, moving the stabilizing unit from the scaffold terminus of the peptide to the N-peptide terminus may increase the stability of the resulting trimeric coiled-coil. For example, it may be possible to further stabilize the chimeric N-peptide described above (i.e., I10N17) by placing the stabilizing cysteine residues at the COOH-terminus of the chimeric peptide. This would be done by adding the mirror image of Cys-Cys-Gly-Gly (SEQ ID NO:28), Gly-Gly-Cys-Cys (SEQ ID NO:82), to the 110N17 chimeric N-peptide sequence, generating a CC-chimeric N-peptide with the following amino acid sequence: IKKKIEAIEKLLQLTVWGIKQLQARILGGCC (SEQ ID NO:83; designated "I10N17CC").

In a further embodiment of the present invention, the scaffold domain of the CC- and derivatized-chimeric N-peptides described herein can be divided such that portions of said domain are located at both the $NH_2$- and COOH-termini of the N-peptide region. In such a situation, the scaffold portions are still fused in helical phase with the N-peptide portion of the chimeric peptides, thus maintaining the α-helical conformation of the resulting peptide. The divided scaffold domain can be derived from either the Suzuki-IZ or GCN4-pI$_Q$I scaffolds, described supra, or modified versions thereof.

The CC-chimeric N-peptides of the present invention comprise a soluble, trimeric coiled-coil scaffold protein fused in helical phase to a sufficient portion of the N-helix heptad region of HIV gp41 (the "N-peptide" portion) and at least two cysteine residues added to either the $NH_2$- or COOH-terminus of the chimeric peptide. Said CC-chimeric N-peptides can attain a trimeric coiled-coil conformation, at which point the cysteine residues contribute to further stabilize said conformation by forming covalent, disulfide bonds between peptides upon oxidation. Alternatively, a single CC-chimeric N-peptide can attain a trimeric coiled-coil conformation with two chimeric N-peptides which are each derivatized to incorporate an electrophilic moiety through the formation of thioether bonds between said peptides, wherein a nucleophilic sulfhydryl of two cysteine residues in the cysteine portion of the CC-chimeric N-peptide forms a thioether bond with the electrophilic moiety of the derivatized-chimeric N-peptides. The CC- and derivatized-chimeric N-peptides of the present invention must comprise a sufficient portion of the N-helix region of gp41 to permit the peptides to bind to the α-helices formed by the C-helix domain of gp41 and, thus, said covalently-stabilized peptides represent a stable and faithful mimetic of the internal, N-helix coiled-coil domain of the pre-hairpin and trimer-of-hairpins structures described supra. Additionally, CC- and derivatized-chimeric N-peptides of the present invention must comprise a sufficient portion of the N-helix region such that the covalently-stabilized peptides either inhibit HIV infection of human cells with low to sub-nanomolar potencies and/or are capable of binding to an antibody that recognizes a conformational epitope located in the N-helix coiled-coil domain of gp41. The N-peptide portion of the chimeric peptides can be fused in helical phase to either the $NH_2$- or COOH-terminus of the scaffold domain.

The HIV-1 gp41 ectodomain represents, approximately, 169 amino acid residues, residues 512-681 as numbered according to their position in HIV-1 gp160 envelope protein. Within this ectodomain are two 4-3 heptad repeat regions located adjacent to the $NH_2$- and COOH-terminal portions of the ectodomain that are predicted to form α-helices, designated as the N- and C-helix regions, respectively. The N-helix and C-helix domains (also known as HR1 and HR2, respectively) are located, approximately, at amino acid positions 541-592 and 623-663 of gp160, respectively (see, e.g., Caffrey et al., 1998, *EMBO J.* 17:4572-4584). Upon crystallization of the α-helical conformation of HIV-1 gp41, Chan et al. (1997, *Cell* 89:263-273; see also U.S. Pat. No. 6,506,554) identified what they consider to be the core fusion-active structure of the gp41 ectodomain, a trimer of two interacting peptides, referred to as N36 and C34 peptides, located within the N-helix and C-helix regions, respectively. Chan et al. showed a minimal, stable, envelope subdomain consisting of said N36 and C34 peptides, whose sequences are as follows: SGIVQQQNNLLRAIEAQQHLLQLTVWGIKQLQARIL (N36; SEQ ID NO:46) and WMEWDREINNYTSLIH-SLIEESQNQQEKNEQELL (C34; SEQ ID NO:47). The crystal structure of the N36/C34 complex is a six-helix bundle in which three N36 helices form an interior, parallel coiled-coil, and three C34 helices pack in an oblique, anti-parallel manner into highly conserved, hydrophobic grooves onto the surface of the N36 trimer (i.e., the trimer-of-hairpins). N36 includes amino acid residue 546 through and including amino acid residue 581, again, numbered according to their position in HIV-1 gp160. Using X-ray crystallography, it was determined that the trimer-of-hairpins structure is punctuated by deep cavities (also called hydrophobic pockets). One such cavity is located at the base (i.e., the COOH-terminal half) of each groove of the N36 α-helix and is filled by a knob-like protrusion from a juxtaposed C34 helix, creating a ball-and-socket arrangement. Three residues from the C-helix (tryptophan-628, tryptophan-631 and isoleucine-635) insert into this cavity, making extensive hydrophobic contacts. Mutational analysis indicates that two N36 residues (leucine-568 and tryptophan-571) comprising this cavity are critical for membrane fusion activity (Cao et al., 1993, *J. Virol.* 67:2747-2755). This cavity has proven to be an attractive target for the development of new anti-viral compounds given that it is reasonable to expect that compounds (e.g., small molecules, antibodies) which bind with high affinity to this cavity, preventing normal N- and C-helix pairing, will be effective HIV inhibitors. In addition, since residues in the cavity are highly conserved among diverse HIV-1 isolates, drugs targeting this site would likely have broad activity against diverse HIV-1 isolates, and possibly HIV-2 isolates as well.

While Chan et al., supra, identified the minimal, stable, envelope subdomains of HIV-1 gp41 to be N36 (SEQ ID NO:46) and C34 (SEQ ID NO:47), other groups have crystallized helical domains of HIV-1 gp41 that form stable, six-helix bundles that are slightly larger than those disclosed by Chan et al. For example, Weissenhom et al. (1997, *Nature* 387:426-430) extends the N36 peptide by five amino acid residues at the $NH_2$-terminus and by seven amino acid residues at the COOH-terminus of the N36 peptide sequence: ARQLLSGIVQQQNNLL-RAIEAQQHLLQLTVWGIKQLQARILAVERYLK (SEQ ID NO:53). Therefore, the N-peptide region of the CC- and derivatized-chimeric N-peptides of the present invention is not necessarily limited to all or a portion of the N36 region disclosed above. Instead, the N-peptide domain of said peptides of the present invention comprises a sufficient amount of the N-helix region of gp41 (identified herein as, approximately, between amino acid residues 541-592 of gp160) to bind to the α-helices formed by the C-helix domain of the glycoprotein. Typically, seven or more amino acid residues from the N-helix domain, up to and including all of the residues of said domain, can comprise the HIV gp41 component of the CC- or derivatized-chimeric N-peptides of the present invention.

In one embodiment, the CC- and derivatized-chimeric N-peptides of the present invention comprise a portion of the gp41 N-helix that includes the amino acid residues which form the hydrophobic pocket or cavity of the central, N-helix coiled-coil. The hydrophobic pocket is approximately 16 Å long, approximately 7 Å wide and approximately 5-6 Å deep. The top of the cavity is lined by leucine-566 (L566) of the left N36 helix and leucine-565 (L565) of the right N36 helix. The left side of the cavity is formed by side chains from the left N36 helix, including amino acid residues (top to bottom): valine-570 (V570), lysine-574 (K574, aliphatic portion) and glutamine-577 (Q577). The right wall of the cavity is formed by amino acid residues leucine-568 (L568), tryptophan-571 (W571) and glycine-572 (G572) of the right N36 helix. The floor of the cavity is composed of threonine-569 (T569), isoleucine-573 (I573) and leucine-576 (L576). Thus, the portion of the gp41 ectodomain that forms the hydrophobic pocket lies in the COOH-terminal half of the N-helix α-helical domain. In one embodiment of the present invention, the chimeric N-peptides covalently-stabilized as described herein comprise at least the 17 amino acids located at the COOH-terminal half of the N36 N-peptide of HIV-1 ("N17"), corresponding to residues 565-581 of the gp160 sequence (LLQLTVWGIKQLQARIL (SEQ ID NO:44)). N17 peptides fused to either an IZ or an IQ scaffold domain form discrete trimers and are potent inhibitors of viral infectivity (see Eckert, D. M. and P. S. Kim, 2001, supra). In particular, the present invention relates to the addition of at least two cysteine residues to either the $NH_2$- or COOH-terminus of the following chimeric N-peptides comprising the N17 peptide of the gp41 N-helix: IZN17 (SEQ ID NO:1), EZN17 (SEQ ID NO:6), IZ17N17 (SEQ ID NO:41) and IQN17 (SEQ ID NO:23).

A strategy for exposing longer segments of the C-helix binding site on the CC- or derivatized-chimeric N-peptides of the present invention involves extending the N-peptide region of the chimeric peptide. Therefore, in another embodiment of the present invention, the CC- and derivatized-chimeric N-peptides that are covalently-stabilized as described herein comprise at least about 23 amino acids located at the COOH-terminus of the N36 N-peptide of HIV-1 (e.g., residues 559-581 of the gp160 sequence, "N23": IEAQQHLLQLTVWGIKQLQARIL (SEQ ID NO:48)). N23 represents one more turn of the α-helical domain formed by the N-helix region of gp41; and when fused to either an IZ-like or an IQ-like scaffold domain, the resulting chimeric N-peptide forms discrete trimers that can inhibit HIV infectivity (see Eckert and Kim, 2001, supra). In particular, the present invention relates to the addition of at least two cysteine residues to either the $NH_2$- or COOH-terminus of the following chimeric N-peptides comprising the N23 peptide of the gp41 N-helix: IZN23 (SEQ ID NO:10), EZN23 (SEQ ID NO:14), IZ17N23 (SEQ ID NO:57) and IQN23 (SEQ ID NO:24). The CC- and derivatized-chimeric N-peptides of the present invention that comprise shortened versions of N36 may be therapeutically advantageous because, for example, they are easier and less expensive to produce than are larger peptides. It is also reasonable to expect that the shortened versions are still large enough to prevent rapid filtration in the kidney. In yet a further embodiment of the present invention, the CC- and derivatized-chimeric N-peptides comprise at least about 36 amino acids of the N-helix of HIV-1, e.g., the entire N36 N-peptide of HIV-1, fused to a stabilizing scaffold as described herein, and at least two cysteine residues added to either the $NH_2$- or COOH-terminus of the sequence (e.g., IZN36 (SEQ ID NO:16), EZN36 (SEQ ID NO:19), IZ17N36 (SEQ ID NO:58) and IQN36 (SEQ ID NO:25)).

Furthermore, in each of the examples described above, the N-peptide domain can be extended by from one to twelve amino acids, mimicking the N-helix α-helical domain identified by Weissenhorn et al., described supra. Thus, for example, the chimeric peptides covalently-stabilized as described herein may comprise all or a COOH-terminal portion of the N36 N-peptide of HIV-1, described by Chan et al., supra, plus up to an additional seven amino acids located at the COOH-terminus of said N-peptide, extending the N-peptide region further into the N-helix domain identified by Weissenhorn et al., supra. Thus, in one embodiment of the present invention, the N-peptide portion of the CC- and derivatized-chimeric N-peptides may further comprise either all or a portion of seven additional amino acids, specifically AVERYLK (SEQ ID NO:49), located COOH-terminal of all or a COOH-terminal portion of the N36 peptide domain. CC-chimeric N-peptides and derivatized-chimeric N-peptides of the present invention that further comprise either all or a portion of these seven amino acid may be useful to overcome a putative immunogenic edge effect identified with N17 peptides (see Example 8). As is described further in Example 8, the extreme COOH-terminus of N17 contains an immunodominant epitope that generates a non-neutralizing response to said N-peptide in mice. The immunodominant epitope, exposed due to its location at the end of the N17 peptide, may be partially masked by the addition of amino acid residues to the COOH-terminus of N17. Thus, in one embodiment, a CC- or derivatized-chimeric N-peptide of the present invention comprises a N-peptide domain designated as "N17+7" (LLQLTVWGIKQLQARILAVERYLK (SEQ ID NO:50)), "N23+7" (IEAQQHLLQLTVWGIKQLQA-RILAVERYLK (SEQ ID NO:51)), or "N36+7" (SGIVQQQNNLLRAIEAQQHLLQLTVWGIKQLQARIL-AVERYLK (SEQ ID NO:52)). These N-peptide domains can be fused to either a Suzuki-IZ-like or GCN4-pI$_O$I-like scaffold domain as described supra. In particular, the present invention relates to the addition of a stabilizing unit (e.g., at least two stabilizing cysteine residues or an electrophilic moiety) to either the NH$_2$- or COOH-terminus of the following chimeric N-peptides comprising the N17+7 peptide of the gp41 N-helix: IZN17+7 (SEQ ID NO:54), EZN17+7 (SEQ ID NO:55), IZ17N17+7 (SEQ ID NO:59), I10N17+7 (SEQ ID NO:92) and IQN17+7 (SEQ ID NO:56). Additionally, the chimeric peptides covalently-stabilized as described herein may comprise all or a NH$_2$-terminal portion of the N36 peptide sequence plus up to an additional five amino acids located at the NH$_2$-terminus of said N-peptide, extending the N-peptide region further into the NH$_2$-terminal region of the Weissenhorn et al. N-helix domain. Thus, the N-peptide portion of the CC- or derivatized-chimeric N-peptides of the present invention may further comprise either all or a portion of five amino acids located at the NH$_2$-terminus of the N36 peptide, specifically ASQLL (SEQ ID NO:84).

In another embodiment of the present, the CC- and derivatized-chimeric N-peptides described herein comprise a portion of the gp41 N-helix domain that does not include the amino acid residues which form the hydrophobic pocket cavity of the central, N-helix coiled-coil. CC- or derivatized-chimeric N-peptides that do not comprise the hydrophobic pocket domain of the N-helix coiled-coil domain may be used to block viral particle-host cell membrane fusion by targeting the gp41 fusion intermediate structure.

Figure 8:
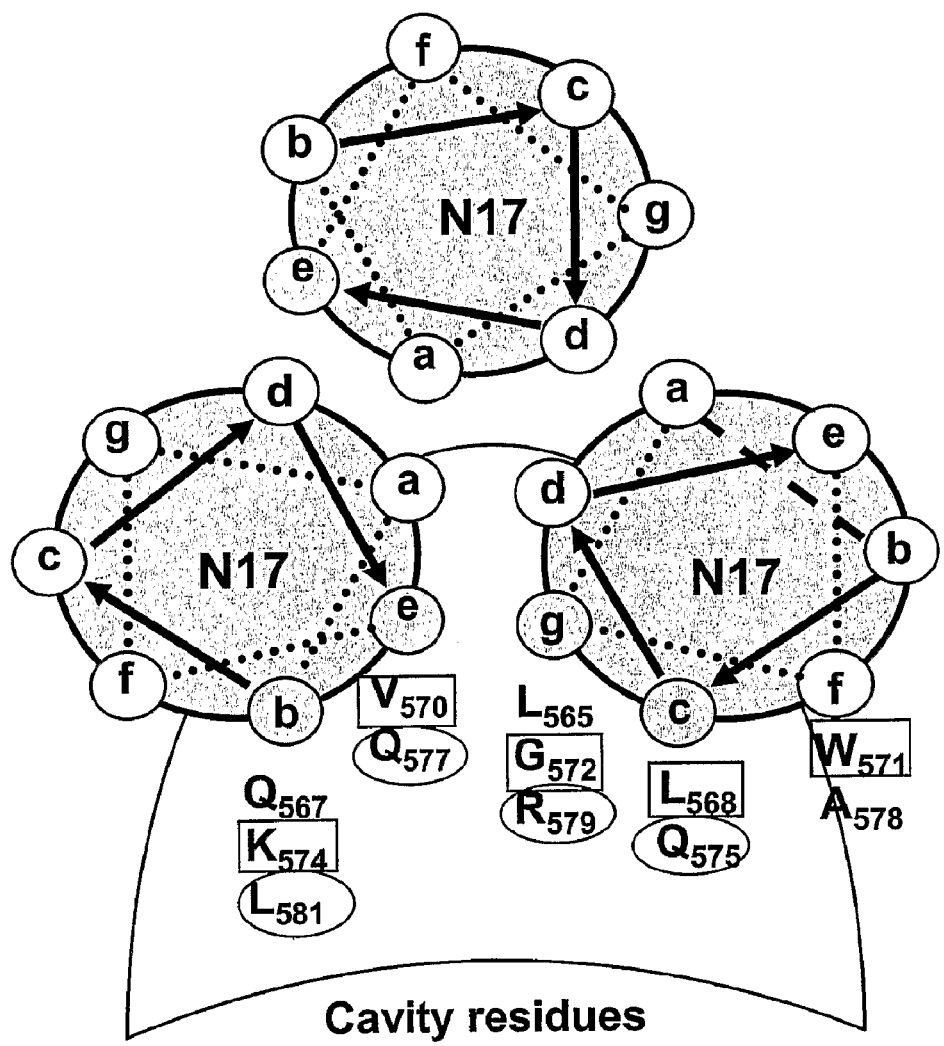
FIG. 8 shows a helical wheel representation of N17 in a coiled-coil configuration delineating the specific amino acid residues of said peptide domain that comprise the epitope to which HIV-neutralizing antibody, D5-IgG (squares), or non-HIV-neutralizing mouse monoclonal antibodies (ovals) generated against IQN17 (SEQ ID NO:23) bind.

The HIV portion of the CC- and derivatized-chimeric N-peptides of the present invention can also be modified versions of the original HIV N-helix heptad domain, provided that the resulting chimeric peptide is either an inhibitor of HIV infection of mammalian cells, as described herein, and/or capable of generating neutralizing antibodies targeting conformational epitopes of fusion intermediates. Any of a wide variety of modifications can be made in the stabilizing scaffold portion of the CC- and derivatized-chimeric N-peptides, as described supra, provided that these changes do not alter the trimerization ability of the resulting α-helix and the proper display of the N-helix region. Changes can also be made in the portion of the CC- and derivatized-chimeric N-peptides which comprises the HIV gp41 sequence (i.e., the N-peptide sequence), provided however that the trimerization ability and surface structure of both the scaffold domain and the HIV N-peptide domain is maintained. For example, non-neutralizing, immunodominant regions (i.e., subunits of an antigenic determinant that are most easily recognized by the immune system and, thus, most influence the specificity of the induced antibody) may exist within the N-peptide sequence used to generate the CC- or derivatized-chimeric N-peptides of the present invention. Indeed, alanine scanning of the IZN17 peptide and subsequent analysis using an interaction assay involving biotinylated-IQN17 and three, non-HIV-neutralizing mouse monoclonal antibodies raised against IQN17 has identified an immunodominant region in the N-helix region. (Example 8). Said immunodominant region, which generates non-neutralizing antibodies, is located in the extreme COOH-terminal portion of N17 comprised within IQN17. Alanine scanning experiments of IZN17, a related peptide, has shown that amino acid residue arginine-579 (R579) appears critical for the binding of the non-neutralizing monoclonal antibodies; and residues glutamine (Q577) and leucine-581 (L581) also participate in the binding but show variable contributions depending on the monoclonal tested. The residues of N17 that are involved in mouse monoclonal binding form a ring at the bottom of the molecule that likely represents an immunodominant epitope in mice in the N-helix domain of IQN17 (see FIG. 8). Interestingly, the amino acid residues lining the hydrophobic pocket of the trimeric, N-helix coiled-coil are located further NH$_2$-terminal of this putative immunodominant epitope. The hydrophobic pocket has been identified as comprising a domain which binds to a newly identified, HIV-neutralizing antibody, D5 IgG; therefore, the hydrophobic pocket is thought to contain a putative neutralizing, conformational epitope (see co-pending U.S. Provisional Application describing D5 IgG, Ser. No. 60/576,012, filed Jun. 1, 2004). Thus, the N-peptide domain used to generate the CC- or derivatized-chimeric N-peptides of the present invention can be modified or shortened in an attempt to minimize the antigenic response of said identified, non-neutralizing immunodominant domain, focusing the immune response to the putative neutralizing epitope within the hydrophobic pocket. For example, in one embodiment of the present invention, the extreme COOH-terminal portion of N36 is mutated at any one or more of the following residues: leucine-581 (L581), arginine-579 (R579), glutamine-577 (Q577) and/or glutamine-575 (Q575). It is preferable that each residue is mutated to an alanine (A) amino acid because alanine can participate in α-helix formation and, thus, will not disrupt the coiled-coil structure of the peptide. Additionally, alanine has a small side chain and, thus, will display the smallest possible binding surface for an antibody. Glycine or proline residues have no side chains and may be considered to be better choices for these mutations; however, said amino acids are known to disrupt α-helix conformation. In one embodiment of the present invention, the N17 sequence fused to a scaffold coiled-coil domain, as described herein, is mutated at all four of the cited residues (L581A, R579A, Q577A and Q575A), forming an N17-like N-peptide domain designated as "N17Ala4" having the following sequence: LLQLTVWGIK ALAAAIA (SEQ ID NO:60). The mutated amino acids are underlined. N17Ala4 can be fused to any of the scaffolds described herein to generate CC- or derivatized-chimeric N-peptides of the present invention, e.g., CCIZN17Ala4 (SEQ ID NO:5), CCEZN17Ala4 (SEQ ID NO:9), CCIZ17N17Ala4 (SEQ ID NO:61) and CCIQN17Ala4 (SEQ ID NO:27). The IZN17Ala4 peptide (SEQ ID NO:4) was generated as described in Example 1 and tested in a single-cycle infectivity assay to determine if it possessed anti-viral activity similar to the parental IZN17 peptide (SEQ ID NO:1). Although IZN17Ala4 inhibits the HIV-1 strain HXB2 with an $IC_{50}$ of only 25 nM (see FIG. 12A), an approximate 125-fold reduction in anti-viral activity relative to the parental peptide IZN17 ($IC_{50}$=0.2 nM), IZN17Ala4 is still capable of interacting with the antibody D5 which recognizes a conformational epitope within the hydrophobic pocket in the gp41 ectodomain (see FIG. 12B). Thus, despite four amino acid substitutions at the C-terminus, the IZN17Ala4 peptide is still capable of assuming a conformation that presents an intact hydrophobic pocket and retains the ability to interact with the native gp41 pre-hairpin structure resulting in anti-viral activity. Additionally, the non-neutralizing, immunodominant region can be truncated or removed entirely in efforts to eliminate the antigenic response to this domain. For example, CCIZN13 (CCGGIKKKEIEAIKKQEAIKK-KIEAIEKLLQLTVWGIKQLQ; SEQ ID NO:95) contains a truncated N17 domain, N13, which consists of only thirteen amino acids (underlined). Shortening the N17 domain in this way removes two of the four amino acids found to contribute to the binding of non-neutralizing antibodies.

The N-peptide portion of the CC- and derivatized-chimeric N-peptides of the present invention can also be modified to further stabilize the peptide as a whole. For example, the N-peptide domain can be modified to incorporate more stabilizing isoleucine residues into the sequence. Thus, for example, in one embodiment of the present invention, N17 (SEQ ID NO:44) can be mutated at "a" and "d" packing positions to incorporate said isoleucine residues as follows: L IQLIWGIKQIQARIL (SEQ ID NO:85; designated "N17Ile"; mutated residues underlined). Said modified N17 peptide can be fused in helical phase to a number of different Suzuki-IZ-like or GCN4-pI$_Q$I-like scaffold domains described herein. In particular, a CC- or derivatized-chimeric N-peptide that is covalently-stabilized via disulfide or thioether bonds, respectively, may comprise a N-peptide domain that has been modified to make said domain more stable, such as N17Ile, fused to a shortened IZ scaffold (e.g., I10 or IZ17). This combination may further stabilize the shortened scaffold, allowing for the proper formation of a faithful mimetic of gp41 fusion intermediate. Thus, in one embodiment of the present invention, a further stabilized N-peptide domain, e.g., N17Ile, is fused in helical phase to the I10 scaffold (e.g., IKKKIEAIEKLIQLWVWGIKQIQARIL (SEQ ID NO:86; designated as "I10N17Ile")) or the IZ17 scaffold (e.g., IKKEIEAIKKEQEAIKKLIQLIVWGIKQIQARIL (SEQ ID NO: 89; designated as "IZ17N17Ile")). These chimeric N-peptides may be covalently-stabilized via disulfide or thioether bonds mediated by the addition of either a Cys-Cys-Gly-Gly (SEQ ID NO:28) trimerizing unit to the NH$_2$-terminus of the peptides or the mirror image of said unit, Gly-Gly-Cys-Cys (SEQ ID NO:82), fused to the COOH-terminus of the peptide: for example, CCGGIKKKIEAIEK-LIQLIVWGIKQIQARIL (SEQ ID NO:87; designated as "CCI10N17Ile"), CCGGIKKEIEAIKKEQEAIEK-LIQLIVWGIKQIQARIL (SEQ ID NO:90; designated as "CCIZ17N17Ile"), IKKKIEAIEKLIQLIVWGIK-QIQARILGGCC (SEQ ID NO:88; designated as "I10N17IleCC"), IKKEIEAIKKEQEAIKKLIQLIVWGIK- QIQARILGGCC (SEQ ID NO:91; designated as "IZ17N17IleCC"), respectively.

It is important to note that the N-peptide portion of the CC- and derivatized-chimeric N-peptides of the present invention can be fused to either the NH$_2$-terminus or the COOH-terminus of the scaffold domain. For example, one of the CC-chimeric N-peptide described above designated as CCIZ2N7 (SEQ ID NO:2) can be altered such that the scaffold and N-peptide portions of the peptide are reversed, generating the following CC-chimeric N-peptide: CCGGLLQLTVW-GIKQLQARILAIKKEIEAIKKEQEAIKKKIEAI (SEQ ID NO:93; designated as "CCN17IZ"). This general scheme can be applied to all of the CC- and derivatized-chimeric N-peptides described herein.

The N-helix portion of HIV gp41 used to generate CC- and derivatized-chimeric N-peptides of the present invention can be isolated from HIV-1, HIV-2, another HIV strain or a strain from another lentiviral species (e.g., simian immunodeficiency virus (SIV), feline immunodeficiency virus (FIV) or Visna virus). The corresponding N-peptide sequences in similar HIV strains and/or immunodeficiency viruses of other species can be easily identified and are known in the art. For example, the amino acid sequences of other lentiviral NH$_2$-terminal α-helical domains that align to the N36 N-peptide of HIV-1 gp41 are listed in Table 2. Additionally, α-helical, coiled-coil domains have been identified in the membrane-fusion proteins of other enveloped viruses (see Singh et al., 1999, supra).

TABLE 2

Lentivirus NH$_2$-terminal heptad domain.

| Virus | Sequence | GenBank Acc. No. |
|---|---|---|
| Simian immuno-deficiency virus (SIV) | AGIVQQQQQLLDVVKRQQELLRLTVWGTK NLQTRVS (SEQ ID NO:62) | P05885 |
| Visna virus | QSLANATAAQQNVLEATYAMVQHVAKGVR ILEARVA (SEQ ID NO:63) | JQ1165 |
| Caprine arthritis encephalitis virus (CAEV) | QTLANATAAQQDALEATYAMVQHVAKGVR ILEARVA (SEQ ID NO:64) | P31627 |
| Feline immuno-deficiency virus (FIV) | ATHQETIEKVTEALKINNLRLVTLEHQVL VIGLKVE (SEQ ID NO:65) | Q04995 |
| Equine infectious anemia virus (EIAV) | NHTFEVENSTLNGMDLIERQIKILYAMIL QTHADVQ (SEQ ID NO:66) | P22427 |
| Bovine immuno-deficiency virus (BIV) | ERVVQNVSYIAQTQDQFTHLFRNINNRLN VLHRRVS (SEQ ID NO:67) | P19556 |

The core chimeric peptide structure of the CC- and derivatized-chimeric N-peptides of the present invention is described above. However, the important difference between the chimeric peptides of this invention in comparison to similar peptides previously disclosed in the art is the addition of at least two cysteine residues to either the NH$_2$- or COOH-terminus and/or the incorporation of an electrophilic moiety to either terminus of the core chimeric peptides for participation in stabilizing disulfide and/or thioether bonds, respectively, between said peptides. Said cysteine residues and electrophilic moieties are optionally separated from the α-helical domain of the chimeric peptides by a linker or spacer region. Covalent cross-links between individual proteins (i.e., intermolecular) or within a single polypeptide chain (i.e., intramolecular) can be formed by the oxidation of cysteine residues. Disulfide bonds are formed by the oxidation of the thiol (—SH) groups in cysteine residues. Intramolecular disulfide bonds stabilize the tertiary structures of proteins, while those that occur intermolecularly are involved in stabilizing protein structure involving one or more polypeptides. Covalent cross-links between individual peptides/proteins can also be formed by chemoselective reactions (e.g., formation of thioether bonds) imposed by incorporating unique, mutually reactive groups into said peptides/proteins to be covalently-linked—one within each segment to be joined (reviewed in Lemieux G. A. and Bertozzi C. R., 1998, *Trends Biotechnol.* 16:506-513; and Borgia, J. A. and Fields G. B., 2000, *Trends Biotechnol.* 15:243-251). One goal of the present invention is to create a covalently-stabilized structure comprised of three chimeric-peptides described above folded together in a trimeric conformation. Said structure can be attained by the trimerization and covalent-stabilization of three CC-chimeric N-peptides, wherein said trimeric structure is stabilized via disulfide bonds between cysteine residues in the cysteine portion of said individual peptides. The cysteine residues that are added to the core α-helical domain of chimeric peptides create disulfide bonds upon oxidation, covalently-stabilizing the trimeric structure formed by three, identical CC-chimeric N-peptides. Alternatively, said structure can be attained by the trimerization and covalent-stabilization of a single CC-chimeric N-peptide with two derivatized-chimeric N-peptides each having an electrophilic moiety, wherein a thioether bond is formed between each thiol-reactive functional group present in the engineered cysteine residues of the CC-chimeric N-peptide and the electrophilic moiety (e.g., an alkyl halide moiety or a Michael acceptor) of each derivatized-chimeric N-peptide. Thus, the disulfide or chemoselective covalent bond linkages between the chimeric peptides of the present invention ensure that peptide monomers (i.e., single, chimeric peptide subunits of the homotrimeric or heterotrimeric coiled-coil structure) do not dissociate, even at very low concentrations.

In one embodiment of the present invention, the core chimeric N-peptides, described supra, are expanded to include at least two cysteine amino acid residues, generating the CC-chimeric N-peptides as described herein. The additional cysteine amino acid residues of the CC-chimeric N-peptides are engineered to reside outside of the core α-helical domain of the chimeric peptides. Additionally, the chimeric N-peptides described supra can be derivatized to incorporate a moiety enabling said peptide to participate in chemoselective ligation reaction (e.g., an electrophilic moiety capable of thioether bond formation). Said chemical moiety is also located at a terminus of the chimeric-N-peptide and outside of the α-helical domain of the chimeric peptide. In comparison, an alternative strategy used by Louis et al. (2003, supra) to generate an internal, trimeric coiled-coil of the gp41 ectodomain mutated actual residues within the N-helix domain to cysteine residues. One of said mutated amino acid residues was located in the "d" position of the α-helical domain, known to be one of two positions of the heptad repeat that forms the interior of the interacting strands of the coiled-coil and also highly conserved among HIV-1 clades (Dong et al., 2001, *Immutnol. Lett.* 75:215-220). The extra-helical placement (i.e., outside of the core α-helical region of the chimeric peptide structure) of the additional cysteine residues in the CC-chimeric N-peptides of the present invention minimizes interference between the coiled-coil conformation of said peptides and the stabilizing disulfide bonds.

Covalently-stabilized trimeric structures containing one or more CC-chimeric N-peptides of the present invention act to mimic the native form of the internal trimer of N-helices that exists in both the pre-hairpin intermediate and trimer-of-hairpins conformations. To help ensure the stabilization of discrete trimers, as opposed to the stabilization of higher order molecular structures encompassing more than one homotrimeric or heterotrimeric coiled-coil containing one or more CC-chimeric N-peptides, exactly two cysteine residues per individual CC-chimeric N-peptide chain can be added to a chimeric N-peptide described herein, favoring formation of a single disulfide bond between each chain of the trimeric structure comprised of three CC-chimeric N-peptides (see, e.g., FIGS. 1 and 2A) or formation of a single thioether bond between a single CC-chimeric N-peptide chain and each of two derivatized-chimeric N-peptides (see, e.g., FIG. 14). Initially, when three CC-chimeric N-peptides physically associate in a parallel orientation, a result of the α-helical structure of the individual polypeptide monomers, the cysteine residues are in close approximation. Under oxidizing conditions, these juxtaposed cysteine residues will spontaneously form disulfide bridges among the three chains. Since a discrete trimer is the most accurate mimetic of the internal, N-helix coiled-coil, covalent-stabilization of said discrete trimers may be advantageous, especially if said trimers are to be used as part of a vaccination regimen for generation of neutralizing antibodies to a conformational epitope in the N-helix domain. Therefore, in one embodiment of the present invention, exactly two cysteine residues are present in the CC-chimeric N-peptides described herein, facilitating the stabilization of the trimeric conformation of said peptides via disulfide or chemoselective (e.g., thioether) bond formation with the thiol-containing cysteine residues. Alternatively, if higher order molecular structures encompassing more than one trimer of CC-chimeric N-peptides are desired, more than two cysteine residues can be added to the core chimeric peptide sequence to help favor the generation of disulfide or chemoselective bonds between individual trimeric structures. In this situation, a high concentration of discrete trimers having more than two, terminal cysteine residues in solution may facilitate the generation of disulfide bonds or chemoselective bonds (e.g., thioether bonds) between homotrimeric structures.

The cysteine residues described herein may be added to the $NH_2$-terminus or COOH-terminus of the core chimeric N-peptide to generate CC-chimeric N-peptides. In one embodiment of the present invention, two cysteine residues are engineered to occupy the first two amino acid residues at the $NH_2$-terminus of a CC-chimeric N-peptide, wherein the scaffold coiled-coil domain is located in the $NH_2$-terminal half of the chimeric peptide. This arrangement ensures that the two engineered cysteine residues are least likely to interfere with the α-helical structure of the N-peptide portion of the chimeric peptide and/or the functionality of said HIV domain, e.g., to interact with C-helices. Alternatively, in another embodiment of the present invention, two cysteine amino acid residues are engineered to occupy the last two amino acid residues at the COOH-terminus of a CC-chimeric N-peptide, wherein the scaffold; coiled-coil domain is located in the $NH_2$-terminal half of the chimeric peptide. This may be necessary, for example, if there is difficulty conjugating a CC-chimeric N-peptide to an immunogenic carrier or an affinity resin via the non-HIV scaffold portion of the chimeric peptide due to the presence of the Cys-Cys sequence located adjacent to the scaffold domain. In another embodiment, two cysteine residues are engineered to occupy the first two amino acid residues at the NH$_2$-terminus of a CC-chimeric N-peptide, wherein the N-peptide domain is located in the NH$_2$-terminal half of the chimeric peptide. In a further embodiment of the present invention, two cysteine residues are engineered to occupy the last two amino acid residues at the COOH-terminus of a CC-chimeric N-peptide, wherein the N-peptide domain is located in the NH$_2$-terminal half of the chimeric peptide. Switching the orientation of the N-peptide and scaffold domains may impact the ability of the resulting CC-chimeric N-peptide to inhibit viral-host cell membrane fusion.

In one embodiment of the present invention, the cysteine residues of the CC-chimeric N-peptides described herein or the electrophilic moiety of the derivatized-chimeric N-peptides described herein are separated from the α-helical portion of the chimeric peptides by a linker or spacer region. Without such a spacer/linker region, for example, the cysteine residues, either located at the $NH_2$- or COOH-terminus of the chimeric peptide, may be included within the helical secondary structure of the peptide. In order to give the cysteine residues of the CC-chimeric N-peptides described herein higher conformational freedom, the cysteines can be separated from the rest of the chimeric N-peptide by a linker/spacer region that does not participate in the α-helical secondary structure of said peptide. Thus, the spacer region will act to break the helical structure of the CC-chimeric N-peptide at that precise location, giving matching cysteine residues on individual peptide chains greater freedom to interact with each other to form intermolecular, stabilizing disulfide bridges. Alternatively, it is important that the electrophilic moiety of the derivatized-chimeric N-peptides of the present invention is separated from the α-helical secondary structure of said peptides in order to minimize any interference between covalent bond formation and coiled-coil formation. The spacer/linker region can comprise a short amino acid sequence known to have the ability to break α-helical secondary structure. In one embodiment of the present invention, CC- or derivatized-chimeric N-peptides of the present invention have a spacer region of at least one amino acid residue located between the α-helical domain of the chimeric peptide (i.e., the scaffold domain fused in helical phase to the N-peptide domain) and either the added cysteine residues or the incorporated electrophilic moiety, respectively. If a single amino acid residue is used as the spacer/linker region, it would be best that said single amino acid has a high likelihood of being able to disrupt the α-helix structure of the peptide, e.g., a glycine or proline residue. Any single D-amino acid, the dextrorotatory isomer of amino acids, can also be used to break the α-helix conformation of the chimeric peptides described herein; however, in such a case, said D-amino acid could only be incorporated by chemical synthesis. *Helix* propensity scales are known in the art, generated by measuring the helix propensity of amino acids (see, e.g., Pace and Scholtz, 1998, *Biophys. J.* 75:422-427; Luque et al., 1996, *Biochemistry* 35:13681-13688). In another embodiment of the present invention, CC- or derivatized-chimeric N-peptides described herein comprise exactly two, consecutive residues separating the incorporated cysteines or electrophilic moiety, respectively, from the α-helical domain of the chimeric peptide, including but not limited to two, consecutive glycine residues or two consecutive D-amino acids. In a further embodiment of the present invention, CC- and derivatized-chimeric N-peptides described herein comprise more than two consecutive residues separating the cysteines or electrophilic moiety, respectively, from the α-helical domain of the chimeric N-peptide, including but not limited to three consecutive glycine residues or three consecutive D-amino acids. Said CC- and derivatized-chimeric N-peptides can also comprise a combination of amino acids in the spacer/linker domain (e.g., one glycine and one proline residue) since both of these amino acids have a high likelihood of disrupting α-helix structure. Generally, if the spacer region of a CC- or derivatized-chimeric N-peptide of the present invention comprises an amino acid sequence, said sequence can be of varied lengths; however, in order to minimize the non-HIV sequences within the chimeric peptide, it is preferred that a minimal number of residues required to break the α-helical structure is used as a spacer. Alternatively, the spacer/linker region can comprise a chemical or synthetic linker, e.g., aminopentanoic acid, aminohexanoic acid, or any amino acid without a C-alpha side chain. Generally, any chemical linker can be used if it can provide enough conformational freedom to allow the appropriate disulfide bridges to form without any perturbation to the coiled-coil.

The cysteine residues present in CC-chimeric N-peptides described herein are generally consecutive amino acid residues. Therefore, in one embodiment of the present invention, the CC-chimeric N-peptides described herein comprise at least two, consecutive cysteine residues-located at either the $NH_2$- or COOH-terminal ends of the peptide, outside of the core α-helical domain of the chimeric peptides, and optionally, separated from the core α-helical domain by a space/linker region. In another embodiment of the present invention, CC-chimeric N-peptides described herein comprise exactly two, consecutive cysteine residues at either the $NH_2$- or COOH-terminal ends of the peptide, outside of the core α-helical domain of the chimeric peptides, and optionally, separated from the core α-helical domain by a space/linker region. One can envision that the cysteine residues described herein do not necessarily have to be consecutive residues, and thus, it may be possible to include a minimal number of amino acid residues between said cysteine residues. It is important, however, that the cysteine residues are not spaced sufficiently far apart so as to enable the generation of intramolecular disulfide bonds between cysteine residues on the same polypeptide chain, leaving them incapable of forming intermolecular disulfide bonds between the individual CC-chimeric N-peptides in a trimeric, coiled-coil conformation.

The CC-chimeric N-peptides and derivatized-chimeric N-peptides of the present invention can further comprise a marker region attached to either the $NH_2$- or COOH-terminus of the chimeric peptide. For example, without interfering with the structure or function of said peptides, well characterized protein tags can be added to aid, for example, in peptide purification or detection by immunoassays. For example, a fluorescent group, an epitope sequence (e.g., the sequence recognized by the anti-hemagglutinin antibody, the Myc epitope, or the FLAG epitope) or a biotin molecule can be added to either the $NH_2$- or COOH-terminus of the chimeric peptides described herein (see, for example, Alarcon et al., 2001, *Transgenic Res.* 10: 183-192; Chavand et al., 2001, *Biochem. Cell Biol.* 79:107-112; Raska et al., 2003, *J. Am. Soc. Mass. Spectrom.* 14:1076-1085). One embodiment of the present invention includes a biotinylated form of the CC-chimeric N-peptides described herein, having a biotin molecule attached to either terminus of the chimeric peptide. In one embodiment of the present invention, a biotin marker is attached to the $NH_2$-terminus of the CC-chimeric N-peptides described herein, wherein the stabilizing scaffold domain is located in the $NH_2$-terminal half of the chimeric peptide and the cysteine residues are located at the $NH_2$-terminus of the chimeric peptide. If the marker (e.g., biotin) and the cysteine residues are located at the same terminus of the chimeric peptide, in order to avoid any steric hindrance with respect to formation of intermolecular disulfide bonds as a result of the marker's close presence to said cysteine residues, a short amino acid spacer region may be added between the marker and the cysteine residues. In one embodiment of the invention, said spacer region comprises one glycine residue. Biotin-CCIZN23 (SEQ ID NO:12) represents an example of a biotin-conjugated CC-chimeric N-peptide described herein that comprises a biotin molecule attached to a CC-chimeric N-peptide (CCIZN23) through the $NH_2$-terminus and having a single glycine residue separating said marker from the chimeric peptide sequence. The spacer region separating the cysteine residues from the marker can also comprise a proline residue or any D-amino acid. Alternatively, the marker (e.g., biotin) and the engineered cysteine residues may be located at different ends of a CC-chimeric N-peptide of the present invention.

Small molecules such as peptides can be poorly immunogenic and, thus, it is often necessary to prepare conjugates to larger macromolecules (carriers) in order to elicit a good immune response to said molecules. Therefore, the present invention further relates to CC- and derivatized-chimeric N-peptides described herein conjugated to an immunogenic carrier. The CC-chimeric N-peptides and/or derivatized-chimeric N-peptides of the present invention can be conjugated as individual peptides which are then subjected to conditions leading to the formation of homotrimeric or heterotrimeric coiled-coil structures comprised of three, individually-conjugated peptides. Alternatively, a covalently-stabilized, homotrimeric or heterotrimeric coiled-coil structure comprised of one or more CC-chimeric N-peptides of the present invention can be conjugated to the immunogenic carrier. The carrier molecule, usually a heterologous protein, can help to evoke and/or elevate an immune response to the HIV portions of the peptides. A CC- or derivatized-chimeric N-peptide and its carrier partner can be linked by non-specific cross-inking agents, monogeneric spacers or bigeneric spacers. There are a number of immunogenic carrier molecules known in the art to which the chimeric peptides of the present invention can be conjugated (see, e.g., Shodel et al., 1996, *J. Biotechnol.* 44:91-96; Lang and Korhonen, 1997, *Behring Inst. Mitt.* 98:400-409; Brennan et al., 2001, *Mol. Biotechnol.* 17:15-26; Pumpens and Grens, 2201, *Intervirology* 44:98-114; and Simpson et al., 1999, *Cell Mol. Life. Sci.* 56:47-61). Said potential immunogenic molecules include but are not limited to *Neisseria meningitidis* OMPC particles, keyhole limpet hemocyanin (KLH), bovine serum albumin (BSA), ovalbumin (OVA), thyroglobulin (TG), HBV-core antigen, HBV-surface antigen, immunogenic proteins such as tetanus or diphtheria toxoid or rotavirus VP6, and HIV capsid particles comprised of p24. Said resulting immunological conjugates can be used as a component of a preventative vaccine for HIV infection, resulting in the generation of HIV-specific, broadly neutralizing antibodies for active immunity against HIV. The vaccine could be formulated with adjuvants known in the art, such as MPL-A, and adsorbed onto either Alum or aluminum phosphate. The antigenic conjugates may also include T cell helper epitopes to effectuate a stronger helper T cell response, including but not limited to a synthetic, non-natural pan HLA DR-binding epitope (PADRE) (see, e.g., Alexander et al., 2000, *J. Immunol.*, 164:1625-1633 and del Guercio et al., 1997, *Vaccine* 15:441-448). Immunogenic conjugates of the chimeric peptides described herein may be prepared by isolating, synthesizing and purifying their component parts (either chimeric peptide or homotrimeric/heterotrimeric coiled-coil and carrier) and then conjugating the two components. Subsequent purification of conjugate mixtures may be performed as desired. Antigenic conjugates of the chimeric peptides and a suitable immunogenic carrier have at least one covalent linkage between the component parts (i.e., chimeric peptide and carrier) and, typically, have more than one chimeric peptide molecule covalently bound to each carrier molecule. If the components are prepared separately, they can be subsequently linked by non-specific cross-linking agents, monogeneric spacers or bigeneric spacers. Methods for non-specific cross-linking are well known in the art and include, but are not limited to, the following: reaction with glutaraldehyde; reaction with N-ethyl-N'-(3-dimethylaminopropyl) carbodiimide, with or without admixture of a succinylated carrier; periodate oxidation of glycosylated substituents followed by coupling to free amino groups of a protein carrier in the presence of sodium borohydride or sodium cyanoborohydride; diazotization of aromatic amino groups followed by coupling on tyrosine side chain residues of the protein; reaction with isocyanates; or reaction of mixed anhydrides. See, generally, Briand et al., 1985, *J. Imm. Meth.* 78:59-69.

In one embodiment of the invention, chimeric peptide immunoconjugates can be formed with a monogeneric spacer. Said spacers are bifunctional and require functionalization of only one of the partners of the reaction pair (e.g., chimeric peptide or carrier) before conjugation takes place. For conjugation procedures using a monogeneric spacer as well as examples of monogeneric spacers, see e.g., Schneerson et al., 1980, *J. Exp. Med.* 152:361-376. and Fujii et al., 1985, *Int. J. Pept. Protein Res.* 26:121-129. In another embodiment of the present invention, conjugates of CC-chimeric N-peptides and an immunogenic carrier can be formed with a bigeneric spacer. Bigeneric spacers are formed after each partner of the reaction pair to be conjugated (e.g., chimeric peptide and carrier) is functionalized with a bifunctional spacer. Conjugation occurs when each functionalized partner is reacted with its opposite partner to form a stable covalent bond(s). See, for example, Marburg et al., 1986, *J. Am. Chem. Soc.* 108:5282-5287; and Marburg et al., U.S. Pat. No. 4,695,624, issued Sep. 22, 1987. Bigeneric spacers are preferred for preparing conjugates in human vaccines since the conjugation reaction is well characterized and easily controlled.

In order to facilitate either the conjugation of the chimeric peptides described herein to, for example, a resin or a carrier, or the derivatization of said peptide with a tag or a moiety, for example, a pegylated chain, the CC-chimeric N-peptides of the present invention can be modified to include one more cysteine residue per chain. In this embodiment of the invention, each peptide chain contains an odd number of cysteines, e.g., three terminal cysteine residues (e.g., CCCIZN17; SEQ ID NO:103). The odd-numbered numbered, terminal cysteine residue can optionally be separated from the remaining contiguous cysteines by means of a flexible, chemical linker, e.g., Ttds (1-amino-4,7,10-trioxa-13-tridecamine succinic acid; —NH—$(CH_2)_3$—O—$(CH_2)_2$—O—$(CH_2)_2$—O—$(CH_2)_3$—NH—CO—$CH_2)_2$—CO—; see Examples 9 and 11). The odd number of cysteines assures that after formation of a covalently-stabilized trimer comprising CC- and/or derivatized-chimeric N-peptides of the present invention, at least one reactive thiol group per covalently-stabilized trimer is available for further reaction with thiol-reactive groups, such as maleimidyl. The linker provides flexibility, solubility and spacing between the disulfide bridges of the trimerization domain and the cysteine residues suitable for conjugation/derivatization. The additional cysteine residue may have a protected thiol group in order to prevent the participation of said cysteine residue in either disulfide or chemoselective bond formation (e.g., thioether bond formation). The protecting group (including, but not limited to, a fluorenylmethoxy ("Fm") or an acetamidomethyl ("Acm") group) may be removed after the formation of the covalently-stabilized, trimeric coiled-coil so that said newly exposed thiol group is available for conjugation reactions.

A preferred aspect of the present invention is disclosed in FIG. 4 as SEQ ID NO:2, designated "CCIZN17." CCIZN17 has the following amino acid sequence: CCG-GIKKEIEAIKKEQEAIKKKIEAIEKLLQLTVWGIKQL-QARIL (SEQ ID NO:2). CCIZN17 represents a CC-chimeric N-peptide wherein the core chimeric peptide sequence, "IZN17," consists of the IZ scaffold domain (underlined above) fused to the $NH_2$-terminus of N17 (SEQ ID NO:44). CCIZN17 further comprises a stabilizing Cys-Cys-Gly-Gly (SEQ ID NO: 28) sequence fused to the $NH_2$-terminus of the core chimeric peptide. The two, consecutive cysteine residues participate in disulfide bond linkages with juxtaposed cysteine residues on closely associated CC-chimeric N-peptides that are formed upon oxidation of the peptides. The two, consecutive glycine residues represent a spacer region, separating the cysteine residues from the α-helical domain of the core chimeric peptide sequence. The glycine spacer region ensures that the cysteine residues are not embroiled in the helical secondary structure of the core peptide sequence, helping to free said cysteines to participate in disulfide linkages. The oxidized product, $(CCIZN17)_3$ (see FIG. 2A), has a molecular weight of 15520 Da, as determined by electrospray mass spectrometry (Example 1). In another embodiment of the present invention, CCIZN17 is linked to a biotin marker through the $NH_2$-terminus of the chimeric peptide, wherein said marker is separated from the consecutive cysteine residues located at the $NH_2$-terminus by an additional glycine residue, "biotin-CCIZN17" (biotin-GCCG-GIKKEIEAIKEQEAIKIAIEKLLQLTVWGIKQLQARIL (SEQ ID NO:68)). When testing $(CCIZN17)_3$ in parallel with IZN17 and other fusion inhibitors (5-Helix, T-20, mAb2F5 and IgGD5; see Example 3), comparing its ability to inhibit HIV in a single-cycle infectivity assay using primary and laboratory isolates, the covalently stabilized trimer displays at least one order of magnitude higher potency against HXB2 and BaL isolates. $(CCIZN17)_3$ also shows a low nanomolar potency against primary isolates such as 89.6, wherein 89.6 is completely resistant towards IZN17. The covalently stabilized $(CCIZN17)_3$ trimer also strongly binds to D5 IgG, a newly identified HIV neutralizing antibody that recognizes a conformational epitope located within the hydrophobic pocket of the N-helix coiled-coil (described further infra; see Example 3). This ensures that the N17 portion of the CC-chimeric N-peptide appropriately displays the HIV sequence, further indicating that said peptide is a faithful mimetic of this portion of the gp41 ectodomain.

Another preferred aspect of the present invention is disclosed in FIG. 4 as SEQ ID NO:13, designated "CCIZN23." CCIZN23 has the following amino acid sequence: CCG-GIKKEIEAIKKEOEAIKKKIEAIEKEIEAQQHLLQLTV-WGIKQLQARIL (SEQ ID NO:13). CCIZN23 represents a CC-chimeric N-peptide wherein the core chimeric peptide sequence consists of an IZ-like scaffold domain (underlined above; comprising "IZ" (SEQ ID NO:31) plus an additional glutamic acid (E) at the COOH-terminus of the IZ scaffold) fused to the $NH_2$-terminus of N23 (SEQ ID NO:48). CCIZN23 further comprises a stabilizing Cys-Cys-Gly-Gly (SEQ ID NO:28) sequence fused to the $NH_2$-terminus of the core chimeric peptide sequence. The two, consecutive cysteine residues participate in disulfide bond linkages, formed upon oxidation, with juxtaposed cysteine residues on closely associated CC-chimeric N-peptides. The two, consecutive glycine residues represent a spacer region, separating the cysteine residues from the α-helical domain of the core chimeric peptide sequence. The glycine spacer region helps to ensure that the cysteine residues are free to participate in disulfide linkages and not embroiled in the helical secondary structure of the rest of the peptide. In another embodiment of the present invention, CCIZN23 is linked to a biotin molecule through the $NH_2$-terminus of the peptide, wherein said biotin molecule is separated from the consecutive cysteine residues located at the $NH_2$-terminus by an additional glycine residue, designated "biotin-CCIZN23" (biotin-GCCGGIKKEE-AIKKEQEAIKKKEAIEKEEEAQQHLLQLTVWGIKQL-QARIL (SEQ ID NO:12)). Upon incubation at neutral pH, biotin-CCIZN23 spontaneously oxidizes to form a covalent trimer, $(biotin-CCIZN23)_3$ (see FIG. 2B), with a molecular weight of 18751 Da, as determined by electrospray mass spectrometry (Example 1). When IZN23 and $(biotin-CCIZN23)_3$ were tested in parallel to compare their ability to inhibit IV in a single-cycle infectivity assay, the covalently stabilized trimer was an order of magnitude more potent (see Example 3).

Another preferred aspect of the present invention is disclosed in FIG. 4 as SEQ ID NO:7, designated "CCEZN17". CCEZN17 has the following amino acid sequence: CCG-GIEKKIEEIEKKIEEIEKKIEEIEKLLQLTVWGIKQLQ-ARIL (SEQ ID NO:7). CCEZN17 represents a CC-chimeric N-peptide wherein the core chimeric peptide sequence, designated "EZN17," consists of the EZ scaffold domain (underlined above; SEQ ID NO:32), described further supra, fused to the $NH_2$-terminus of N17 (SEQ ID NO:44). CCEZN17 further comprises a stabilizing Cys-Cys-Gly-Gly (SEQ ID NO:28) sequence fused to the $NH_2$-terminus of the core chimeric peptide. The two, consecutive, cysteine residues can participate in disulfide bond linkages with juxtaposed cysteine residues on closely associated CC-chimeric N-peptides upon oxidation. The two, consecutive glycine residues represent a spacer region, separating the cysteine residues from the α-helical domain of the core chimeric peptide sequence. The glycine spacer region helps to ensure that the cysteine residues are not embroiled in the helical secondary structure of the rest of the peptide, freeing them to participate in disulfide linkages. In another embodiment of the present invention, CCEZN17 is linked to a biotin molecule through the $NH_2$-terminus of the chimeric peptide, wherein said biotin molecule is separated from the consecutive cysteine residues located at the $NH_2$-terminus by an additional glycine residue, "biotin-CCEZN17" (biotin-GCCGGIEKKIEEIEKKEEE-IEKKIEEIEKLLQLTVWGIKQLQARIL (SEQ ID NO:69)). CCEZN17 was designed as a more favorable antigen to conjugate to OMPC because it has a more acidic isoelectric point than CCIZN17, more preferable for conjugation purposes (see Example 6). Although the core chimeric peptide, EZN17, displays a weak anti-viral activity, it strongly binds to D5 IgG (see Example 6), indicating that the chimeric peptide faithfully displays the hydrophobic pocket domain of the N-peptide. Thus, CCEZN17 represents a derivative of EZN17 that is capable of forming a covalently-stabilized trimer and can be used as an immunogen for generation of neutralizing antibodies to HIV.

Another preferred aspect of the present invention is disclosed in FIG. 4 as SEQ ID NO:5, designated "CCIZN17Ala4." CCIZN17Ala4 has the following amino acid sequence: CCGGIKKEIEAIKEQEAIKKKIEAIEK-LLQLTVWGIKALAAAIA (SEQ ID NO:5). CCIZN17Ala4 represents a CC-chimeric N-peptide comprising the IZ scaffold domain (underlined above; SEQ ID NO:31) fused to the NH$_2$-terminus of a N17-derived sequence, wherein said N17-derived sequence represents the "N17" peptide (SEQ ID NO:44) that has been mutated at four amino acid residues (twice underlined above) to alanine residues, "N17Ala4" (SEQ ID NO:60). N17Ala4 is designed to eliminate an immunodominant domain in the N17 peptide known to generate non-neutralizing antibodies in mice and, thus, helping to focus the antigenic response to this N17-derived peptide to a neutralizing, conformational epitope known to exist in the hydrophobic pocket located adjacent to said immunodominant domain. CCIZN17Ala4 further comprises a stabilizing Cys-Cys-Gly-Gly (SEQ ID NO:28) sequence fused to the $NH_2$-terminus of the core chimeric peptide. The two, consecutive cysteine residues can participate in disulfide bond formation with juxtaposed cysteine residues on closely associated CC-chimeric N-peptides upon oxidation. The two, consecutive glycine residues represent a spacer region, separating the cysteine residues from the α-helical domain of the core chimeric peptide sequence. The glycine spacer region helps to ensure that the cysteine residues are not embroiled in the helical secondary structure of the rest of the peptide, freeing them to participate in disulfide linkages. In another embodiment of the present invention, CCIZN17Ala4 is linked to a biotin molecule marker through the $NH_2$-terminus of the chimeric peptide, wherein said marker is separated from the consecutive cysteine residues located at the $NH_2$-terminus by an additional glycine residue, "biotin-CCIZN17Ala4" (biotin-GCCGGIKKEIEAIKKEQEAIKKKIEAIEKLLQLTVWGIKALAAAIA (SEQ ID NO:70)).

Another preferred aspect of the present invention is disclosed in FIG. 4 as SEQ ID NO:9, designated CCEZN17Ala4. CCEZN17Ala4 has the following amino acid sequence: CCGGIEKKIEEIEKKIEEIEKKIEEIEKLLQLTVWGIKALAAAIA (SEQ ID NO:9). CCEZN17Ala4 represents a CC-chimeric N-peptide wherein the core chimeric peptide sequence consists of the EZ scaffold domain (single underlined above; SEQ ID NO:32) fused to the $NH_2$-terminus of a N17-derived sequence, wherein said N17-derived sequence represents the N17 peptide that has been mutated at four amino acid residues (twice underlined above) to alanine residues, "N17Ala4" (SEQ ID NO:60), explained supra. CCEZN17Ala4 further comprises a stabilizing Cys-Cys-Gly-Gly (SEQ ID NO:28) sequence fused to the $NH_2$-terminus of the core chimeric peptide. The two, consecutive cysteine residues can participate in disulfide bond formation with juxtaposed cysteine residues on closely associated CC-chimeric N-peptides upon oxidation. The two, consecutive glycine residues represent a spacer region, separating the cysteine residues from the α-helical domain of the core chimeric peptide sequence. The glycine spacer region helps to ensure that the cysteine residues are not embroiled in the helical secondary structure of the rest of the peptide, freeing them to participate in disulfide linkages. In another embodiment of the present invention, CCEZN17Ala4 is linked to a biotin molecule through the $NH_2$-terminus of the chimeric peptide, wherein said marker is separated from the consecutive, stabilizing cysteine residues located at the $NH_2$-terminus by an additional glycine residue, "biotin-CCEZN17Ala4" (biotin-GCCGGIEKKIEEIEKKIEEIEKKIEEIEKLLQLTVWGIKALAAAIA (SEQ ID NO:71)).

A preferred aspect of the present invention is disclosed in FIG. 4 as SEQ ID NO:21, designated "SCCIZN17." SCCIZN17 has the following amino acid sequence: SGGCCGGIKKEIEAIKKEQEAIKKKIEAIEKLLQLTVWGIKQLQARIL (SEQ ID NO:21). SCCIZN17 represents a CC-chimeric N-peptide wherein the core chimeric peptide sequence, "IZN17," consists of the IZ scaffold domain (underlined above; SEQ ID NO:31) fused to the $NH_2$-terminus of N17 (SEQ ID NO:44). SCCIZN17 further comprises a Cys-Cys-Gly-Gly (SEQ ID NO:28) sequence fused to the $NH_2$-terminus of the core chimeric peptide. The two, consecutive cysteine residues participate in disulfide bond linkages with juxtaposed cysteine residues on closely associated CC-chimeric N-peptides that are formed upon oxidation of the peptides. The two, consecutive glycine residues represent a spacer region, separating the cysteine residues from the α-helical domain of the core chimeric peptide sequence. The glycine spacer region ensures that the cysteine residues are not embroiled in the helical secondary structure of the core peptide sequence, helping to free said cysteines to participate in disulfide linkages. SCCIZN17 further comprises a Ser-Gly-Gly sequence fused to the $NH_2$-terminus of the consecutive cysteine/glycine residues. The Ser-Gly-Gly sequence was added to facilitate the conjugation of the CC-chimeric N-peptide to an affinity resin (see Example 2 for further details). The oxidized product, $(SCCIZN17)_3$ (see FIG. 3A), has a molecular weight of 15995 Da, as determined by electrospray mass spectrometry (Example 2).

The CC- and derivatized-chimeric N-peptides described herein can be used for a number of different purposes. Covalently-stabilized, chimeric peptides may be useful as anti-HIV therapeutic and/or prophylactic agents or drugs to prevent HIV infection in humans. The mechanism of action of such an anti-HIV agent is to inhibit the fusion process of the virus. Indeed, some of the covalently-stabilized, trimeric coiled-coils described herein are potent inhibitors of HIV-1 infectivity (i.e., viral membrane fusion), active at subnanomolar concentrations. Thus, unlike standard anti-HIV therapy that targets viral proteins after HIV entry into host cells, the covalently-stabilized, chimeric peptides described herein that are shown to be potent inhibitors of HIV infectivity can be used prophylactically to either prevent infection or reduce the extent to which infection occurs. Therefore, in one embodiment of the present invention, a CC-chimeric N-peptide described herein that has the capacity of inhibiting viral activity at low to subnanomolar concentrations (e.g., CCIZN17 and CCIZN23) is used to reduce HIV infection in an individual. In this embodiment, said covalently-stabilized, chimeric peptide is administered to an individual in sufficient quantity to reduce (totally or partially) MV infection of the individual's cells. A dose of said chimeric peptide sufficient to reduce HIV infection (an "effective dose") is administered in such a manner (e.g., by injection, topical administration, intravenously) that it inhibits, totally or partially, HIV entry into cells. A pharmaceutically acceptable composition suitable for patient administration will contain an effective amount of the peptide in a formulation which both retains biological activity while also promoting maximal stability during storage within an acceptable temperature range. This peptide-based pharmaceutical composition may optionally comprise a pharmaceutically acceptable carrier. These peptides could be used in combination with a variety of anti-retrovirals to inhibit HIV replication. Classes of anti-retrovirals that could be used with CC-chimeric N-peptide-based compositions include, but are not limited to, nucleoside reverse transcriptase inhibitors (NRTIs), non-nucleoside reverse transcriptase inhibitors (NNRTIs) and protease inhibitors (PIs).

Since the covalently-stabilized, trimeric coiled-coils of the present invention represent stable, faithful mimetics of the internal, N-helix coiled-coil of gp41, they also are useful as immunogens to raise a neutralizing antibody response targeting HIV fusion intermediates. Therefore, the present invention relates to methods of using a covalently-stabilized chimeric peptide as described herein as an immunogen to elicit HIV-specific antibodies to either prevent or reduce HIV infection. The CC-chimeric N-peptide-related immunogens, when administered alone or in combined modality and/or prime/boost regimen, will offer a prophylactic advantage to previously uninfected individuals and/or provide a therapeutic effect by reducing viral load levels within an infected individual, thus prolonging the asymptomatic phase of HIV infection. When the covalently-stabilized chimeric peptides described herein, or immunogenic conjugates thereof, are capable of eliciting HIV neutralizing immune responses to the HIV component of chimeric peptides, said peptides/conjugates may be administered to mammals in immunologically effective amounts, with or without additional immunomodulatory, anti-viral or antibacterial compounds. Said peptides/conjugates will be useful for inducing mammalian immune responses against the HIV peptidyl portion of the conjugates, for inducing HIV-neutralizing antibodies in mammals, for making immunogens and/or immunogenic compositions comprising said covalently-stabilized CC-chimeric N-peptides described herein for administration to humans to prevent contraction of HIV infection or disease including AIDS, or for administration to humans afflicted with HIV infection or disease including AIDS. Dosages of between 10 µg and 500 µg of conjugated, covalently-stabilized CC-chimeric-N-peptides, and preferably between 50 µg and 300 µg of conjugate, are administered to a mammal to induce anti-HIV or HIV-neutralizing immune responses. About two to four weeks after the initial administration, a booster dose may be administered, and then again whenever serum antibody titers diminish. The conjugate should be given intramuscularly at a concentration of between 10 µg/ml and 1 mg/ml, and preferably between 50 and 500 µg/ml, in a volume sufficient to make up the total required for immunological efficacy. Importantly, in order to help minimize the generation of antibodies against the scaffold domain of the covalently-stabilized homotrimeric gp41 mimetics described herein, the prime/boost regimen can be designed such that the covalently-stabilized trimeric structure used for prime injection has as different scaffold domain as the covalently-stabilized trimeric structure used for boost injections (e.g., primer with (CCIZN17)$_3$, and boost with (CCEZN17)$_3$). Adjuvants may or may not be added during the preparation of the immunogenic compositions of this invention. For example, alum is the typical and preferred adjuvant in human vaccines, especially in the form of a thixotropic, viscous, and homogeneous aluminum hydroxide gel. One embodiment of this invention is the prophylactic vaccination of patients with a suspension of alum adjuvant as vehicle and a cocktail of covalently-stabilized chimeric peptides, or immunoconjugates thereof, as the antigens.

And finally, since the covalently-stabilized chimeric peptides of the present invention present faithful mimetics of the internal N-helix coiled-coil of the fusogenic structure of gp41, said chimeric peptides are useful as a reagent for the identification of inhibitors (e.g., small molecules, scFvs) that bind to HIV fusion intermediates. Therefore, the present invention also relates to methods of screening for and selecting HIV anti-viral compounds. For example, an antibody/peptide/test compound interaction assay involving a neutralizing antibody that recognizes a conformation epitope within the internal N-helix coiled-coil (e.g., D5 IgG) and the covalently-stabilized chimeric peptides of the present invention may be devised. Such interaction assays may be utilized for the purpose of high throughput screening to identify small molecules that associate with the epitope to which to neutralizing antibody binds (e.g., in the case of D5 IgG, the hydrophobic pocket of HR1) and displace the antibody. Such small molecules may, in turn, represent HIV fusion inhibitors if they successfully prevent the intramolecular interaction of N- and C-helices of the gp41 ectodomain. The compound to be tested may be a peptide, a protein, a non-proteinaceous organic or inorganic molecule, DNA (single or double stranded) or RNA (such as siRNA or shRNA).

Various antibody/peptide-based assays known in the art may be used which incorporate and rely on a covalently-stabilized chimeric peptide of the present invention as an essential reagent in screening for a new HIV anti-viral compound, including but not limited to an ELISA assay, a RIA assays, a Western blot analysis, any homogenous assay relying on a detectable biological interaction not requiring separation or wash steps (e.g., see AlphaScreen™ from PerkinElmer®) and/or SPR-based technology (e.g., see BIACore). To this end, the present invention relates to any such assay, regardless of the known methodology employed, which measures the ability of a test compound to compete with the binding of a neutralizing antibody that recognizes a conformational epitope (e.g., D5 IgG) to a covalently-stabilized CC-chimeric N-peptide described herein. For screening, one component (component 1) of the assay would consist of a covalently-stabilized CC-chimeric N-peptide, including but not limited to covalently-stabilized CCIZN17, CCIZN17Ala4 and CCEZN17 trimers. These CC-chimeric N-peptides could also be modified by covalent addition of a moiety to enable detection; such moieties include but are not limited to biotin. The other primary assay component (component 2) would include consist of a neutralizing antibody that specifically binds to a conformation epitope, including but not limited to an epitope located within the hydrophobic pocket of the gp41. To facilitate detection, the antibody component could also be modified by covalent addition of moieties such as fluorescein, AlexaFluor647 (AlexaFluor647-NHS from Molecular Probes), or Europium chelates (e.g., Eu-LANCE-NHS from Wallac Perkin Elmer).

A screening assay designed to detect antibody/covalently-stabilized chimeric peptide interaction in the presence or absence of a test would take any number of forms, of which only a few examples are presented herein for clarification, and not limitation. One mode would be a traditional enzyme-linked immunosorbent assay (ELISA) in which the biotin-labeled component 1 (peptide) is immobilized in a microtiter plate well coated and allowed to react with streptavidin-linked component 2 (antibody) in the presence or absence of competitors, and antibody remaining bound (after washing) is detected using an enzyme-labeled anti-human IgG or an enzyme-labeled Protein A. A second format, discussed infra, uses AlphaScreen™ assay technology (PerkinElmer) in which the donor bead is coated with Streptavidin and the acceptor bead is coated with Protein A. In this format, biotinylated component 1 (peptide) is mixed with component 2 (antibody) in the presence or absence of competitor and allowed to react. After binding, complexes of component 1 and component 2 are detected by adding the donor and acceptor beads, waiting for binding, and measuring emitted light in a Fusion detector (Wallac Perkin Elmer) according to the manufacturer's instructions. A third format, also a homogeneous binding format, could rely on homogeneous time-resolved fluorescence (HTRF) technology. In this format, biotinylated component 1 (peptide) is mixed, in the presence or absence of a competitor, with component 2 (antibody) that has been covalently derivatized with AlexaFluor647. After binding, complexes of component 1 and component 2 are detected by adding Streptavidin (derivatized with Europium chelates, from Molecular Probes) and measuring fluorescence resonance energy transfer (FRET) in a microplate fluorometer according to the manufacturer's instructions. Alternatively, the HTRF assay could be done using component 2 derivatized with Europium chelate and Streptavidin derivatized with XL-665.

Another available screening strategy which allows for incorporation of the covalently-stabilized chimeric peptides of the present invention is the use surface plasmon resonance (SPR)-based biomolecular interaction analysis, such as with a BIACore 3000 instrument. Such an instrument provides several advantages over traditional immunoassays. First, use of SPR technology removes the need to use labeled reagents. Instead, an assay reagent is immobilized on a sensor chip (e.g., a streptavidin (SA) or carboxymethyldextran (CM5)), which are available from BIACore (Piscataway, N.J.). Second, formation of antibody/antigen/test compound complexes can be followed in real time, allowing for retrieval of information regarding reaction kinetics and affinity measurements (Kd). This technology is also amenable to analysis of test compounds, such as small organic molecules, to select a test compound which interacts with the epitope similar antibody binding site on the covalently-stabilized chimeric peptides. A covalently-stabilized, biotinylated chimeric peptide (including but in no way limited to CCIZN17, CCIZN17Ala4 and/or CCEZN17 trimers) that represents a stable, faithful, mimetic of the gp41 fusion intermediate will be useful in BIACore-based screens of inhibitors targeting the N-helix of the HIV gp41 ectodomain. Said peptides can be immobilized by flowing a solution of 1 nM peptide in HBS (Hepes Buffered Saline) plus 10× Tween for 1-4 minutes over a SA chip. Manual injection is used until the bound peptide reaches 10 resonance units (RU), sufficient to bind 100 RU of analyte full antibody. Alternatively, a BIACore assay may be based upon immobilization of an neutralizing antibody, as described supra, preferably on a CM5 chip. Such a sensor chip is first surface-activated by EDC (N-ethyl-N'-(3-dimethyl aminopropyl)-carbodiimide hydrochloride) and NHS (N-hydroxysuccinimide) following the manufacturer's instructions. Immobilization of the antibody may be carried out at 1-5 µg/mL in acetate buffer, pH 4.8 (mixing BIACore supplied buffers) using the inbuilt immobilization wizard control template, with target immobilization set at 1500-1800 RU. Flow rates are normally 20 µl/min during association-dissociation phases, and 50 µl/min during surface regeneration with a single wash of 15 mM HCl. The kinetics wizard may be used to design the affinity measurement experiments, with duplicates and controls run as prompted to detect diffusion-limited kinetics. Peptide concentrations are chosen to give data for concentrations above and below the Kd value, with two-fold or four-fold dilution series. The association time is typically 3 min, dissociation 5-10 min while association-dissociation measurements are made at 25° C. in HBS+10× Tween, which should eliminate non-specific binding events. Analysis of data is by the BIACore curve-fitting software, selecting data from smooth regions with significant change in RU. It will be evident to the artisan that BIACore technology will allow for multiple assay formats in the context of a screen for HIV fusion inhibitors. A direct binding assay may be used where one or the other of either a CC-chimeric N-peptide, HIV fusion mimetic or a neutralizing antibody that recognizes a conformational epitope within the internal, N-helix coiled-coil is immobilized to an appropriate sensor chip. With a chip containing immobilized peptide, either an assay which measures the direct binding of a test compound to said covalently-stabilized chimeric peptides or a surface competition assay measuring binding competition between a test compound and a neutralizing antibody which specifically binds an epitope of interest in contemplated. Alternatively, a neutralizing antibody which specifically binds an epitope of interest within the internal, N-helix coiled-coil of the pre-hairpin gp41 complex, including but not limited to D5 IgG, may be immobilized on a sensor chip and used in a surface competition assay with a test compound and a covalently-stabilized chimeric peptide coiled-coil.

A variety of antibody/peptide interaction assays can be used to detect anti-viral compounds using the covalently-stabilized chimeric peptides of the present invention. The assay may be a simple "yes/no" assay to determine whether there is a change in the ability to form a antibody/antigen complex. The assay is easily made quantitative by utilizing any number of methods, especially an ELISA-based assay, a homogenous assay, or an SPR-based assay. To this end, the present invention relates in part to methods of identifying an anti-viral compound that binds to an epitope within the internal, N-helix coiled-coil of gp41, including but not limited to the hydrophobic pocket of said coiled-coil structure, and displaces a neutralizing antibody that likewise recognizes said epitope, preventing intramolecular interaction of the N- and C-helices of the gp41 ectodomain. Such methodology comprises (a) incubating a test compound along with (i) a covalently-stabilized trimeric coiled-coil of the present invention and (ii) an antibody, including but not limited to a neutralizing antibody, that recognizes a conformational epitope within the internal, N-helix coiled-coil of the gp41 ectodomain, including but not limited to a neutralizing antibody that recognizes the hydrophobic pocket of said coiled-coil; (b) measuring the effect the test compound has on the affinity of component (i) for component (ii); and (c) comparing that effect the test compound has on the affinity of component (i) for component (ii) versus the affinity of component (i) for component (ii) in the absence of the test compound. A decrease in component (i) and component (ii) affinity in the presence of the test compound, indicates that the test compound is a compound which interacts with and possesses a quantitative (i.e., measurable) affinity for a conformational epitope within the N-helix coiled-coil of gp41. Any such test compound is considered a potential EV anti-viral lead compound (e.g., a HIV fusion inhibitor).

The CC- and derivatized-chimeric N-peptides of the present invention can be produced by a variety of methods. For example, they can be chemically synthesized. Long peptides may be synthesized on solid-phase supports using an automated peptide synthesizer as described by Kent et al., 1985, "Modern Methods for the Chemical Synthesis of Biologically Active Peptides," Alitalo et al. (Eds.), *Synthetic Peptides in Biology and Medicine*, Elsevier pp. 29-57. Manual solid-phase synthesis may be performed as described, for example, in Merrifield, 1963, *Am. Chem. Soc.* 85:2149, or known improvements thereof. Solid-phase peptide synthesis may also be performed by the Fmoc method, which employs very dilute base to remove the Fmoc protecting group. Solution-phase synthesis is usually feasible only for selected smaller peptides. For preparing cocktails of closely related peptides, see, e.g., Houghton, 1985, *Proc. Natl. Acad. Sci. USA* 82:1242-1246. The chimeric peptides of the present invention can be produced as a continuous peptide or as components that are joined or linked after they are formed.

Alternatively, the chimeric peptides of the present invention can be produced, using known methods and expression systems, by expressing chimeric peptide-encoding DNA, which can be a single DNA that encodes the entire chimeric peptide. The chimeric peptide gene may be recombinantly expressed by molecular cloning into an expression vector (e.g., pcDNA3.neo, pcDNA3.1, pCR2.1, pBlueBacHis2 or pLITMUS28) containing a suitable promoter and other appropriate transcription regulatory elements, and transferred into prokaryotic or eukaryotic host cells to produce the chimeric peptide. Expression vectors are defined herein as DNA sequences that are required for the transcription of cloned DNA and the translation of their mRNAs in an appropriate host. Such vectors can be used to express recombinant DNA in a variety of recombinant host cells such as bacteria, yeasts, blue green algae, plant cells, insect cells and mammalian cells. An appropriately constructed expression vector should contain the following components: an origin of replication for autonomous replication in host cells; selectable markers; a limited number of useful restriction enzyme sites; and active promoters. Expression vectors may include, but are not limited to, cloning vectors, modified cloning vectors, specifically designed plasmids or viruses. Commercially available mammalian expression vectors may be suitable for recombinant chimeric peptide expression. Also, a variety of commercially available bacterial, fungal cell, and insect cell expression vectors may be used to express recombinant mimotopes in the respective cell types. A promoter is defined as a DNA sequence that directs RNA polymerase to bind to DNA and initiate RNA synthesis. A strong promoter is one which causes mRNAs to be initiated at high frequency. Techniques for such manipulations can be found in Sambrook et al., 1989, *Molecular Cloning: A Laboratory Manual*, Cold Spring Harbor Laboratory, Cold Spring Harbor, N.Y., and are well known and available to an artisan of ordinary skill in the art. The expression vector containing the appropriate gene coding for a chimeric peptide may be introduced into host cells via any one of a number of techniques, including but not limited to transformation, transfection, protoplast fusion, and electroporation. The expression vector-containing cells are individually analyzed to determine whether they produce the chimeric peptide of interest. Identification of chimeric peptide-expressing cells may be done by several means, including but not limited to immunological reactivity with anti-HIV peptide antibodies. Recombinant chimeric peptides may possess additional and desirable structural modifications not shared with the same organically synthesized-peptide, such as adenylation, carboxylation, glycosylation, hydroxylation, methylation, phosphorylation or myristoylation. These added features may be chosen or preferred as the case may be, by the appropriate choice of recombinant expression system.

Following expression of a chimeric peptide gene in a host cell, chimeric peptide may be recovered. Several protein purification procedures are available and suitable for use, including purification from cell lysates and extracts, or from conditioned culture medium, by various combinations of, or individual application of, salt fractionation, ion exchange chromatography, size exclusion chromatography, hydroxylapatite adsorption chromatography and hydrophobic interaction chromatography. In addition, chimeric peptides can be separated from other cellular proteins by use of an immunoaffinity column made with monoclonal or polyclonal antibodies specific for the chimeric peptide. As used herein, "purified" and "isolated" are utilized interchangeably to stand for the proposition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in pure quantities.

All publications mentioned herein are included for the purpose of describing and disclosing methodologies and materials that might be used in connection with the present invention. Nothing herein is to be construed as an admission that the invention is not entitled, to antedate such disclosure by virtue of prior invention.

Having described preferred embodiments of the invention with reference to the accompanying figures, it is to be understood that the invention is not limited to those precise embodiments, and that various changes and modifications may be effected therein by one skilled in the art without departing from the scope or spirit of the invention as defined in the appended claims.

The following examples are provided to illustrate the present invention without, however, limiting the same hereto.

EXAMPLE 1

Peptide Synthesis and Covalent-Stabilization

Synthesis of IZN17 and CCIZN17—The peptides IZN17 (SEQ ID NO:1) and CCIZN17 (SEQ ID NO:2) were synthesized by solid phase using Fmoc/t-Bu chemistry on a Pioneer Peptide Synthesizer (Applied Biosystems). The resin used was the Fmoc-Linker AM-Champion, 1% cross-linked (Biosearch Technologies, Inc.), a PEG-PS based resin derivatized with a modified Rink linker p-[(R,S)-α-[9H-Fluoren-9-yl-methoxyformamido]-2,4-dimethoxybenzyl]-phenoxyacetic acid (Rink, H., 1987, *Tetrahedron Lett.* 28:3787-3789; Bernatowicz, M. S. et al., 1989, *Tetrahedron Lett.* 30:4645-4667). All the acylation reactions were performed for 60-120 minutes with 4-fold excess of activated amino acid over the resin free amino groups. Amino acids were activated with equimolar amounts of HBTU (2-(1H-benzotriazole-1-yl)-1,1,3,3-tetramethyluronium hexafluorophosphate) and a 2-fold molar excess of DIEA (N,N-diisopropylethylamine). The side chain protecting groups were as follows: tert-butyl for glutamic acid (Glu) and threonine (Thr); trityl for cysteine (Cys) and glutamine (Gln); tert-butoxy-carbonyl for lysine (Lys) and tryptophan (Trp); and, 2,2,4,6,7-pentamethyldihydrobenzofuran-5-sulfonyl for arginine (Arg). The acetylation reaction was performed at the end of the peptide assembly by reaction with a 10-fold excess of acetic anhydride in N,N-dimethylformamide (DMF). At the end of the synthesis, the dry peptide-resin was treated with 88% trifluoroacetic acid (TFA), 5% phenol, 2% triisopropylsilane and 5% water (Sole, N. A. and G. Barany, 1992, *J. Org. Chem.* 57:5399-5403) for 1.5 hours at room temperature. The resin was filtered and the solution was added to cold methyl-t-butyl ether in order to precipitate the peptide. After centrifugation, the peptide pellets were washed with fresh, cold methyl-t-butyl ether to remove the organic scavengers. The process was repeated twice. The final pellets were dried, resuspended in $H_2O$, 20% acetonitrile and lyophilized.

The crude peptide IZN17 (SEQ ID NO:1) was purified by reverse-phase HPLC using semi-preparative Waters RCM Delta-Pak™ $C_{-4}$ cartridges (40×200 mm, 15 µm) and using as eluents (A) 0.1% TFA in water and (B) 0.1% TFA in acetonitrile. The following gradient of eluent B was used: 40%-60% over 20 min, flow rate 80 mL/min. Analytical HPLC was performed on a Phenomenex, Jupiter $C_4$ column (150×4.6 mm, 5 µm) with the following gradient of eluent B: 40%-60% B (in 20 min)-80% (in 3 min), flow rate 1 mL/min. The purified peptide was characterized by electrospray mass spectrometry on a Micromass LCZ platform.

The crude peptide CCIZN17 (SEQ ID NO:2) was purified by gel permeation chromatography (GPC) on a 700×26 mm column packed with a Toyopearl HW-50S resin, using 30% acetonitrile in water, 0.1% TFA as eluent. In a typical run, 300 mg of crude peptide was dissolved in 12 mL of eluent and directly loaded on the column, flow rate 1 mL/min. Analytical HPLC of eluted fractions was performed on a Beckman HPLC with a Phenomenex, Jupiter $C_4$ column (150×4.6 mm, 5 µm) with the following gradient of eluent B (above): 40%-60% B (in 20 min)-80% (in 3 min), flow rate 1 mL/min. On the basis of the purity, the fractions were pooled and further purified by reverse phase HPLC using semi-preparative Waters RCM Delta-Pak™ $C_{-4}$ cartridges (40×200 mm, 15 µm) and using as eluents (A) 0.1% TFA in water and (B) 0.1% TFA in acetonitrile. The following gradient of eluent B was used: 35%-50% over 20 min, flow rate 80 mL/min. The purified peptide was characterized by electrospray mass spectrometry on a Micromass LCZ platform spectrometer. The theoretical, average molecular weight (MW)) is 5175 Da; while the found MW is 5175 Da.

Oxidation of CCIZN17 to $(CCIZN17)_3$—The purified peptide precursor (12 mg), CCIZN17 (SEQ ID NO:2), was dissolved in 0.1 M Hepes, pH 7.3 (USB Corp.) at a concentration of 1 mg/mL. Under this condition, CCIZN17 is slowly oxidized by the air to the covalent trimer $(CCIZN17)_3$ ([SEQ ID NO:2]$_3$), see FIG. 2A. The oxidation reaction was monitored by LC-MS analysis using a Waters-Micromass LCZ Platform with a Phenomenex, Jupiter $C_4$ column (150×4.6 mm, 5 µm) using as eluents (A) 0.1% TFA in water and (B) 0.1% TFA in acetonitrile. The following gradient of eluent B was used: 40%-60% B (in 20 min)-80% (in 3 min), flow rate 1 mL/min. Under these chromatographic conditions, CCIZN17 elutes at $t_R$=13.25'. The oxidation reaction proceeds smoothly in 3 hours with formation of one main product eluting at $t_R$=15' whose mass corresponds to that of one molecule comprising three CCIZN17 peptide chains having a reduction of mass consistent with formation of three disulfide bridges ([CCIZN17]$_3$, see FIG. 2A). The overall yield of the oxidation reaction is more than 80%. To the solution (12 mL) was added 24 µL of TFA, and the solution was directly loaded on a 700×26 mm column, packed with a TSKgel Toyopearl HW-50S resin, using as eluent $H_2O$/acetonitrile, 70/30, 0.1% TFA, flow rate 1 mL/min. The eluted fractions were analyzed by HPLC with a Phenomenex, Jupiter $C_4$ column (150×4.6 mm, 5 µm) using as eluents: (A) 0.1% TFA in water and (B) 0.1% TFA in acetonitrile. The following gradient of eluent B was used: 40%-60% B (in 20 min)-80% (in 3 min), flow rate 1 mL/min on the LC-MS Waters-Micromass LCZ Platform. The pooled fractions corresponding to the covalent trimer were further analyzed by mass spectrometry on an ESI-QqToF (Applied Biosystems) in a positive mode ($ES^+$), nanospray 1 µl injection. The expected MW is 15520.2 Da; while the found MW is 15520.1 Da.

Synthesis of Biotin-IZN17—IZN17 (SEQ ID NO:1) was synthesized following the same protocol as described for synthesis of IZN17 and CCIZN17. The reaction with Biotin was performed at the end of the peptide assembly by reaction with a 4-fold excess of Biotin activated with an equimolar amount of DIPC (N,N'-diisopropylcarbodiimide) and HOBt (1-hydroxybenzotriazole), overnight. The crude peptide, Biotin-IZN17 (SEQ ID NO: 3), was purified by reverse-phase HPLC on semi-preparative Waters RCM Delta-Pak™ $C_{-4}$ cartridges (40×200 mm, 15 µm) using as eluents (A) 0.1% TFA in water and (B) 0.1% TFA in acetonitrile. The following gradient of eluent B was used: 35%-55% over 25 min, flow rate 80 mL/min. Analytical HPLC was performed on a Phenomenex, Jupiter $C_4$ column (150×4.6 mm, 5 µm) with the following gradient of eluent B: 45%-60% B (in 20 min)-80% (in 3 min), flow rate 1 mL/min. The purified peptide was characterized by electrospray mass spectrometry on a Micromass LCZ platform. The theoretical average MW is 5281.52 Da, and the found MW is 5281.0 Da.

Synthesis of Biotin-IZN23 and Biotin-CCIZN23—Biotin-IZN23 (SEQ ID NO:11) and Biotin-CCIZN23 (SEQ ID NO:12) were synthesized following the same protocols as outlined for synthesis of IZN17 (SEQ ID NO:1) and CCIZN17 (SEQ ID NO:2), see above, except that the last 20 amino acids were activated with equimolar amounts of HATU (N-[(dimethylamino)-1H-1,2,3-triazolo-[4,5-b]pyridinylmethylene)]-N-methylmethanaminium hexafluorophosphate N-oxide) and a 2-fold molar excess of DIEA (N,N-diisopropylethylamine). The side chain protecting groups were as follows: tert-butyl for glutamic acid (Glu) and threonine (Thr); trityl for histidine (His), cysteine (Cys) and glutamine (Gln); tert-butoxy-carbonyl for lysine (Lys) and tryptophan (Trp); and, 2,2,4,6,7-pentamethyldihydrobenzofuran-5-sulfonyl for arginine (Arg).

The reaction with Biotin was performed at the end of the peptide assembly process by reaction with a 4-fold excess of Biotin activated with an equimolar amount of DIPC(N,N'-diisopropylcarbodiimide) and HOAt (7-aza-1-hydroxybenzotriazole), overnight. The crude peptide Biotin-IZN23 (SEQ ID NO:11) (270 mg dissolved in 16 mL $H_2O$/acetonitrile, 70/30, 0.1% TFA) was purified by gel permeation chromatography (GPC) on TSK-gel Toyopearl HW-50S resin (700× 26 mm column), using 30% acetonitrile in water as eluent, 0.1% TFA, flow rate 1 ml/min. The pooled fractions (purity 80%) obtained by GPC (30% yield) were further purified to >95% purity by semi-preparative reversed phase HPLC on Jupiter $C_4$ column (250×21.2 mm, 10 µm, 300 A, Phenomenex), flow rate 25 mL/min, using as eluents: (A) 0.1% TFA in water and (B) 0.1% TFA in acetonitrile. The following gradient of eluent B was used: 35%-50% over 20 min. Analysis of the crude peptide, the eluted fractions and the purified pool was carried out by analytical HPLC on Jupiter $C_4$ column (150×4.6 mm, 5 µm, 300 A, Phenomenex), flow rate 1 mL/min, using as eluents: (A) 0.1% TFA in water and (B) 0.1% TFA in acetonitrile. The following gradient of eluent B was used: 35%-50% over 20 min-80% over 3 minutes. The purified peptide was characterized by mass spectrometry on a Micromass LCZ platform $ES^+$. The found MW is 5989.0 Da, and the calculated average MW is 5989.22 Da.

The crude Biotin-CCIZN23 (SEQ ID NO:12) peptide was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC (25% yield) were further purified to >95% purity by semi-preparative reversed phase HPLC on Jupiter $C_4$ column (250× 21.2 mm, 10 µm, 300 A, Phenomenex), flow rate 25 mL/min, using as eluents (A) 0.1% TFA in water and (B) 0.1% TFA in acetonitrile. The following gradient of eluent B was used: 35%-50% over 20 min, flow rate 80 mL/min. Analysis of the crude peptide, the eluted fractions and the purified pool was carried out by analytical HPLC on Jupiter $C_4$ column (150× 4.6 mm, 5 µm, 300 A, Phenomenex), flow rate 1 mL/min, using as eluents: (A) 0.1% TFA in water and (B) 0.1% TFA in acetonitrile. The following gradient of eluent B was used: 35%-50% over 20 min-80% over 3 minutes. The purified peptide was characterized by mass spectrometry on a Micromass LCZ platform $ES^+$. The found MW is 6252.0 Da, and the calculated average MW is 6252.5 Da.

Oxidation of Biotin-CCIZN23 to $(Biotin-CCIZN23)_3$— The purified peptide precursor (7 mg), Biotin-CCIZN23 (SEQ ID NO:12), was dissolved in 0.1 M Hepes, pH 7.3 (USB Corp.) at a concentration of 1 mg/mL. Under this condition, the Biotin-CCIZN23 is slowly oxidized overnight by air to the covalent trimer (Biotin-CCIZN23)$_3$ (SEQ ID NO:12)$_3$, see FIG. 2B. The oxidation reaction was monitored by HPLC-MS analysis using a Waters-Micromass LCZ Platform with a Phenomenex, Jupiter C$_4$ column (150×4.6 mm, 5 μm) with the following gradient of eluent B (above): 30%-60% B (in 20 min)-80% (in 3 min), flow rate 1 mL/min. In these chromatographic conditions, Biotin-CCIZN23 elutes at t$_R$=13.74'. The oxidation reaction yield was about 70% with formation of one main product eluting at t$_R$=11', whose mass corresponds to that of one molecule comprising three Biotin-CCIZN23 peptide chains having a reduction of mass consistent with formation of three disulfide bridges (expected MW is 18751.64 Da; found MW is 18751.0 Da). To the solution (7 mL), 14 μL of TFA was added, and the solution was directly loaded on a Phenomenex Jupiter C$_4$ column (250×21.6 mm) using as eluents: (A) 0.1% TFA in water and (B) 0.1% TFA in acetonitrile, flow rate 25 mL/min. The following gradient of eluent B was used: 30%-30% (for 5 min)-50% B (in 20 min)-80% (in 3 min). The eluted fractions were analyzed by HPLC with a Phenomenex, Jupiter C$_4$ column (150×4.6 mm, 5 μm) with the following gradient of B: 30%-60% B (in 20 min)-80% (in 3 min), flow rate 1 mL/min on the Waters-Micromass LCZ Platform. The pooled fractions corresponding to the covalent trimer were collected and freeze-dried with an overall yield of 2 mg of purified (Biotin-CCIZN23)$_3$ (see FIG. 2B).

Synthesis of Biotin-IZN36—Biotin-IZN36 (SEQ ID NO:12) was synthesized following the same protocols as outlined for the synthesis of IZN17 and CCIZN17, see above, except that the amino acids were activated with equimolar amounts of HATU (N-[(dimethylamino)-1H-1,2,3-triazolo-[4,5-b]pyridinylmethylene)]-N-methylmethanaminium hexafluorophosphate N-oxide) and a 2-fold molar excess of DIEA (N,N-diisopropylethylamine). The side chain protecting groups were as follows: tert-butyl for glutamic acid (Glu), serine (Ser) and threonine (Thr); trityl for histidine (His), asparagine (Asn), cysteine (Cys) and glutamine (Gln); tert-butoxy-carbonyl for lysine (Lys) and tryptophan (Trp); and, 2,2,4,6,7-pentamethyldihydrobenzofuran-5-sulfonyl for arginine (Arg).

The reaction with Biotin was performed at the end of the peptide assembly by reaction with a 4-fold excess of Biotin activated with an equimolar amount of DIPC(N,N'-diisopropylcarbodiimide) and HOBt (1-hydroxybenzotriazole), overnight. The crude peptide Biotin-IZN36 was purified by reverse-phase HPLC on semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of eluent B was used: 35%-50% over 25 min, flow rate 80 mL/min. Analytical HPLC was performed on a Phenomenex, Jupiter C$_4$ column (150×4.6 mm, 5 μm) with the following gradient of eluent B: 40%-60% B (in 20 min)-80% (in 3 min), flow rate 1 mL/min. The purified peptide was characterized by electrospray mass spectrometry on a Perkin-Elmer API-100. The theoretical average MW is 7653.18 Da; and the found MW is 7653.4 Da.

Synthesis of IZN17Ala-4—IZN17Ala4 (SEQ ID NO:4) was synthesized following the same protocol as described for IZN17 (SEQ ID NO:1) and CCIZN17 (SEQ ID NO:2). The acetylation reaction was performed at the end of the peptide assembly by reaction with a 10-fold excess of acetic anhydride in DMF. The crude peptide, IZN17Ala4 (SEQ ID NO:4), was purified by reverse-phase HPLC on semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of eluent B was used: 40%-60% over 25 min, flow rate 80 mL/min. Analytical HPLC was performed on a Phenomenex, Jupiter C$_4$ column (150×4.6 mm, 5 μm) with the following gradient of eluent B: 45%-65% B (in 20 min)-80% (in 3 min), flow rate 1 mL/min. The purified peptide was characterized by electrospray mass spectrometry on a Micromass LCZ platform. The theoretical average MW is 4613.7 Da, and the found MW is 4613.0 Da.

Synthesis of CCIZN17Ala-4—CCIZN17Ala4 (SEQ ID NO:5) was synthesized following the same protocol as described for IZN17 (SEQ ID NO:1) and CCIZN17 (SEQ ID NO:2). The acetylation reaction was performed at the end of the peptide assembly by reaction with a 10-fold excess of acetic anhydride in DMF. The crude peptide, CCIZN17Ala4 (SEQ ID NO:5), was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC (25% yield) were further purified to >95% purity by reverse-phase HPLC on semi-preparative Waters RCM Delta-Pak™ C$_{-4}$ cartridges (40×200 mm, 15 μm), flow rate 80 mL/min, using as eluents (A) 0.1% TFA in water and (B) 0.1% TFA in acetonitrile. The following gradient of eluent B was used: 45%-55% over 25 min, flow rate 80 mL/min. Analysis of the crude peptide, the eluted fractions and the purified pool was carried out by analytical HPLC on Jupiter C$_4$ column (150×4.6 mm, 5 μm, 300 A, Phenomenex), flow rate 1 mL/min, using as eluents: (A) 0.1% TFA in water and (B) 0.1% TFA in acetonitrile. The following gradient of eluent B was used: 50%-60% over 20 min-80% over 3 minutes. The purified peptide was characterized by mass spectrometry on a Micromass LCZ platform ES$^+$. The found MW is 4934.0 Da, and the calculated average MW is 4933.0 Da.

Oxidation of CCIZN17Ala4 to (CCIZN17Ala4)$_3$— The purified peptide precursor (26 mg), CCIZN17Ala4 (SEQ ID NO:5), was dissolved in 0.1 M Hepes, pH 7.3 (USB Corp.) at a concentration of 5 mg/mL. Under this condition, CCIZN17Ala4 is slowly oxidized by the air to the covalent trimer (CCIZN17Ala4)$_3$ ([SEQ ID NO:5]$_3$). The oxidation reaction was monitored by LC-MS analysis using a Waters-Micromass LCZ Platform with a Phenomenex, Jupiter C$_4$ column (150×4.6 mm, 5 μm) using as eluents (A) 0.1% TFA in water and (B) 0.1% TFA in acetonitrile. The following gradient of eluent B was used: 45%-70% B (in 20 min)-80% (in 3 min), flow rate 1 mL/min. Under these chromatographic conditions, CCIZN17 elutes at t$_R$=12.52'. The oxidation reaction proceeds smoothly in 3 hours with formation of one main product eluting at t$_R$=17' whose mass corresponds to that of one molecule comprising three CCIZN17Ala4 peptide chains having a reduction of mass consistent with formation of three disulfide bridges ([CCIZN17Ala4)$_3$). The overall yield of the oxidation reaction is more than 80%. To the solution was added 45 μL of TFA, and the solution was directly loaded on a 700×26 mm column, packed with a TSKgel Toyopearl HW-50S resin, using as eluent H$_2$O/acetonitrile, 70/30, 0.1% TFA, flow rate 1 mL/min. The eluted fractions were analyzed by HPLC with a Phenomenex, Jupiter C$_4$ column (150×4.6 mm, 5 μm) using as eluents: (A) 0.1% TFA in water and (B) 0.1% TFA in acetonitrile. The following gradient of eluent B was used: 50%-70% B (in 20 min)-80% (in 3 min), flow rate 1 mL/min on the LC-MS Waters-Micromass LCZ Platform in a positive mode (ES$^+$). The expected MW is 14796.2.2 Da; while the found MW is 14797.1 Da.

EXAMPLE 2

Preparation of Affinity Purification Resin with (SCCIZN17)$_3$

Synthesis of SCCIZN17—SCCIZN17 (SEQ ID NO:21) was synthesized following the same protocols as outlined for the synthesis of IZN17 and CCIZN17 (see Example 1) except that the N-terminal serine (Ser) was left with the NH$_2$-terminal free amine. The crude peptide (250 mg dissolved in 15 mL H$_2$O/acetonitrile, 70/30, 0.1% TFA) was purified by gel permeation chromatography (GPC) on TSK-gel Toyopearl HW-50S resin (700×26 mm column), using 30% acetonitrile in water as eluent, 0.1% TFA, flow rate 1 mL/min. Analytical HPLC of eluted fractions was performed on a Beckman HPLC with a Phenomenex, Jupiter C$_4$ column (150×4.6 mm, 5 µm) with the following gradient of eluent B (above): 35%-50% B (in 20 min)-80% (in 3 min), flow rate 1 ml/min. On the basis of the purity, the fractions were pooled and further purified by reverse phase HPLC with semi-preparative Waters RCM Delta-Pak™ C$_4$ cartridges (40×200 mm, 15 µm) using eluents (A) 0.1% TFA in water and (B) 0.1% TFA in acetonitrile. The following gradient of eluent B was used: 30%-45% over 20 min, flow rate 80 mL/min. The purified peptide was characterized by electrospray mass spectrometry on a Micromass LCZ platform (MW found: 5228.0 Da).

Oxidation of SCCIZN17 to (SCCIZN17)$_3$— The purified peptide precursor (11 mg), SCCIZN17 (SEQ ID NO:21), was dissolved in 0.1 M Hepes, pH 7.3 (USB Corp.) at a concentration of 1 mg/mL. The oxidation reaction was monitored by HPLC-MS analysis using a Waters-Micromass LCZ Platform with a Phenomenex, Jupiter C$_4$ column (150×4.6 mm, 5 µm) with the following gradient of eluent B (above): 35%-55% B (in 20 min)-80% (in 3 min), flow rate 1 mL/min. SCCIZN17, whose retention time in the HPLC-MS analysis is $t_R$=15.35', was slowly oxidized overnight by air, with the formation of one main product (eluting at $t_R$=14.5') whose mass corresponds to that of one molecule comprising three SCCIZN17 peptide chains linked together and a reduction of mass consistent with the formation of three disulfide bridges ([SC-CIZN17]$_3$, see FIG. 3A). The oxidation reaction yield was about 70%. To the solution (11 mL), 24 µL of TFA was added, and the solution was directly loaded on a 700×26 mm column, packed with a TSKgel Toyopearl HW-50S resin, using as eluent H$_2$O/acetonitrile, 70/30, 0.1% TFA, flow rate 1 mL/min. The eluted fractions were analyzed by HPLC with a Phenomenex, Jupiter C$_4$ Column (150×4.6 mm, 5 µm) using as eluents: (A) 0.1% TFA in water and (B) 0.1% TFA in acetonitrile. The following gradient of eluent B was used: 35%-55% B (in 20 min)-80% (in 3 min), flow rate 1 mL/min on the LC-MS Waters-Micromass LCZ Platform. The pooled fractions corresponding to the covalent trimer were pooled, freeze-dried and further analyzed by mass spectrometry analysis on a Micromass LCZ platform. The expected MW is 15994.5 Da; and the found MW is 15995.0 Da.

Results—Affinity columns can be used as part of a vaccine validation process. For example, possible vaccine antigens can be used to immunize laboratory animals (e.g., mice) whose antisera are then tested for presence of antibodies to said putative antigen. An affinity column can be used to test the presence of said antibodies, wherein the putative antigen is conjugated to the resin of the column, capturing and extracting antibodies with an affinity for the antigen from the antisera that flows through the column. Similar experiments can be designed to further validate use of the CC-chimeric N-peptides of the present invention as IV immunogens. To this end, a new peptide was designed, designated as "SCCIEN17" (SEQ ID NO:21), which was able to selectively form the three disulfide bonds to produce the covalent trimer (SCCIZN17)$_3$ (FIG. 3A). This peptide comprises a moiety suitable for conjugation to an affinity resin. In particular, the design of SSCCIZN17 makes use of a serine (Ser) residue at the NH$_2$-terminus of the peptide chain that can be easily and selectively oxidized by periodate to an aldehyde function and can be selectively used in a conjugation reaction with a hydrazide moiety. This strategy has been known for many years (Fields and Dixon, 1968, *Biochem. J.* 108:883-887) and has been exploited for the synthesis of bioconjugates through formation of hydrazone, thiazolidine or oxime (—ON=CH—CO—) bonds (Geoghegan and Stroh, 1992, *Bioconjugate Chem.* 3:138-146; Rose et al., 1996, *Bioconjugate Chem.* 7:552-556). The above strategy has been exploited for use with peptides displaying multiple cysteine residues (Kinzel et al., 2003, *J. Peptide Sci.* 9:375-385). For the design of SCCIZN17 (SEQ ID NO:21), a NH$_2$-terminal, amine free serine (Ser) residue plus two glycine (Gly) residues acting as a spacer were added at the NH$_2$-terminus of CCIZN17. The resulting SCCIZN17 peptide was first oxidized as described for CCIZN17 and purified to produce (SCCIZN17)$_3$ (see FIG. 3A). The covalently-stabilized trimer, (SCCIZN17)$_3$, was then oxidized with sodium periodate to obtain (0=CH—CO-GGCCIZN17)$_3$ which is conjugated to a sepharose-hydrazide resin (the oxidation to (0=CH—CO-GGCCIZN17).

An affinity column was prepared using the covalently-stabilized (SCCIZN17)$_3$ coiled-coil. The covalently-stabilized coiled-coil was dissolved in 0.115 mL 50 mM Hepes, pH 7.3 at a concentration of 26 mg/mL. The dissolved coiled-coil (0.090 mL) was mixed with 0.010 mL of sodium meta-periodate (18.84 mg/mL; Pierce #20504) which was dissolved in 50 mM Hepes, pH 7.3. The mixture was incubated in the dark, at room temperature, for 6 min, at which time 95 µl of the reaction mix was injected onto a Waters Symmetry300 C18 reverse phase column and purified using a gradient of 5%-80% acetonitrile in 0.1% TFA. The solvent was removed and the oxidized peptide was re-dissolved in 0.1 M Hepes, pH 7.3 at a concentration of 1.5 mg/mL. Pierce Ultralink hydrazide resin (0.5 mL; Pierce #53149) was placed in a disposable column and washed with 10 mL of 0.1 M Hepes, pH 7.3. Excess buffer was removed from the resin, and 1.1 mL of peptide plus 2 mL of Hepes buffer were added to the resin and mixed gently, end over end, overnight, at room temperature. The following morning, the supernatant was removed from the resin and analyzed by reverse phase HPLC for peptide content. Binding efficiency was determined to be 98%. The column washed with phosphate buffered saline containing 0.02% sodium azide and stored at 2-8° C.

EXAMPLE 3

Anti-Viral Activity of Covalently-Stabilized CC-Chimeric N-Peptides

Single-cycle HIV infectivity assay—HIV strains B2, BaL, 89.6, MN-1, and NL4-3 were purchased from Advanced Biotechnology Inc. (Bethesda, Md.). SHIV-89.6P (Reimann et al., 1996, *J. Virol.* 70:6922-6928) was obtained from N. Letvin (Beth Israel Hospital, Boston, Mass.) and passaged three times in human peripheral blood lymphocytes prior to use in the assay. HIV pseudotyped with the VSV-G protein was generated by transfecting 293T cells with the proviral DNA construct R8Δenv (Trono et al., 1989, *Cell* 59:113-120; Gallay et al., 1995, *Cell* 83:569-576) and pCMV-VSV-G (Wu et al., 1999, *J. Virol.* 73:2126-2135; gift of J. Kappes, University of Alabama Birmingham). P4-2/R5 cells (Charneau et al., 1992, *J. Virol.* 66:2814-2820; Deng et al., 1996, *Nature* 381: 661-666; gift of N. Landau, Salk Institute) are HeLa cells stably expressing human CD4 and CCR5 and harboring a β-galactosidase reporter gene driven by a tat-responsive fragment of the HUV-2 LTR. P4-2/R5 cells were maintained at 37° C. and 5% $CO_2$ in phenol red-free Dulbecco's modified Eagle's medium, 10% fetal bovine serum (FBS). For infectivity assays, cells were seeded in 96-well plates (Costar) at $2.5 \times 10^3$ cells/well and infected the following day with the various strains of HIV-1 at a multiplicity of infection of 0.01 in the presence of peptides. After incubating an additional 48 h at 37° C./5% $CO_2$, cells were lysed and O-galactosidase activity was quantified using GalScreen chemiluminescent substrate (Tropix, Bedford, Mass.) according to the manufacturer's instructions.

Description of D5 IgG—D5 IgG HIV-neutralizing antibody is described in detail in a co-pending application. Briefly, to identify antibodies targeting the HIV-1 gp41 ectodomain, phage display technology from Cambridge Antibody Technology (CAT) was utilized in conjunction with two specific selecting peptides, 5-Helix (Root, M. J. et al., 2001, *Science* 291:884-888) and IZN36 (SEQ ID NO:16; Eckert, D. M. and P. S. Kim, 2001, supra), both presenting the groove structure formed by adjacent N-helix coiled-coil domains in the gp41 trimer-of-hairpins conformation. 5-Helix is composed of a series of three alternating N36 N-peptides and two C34 C-peptides derived from N-helix and C-helix domains, respectively, which are united by small peptidic linkers. This artificial peptide folds into a 5-helical bundle due to the absence of one C-peptide, thus exposing one of three potential grooves. IZN36 (SEQ ID NO:16) is a chimeric peptide composed of a segment of amino acids that form a Leucine zipper (an IZ scaffold motif consisting of "IZ" (SEQ ID NO:31) plus and additional Glu-Ile sequence at the COOH-terminus of the scaffold) and the N36 N-peptide. Both 5-Helix and ZN36 represent potent inhibitors of HIV infection. Libraries of bacteriophages encoding selected regions of human IgG heavy and light chains (scFvs) were screened using biotinylated 5-Helix and IZN36 peptides. ScFvs that bound both peptides were tested for neutralizing capacity, and scFv-associated anti-viral activity was confirmed in a single-cycle HIV infectivity assay. D5-scFvs emerged as a bona fide inhibitor of HIV entry. Transfer of variable heavy (VH) and variable light (VL) regions from the scFv into a full length IgG preserved anti-viral activity.

The binding site for the D5 antibody was localized to the hydrophobic pocket region formed by the COOH-terminal half of the N-helix domain. Specifically, amino acids leucine-568 (L568), tryptophan-571 (W571) and lysine-574 (K574) appear critical for antibody binding, and valine-570 (V570) appears to also contribute to a lesser extent (see FIG. 8). By interacting with the hydrophobic pocket of the N-helix domain, D5 IgG possesses the functional capacity of preventing the in vitro interaction of N- and C-peptides. Therefore, the D5 antibody is the first example of an antibody that shows anti-viral activity by targeting a gp41 fusion intermediate.

Results—IZN17 (SEQ ID NO:1) and $(CCIZN17)_3$ (SEQ ID NO:2) were tested in parallel to compare their individual ability to inhibit HIV in a single-cycle infectivity assay, using primary and laboratory isolates and VSV-G-HIV (HIV pseudotyped with G protein of Vesicular Stomatitis Virus) as a negative control. In the same assay, other fusion inhibitors like 5-Helix (Root et al., 2001, supra) 291:884-888), T-20 (Fuzeon™; Kilby et al., 1999, *Nat. Med.* 4:1302-1307), mAb2F5 (Muster et al., 1993, *J. Virol.* 67:6642-6647) and IgGD5 (see above) were tested for comparison (Table 3). In particular, T-20 is the fusion inhibitor recently approved in humans.

TABLE 3

Anti-viral activity of fusion inhibitors. Numbers represent $IC_{50}$ values (nM); "n" is the number of independent experiments.

| HIV Strain | D5 IgG | IZN17 | $(CCIZN17)_3$ | 5-Helix | T-20 | 2F5 IgG | Biotin-IZN23 | Biotin-$(CCIZN23)_3$ |
|---|---|---|---|---|---|---|---|---|
| HXB2 | 310 (n = 6) | 1.7 (n = 7) | 0.04 (n = 8) | 48 (n = 4) | 5.3 (n = 7) | 0.53 (n = 4) | 2.173 | 0.316 |
| BaL | 93 (n = 4) | 3.2 (n = 3) | 0.34 (n = 1) | 36 (n = 1) | 2.4 (n = 1) | 9 (n = 1) | | |
| 89.6 | 1750 (n = 2) | No activity | 8 (n = 2) | 213 (n = 1) | 29 (n = 1) | 17 (n = 1) | | |
| SHIV89.6p | | | 6.9 (n = 1) | | | | | |
| MN-1 | 393 (n = 4) | | 0.9 (n = 2) | | | | | |
| NL43 | 226 (n = 1) | | 0.1 (n = 1) | | | | | |
| VSVG con. | No activity | | No activity | | | | | |

The data reported in Table 3 shows that the covalently-stabilized $(CCIZN17)_3$ trimer displays at least one order of magnitude higher potency than IZN17 with HXB2 and BaL strains. This covalently-stabilized trimer also shows a low nanomolar potency against primary HIV isolates such as 89.6 which is completely resistant towards IZN17. Overall, $(CCIZN17)_3$ shows anti-viral activity against various HIV strains, either in the picomolar or the low nanomolar range, with potencies higher than any other fusion inhibitor as shown in Table 3. Thus, $(CCIZN17)_3$ is the most potent HIV fusion inhibitor described so far.

Biotin-IZN23 and (Biotin-$CCIZN23)_3$ were also tested in parallel to compare their ability to inhibit HIV in a single-cycle infectivity assay (HIV HXB2 strain). Biotin-IZN23 showed an $IC_{50}$(nM) of 2.173; while (Biotin-$CCIZN23)_3$ showed an $IC_{50}$(nM) of 0.316. Thus, the covalently-stabilized trimeric construct shows an increased inhibitory potency with respect to the monomeric construct.

EXAMPLE 4

Binding of CC-Chimeric N-Peptides to D5 IgG

AlphaScreen™ binding assay—A homogeneous AlphaScreen™ detection kit (PerkinElmer Cat.#6760612) was used. Biotinylated peptides were coupled to donor beads conjugated to streptavidin, and IgGD5 was captured by Protein A coupled to acceptor beads. The coated bead complexes were mixed together and incubated in 96-well plates overnight in the dark at room temperature. The plates were then analyzed on a Fusion α-FP HT instrument which excites the donor beads at 680 nm. A singlet oxygen is emitted by the donor beads. If the acceptor beads are in proximity due to a peptide/antibody interaction, the singlet oxygen is captured by the acceptor beads which emit light at 520-620 nm. The instrument records these emissions.

Figure 6:
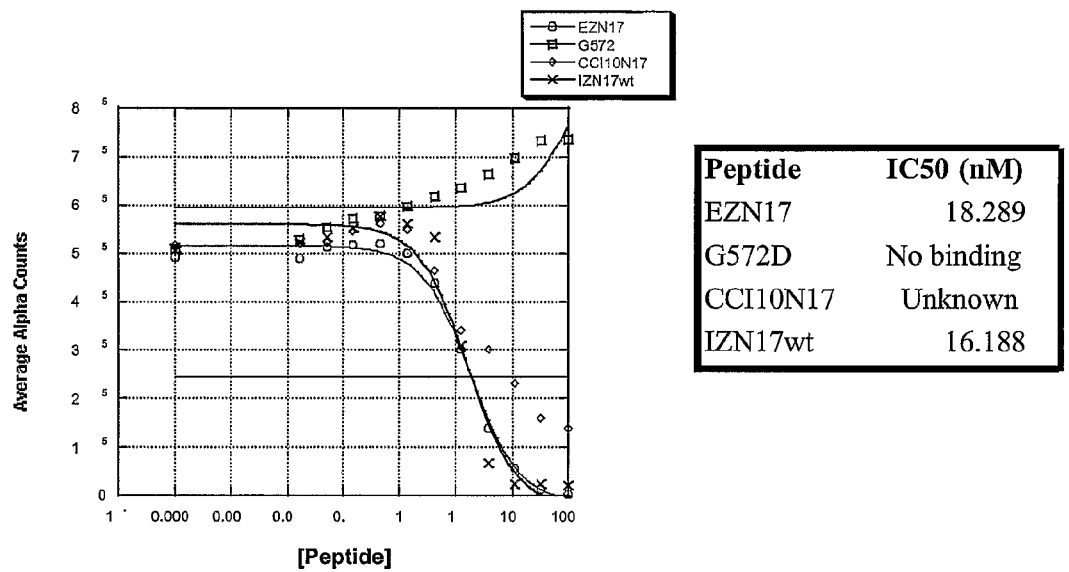
FIG. 6 shows the ability of peptides EZN17 (SEQ ID NO:6) and (CCI10N17)$_3$ (SEQ ID NO:20)$_3$ to inhibit binding of D5 IgG to biotinylated-IZN17 in an AlphaScreen™-based assay format. Wildtype IZN17 peptide was included as a positive control, previously shown to inhibit D5 binding in this assay. The IZN17G572D peptide was included as a negative control due to its inability to bind D5 IgG. Note that peptide (CCI10N17)$_3$ clearly inhibits the binding of D5 antibody to biotinylated-IZN17, but an IC$_{50}$ could not be derived using the range of concentrations tested.
Figure 7:
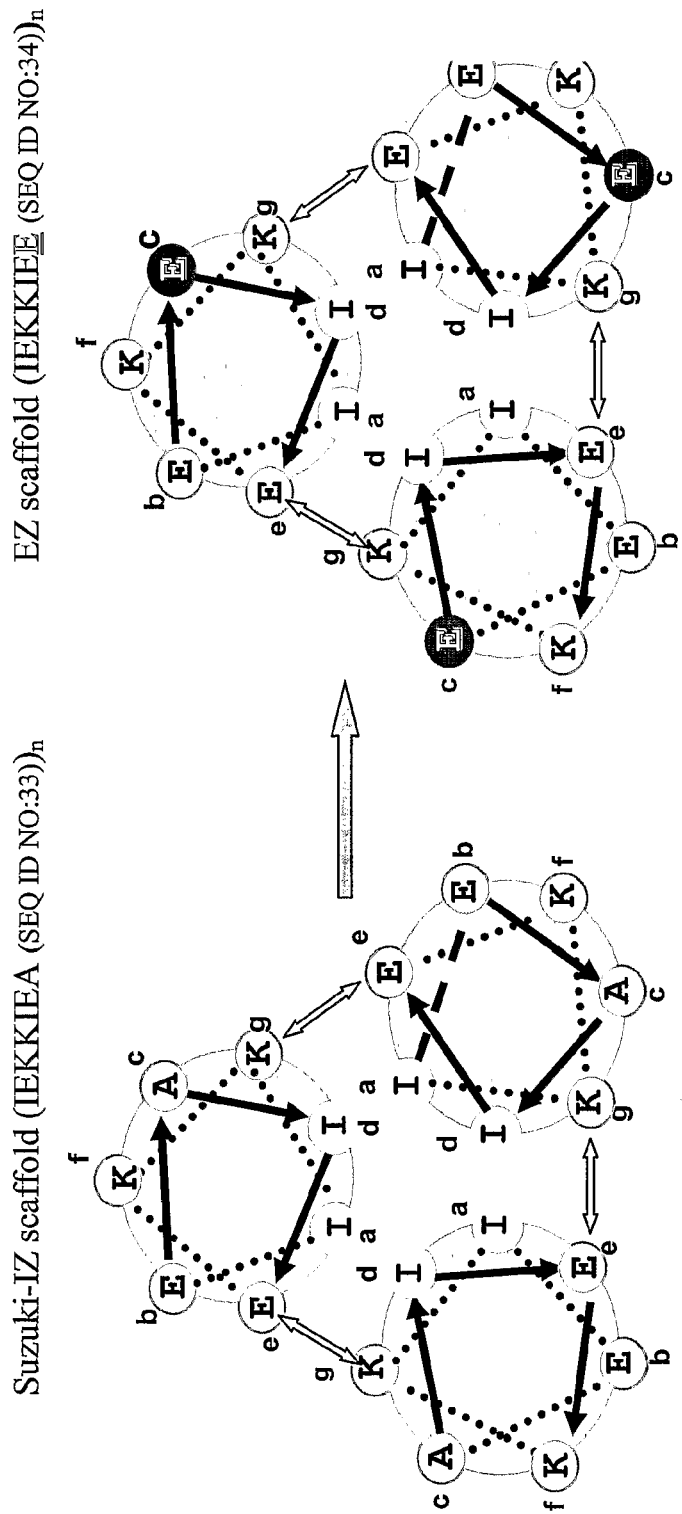
FIG. 7 shows a helical wheel representation of the Suzuki-IZ (left) and EZ (right) heptad repeats. Three Suzuki-IZ helices and three EZ helices are represented as helical projections. The view is from the top of the complex. The helices interact through "knobs-into-holes" packing interactions at the "a" and "d" positions. In the EZ heptad repeat, the Ala residue at position "c" in each helix is mutated to a Glu residue.

Results—In addition to determining the anti-viral activity of CC-chimeric N-peptides of the present invention against HIV (see Example 3), said peptides were analyzed for their ability to compete the interaction of a neutralizing antibody which binds the hydrophobic pocket located within the internal, N-helix coiled-coil of the gp41 ectodomain, D5 IgG, with either biotinylated 5-Helix (FIG. 13) or biotinylated IZN17 (FIG. 6). This test determines whether the covalently-stabilized, homotrimeric or heterotrimeric CC-chimeric N-peptides can preserve the structure of the internal, N-helix coiled-coil of gp41. While the covalently-stabilized CCIZN17 coiled-coil is approximately 10-fold more potent against HIV-HXB2 than the parental IZN17 peptide (see Example 3), (CCIZN17)$_3$ also prevents the binding of D5 IgG to 5-Helix more effectively than the parental peptide, producing an IC$_{50}$ of 0.86 nM, approximately 4-fold more potent than IZN17 (FIG. 13). Neither EZN17 nor CCEZN17 peptides appear to have significant anti-viral activity (see FIGS. 12A and 13), yet both peptides interact with D5 IgG in the bio-5-Helix/D5 IgG (FIG. 13) and bio-IZN17/D5 IgG (FIG. 6) interaction assays (see also Example 6), suggesting that the hydrophobic pocket is likely preserved in these peptides. The lack of anti-viral activity could be attributable to the global negative charge carried by the EZ scaffold which may prevent access of the peptide to the native pre-hairpin structure of gp41 on the envelope of a virus undergoing fusion. Both peptides designed with the shortened "110" scaffold (CCI10N17 and I10N17CC) (see Example 5) are less potent anti-virals when compared with the parental IZN17 and CCIZN17 peptides (FIG. 13), yet they appear to prevent the binding of D5 IgG with comparable or superior potency to IZN17 and CCIZN17 (see FIG. 13). This indicates that the hydrophobic pocket in these peptides is fully preserved. The COOH-terminal covalent cross-link (110N17CC) appears to reduce anti-viral potential and D5 binding when compared to NH$_2$-terminal positioning of the cross-ink (CCI10N17). Peptides IZN17Ala4 and CCIZN17Ala4 (see Example 1), in which four COOH-terminal residues that comprise an imunundominant but non-HIV neutralizing epitope (see Example 8) were substituted with alanine residues, appear to retain anti-viral activity (see FIGS. 12A and 13); however, these peptides are clearly less potent than IZN17. Both peptides bind D5 IgG but precise IC$_{50}$s could not be determined (FIG. 13).

EXAMPLE 5

Ramification of Trimming the IZ Scaffold

Synthesis of CCI10N17—CCI10N17 (SEQ ID NO:20) was synthesized following the same protocols as outlined for synthesis of IZN17 and CCIZN17 (see Example 1). The crude CCI10N17 peptide was purified by reverse-phase HPLC with a semi-preparative Waters RCM Delta-Pak™ C$_4$ cartridges (40×200 mm, 15 μm) using as eluents (A) 0.1% TFA in water and (B) 0.1% TFA in acetonitrile. The following gradient of eluent B was used: 40%-60% over 20 min, flow rate 80 mL/min. Analytical HPLC was performed on a Phenomenex, Jupiter C$_4$ column (150×4.6 mm, 5 μm) with the following gradient of eluent B: 40%-60% B (in 20 min)-80% (in 3 min), flow rate 1 mL/min. The purified peptide was characterized by electrospray mass spectrometry on a Micromass LCZ platform (MW found: 3536.0 Da).

Oxidation of CCI10N17 to (CCI10N17)$_3$—The purified peptide precursor (10 mg), CCI10N17 (SEQ ID NO:20), was dissolved in 0.1 M Hepes, pH 7.3 (USB Corp.) at a concentration of 1 mg/mL. The oxidation reaction was monitored by HPLC-MS analysis using a Waters-Micromass LCZ Platform with a Phenomenex, Jupiter C$_4$ column, (150×4.6 mm, 5 μm) using as eluents (A) 0.1% TFA in water and (B) 0.1% TFA in acetonitrile. The following gradient of eluent B was used: 50%-80% B (in 20 min), flow rate 1 mL/min. CCI10N17, whose retention time in the HPLC-MS analysis is 6.7', was slowly oxidized in 5 hours by air, with the formation of two main products: (1) one product eluting at $t_R$=15.6 (yield 40%) represents the putative covalent trimer (CCI10N17)$_3$ (SEQ ID NO:20), whose mass corresponds to that of one molecule of three CCI10N17 peptide chains linked together, (CCI10N17)$_3$ (see FIG. 2C), and with a reduction of mass consistent with formation of three disulfide bridges (expected MW is 10603.23 Da, found MW is 10603.0 Da); (2) the other product eluting at $t_R$=18.39 (yield 40%), corresponds to a molecule whose mass is that of one molecule of four CCI10N17 peptide chains linked together with a reduction of mass consistent with formation of four disulfide bridges (14137.0 Da). After five hours, 20 μL of TFA was added to the solution (10 mL), and the solution was directly loaded on a Phenomenex Jupiter C$_4$ column (250×21.6 mm) using as eluents: (A) 0.1% TFA in water and (B) 0.1% TFA in acetonitrile, flow rate 25 mL/min. The following gradient of eluent B was used: 50%-58% B (in 30 min). The eluted fractions were analyzed by HPLC with a Phenomenex, Jupiter C$_4$ column (150×4.6 mm, 5 μm) with the following gradient of eluent B: 50%-80% B (in 30 min), flow rate 1 mL/min on the Waters-Micromass LCZ Platform. The pooled fractions corresponding to the covalent trimer (expected MW of 10603.23 Da; found MW of 10603.0 Da) were collected and freeze-dried.

Synthesis of IZN17G572D—Peptide IZN17G572D (SEQ ID NO:22) was synthesized as per the same protocol used to synthesize IZN17 (SEQ ID NO:1), see Example 1. The acetylation reaction was performed at the end of the peptide assembly by reaction with a 10-fold excess of acetic anhydride in DMF. The crude peptide, IZN17G572D (SEQ ID NO:22), was purified by reverse-phase HPLC on semi-preparative Waters RCM Delta-Pak™ C$_4$ cartridges (40×200 mm, 15 μm) using as eluents (A) 0.1% TFA in water and (B) 0.1% TFA in acetonitrile. The following gradient of eluent B was used: 35%-55% over 25 min, flow rate 80 mL/min. Analytical HPLC was performed on a Phenomenex, Jupiter C$_4$ column (150×4.6 mm, 5 μm) with the following gradient of B: 40%-60% B (in 20 min)-80% (in 3 min), flow rate 1 mL/min. The purified peptide was characterized by electrospray mass spectrometry on a Micromass LCZ platform: theoretical average MW is 4913.0 Da, and found MW is 4911.0 Da.

Alphascreen™ binding assay—See Example 4.

Single cell infectivity assay—See Example 3.

Results—When designing CC-chimeric N-peptides of the present invention, both the role of the solubilizing, trimerizing scaffold (e.g., the "IZ" coiled-coil) and the covalent, trimerizing unit (e.g., CCGG (SEQ ID NO:28)) need to be considered. To this respect, there are a number of configurations that should be considered in order to identify the key and optimal requirements for the CC-chimeric N-peptides of the present invention for the development of either an anti-viral agent or an antigen for immunization or screening purposes.

Initially, the "IZ" solubilizing, trimerizing domain (SEQ ID NO: 31), described infra, was used to generate CC-chimeric N-peptides. As explained previously, in the case of IZN17 (SEQ ID NO:1), the IZ scaffold is composed of 24 amino acid residues. Addition of a covalent, trimerizing unit (CCGG; SEQ ID NO:28) at the $NH_2$-terminus of IZ has a great impact on the stabilization of the IZN-peptides (see Example 3). To help define the minimum length to which the IZ scaffold of the CCIZN-peptides of the present invention could be reduced while still being able to generate a faithful, stable mimetic of gp41 fusion intermediate, a CC-peptide N-peptide was designed comprising a shortened IZ scaffold, designated as "CCI10N17" (SEQ ID NO:20). The experimental benchmark for resulting CC-chimeric N-peptides to maintain the ability to generate a faithful, stable mimetic of gp41 fusion intermediate is either (1) retaining optimal broad anti-viral activity and/or (2) binding to a conformational epitope located within the N-helix coiled-coil domain of gp41 (e.g., IgGD5) to the extent achieved, for example, by (CCIZN17)$_3$ (see Example 4). Trimming of the scaffold may be advantageous for many purposes. First, manufacturing of a smaller molecular weight inhibitor or immunogen precursor can be less expensive and/or less complicated. Second, a smaller scaffold may provide a better inhibitory profile to the N-peptide portion of CC-chimeric N-peptides by reducing any possible interference of the scaffold with the HIV fusion machinery. Third, for perspectives relating to generating an immune response to the CC-chimeric N-peptides, a smaller scaffold reduces the content of non-HIV residues and, thus, may help to focus the immune response towards the HIV N-peptide portion of the peptide.

The IZ-like scaffold in CCI10N17 (SEQ ID NO:20) comprises only the ten COOH-terminal residues of the "IZ" scaffold, with addition of the covalent trimerizing unit (CCGG (SEQ ID NO:28)) at the $NH_2$-terminus of the peptide. The non-covalently-stabilized CCI10N17 coiled-coil (i.e., the coiled-coil formed under non-oxidizing conditions) was dissolved at neutral pH, and its secondary structure content was determined by circular dichroism spectroscopy (CD). This CCI10N17 coiled-coil was found to be only 61% helical at 15 µM concentration, while the IZN17 (SEQ ID NO:1) coiled-coil is fully helical under the same conditions. This suggests that scaffold length is critical for formation of the non-covalently-stabilized, chimeric N-peptide coiled-coil molecules.

In order to understand the role of the covalent trimerizing unit (CCGG; SEQ ID NO:28), the CCI10N17 peptide was dissolved to permit air oxidation under the same conditions as previously shown for CCIZN17, to generate covalently-stabilized coiled-coil molecules, (CCI10N17)$_3$. As opposed to forming a discrete, coiled-coil molecule as seen in the similar reaction with CCIZN17 (with >80% yield), in the case of CCI10N17, two main products were generated: a trimer (CCI10N17)$_3$ and a tetramer, each one with a comparable yield of about 40%. The trimer (CCI10N17)$_3$ was analyzed by CD and denaturation studies for analysis of both its secondary structure content and stability. The helical content of this molecule was only 85% with a melting curve showing a low cooperatively profile and a low melting point of about 60° C. Overall the data suggest that the covalent trimerizing unit has only a marginal role in stabilization of the helical structure (from 61% to 85%), and a longer scaffold is essential for providing key contacts that stabilize the trimer.

The (CCI10N17)$_3$ trimer was also tested for its ability to both inhibit HIV and bind to D5 IgG. Consistent with previous observations, the (CCI10N17)$_3$ trimer is a much less potent HIV inhibitor than (CCIZN17)$_3$. The $IC_{50}$ for (CCI10N17)$_3$ is approximately 150-fold less than that for (CCIZN17)$_3$, 24 nM versus 0.132 nM, respectively (FIG. 13). Additionally, the $IC_{50}$ for (CCI10N17)$_3$ is approximately 10-fold less than that for the non-covalently-stabilized IZN17 peptide (1.68 nM). (CCI10N17)$_3$ was also tested for binding to the D5 IgG antibody in both a biotinylated-5-Helix/D5 IgG and a biotinylated-IZN17/D5 IgG interaction assay. Consistent with previous observation, (CCI10N17)$_3$ competes for binding of D5 IgG to Biotin-IZN17 (SEQ ID NO:3), but is somewhat less effective than 112N7 (see FIG. 6; $IC_{50}$ of CCI10N17 could not be derived using the available experimental data). In this experiment, the chimeric peptide designated as "IZN17G572D" (SEQ ID NO:22) was used as a negative control since the G572D mutation in the N17 HIV domain (HIV-1 HXB-2) is known to abolish binding to D5 IgG. The covalently-stabilized CCI10N17 coiled-coil also competes for binding of D5 IgG to Biotin-5-Helix (see FIG. 13).

EXAMPLE 6

A More Favorable Scaffold Protein Designed for Conjugation Purposes

Synthesis of EZN17—EZN17 (SEQ ID NO:6) was synthesized following the same protocol as described for IZN17 (SEQ ID NO:1) and CCIZN17 (SEQ ID NO:2). The acetylation reaction was performed at the end of the peptide assembly by reaction with a 10-fold excess of acetic anhydride in DMF. The crude peptide, EZN17 (SEQ ID NO:6), was purified by reverse-phase HPLC on semi-preparative Waters RCM Delta-Pak™ $C_{-4}$ cartridges (40×200 mm, 15 µm) using as eluents (A) 0.1% TFA in water and (B) 0.1% TFA in acetonitrile. The following gradient of eluent B was used: 45%-65% over 25 min, flow rate 80 mL/min. Analytical HPLC was performed on a Phenomenex, Jupiter $C_4$ column (150×4.6 mm, 5 µm) with the following gradient of eluent B: 30%-70% B (in 20 min)-80% (in 3 min), flow rate 1 mL/min. The purified peptide was characterized by electrospray mass spectrometry on a Micromass LCZ platform. The theoretical average MW is 5015.06 Da, and the found MW is 5013.0 Da.

Synthesis of CCEZN17—CCEZN17 (SEQ ID NO:7) was synthesized following the same protocols as for IZN17 (SEQ ID NO: 1) and CCIZN17 (SEQ ID NO:2), see Example 1. The acetylation reaction was performed at the end of the peptide assembly by reaction with a 10-fold excess of acetic anhydride in DMF. The crude peptide, CCEZN17 (SEQ ID NO:7), was purified by reverse-phase HPLC on semi-preparative Waters RCM Delta-Pak™ $C_{-4}$ cartridges (40×200 mm, 15 µm) using as eluents (A) 0.1% TFA in water and (B) 0.1% TFA in acetonitrile. The following gradient of eluent B was used: 45%-60% over 25 min, flow rate 80 mL/min. Analytical HPLC was performed on a Phenomenex, Jupiter $C_4$ column (150×4.6 mm, 5 µm) with the following gradient of eluent B: 45%-65% B (in 20 min)-80% (in 3 min), flow rate 1 mL/min. The purified peptide was characterized by electrospray mass spectrometry on a Micromass LCZ platform: theoretical average MW is 5335.0 Da, and found MW is 5333.0 Da.

Oxidation of CCEZN17 to (CCEZN17)$_3$—The purified peptide precursor (14 mg), CCEZN17 (SEQ ID NO:7), was dissolved in 0.1 M Hepes, pH 7.5 (USB Corp.) at a concentration of 0.5 mg/mL. The pH was raised to 10 by addition of NaOH to favor solubilization of precursor peptide. The oxidation reaction was monitored by HPLC-MS analysis using a Waters-Micromass LCZ Platform with a Phenomenex, Jupiter $C_4$ column (150×4.6 mm, 5 µm) with the following gradient of eluent B (above): 30%-70% B (in 20 min)-80% (in 3 min), flow rate 1 mL/min. CCEZN17, whose retention time in the HPLC-MS analysis is $t_R$=16.4', was slowly oxidized overnight by air, with the formation of one main product (eluting at $t_R$=10') whose mass corresponds to that of a molecule of three CCEZN17 peptide chains linked together and having a reduction of mass consistent with formation of three disulfide bridges, ([CCEZN17]$_3$, see FIG. 3B). To the solution (28 mL), 90 µl of TFA was added, and the solution was directly loaded on a 700×26 mm column, packed with TSKgel Toyopearl HW-50S resin, using as eluent $H_2O$/acetonitrile, 70/30, 0.1% TFA, flow rate 1 mL/min. The eluted fractions were analyzed by HPLC with a Phenomenex, Jupiter $C_4$ column (150×4.6 mm, 5 µm) using as eluents: (A) 0.1% TFA in water and (B) 0.1% TFA in acetonitrile. The following gradient of eluent B was used: 30%-60% B (in 20 min)-80% (in 3 min), flow rate 1 mL/min on the LC-MS Waters-Micromass LCZ Platform. The fractions corresponding to the covalent trimer were pooled, freeze-dried and further analyzed by mass spectrometry analysis on a Micromass LCZ platform. The expected MW is 16000.3 Da; and the found MW is 15998.0 Da.

Single cell infectivity assay—See Example 3.
Alphascreen™ binding assay—See Example 4.
Results—The "EZ" scaffold (IEKKIEEIEKKEEIEK-KIEEIEK; SEQ ID NO: 32) was designed to facilitate conjugation of CCEZN-peptides (i.e., CC-chimeric N-peptides comprising the EZ scaffold fused to all or a portion of the N-helix domain of gp41) to *Neisseria meningitidis* OMPC particles, an immunogenic carrier. The covalent addition of a peptide to a carrier frequently results in irreversible precipitation of the conjugate, as is the case with OMPC-peptide conjugates. To prevent this, the maximum number of peptide moles that can be incorporated on a mole of OMPC (i.e., the peptide "load") must be carefully controlled. For many peptide sequences, even after optimization, it is not possible to achieve a good load of peptide onto OMPC. A strategy was recently developed that enables the straightforward conjugation of a peptide of any sequence to OMPC (see Bianchi, E. et al., U.S. Provisional Application Ser. No. 60/530,867, "A Method to Make a Peptide-Carrier Conjugate with a High Immunogenicity," filed on Dec. 18, 2003). This method ensures that the peptide load will be above a certain threshold, a factor critical to obtaining a satisfactory immune response against the peptide epitope. The method entails manipulation of the pI ("isoelectric point") of the peptide sequence, adjusting its value to, optimally, between approximately 3.5-5.0. To achieve a pI within this range, the peptide can be modified outside of its active, immunogenic domain, ensuring maintenance of the peptide's immunological properties. For example, IZN17 (<u>IKKEIEAIKKEQEAIKKKIEAIEK</u>LLQLTVWGIKQLQARIL; SEQ ID NO:1; scaffold portion underlined) has a very high pI of 10.7, not within the optimal range of between ~3.5-5.0 for conjugation to OMPC. Because the high pI value of IZN17 is mostly determined by the large number of basic amino acid residues present on the "IZ" scaffold, a new scaffold was designed, the "EZ" scaffold, with a more acidic character.

The Suzuki-IZ scaffold, the scaffold motif from which the "IZ" scaffold is derived, has a heptad repeat sequence of $(IEKKIEA)_n$ (SEQ ID NO:33). To generate the EZ scaffold, this heptad repeat sequence was modified to a $(IEKKIEE)_n$ (SEQ ID NO:34) heptad repeat by mutating the alanine residue at position "c" of the heptad repeat to glutamic acid (see FIG. 7). A chimeric N-peptide comprising this modified scaffold domain is "EZN17", having the following amino acid sequence: (<u>IEKKIEEIEKKIEEIEKKIEEIEK</u>LLQLTVWGIKQLQARIL; SEQ ID NO:6; scaffold portion underlined). The pI of this chimeric peptide is 5.2. Analysis of EZN17 by circular dichroism spectroscopy shows that this peptide is still able to adopt a fully helical conformation with a typical coiled-coil signature. However, when tested for its ability to inhibit HIV infectivity of single cells, the anti-viral activity of EZN17 is several orders of magnitude less potent than IZN17 (see FIG. 12A). Despite this observation, EZN17 still binds to IgGD5 in a bio-IZN17/D5 IgG interaction assay, having an affinity comparable to IZN17 (see FIG. 6). These observations indicate that the acidic EZ scaffold interferes with the resulting peptide's ability to inhibit HIV infectivity, probably due to the charge of the scaffold or possible steric hindrance with the HIV fusion machinery; however, since the resulting peptide properly presents the conformational epitope recognized by D5, it still folds accurately to form a faithful mimetic of the gp41 fusion intermediate.

EXAMPLE 7

Covalently-Stabilized CC-Chimeric N-Peptides are Stable Mimetics of Gp41 Ectodomain at Low Concentrations Materials and Methods—A BIACore 3000 instrument was used for measurements, in conjunction with chips SA (immobilized streptavidin surface) or C5 (activatable carboxyl groups on surface) supplied by BIACore (Piscataway, N.J.). Biotinylated peptides were immobilized by flowing a solution of 1 nM peptide in HBS (Hepes Buffered Saline) plus 10× Tween for 1-4 minutes over a SA chip. Manual injection was used till the bound peptide reached 10 resonance units (RU), sufficient to bind 100 RU of analyte full antibody. For the C5 chips, following surface activation by EDC (N-ethyl-N'-(3-dimethyl aminopropyl)-carbodiimide hydrochloride) and NHS (N-hydroxysuccinimide), immobilization of D5-IgG was carried out at 1-5 μg/mL in acetate buffer, pH 4.8 (mixing BIACore supplied buffers) using the inbuilt immobilization wizard control template, with target immobilization set at 1500-1800 RU. This was found to immobilize sufficient active D5-IgG to bind up to 100 RU of analyte peptide. Flow rates were 20 μl/min during association-dissociation phases, and 50 μl/min during surface regeneration with a single wash of 15 mM HCl, determined to be sufficient to release all bound peptide. The kinetics wizard was used to design the affinity measurement experiments, with duplicates and controls run as prompted to detect diffusion-limited kinetics. Analyte concentrations were chosen to give data for concentrations above and below the Kd value, with two-fold or four-fold dilution series. The association time was typically 3 min, dissociation 5-10 min. All association-dissociation measurements were made at 25° C. in HBS+10× Tween, which was determined to eliminate non-specific binding events. Analysis of data was by the BIACore curve-fitting software, selecting data from smooth regions with significant change in RU. First, dissociation rate was estimated. Data from all but the most dilute analyte samples were readily fitted and were closely similar. However, for samples below 0.25 nM, baseline drift began to degrade the data and made off-rate estimates unreliable. Using the best fit off-rate, the association curves were each fitted in the BIACore software to obtain an on-rate. All concentrations used yielded readily fitted on-rate data.

Results—Further evidence of the impact of covalent stabilization of the chimeric peptides described herein comes from binding experiments with a newly identified, HIV neutralizing antibody, D5 IgG (described in Example 3). D5 IgG was recently discovered in a joint effort between Merck and CAT. D5 IgG is the first example of an antibody that shows antiviral activity via targeting a gp41 fusion intermediate. D5 was originally selected by screening CAT scFvs libraries using a hybrid selection protocol. CAT scFvs libraries were first selected on Biotinylated-5-Helix (on solid phase). The second round of selection used Biotinylated-IZN36 as the selector; however, a relatively high concentration of the peptide was required (250 nM). Additionally, the Biotinylated-IZN36 needed to be in solution (as opposed to on solid phase) after determining that said peptide was an unsuitable selector when immobilized. The requirement of a high concentration of Biotinylated-IZN36 in the second round could be explained if the neutralizing, antigenic domain of the peptide represents a conformational epitope whose presence and stability depends on the trimerization equilibrium of the IZN36 chains. At a low concentration, at which selections are normally performed, the IZN36 peptide is in an equilibrium monomer:trimer state and, thus, may not fully display a conformational, neutralizing epitope. Therefore a high concentration of IZN36 would be needed to drive the equilibrium completely toward the trimeric state. It may be possible to overcome this concentration dependence by using the covalently-stabilized, chimeric peptides described in the present invention. This was, indeed, confirmed using surface plasmon resonance (SPR), i.e. BIACore binding experiments. BIACore assays require stability of a species linked to a BIACore chip; thus, a linked species whose stability and oligomerization state is dependent upon concentration is disfavored.

Figure 5A:
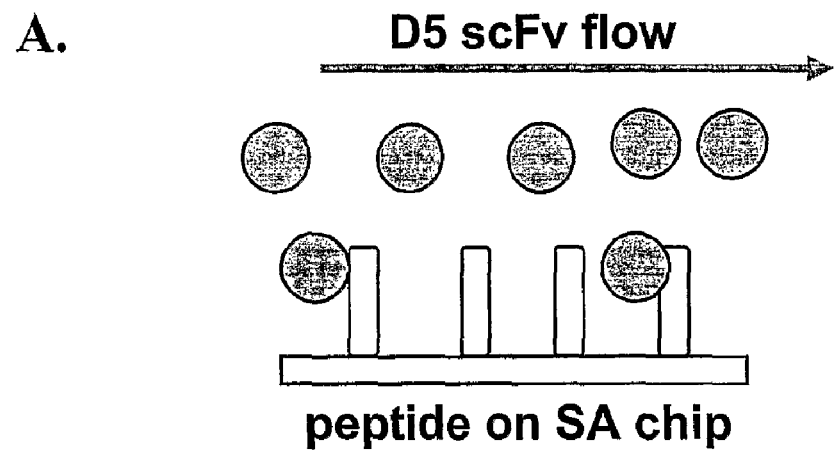
FIG. 5A-B shows a schematic representation of two configurations of BIACore experiments performed as described in Example 7. In (A), biotinylated-chimeric peptides described herein are affixed to a steptavidin ("SA")-coated chip and analyzed for binding to a soluble HIV-neutralizing antibody, D5-scFv. In (B), D5-IgG is affixed to a carboxymethyl dextran ("CM5")-coated chip and analyzed for binding to biotinylated-chimeric peptides in solution.
Figure 5B:
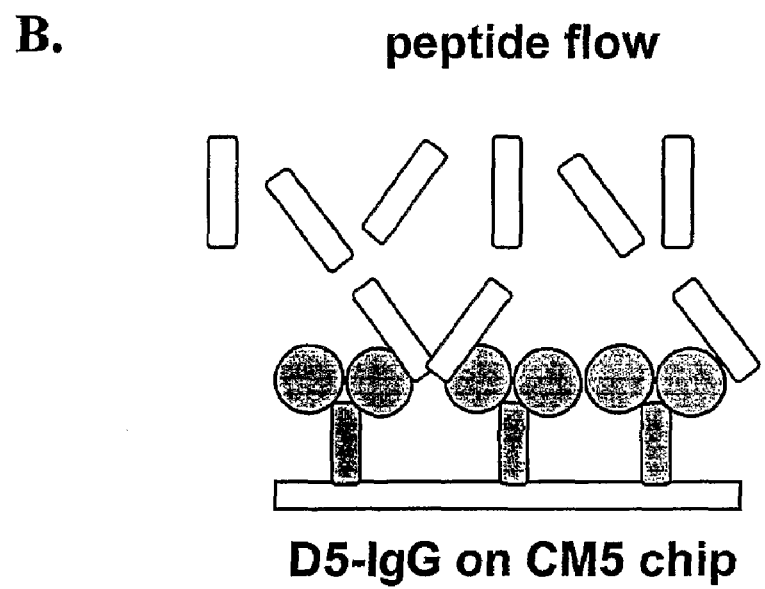

To confirm this hypothesis, biotinylated analogues of IZN36 (Biotin-IZN36) and the covalently-stabilized CCIZN23 trimer ([biotin-CCIZN23]$_3$; see FIG. 2B) were first coated on streptavidin ("SA") coated chips and analyzed for binding to soluble D5-scFv (FIG. 5A). The constant of dissociation for the same binding interactions (biotin-IZN36/D5-scFv and (biotin-CCIZN23)$_3$/D5-scFv) were then analyzed in a similar experiment, but this time having D5 IgG immobilized on a CM5 chip and keeping the peptides, biotin-IZN36 and (biotin-CCIZN23)$_3$ in solution (FIG. 5B) (see Results in Table 4).

TABLE 4

Dissociation constants, $K_d$ (nM), of BIACore binding assays.

| BIACore Assay Format | IZN36 | CCIZN23 |
|---|---|---|
| Peptide on SA chip/ D5-scFV in solution | >1000 | 0.2 |
| D5 IgG on CM5 chip/ Peptide in solution | 0.17 | 0.22 |

As shown in Table 4, the affinities measured for the biotin-IZN36/D5 interaction vary according to the BIACore configuration used. This observation, however, is not seen for the (biotin-CCIZN23)$_3$/D5 interaction. In particular, the $K_d$ for biotin-IZN36/D5 is 0.17 nM when D5 is affixed to the chip, while it is more than 1 μM when IZN36 is immobilized. On the contrary, the $K_d$ for the covalently-stabilized (CCIZN23)$_3$/D5 interaction is about 0.2 nM when either affixed to the chip or in solution. These data demonstrate that the covalently-stabilized, trimeric CCIZN23 construct is a stable, faithful, mimetic of gp41 fusion intermediate that is preserved at low concentrations, validating its use as an antigen to elicit an HIV-specific immune response and as an optimal selector for the screening of inhibitors targeting the N-helix of the HIV gp41 ectodomain.

EXAMPLE 8

Identification of N17 Epitopes that Bind to Either HIV Neutralizing or Non-Neutralizing MAbs Alanine-scanned IZN17 peptide synthesis—The peptides (see Table 5) were synthesized by solid phase using Fmoc/t-Bu chemistry on a peptide multisynthesizer APEX 396 (Advanced Chemtech) using a 40-well reaction block. Each peptide was synthesized in a single well using 0.3 g of a resin Fmoc-Linker AM-Champion, 1% cross-linked (Biosearch Technologies, Inc.), a PEG-PS based resin derivatized with a modified Rink linker p-[(R,S)-α-[9H-Fluoren-9-yl-methoxy-formamido]-2,4-dimethoxybenzyl]-phenoxyacetic acid (Rink, 1987, supra; Bernatowicz et al., 1989, supra). All the amino acids were dissolved at a 0.5 M concentration in a solution of 0.5M HOBt (Hydroxybenzotriazole) in DMF. The acylation reactions were performed for 60 min with 6-fold excess of activated amino acid over the resin free amino groups. The first fourteen amino acids were activated with equimolar amounts of HBTU (2-(1H-benzotriazole-1-yl)-1,1,3,3-tetramethyluronium hexafluorophosphate) and a 2-fold molar excess of DIEA (N,N-diisopropylethylamine). The last twenty-seven amino acids were activated with equimolar amounts of HATU (N-[(dimethylamino)-1H-1,2,3-triazolo-[4,5-b]pyridinylmethylene)]-N-methylmethanaminium hexafluorophosphate N-oxide) and a 2-fold molar excess of DIEA (N,N-diisopropylethylamine). The side chain protecting groups were: tert-butyl for Glu and Thr; trityl for Cys and Gln; tert-butoxy-carbonyl for Lys, Trp; and, 2,2,4,6,7-pentamethyldihydrobenzofuran-5-sulfonyl for Arg. The acetylation reaction was performed at the end of the peptide assembly by reaction with a 10-fold excess of acetic anhydride in DMF. At the end of the synthesis, the dry peptide-resins were individually treated with 20 mL of the cleavage mixture, 88% TFA, 5% phenol, 2% triisopropylsilane and 5% water (Sole and Barany, 1992, supra) for 1.5 hours at room temperature. Each resin was filtered and the solution was added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in H$_2$O, 20% acetonitrile, and lyophilized.

The crude peptide "IZN17A1" (SEQ ID NO:72) was purified by reverse-phase HPLC using a semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of B was used: 40%-60% over 20 min, flow rate 80 mL/min. Analytical HPLC was performed on a Phenomenex, Jupiter C$_4$ column (150×4.6 mm, 5 μm) with the following gradient of B: 40%-60% B (in 20 min)-80% (in 3 min), flow rate 1 mL/min. The purified peptide was characterized by electrospray mass spectrometry on a Micromass LCZ platform spectrometer. The theoretical, average molecular weight (MW) is 4812.9 Da; while the found MW is 4813.0 Da.

The crude peptide "IZN17A3" (SEQ ID NO:73) was purified using the same conditions used for IZN17A1. The purified peptide was characterized by electrospray mass spectrometry on a Micromass LCZ platform spectrometer. The theoretical, average molecular weight (MW) is 4797.9 Da; while the found MW is 4798.0 Da.

The crude peptide "IZN17A4" (SEQ ID NO:74) was purified using the same conditions used for IZN17A1. The purified peptide was characterized by electrospray mass spectrometry on a Micromass LCZ platform spectrometer. The theoretical, average molecular weight (MW) is 4812.9 Da; while the found MW is 4813.0 Da.

The crude peptide "IZN17A6" (SEQ ID NO:75) was purified using the same conditions used for IZN17A1. The purified peptide was characterized by electrospray mass spectrometry on a Micromass LCZ platform spectrometer. The theoretical, average molecular weight (MW) is 4826.9 Da; while the found MW is 4827.0 Da.

The crude peptide "IZN17A7" (SEQ ID NO:76) was purified by reverse-phase HPLC using a semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of B was used: 35%-55% over 20 min, flow rate 80 mL/min. Analytical HPLC was performed on a Phenomenex, Jupiter C$_4$ column (150×4.6 mm, 5 μm) with the following gradient of B: 35%-65% B (in 20 min)-80% (in 3 min), flow rate 1 mL/min. The purified peptide was characterized by electrospray mass spectrometry on a Micromass LCZ platform spectrometer. The theoretical, average molecular weight (MW) is 4739.9 Da; while the found MW is 4739.0 Da.

The crude peptide "IZN17A10" (SEQ ID NO:77) was purified by reverse-phase HPLC using a semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of B was used: 45%-65% over 20 min, flow rate 80 mL/min. Analytical HPLC was performed on a Phenomenex, Jupiter C$_4$ column (150×4.6 nm, 5 μm) with the following gradient of B: 45%-70% B (in 20 min)-80% (in 3 min), flow rate 1 mL/min. The purified peptide was characterized by electrospray mass spectrometry on a Micromass LCZ platform spectrometer. The theoretical, average molecular weight (MW) is 4797.9 Da; while the found MW is 4798.0 Da.

The crude peptide "IZN17A11" (SEQ ID NO:78) was purified by reverse-phase HPLC using a semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of B was used: 35%-55% over 20 min, flow rate 80 mL/min. Analytical HPLC was performed on a Phenomenex, Jupiter C$_4$ column (150×4.6 mm, 5 μm) with the following gradient of B: 40%-60% B (in 20 min)-80% (in 3 min), flow rate 1 mL/min. The purified peptide was characterized by electrospray mass spectrometry on a Micromass LCZ platform spectrometer. The theoretical, average molecular weight (MW) is 4797.9 Da; while the found MW is 4796.0 Da.

The crude peptide "IZN17A13" (SEQ ID NO:79) was purified by reverse-phase HPLC using a semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of B was used: 45%-70% over 20 min, flow rate 80 mL/min. Analytical HPLC was performed on a Phenomenex, Jupiter C$_4$ column (150×4.6 mm, 5 μm) with the following gradient of B: 45%-70% B (in 20 min)-80% (in 3 min), flow rate 1 mL/min. The purified peptide was characterized by electrospray mass spectrometry on a Micromass LCZ platform spectrometer. The theoretical, average molecular weight (MW) is 4797.9 Da; while the found MW is 4797.0 Da.

The crude peptide "IZN17A15" (SEQ ID NO:80) was purified by reverse-phase HPLC using a semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of B was used: 40%-55% over 20 min, flow rate 80 mL/min. Analytical HPLC was performed on a Phenomenex, Jupiter C$_4$ column (150×4.6 mm, 5 μm) with the following gradient of B: 35%-65% B (in 20 min)-80% (in 3 min), flow rate 1 mL/min. The purified peptide was characterized by electrospray mass spectrometry on a Micromass LCZ platform spectrometer. The theoretical, average molecular weight (MW) is 4769.9 Da; while the found MW is 4769.0 Da.

The crude peptide "IZN17A17" (SEQ ID NO:81) was purified by reverse-phase HPLC using a semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of B was used: 35%-55% over 20 min, flow rate 80 mL/min. Analytical HPLC was performed on a Phenomenex, Jupiter C$_4$ column (150×4.6 mm, 5 μm) with the following gradient of B: 45%-60% B (in 20 min)-80% (in 3 min), flow rate 1 mL/min. The purified peptide was characterized by electrospray mass spectrometry on a Micromass LCZ platform spectrometer. The theoretical, average molecular weight (MW) is 4812.9 Da; while the found MW is 4812.0 Da.

The synthesis protocol for "IZN17G572D" (SEQ ID NO:22) is provided in Example 5.

TABLE 5

Mutated IZN17 sequences generated by alanine scanning of IZN17 (SEQ ID NO:1), mutating said sequence by alanine substitutions at positions L565, Q567, L568, V570, W571, K574, Q575, Q577, R579 or L581. A lower case "a" signifies the amino acid that has been substituted by an alanine residue. Bold amino acids represent the N-peptide portion of the mutated, chimeric N-peptide.

| SEQ ID NO: | NAME | MW | SEQUENCE |
|---|---|---|---|
| 72 | IZN17A1 | 4813.0 | IKKEIEAIKKEQEAIKKKIEAIEKaLQLTVWGIKQLQARIL |
| 73 | IZN17A3 | 4797.9 | IKKEIEAIKKEQEAIKKKIEAIEKLLaLTVWGIKQLQARIL |
| 74 | IZN17A4 | 4812.9 | IKKEIEAIKKEQEAIKKKIEAIEKLLQaTVWGIKQLQARIL |
| 75 | IZN17A6 | 4826.9 | IKKEIEAIKKEQEAIKKKIEAIEKLLQLTaWGIKQLQARIL |
| 76 | IZN17A7 | 4739.9 | IKKEIEAIKKEQEAIKKKIEAIEKLLQLTVaGIKQLQARIL |
| 77 | IZN17A10 | 4797.9 | IKKEIEAIKKEQEAIKKKIEAIEKLLQLTVWGIaQLQARIL |
| 78 | IZN17A11 | 4797.9 | IKKEIEAIKKEQEAIKKKIEAIEKLLQLTVWGIKaLQARIL |
| 79 | IZN17A13 | 4797.9 | IKKEIEAIKKEQEATKKKIEAIEKLLQLTVWGIKQLaARIL |
| 80 | IZN17A15 | 4769.9 | IKKEIEAIKKEQEAIKKKIEAIEKLLQLTVWGIKQLQAaIL |
| 81 | IZN17A17 | 4812.9 | IKKEIEAIKKEQEAIKKKIEAIEKLLQLTVWGIKQLQARIa |

All the peptides are Acetyl N-terminus and Amide C-terminus

Synthesis of CCIZN13—CCIZN13 (SEQ ID NO:95) was synthesized following the same protocol as described for IZN17 (SEQ ID NO:1) and CCIZN17 (SEQ ID NO:2). The acetylation reaction was performed at the end of the peptide assembly by reaction with a 10-fold excess of acetic anhydride in DMF. The crude peptide, CCIZN13 (SEQ ID NO:95), was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC were further purified to >95% purity was purified by reverse-phase HPLC on semi-preparative Waters RCM Delta-Pak™ $C_{-4}$ cartridges (40×200 mm, 15 µm) flow rate 80 in mL/min, using as eluents (A) 0.1% TFA in water and (B) 0.1% TFA in acetonitrile. The following gradient of eluent B was used: 30%-45% over 25 min, flow rate 80 mL/min. Analysis of the crude peptide, the eluted fractions and the purified pool was carried out by analytical HPLC on Jupiter $C_4$ column (150×4.6 mm, 5 µm, 300 A, Phenomenex), flow rate 1 mL/min, using as eluents: (A) 0.1% TFA in water and (B) 0.1% TFA in acetonitrile. The following gradient of eluent B was used: 35%-50% over 20 min-80% over 3 minutes. The purified peptide was characterized by mass spectrometry on a Micromass LCZ platform $ES^+$. The found MW is 4721.0 Da, and the calculated average MW was 4721.7.0 Da.

Oxidation of CCIZN13 to $(CCIZN13)_3$—The purified peptide precursor (20 mg), CCIZN13 (SEQ ID NO:95), was dissolved in 0.1 M Hepes, pH 7.3 (USB Corp.) at a concentration of 5 mg/mL. Under this condition, CCIZN13 is slowly oxidized by the air to the covalent trimer $(CCIZN13)_3$ ([SEQ ID NO:95]$_3$). The oxidation reaction was monitored by LC-MS analysis using a Waters-Micromass LCZ Platform with a Phenomenex, Jupiter $C_4$ column (150×4.6 mm, 5 µm) using as eluents (A) 0.1% TFA in water and (B) 0.1% TFA in acetonitrile. The following gradient of eluent B was used: 35%-55% B (in 20 min)-80% (in 3 min), flow rate 1 mL/min. Under these chromatographic conditions, CCIZN13 elutes at $t_R$=12.57'. The oxidation reaction proceeds smoothly with formation of one main product eluting at $t_R$=15' whose mass corresponds to that of one molecule comprising three CCIZN13 peptide chains having a reduction of mass consistent with formation of three disulfide bridges $(CCIZN13)_3$. The overall yield of the oxidation reaction is more than 80%. To the solution was added 45 µL of TFA, and the solution was directly loaded on a 700×26 mm column, packed with a TSKgel Toyopearl HW-50S resin, using as eluent $H_2O$/acetonitrile, 70/30, 0.1% TFA, flow rate 1 mL/min. The eluted fractions were analyzed by HPLC with a Phenomenex, Jupiter $C_4$ column (150×4.6 mm, 5/µm) using as eluents: (A) 0.1% TFA in water and (B) 0.1% TFA in acetonitrile. The following gradient of eluent B was used: 35%-55% B (in 20 min)-80% (in 3 min), flow rate 1 mL/min on the LC-MS Waters-Micromass LCZ Platform. in a positive mode ($ES^+$). The expected MW is 14158.0 Da; while the found MW was 14159.29 Da.

Alphascreen™ Assay—See Example 4.

Mouse Monoclonal Antibodies—Anti-IQN17 monoclonal antibodies A, B and C were made by immunizing mice via intra-peritoneal injection with IQN17 (SEQ ID NO:23) peptide prepared in various adjuvants. Splenocytes from immunized animals were harvested and fused to a mouse myeloma cell line to produce antibody-secreting hybridomas. Hybridoma-producing antibodies reactive with IQN17, as determined by IQN17-specific ELISA, were injected into mice to produce ascitic fluid from which the three mAbs were purified using protein A columns.

Delineation of a N17 Neutralizing Epitope—To identify specific amino acids of the hydrophobic pocket that are required for attachment of a newly-identified, HIV neutralizing antibody, D5-IgG, a series of mutant IZN17 peptides were tested for ability to compete the binding of D5-IgG with biotinylated IQN17 in an AlphaScreen™ format. Amino acid substitutions were engineered into IZN17, specifically targeting solvent exposed residues. First, an IZN17 mutant in which Glycine at position 572 was replaced with aspartic acid was tested ("IZN17G572D"; SEQ ID NO:22). This mutation effectively introduces a large side-chain into the hydrophobic pocket of IZN17 thus filling this cavity. This G572D mutant is completely incapable of competing D5 binding to IQN17 indicating that introduction of a bulky side chain into the hydrophobic pocket impedes binding of D5-IgG (FIG. 9A). This result further indicates that the binding site of D5 is in the hydrophobic pocket. Three additional IZN17 mutants are incapable of competing D5 binding. Alanine substitutions at positions K574 (IZN17A10; SEQ ID NO:77), L568 (IZN17A4; SEQ ID NO:74) and W571 (IZN17A7; SEQ ID NO:76) in IZN17 (see Tables 5 and 6) completely abolish binding of D5 indicating that these three amino acids likely form the D5 epitope (FIG. 9B). One additional mutant (V570A; IZN17A6; SEQ ID NO:75) appears to compete for D5 binding less effectively than wildtype IZN17 peptide, perhaps suggesting that V570 forms a minor contact point for D5-IgG. The three critical amino acids for D5 binding are identified in FIG. 8 by the squared residues, located in the cavity formed by three adjacent N17 segments. For a summary, see FIG. 11.

The alanine scanned, IZN17 mutants described above (SEQ ID NOs: 72-81), in addition to IZN17G572D (SEQ ID NO:22), were characterized by both circular dichroism spectroscopy and thermal denaturation studies and compared to IZN17 for the ability of forming stable coiled-coil structures. All the mutants are fully helical and show a high stability with denaturation curves having a melting point above 100° C. When thermal denaturations were performed in the presence of a low concentration of denaturant, such as 2M guanidinium chloride (2M, GdnHCl), the melting points for the mutants compare well with that obtained for IZN17, as shown in Table 6. Thus, any decrease in D5-IgG binding by any mutant generated as described can only be interpreted in terms of lack of binding contributions.

TABLE 6

| SEQ ID NO: | NAME | D5[1] | $T_m$ (2M GdnHCl)[2] |
|---|---|---|---|
| 1 | IZN17 | ++++ | 61.5° C. |
| 72 | IZN17A1 | ++++ | 51.7° C. |
| 73 | IZN17A3 | ++++ | 64.7° C. |
| 74 | IZN17A4 | – | 58.2° C. |
| 75 | IZN17A6 | +/– | 56.4° C. |
| 76 | IZN17A7 | – | 61.4° C. |
| 22 | IZN17G572D | – | 62.1° C. |
| 77 | IZN17A10 | – | 68.1° C. |
| 78 | IZN17A11 | ++++ | 66.0° C. |
| 79 | IZN17A13 | ++++ | 71.5° C. |
| 80 | IZN17A15 | ++++ | 77.2° C. |
| 81 | IZN17A17 | ++++ | 60.6° C. |

[1]5-Helix/D5-IgG competition assay;
[2]midpoint of thermal denaturation in 2M GdnHCl.

Delineation of a N17 Non-Neutralizing Epitope—Protein-A purified preparations of three IQN17-directed mouse mAbs (A, B, C) were utilized to identify optimal interaction conditions between biotinylated-IQN17 and each of the three mouse mAbs using Alphascreen™ technology (Perkin Elmer). Using these peptide/antibody interaction assays, a panel of mutant IZN17 peptides in which solvent exposed residues were mutated to alanine residues was titrated to identify amino acids in the N17 segment of the peptide that are critical for binding of the antibodies. Mutant peptides that failed to compete mAb binding to IQN17 revealed key amino acids that comprise the individual epitopes of the three IQN17-directed mAbs (see FIG. 11). Mouse mAb A appears to critically depend on amino acids K574, R579 and L581. Amino acids Q575 and Q577 also appear to represent contact points for the antibody but are not essential for binding. Thus, the epitope of mAb A is comprised of the amino acids K574, R579, L581, Q575 and Q577. In the case of mouse mAb B, the amino acid R579 appears essential for the antibody's interaction with IZN17. While Q577 and L581 also appear to be contacted by the antibody, these two amino acids are not essential for binding. The epitope of mAb B appears to be the smallest as it involves only three amino acids (Q577, R579, L581). Finally, in the case of mouse mAb C, three amino acids appear to be essential for this antibody to interact with IZN17: Q577, R579 and L581. An additional contact appears to be made at Q575, but this interaction is not critical for mAb C to bind IZN17. In conclusion, the epitopes of these three mouse mAbs that were raised against IQN17 are subtly different yet all three epitopes appear to be centered on the three amino acids Q577, R579 and L581, while R579 is essential for the binding of all three antibodies (see FIG. 11). These residues are identified by ovals in FIG. 8.

In order to focus an immune response to the hydrophobic pocket region of the HIV N-helix, the immunodominant non-neutralizing epitope present at the carboxy terminus of the N17 peptide was removed in the CC-chimeric N-peptide, CCIZN13 (SEQ ID NO:95). The CCIZN13 monomer was oxidized to the covalent trimeric (CCIZN13)$_3$ (SEQ ED NO. 95) and characterized for antiviral activity, showing an IC$_{50}$ of 85.3 nM against HIV HXB2 (FIG. 13). The reduced potency is in agreement with antiviral activities shown by the alanine-scanned mutants of IZN17 (mutant Q577A at A15; see Example 8). (CCIZN13)$_3$ also shows a two-fold decrease in the ability to bind D5 IgG with respect to (CCIZN17)$_3$ (FIG. 13).

EXAMPLE 9

Design of C-Ttds-CCEZN Peptides

Synthesis of C-Ttds-CCEZN17—C-Ttds-CCEZN17 (C-Tds-SEQ ID NO:7) was synthesized following the same protocol as described for IZN17 (SEQ ID NO:1) and CCIZN17 (SEQ ID NO:2). The reaction with Ttds (1-amino-4,7,10-trioxa-13-tridecamine succinic acid; —NH—(CH$_2$)$_3$—O—(CH$_2$)$_2$—O—(CH$_2$)$_2$—O—(CH$_2$)$_3$—NH—CO—CH$_2$)$_2$—CO—) was performed by reaction with a 3-fold excess of Ttds activated with an equimolar amount of DIPC (N,N'-diisopropylcarbodiimide) and HOBt (1-hydroxybenzotriazole), for three hours. The acetylation reaction was performed at the end of the peptide assembly by reaction with a 10-fold excess of acetic anhydride in DMF. The crude peptide, C-Ttds-CCEZN17 (C-Tds-SEQ ID NO:7), was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC (25% yield) were further purified to >95% purity by reverse-phase HPLC on semi-preparative Waters RCM Delta-Pak™ C$_{-4}$ cartridges (40×200 mm, 15 μm), flow rate 80 mL/min, using as eluents (A) 0.1% TFA in water and (B) 0.1% TFA in acetonitrile. The following gradient of eluent B was used: 40%-60% over 25 min, flow rate 80 mL/min. Analysis of the crude peptide, the eluted fractions and the purified pool was carried out by analytical HPLC on Jupiter C$_4$ column (150× 4.6 mm, 5 μm, 300 A, Phenomenex), flow rate 1 mL/min, using as eluents: (A) 0.1% TFA in water and (B) 0.1% TFA in acetonitrile. The following gradient of eluent B was used: 45%-65% over 20 min-80% over 3 minutes. The purified peptide was characterized by mass spectrometry on a Micromass LCZ platform ES$^+$. The found MW is 5739.0 Da, and the calculated average MW is 5740.0 Da.

Oxidation of C-Ttds-CCEZN17 and Derivatization with Maleimidobutyric Acid—The purified peptide precursor, C-Ttds-CCEZN17 (C-Tds-SEQ ID NO:7), was dissolved in 0.1 M Hepes, pH 7.3 (USB Corp.) at a concentration of 1 mg/mL. Under this condition, C-Ttds-CCEZN17 is slowly oxidized by the air to the covalent trimer (C-Ttds-CCEZN17)$_3$ ([C-Tds-SEQ ID NO:7]$_3$). The oxidation reaction was monitored by LC-MS analysis using a Waters-Micromass LCZ Platform with a Phenomenex, Jupiter C$_4$ column (150×4.6 mm, 5 μm) using as eluents (A) 0.1% TFA in water and (B) 0.1% TFA in acetonitrile. The following gradient of eluent B was used: 30%-70% B (in 20 min)-80% (in 3 min), flow rate 1 mL/min. The oxidation reaction proceeds smoothly overnight with formation of a product whose mass corresponds to that of one molecule comprising three C-Ttds-CCEZN17 peptide chains having a reduction of mass consistent with formation of four disulfide bridges and still having one free thiol on one of the nine total cysteine residues. ([C-Ttds-CCEZN17]$_3$). The found MW is 17395.0 Da.

An aliquot of the solution was incubated with a 3 molar excess of maleimidobutyric acid (MW 183 Da) (50 μl of a 1 mg/mL water solution added to 0.5 mL of peptide solution). After 30 minutes incubation, HPLC/MS analysis revealed the introduction of a single maleimidobutiryl group on the trimeric species (found MW is 1739, and calculated average MW is 17395) confirming the presence of a single free Cys residue able to react with a maleimide group.

Results—A CCEZN17-derived peptide was designed having a free thiol group useful to confer particular features to the CC-chimeric N-peptide, such as conjugation of the peptide to a resin or a carrier, or derivatization with a tag or any moiety (e.g., a pegylated chain). The design of this peptide can be applied to other CC-chimeric N-peptides described herein, including CC-chimeric N-peptides comprising HIV N-peptide portions of different length, wherein the core CC-chimeric N-peptide is modified to include one more cysteine residue per chain. Thus, each peptide chain will contain an odd number of cysteine residues (i.e., three in this example). The odd cysteine is separated from the other contiguous cysteine residues by means of a flexible and long linker. In the present example, the linker Ttds (1-amino-4,7,10-trioxa-13-tridecamine succinic acid; —NH—(CH$_2$)$_3$—O—(CH$_2$)$_2$—O—(CH$_2$)$_2$—O—(CH$_2$)$_3$—NH—CO—CH$_2$)$_2$—CO—) was chosen. The odd number of cysteine residues assures that after oxidation to from the covalently-stabilized trimer molecule, at least one reactive thiol group per trimer is available for further reaction with thiol-reactive groups (e.g., maleimidyl). The linker, such as Ttds, provides flexibility, solubility and spacing between the trimerization domain and the free thiol-containing cysteine residues suitable for conjugation/derivatization.

This strategy was validated by means of a reaction with a test compound, maleimidobutyric acid. The C-Ttds-CCEZN17 monomer (MW 5739 Da) was incubated at 1 mg/ml to permit air oxidation, forming a covalently-stabilized, trimer molecule. The reaction was followed by LC-MS analysis. After a 24 hour incubation, the main oxidized product corresponded to a trimeric species with four disulfide bridges (MW 17209 Da), indicating that eight out of nine cysteine residues within the trimer structure were engaged in disulfide bridges. The reactivity of one, residual thiol group was tested by incubation with 3 molar excess of maleimidobutyric acid. After a 30 minute reaction, the HPLC-MS analysis showed the formation of a compound corresponding to the product of a single maleimidylbutiric acid on the trimeric species (MW 17395).

EXAMPLE 10

Alterations to the Scaffold Domain

Synthesis of N17IZ—N17IZ (SEQ ID NO:94) was synthesized following the same protocol as described for IZN17 (SEQ ID NO:1) and CCIZN17 (SEQ ID NO:2). The acetylation reaction was performed at the end of the peptide assembly by reaction with a 10-fold excess of acetic anhydride in DMF. The crude peptide, N17IZ (SEQ ID NO:94), was purified by reverse-phase HPLC on semi-preparative Waters RCM Delta-Pak™ $C_{-4}$ cartridges (40×200 mm, 15 µm) using as eluents (A) 0.1% TFA in water and (B) 0.1% TFA in acetonitrile. The following gradient of eluent B was used: 30%-50% over 25 min, flow rate 80 mL/min. The purified peptide was characterized by electrospray mass spectrometry on a Micromass LCZ platform. The theoretical average MW is 4667.0 Da, and the found MW was 4668.77 Da.

Synthesis of CCIZN11IZ—CCIZN11IZ (SEQ ID NO: 96) was synthesized following the same protocol as described for IZN17 (SEQ ID NO:1) and CCIZN17 (SEQ ID NO:2). The pooled fractions (purity 70%) obtained by GPC (see above) were further purified to >95% purity by reverse-phase HPLC on semi-preparative Waters RCM Delta-Pak™ $C_{-4}$ cartridges (40×200 mm, 15 µm) flow rate 80 mL/min, using as eluents (A) 0.1% TFA in water and (B) 0.1% TFA in acetonitrile. The following gradient of eluent B was used: 35%-50% over 25 min, flow rate 80 mL/min. Analysis of the crude peptide, the eluted fractions and the purified pool was carried out by analytical HPLC on Jupiter $C_4$ column (150×4.6 mm, 5 µm, 300 A, Phenomenex), flow rate 1 mL/min, using as eluents: (A) 0.1% TFA in water and (B) 0.1% TFA in acetonitrile. The following gradient of eluent B was used: 40%-60% over 20 min-80% over 3 minutes. The purified peptide was characterized by mass spectrometry on a Micromass LCZ platform $ES^+$. The found MW is 5406.0 Da, and the calculated average MW was 5405.3 Da.

Oxidation of CCIZN11IZ to $(CCIZN11IZ)_3$—The purified peptide precursor (35 mg), CCIZN11IZ (SEQ ID NO:96), was dissolved in 0.1 M Hepes, pH 7.3 (USB Corp.) at a concentration of 5 mg/mL. Under this condition, CCIZN11IZ is slowly oxidized by the air to the covalent trimer $(CCIZN11IZ)_3$ ([SEQ ID NO:96]$_3$). The oxidation reaction was monitored by LC-MS analysis using a Waters-Micromass LCZ Platform with a Phenomenex, Jupiter $C_4$ column (150×4.6 mm, 5 µm) using as eluents (A) 0.1% TFA in water and (B) 0.1% TFA in acetonitrile. The following gradient of eluent B was used: 40%-60% B (in 20 min)-80% (in 3 min), flow rate 1 mL/min. Under these chromatographic conditions, CCIZN11IZ elutes at $t_R$=12.07'. The oxidation reaction proceeds smoothly with formation of one main product eluting at $t_R$=12.8' whose mass corresponds to that of one molecule comprising three CCIZN11IZ peptide chains having a reduction of mass consistent with formation of three disulfide bridges $(CCIZN11IZ)_3$. The overall yield of the oxidation reaction is more than 70%. To the solution was added 100 µL of TFA, and the solution was directly loaded on a 700×26 mm column, packed with a TSKgel Toyopearl HW-50S resin, using as eluent $H_2O$/acetonitrile, 40/60, 0.1% TFA, flow rate 1 mL/min. The eluted fractions were analyzed by HPLC with a Phenomenex, Jupiter $C_4$ column (150×4.6 mm, 5 µm) using as eluents: (A) 0.1% TFA in water and (B) 0.1% TFA in acetonitrile. The following gradient of eluent B was used: 40%-60% B (in 20 min)-80% (in 3 min), flow rate 1 mL/min on the LC-MS Waters-Micromass LCZ Platform. in a positive mode ($ES^+$). The expected MW is 16210.85 Da; while the found MW was 16215 Da.

Synthesis of SZN17 (SEQ ID NO:97) was synthesized following the same protocol as described for IZN17 (SEQ ID NO:1) and CCIZN17 (SEQ ID NO:2). After acetylation, the crude peptide, SZN17 (SEQ ID NO:97), was purified by reverse-phase HPLC on semi-preparative Waters RCM Delta-Pak™ $C_{-4}$ cartridges (40×200 mm, 15 µm) using as eluents (A) 0.1% TFA in water and (B) 0.1% TFA in acetonitrile. The following gradient of eluent B was used: 40%-55% over 20 min, flow rate 80 mL/min. The purified peptide was characterized by electrospray mass spectrometry on a Micromass LCZ platform. The theoretical average MW is 4841 Da, and the found MW was 4841 Da.

Synthesis of CCS17N17 (SEQ ID NO:100) was synthesized following the same protocol as described for IZN17 (SEQ ID NO:1) and CCIZN17 (SEQ ID NO:2). The acetylation reaction was performed at the end of the peptide assembly by reaction with a 10-fold excess of acetic anhydride in DMF. The crude peptide, CCS17N17 (SEQ ID NO:100), was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC were further purified to >95% purity was purified by reverse-phase HPLC on semi-preparative Waters RCM Delta-Pak™ $C_{-4}$ cartridges (40×200 mm, 15 µm) flow rate 80 mL/min, using as eluents (A) 0.1% TFA in water and (B) 0.1% TFA in acetonitrile. The following gradient of eluent B was used: 40%-55% over 20 min, flow rate 80 mL/min. Analysis of the crude peptide, the eluted fractions and the purified pool was carried out by analytical HPLC on Jupiter $C_4$ column (150× 4.6 mm, 5 µm, 300 A, Phenomenex), flow rate 1 mL/min, using as eluents: (A) 0.1% TFA in water and (B) 0.1% TFA in acetonitrile. The following gradient of eluent B was used: 45%-60% over 20 min-80% over 3 minutes. The purified peptide was characterized by mass spectrometry on a Micromass LCZ platform $ES^+$. The found MW is 4350.0 Da, and the calculated average MW was 4350.0 Da.

Oxidation of CCS17N7 to $(CCS17N17)_3$—The purified peptide precursor (17 mg), CCS17N17 (SEQ ID NO:100), was dissolved in 0.1 M Hepes, pH 7.3 (USB Corp.) at a concentration of 2 mg/mL. Under this condition, CCS17N17 is slowly oxidized by the air to the covalent trimer $(CCS17N17)_3$ ([SEQ ID NO:100]$_3$). The oxidation reaction was monitored by LC-MS analysis using a Waters-Micromass LCZ Platform with a Phenomenex, Jupiter $C_4$ column (150×4.6 mm, 5 µm) using as eluents (A) 0.1% TFA in water and (B) 0.1% TFA in acetonitrile. The following gradient of eluent B was used: 45%-70% B (in 20 nm in)-80% (in 3 min), flow rate 1 mL/min. Under these chromatographic conditions, CCS17N17 elutes at $t_R$=10.72'. The oxidation reaction proceeds smoothly with formation of one main product eluting at $t_R$=7.6' whose mass corresponds to that of one molecule comprising three CCS17N17 peptide chains having a reduction of mass consistent with formation of three disulfide bridges $(CCS17N17)_3$. The overall yield of the oxidation reaction is more than 70%. To the solution was added 100 µL of TFA, and the solution was purified by reverse-phase HPLC on semi-preparative Phenomenex Jupiter $C_4$ column (21.2× 250 mm, 15 µm) flow rate 80 mL/min, using as eluents (A) 0.1% TFA in water and (B) 0.1% TFA in acetonitrile. The following gradient of eluent B was used: 35%-50% over 20 min, flow rate 80 mL/min. The eluted fractions were analyzed by HPLC with a Phenomenex, Jupiter $C_4$ column (150×4.6 mm, 5 μm) using as eluents: (A) 0.1% TFA in water and (B) 0.1% TFA in acetonitrile. The following gradient of eluent B was used: 45%-65% B (in 20 min)-80% (in 3 min), flow rate 1 mL/min on the LC-MS Waters-Micromass LCZ Platform. in a positive mode ($ES^+$). The expected MW is 13042 Da; while the found MW is 13043 Da.

Synthesis of CCS10N17 (SEQ ID NO:102) was synthesized following the same protocol as described for IZN17 (SEQ ID NO:1) and CCIZN17 (SEQ ID NO:2). The acetylation reaction was performed at the end of the peptide assembly by reaction with a 10-fold excess of acetic anhydride in DMF. The crude peptide, CCS10N17 (SEQ ID NO:102), was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC were further purified to >95% purity was purified by reverse-phase HPLC on semi-preparative Waters RCM Delta-Pak™ $C_{-4}$ cartridges (40×200 mm, 15 μm) flow rate 80 mL/min, using as eluents (A) 0.1% TFA in water and (B) 0.1% TFA in acetonitrile. The following gradient of eluent B was used: 40%-55% over 20 min, flow rate 80 mL/min. Analysis of the crude peptide, the eluted fractions and the purified pool was carried out by analytical HPLC on Jupiter $C_4$ column (150× 4.6 mm, 5 μm, 300 A, Phenomenex), flow rate 1 mL/min, using as eluents: (A) 0.1% TFA in water and (B) 0.1% TFA in acetonitrile. The following gradient of eluent B was used: 45%-60% over 20 min-80% over 3 minutes. The purified peptide was characterized by mass spectrometry on a Micromass LCZ platform $ES^+$. The found MW is 3538.0 Da, and the calculated average MW was 3537.0 Da.

Oxidation of CCS10N7 to $(CCS10N17)_3$—The purified peptide precursor (20 mg), CCS10N17 (SEQ ID NO:102), was dissolved in 0.1 M Hepes, pH 7.3 (USB Corp.) at a concentration of 5 mg/mL. Under this condition, CCS10N17 is slowly oxidized by the air to the covalent trimer $(CCS10N17)_3$ ([SEQ ID NO:102]$_3$). The oxidation reaction was monitored by LC-MS analysis using a Waters-Micromass LCZ Platform with a Phenomenex, Jupiter $C_4$ column (150×4.6 mm, 5 μm) using as eluents (A) 0.1% TFA in water and (B) 0.1% TFA in acetonitrile. The following gradient of eluent B was used: 50%-80% B (in 23 min), flow rate 1 mL/min. The oxidation reaction proceeded overnight with formation of multiple products that correspond to dimer, trimer and tetrameric species. The overall yield of formation of the trimeric product is about 30%. To the solution was added 100 μL of TFA, and the solution was purified by reverse-phase HPLC on semi-preparative Phenomenex Jupiter $C_{-4}$ column (21.2×250 mm, 15 μm) flow rate 25 mL/min, using as eluents (A) 0.1% TFA in water and (B) 0.1% TFA in acetonitrile. The following gradient of eluent B was used: 45%-70% over 25 min. The eluted fractions were analyzed by HPLC with a Phenomenex, Jupiter $C_4$ column (150×4.6 mm, 5 μm) using as eluents: (A) 0.1% TFA in water and (B) 0.1% TFA in acetonitrile. The following gradient of eluent B was used: 45%-65% B (in 20 min)-80% (in 3 min), flow rate 1 mL/min on the LC-MS Waters-Micromass LCZ Platform. in a positive mode ($ES^+$). The expected MW is 10606 Da; while the found MW was 10607 Da.

Alphascreen™ binding assay—See Example 4
Single cell infectivity assay—See Example 3
Results—In conjunction with the N17 sequence, the role of the IZ coiled-coil on antiviral potency was further investigated. An analog of IZN17 was prepared reversing the location of the scaffold and HIV domain of the N-peptide, forming N17IZ (SEQ ID NO:94), wherein the IZ domain is positioned carboxy terminal to the N17 sequence. An extra alanine residue was included between the N17 and IZ sequences to maintain the alternating heptad repeat ("a" to "g") in frame. Examination of the structure of the post-fusion, trimer-of-hairpins (i.e., 6-helix bundle) suggests that while IZN17 should be able to capture the N-terminal portion of the C-helix of gp41, a partial twist of the C-terminal portion of the C-helix may be necessary to avoid clashing against the coiled-coil grog of the IZ scaffold. Placing the IZ scaffold domain at the carboxy terminus of the N-peptide may minimize any potential steric hindrance due to the C residues during inhibition. By contrast, despite maintaining very high structural stability, N17IZ is more than two orders of magnitude less active than IZN17 in antiviral assays, with an antiviral potency of 800 nM against HIV HXB2 (see FIG. 13). This suggests that the C-terminal location of the IZ scaffold domain may clash with some region of the fusion intermediate, other than the C-helix. While N17IZ can still bind D5 IgG, it does so with less efficiency (see FIG. 13).

CCIZN11IZ (SEQ ID NO:96) was designed with the goal of focusing the immune response to the hydrophobic pocket of the EIV N-helix by reducing the HIV portion of the CC-chimeric N-peptide to only 11 residues. To further stabilize the shortened coiled-coil, eight more IZ residues were added to the carboxy terminus. This may also avoid an immune response targeting the HIV portion at only one edge of the coiled-coil, with recognition from the bottom (the tip). The covalently-stabilized form of CCIZN11IZ, $(CCIZN11IZ)_3$, shows high activity in antiviral assays, with a potency of 0.3 nM against HIV HXB2 (FIG. 13). The homotrimer also binds D5 IgG (FIG. 13).

A new peptide, SZN17 (SEQ ID NO:97), was prepared having as the scaffold an unmodified portion of the Suzuki-IZ scaffold (Suzuki et al., 1998, supra; SEQ ID NO:29), herein named "SZ" (IEKKIEAIEKKIEAIEKKIEAIEK; SEQ ID NO:112). In comparison, the IZ scaffold described herein is based on the Suzuki scaffold with additional mutations to both avoid degeneracy (described further supra). SZN17 was prepared to test the possibility that said mutations may destabilize the trimeric coiled-coil. The stability of SZN17 was compared with that of IZN17 using thermal denaturation analysis performed in the presence of 2M guanidine hydrochloride (GdnHCl). The midpoint of thermal denaturation in 2M GdnHCl for IZN17 is 61.5° C. SZN17 proved to be more stable than IZN17, showing a midpoint of thermal denaturation in 2M GdnHCl of >90° C. SZN17 also displayed relatively potent antiviral activity, with an $IC_{50}$ of 1.5 against HIV BXB2 in the described single-cell infectivity assay (FIG. 13). Because of the apparent increased stability of the SZ scaffold, chimeric N-peptides having shorter SZ scaffold domains (e.g., consisting of 10-17 amino acids) may be generated wherein said peptides will preserve the stable presentation of the HIV portion (e.g., S17N17 (SEQ ID NO:99); S10N17 (SEQ ID NO:101)).

A shorter CC-chimeric N-peptide based on the Suzuki ("SZ") scaffold was prepared, CCS17N17 (SEQ ID NO:100). The covalent trimeric form, $(CCS17N17)_3$, was generated using the same conditions as described previously. The trimeric coiled-coil was analyzed by circular dichroism spectroscopy for an estimate of secondary structure content, and its stability was evaluated by thermal denaturation studies. $(CCS17N17)_3$ is very stable, having a melting point above 90° C. even in the presence of 2M guanidine hydrochloride. The "SZ" was further minimized in S10N17 (SEQ ID NO:101). This minimal, scaffolded peptide is highly stable as determined by thermal denaturation experiments by CD, showing a melting temperature of about 60° C. in the presence of 2M guanidinium chloride. In comparison, a similar construct based on the IZ scaffold, (CC110N17)$_3$, showed a much lower stability with a melting temperature of 60° C. in a simple buffer solution at pH 7.3.

To define a minimalist stable peptide construct which helps to focus an immune response towards the HIV portion of the peptide mimetic that is also capable of being conjugated to an immogenic carrier, such as OMPC, the "S10" scaffold sequence (IEKKIEAIEK; SEQ ID NO:113) was mutated in 3 residues in order to provide an N17-derived peptide with an overall pI of between 3-5. Peptides with a pI within this range have been shown to be more amenable to OMPC conjugation (see supra). The three amino acid residues at positions "c" and "f" of the heptad repeat of the S10 (SEQ ID NO:113) scaffold were mutated to glutamic acid residues, while the "e" and "g" positions were left unaltered due to their location at the interhelical interface (Glu-Lys couples). This generated a peptide construct, E10N17 (SEQ ID NO:108), with a pI of 4.2 which is a good candidate for conjugation to OMPC.

EXAMPLE 11

Covalent-Stabilization of Peptide Mimetics with Thioether Bonds

Synthesis of Br-acetyl-GGGIZN17 (peptide 2 in Table 7)—GGGIZN17 (SEQ ID NO:104) was synthesized following the same protocol as previously described for IZN17 (see Example 1). The bromoacetylation reaction was performed at the end of the peptide assembly by reaction with a 10-fold excess of bromoacetic anhydride in DMF. The crude peptide, Br-acetyl-GGGIZN17 (peptide 2 in Table 7), was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC were further purified to >95% purity by reverse-phase HPLC on semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of eluent B was used: 35%-50% over 20 min, flow rate 80 mL/min. Analysis of the crude peptide, the eluted fractions and the purified pool was carried out by analytical HPLC on Jupiter C$_4$ column (150×4.6 mm, 5 μm, 300 A, Phenomenex), flow rate 1 mL/min, using as eluents: (A) 0.1% TFA in water and (B) 0.1% TFA in acetonitrile. The following gradient of eluent B was used: 40%-60% over 20 min-80% over 3 minutes. The purified peptide was characterized by electrospray mass spectrometry on a Micromass LCZ platform. The theoretical average MW is 5106 Da, and the found MW was 5106 Da.

Synthesis of NH$_2$—C(Fm)Ttds-CCIZN17 (peptide 1 of Table 7)—CCCIZN17 (SEQ ID NO:103) was first synthesized following the same protocol as previously described for IZN17. The reaction with Ttds (1-amino-4,7,10-trioxa-13-tridecamine succinic acid (—NH—(CH$_2$)$_3$—O—(CH$_2$)$_2$—O—(CH$_2$)$_2$—O—(CH$_2$)$_3$—NH—CO—CH$_2$)$_2$—CO—) was performed by reaction with a 3-fold excess of Ttds activated with an equimolar amount of DIPC(N,N'-diisopropylcarbodiimide) and HOBt (1-hydroxybenzotriazole), for three hours. The N-terminal residue C(Fm) was acylated as Boc-Cys(Fm)-OH. The crude peptide, C(Fm)Ttds-CCIZN17, was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC were further purified to >95% purity by reverse-phase HPLC on semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of eluent B was used: 35%-50% over 20 min, flow rate 80 mL/min. Analysis of the crude peptide, the eluted fractions and the purified pool was carried out by analytical HPLC on Jupiter C$_4$ column (150×4.6 mm, 5 μm, 300A, Phenomenex), flow rate 1 mL/min, using as eluents: (A) 0.1% TFA in water and (B) 0.1% TFA in acetonitrile. The following gradient of eluent B was used: 40%-60% over 20 min-80% over 3 minutes. The purified peptide was characterized by electrospray mass spectrometry on a Micromass LCZ platform. The theoretical average MW is 5718 Da, and the found MW was 5718 Da.

Synthesis of NH$_2$—C(Fm)(thioIZN17)$_3$—covalent trimerization by formation of thioether bonds—The purified peptide precursor (45 mg), Br-acetyl-GGGIZN17 (peptide 2 in Table 7), was dissolved in 6 M guanidinium chloride, 0.25M Tris HCl, pH 8.5, 2 mM EDTA at a concentration of 0.83 mg/mL. To this solution was added the other peptide precursor, NH$_2$—C(Fm)Ttds-CCIZN17 (peptide 1 in Table 7) (19 mg; 0.35 mg/mL). The actual molar ratio of the two peptide precursors was 2.6:1, Br-acetyl-GGGIZN17: NH$_2$—C(Fm) Ttds-CCIZN17. The trimerization reaction was monitored by LC-MS analysis using a Waters-Micromass LCZ Platform with a Phenomenex, Jupiter C$_4$ column (150×4.6 mm, 5 μm) using as eluents (A) 0.1% TFA in water and (B) 0.1% TFA in acetonitrile. The following gradient of eluent B was used: 40%-60% B (in 20 min)-80% (in 3 min), flow rate 1 mL/min. Under these chromatographic conditions, Br-acetyl-GGGIZN17 elutes at t$_R$=13.17' and NH$_2$—C(Fm)Ttds-CCIZN17 eluted at t$_R$=14.15'. The thioether formation reaction proceeded smoothly. After two hours, two products were formed. The main peak corresponded to a dimeric species (with one thioether bond formed) eluting at t$_R$=17.39' and whose mass corresponds to one molecule comprising one NH$_2$—C(Fm)Ttds-CCIZN17 peptide chain ligated via a thioether bond to an acetyl-GGGIZN17 peptide chain. The second product eluted at t$_R$=17.8' and corresponded to that of one molecule comprising one C(Fm)Ttds-CCIZN17 peptide chain ligated via two thioether bonds to two acetyl-GGGIZN17 peptide chains. The dimeric species reacted overnight to form the trimeric product NH$_2$—C(Fm)(thioIZN17)$_3$. The overall yield of the trimerization reaction was more than 90%. To the solution was added 100 μL of TFA, and the solution was directly purified by reverse-phase HPLC on semi-preparative Waters RCM Delta-Pak™ C$_{-4}$ cartridges (40×200 mm, 15 μm) using as eluents (A) 0.1% TFA in water and (B) 0.1% TFA in acetonitrile. The following gradient of eluent B was used: 0-40% (over 5 min)-60% over 30 min, flow rate 80 mL/min. The eluted fractions were analyzed by HPLC with a Phenomenex, Jupiter C$_4$ column (150×4.6 mm, 5 μm) using as eluents: (A) 0.1% TFA in water and (B) 0.1% TFA in acetonitrile. The following gradient of eluent B was used: 40%-60% B (in 20 min)-80% (in 3 min), flow rate 1 mL/min on the LC-MS Waters-Micromass LCZ Platform in a positive mode (ES$^+$). The expected MW is 15766 Da; while the found MW was 15767 Da.

Deprotection of NH$_2$-terminal cysteine of NH$_2$—C(Fin) (thioIZN17)$_3$ to form NH$_2$—C(thioIZN17)$_3$—The purified coiled-coil precursor, NH$_2$—C(Fm)(thioIZN17)$_3$, was incubated in 10% piperidine in DMF at a concentration of 5 mg/ml. The solution was quenched by addition of TFA and purified by gel permeation chromatography (GPC) on TSK-gel Toyopearl HW-50S resin (700×26 mm column), using 30% acetonitrile in water as eluent, 0.1% TFA, flow rate 1 mL/min. The purified peptide was characterized by electrospray mass spectrometry on a Micromass LCZ platform. The theoretical average MW is 15589 Da, and the found MW was 15589 Da.

Synthesis of ac-C(Acm)Ttds-CCIZN17 (peptide 3 in Table 7)—CCCIZN17 (SEQ ID NO:103) was synthesized following the same protocol as previously described for IZN17. The reaction with Ttds (1-amino-4,7,10-trioxa-13-tridecamine succinic acid (—NH—$(CH_2)_3$—O—$(CH_2)_2$—O—$(CH_2)_2$—O—$(CH_2)_3$—NH—CO—$(CH_2)_2$—CO—) was performed by reaction with a 3-fold excess of Ttds activated with an equimolar amount of DIPC (N,N'-diisopropylcarbodiimide) and HOBt (1-hydroxybenzotriazole), for three hours. The N-terminal residue C(Acm) was acylated as Fmoc-Cys (Acm)-OH. After deprotection of the Fmoc-group, the peptide was acetylated by reaction with a 10-fold excess of acetic anhydride in DMF. The crude peptide, ac-C(Acm)Ttds-CCIZN17 (peptide 3 in Table 7), was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC were further purified to >95% purity by reverse-phase HPLC on semi-preparative Waters RCM Delta-Pak™$C_{-4}$ cartridges (40×200 mm, 15 μm) using as eluents (A) 0.1% TFA in water and (B) 0.1% TFA in acetonitrile. The following gradient of eluent B was used: 35%-50% over 20 min, flow rate 80 mL/min. Analysis of the crude peptide, the eluted fractions and the purified pool was carried out by analytical HPLC on Jupiter $C_4$ column (150×4.6 mm, 5 μm, 300 A, Phenomenex), flow rate 1 mL/min, using as eluents: (A) 0.1% TFA in water and (B) 0.1% TFA in acetonitrile. The following gradient of eluent B was used: 40%-60% over 20 min-80% over 3 minutes. The purified peptide was characterized by electrospray mass spectrometry on a Micromass LCZ platform. The theoretical average MW is 5253 Da, and the found MW was 5254 Da.

Synthesis of ac-C(Acm)(thioIZN17)$_3$—covalent trimerization by formation of thioether bonds—The purified peptide precursor (36.5 mg), Br-acetyl-IZN17 (peptide 2 in Table 7), was dissolved in 6 M guanidinium chloride, 0.25M Tris HCl, pH 8.5, 2 mM EDTA at a concentration of 1.26 mg/mL. To this solution was added the other peptide precursor, ac-C(Acm)Ttds-CCIZN17 (peptide 3 in Table 7) (15 mg; 0.71 mg/mL). The molar ratio of the two peptide precursors was 2.6:1, Br-acetyl-IZN17:ac-C(Acm)Ttds-CCIZN17. The trimerization reaction was monitored by LC-MS analysis using a Waters-Micromass LCZ Platform with a Phenomenex, Jupiter $C_4$ column (150×4.6 mm, 5 μm) using as eluents (A) 0.1% TFA in water and (B) 0.1% TFA in acetonitrile. The following gradient of eluent B was used: 45%-60% B (in 20 min)-80% (in 3 min), flow rate 1 mL/min. The thioether formation reaction proceeded smoothly. After one hour, two products were formed; the main peak corresponded to the trimer, ac-C(Acm)(thioIZN17)$_3$ (with two thioether bonds formed) eluting at $t_R$=15.9' and whose mass corresponds to that of one molecule comprising one ac-C(Acm)Ttds-CCIZN17 peptide chain ligated via two thioether bonds to two Br-acetyl-IZN17 peptide chains. The second product eluted at $t_R$=14.5' and corresponded to that of one molecule comprising one ac-C(Acm)Ttds-CCIZN17 peptide chain ligated via one thioether bond to one Br-acetyl-IZN17 peptide chain. The dimeric species reacted overnight to form the trimeric product ac-C(Acm)(thioIZN17)$_3$. The overall yield of the trimerization reaction was more than 90%. To the solution was added 100 μL of TFA, and the solution was directly purified by gel permeation chromatography (GPC) on TSK-gel Toyopearl HW-50S resin (700×26 mm column), using 30% acetonitrile in water as eluent, 0.1% TFA, flow rate 1 mL/min. The eluted fractions were analyzed by HPLC with a Phenomenex, Jupiter $C_4$ column (150×4.6 mm, 5 μm) using as eluents: (A) 0.1% TFA in water and (B) 0.1% TFA in acetonitrile. The following gradient of eluent B was used: 45%-60% B (in 20 min)-80% (in 3 min), flow rate 1 mL/min on the LC-MS Waters-Micromass LCZ Platform in a positive mode (ES$^+$). The expected MW was 15700 Da; while the found MW was 15702 Da.

Deprotection of NH$_2$-terminal cysteine of ac-C(Acm) (thioIZN17)$_3$ to form ac-C(thioIZN17)$_3$—The purified coiled-coil precursor ac-C(Acm)(thioIZN17)$_3$ was dissolved at a concentration of 20 mg/ml with TFA, anisole 2% and 50 eq. AgOTf (silver trifluoromethanesulfonate) at 4° C. for 3 hours. Ice-cold, dry ether was added to the reaction mixture and the precipitate was isolated by centrifugation. The precipitate washed twice with ice-cold, dry ether. The peptide was redissolved in H$_2$O/acetonitrile, 0.1% TFA and purified by gel permeation chromatography (GPC) on TSK-gel Toyopearl HW-50S resin (700×26 mm column), using 30% acetonitrile in water as eluent, 0.1% TFA, flow rate 1 mL/min. The purified peptide was characterized by electrospray mass spectrometry on a Micromass LCZ platform. The theoretical average MW was 15589 Da, and the found MW was 15589 Da.

Synthesis of Br-acetyl-GGGS17N17 (peptide 5 in Table 7)—GGGS17N17 (SEQ ID NO:106) was synthesized following the same protocol as previously described for IZN17 (see Example 1). The bromoacetylation reaction was performed at the end of the peptide assembly by reaction with a 10-fold excess of bromoacetic anhydride in DMF. The crude peptide, Br-acetyl-S17N17, was purified by gel permeation chromatography (GPC) on TSK-gel Toyopearl HW-50S resin (700×26 mm column), using 30% acetonitrile in water as eluent, 0.1% TFA, flow rate 1 mL/main. The pooled fractions (purity 70%) obtained by GPC were further purified to >95% purity by reverse-phase HPLC on semi-preparative Waters RCM Delta-Pak™ $C_{-4}$ cartridges (40×200 mm, 15 μm) using as eluents (A) 0.1% TFA in water and (B) 0.1% TFA in acetonitrile. The following gradient of eluent B was used: 40%-55% over 20 min, flow rate 80 mL/min. Analysis of the crude peptide, the eluted fractions and the purified pool was carried out by analytical HPLC on Jupiter $C_4$ column (150×4.6 mm, 5 μm, 300 A, Phenomenex), flow rate 1 mL/inn, using as eluents: (A) 0.1% TFA in water and (B) 0.1% TFA in acetonitrile. The following gradient of eluent B was used: 40%-60% over 20 min-80% over 3 minutes. The purified peptide was characterized by electrospray mass spectrometry on a Micromass LCZ platform. The theoretical average MW is 4279 Da, and the found MW was 4279 Da.

Synthesis of ac-C(Acm)Ttds-CCS17N17 (peptide 4 in table 7)—CCCS17N17 (SEQ ID NO:105) was synthesized following the same protocol as previously described for IZN17. The N-terminal residue C(Acm) was acylated as Fmoc-Cys(Acm)-OH. After deprotection of the Fmoc-group, the peptide was acetylated by reaction with a 10-fold excess of acetic anhydride in DMF. The crude peptide, ac-C(Acm) Ttds-CCS17N17, was purified by gel permeation chromatography (GPC) on TSK-gel Toyopearl HW-50S resin (700×26 mm column), using 30% acetonitrile in water as eluent, 0.1% TFA, flow rate 1 mL/min. The pooled fractions (purity 70%) obtained by GPC were further purified to >95% purity by reverse-phase HPLC on semi-preparative Waters RCM Delta-Pak™ $C_{-4}$ cartridges (40×200 mm, 15 μm) using as eluents (A) 0.1% TFA in water and (B) 0.1% TFA in acetonitrile. The following gradient of eluent B was used: 40%-55% over 20 min, flow rate 80 mL/min. Analysis of the crude peptide, the eluted fractions and the purified pool was carried out by analytical HPLC on Jupiter $C_4$ column (150×4.6 mm, 5 µm, 300 A, Phenomenex), flow rate 1 mL/min, using as eluents: (A) 0.1% TFA in water and (B) 0.1% TFA in acetonitrile. The following gradient of eluent B was used: 40%-60% over 20 min-80% over 3 minutes. The purified peptide was characterized by electrospray mass spectrometry on a Micromass LCZ platform. The theoretical average MW is 4826 Da, and the found MW was 4826 Da.

Synthesis of ac-C(Acm)(thioS17N17)$_3$—covalent trimerization by formation of thioether bonds—The purified peptide precursor (64 mg), Br-acetyl-GGGS17N17 (peptide 5 in Table 7), was dissolved in 6.6 mL of 6 M guanidinium chloride, 0.25M Tris HCl, pH 8.5, 2 mM EDTA at a concentration of 10 mg/mL. To this solution was added the other peptide precursor, ac-C(Acm)Ttds-CCS17N17 (peptide 4 in Table 7) (33 mg; 5 mg/mL). The molar ratio of the two peptide precursors was 2.2:1, Br-acetyl-GGGS17N17: ac-C(Acm)Ttds-CCS17N17. The trimerization reaction was monitored by LC-MS analysis using a Waters-Micromass LCZ Platform with a Phenomenex, Jupiter C$_4$ column (150×4.6 mm, 5 µm) using as eluents (A) 0.1% TFA in water and (B) 0.1% TFA in acetonitrile. The following gradient of eluent B was used: 45%-60% B (in 20 min)-80% (in 3 min), flow rate 1 mL/min. The thioether formation reaction proceeded smoothly. After one hour, two products are formed; the main peak corresponds to the trimer, ac-C(Acm)(thioS17N17)$_3$ (with two thioether bonds formed) eluting at $t_R$=16.97' whose mass corresponds to that of one molecule comprising one ac-C(Acm)Ttds-CCS17N17 ligated via two thioether bonds to two Br-acetyl-GGGS17N17 peptide chains. The second product elutes at $t_R$=21.6', corresponds to that of one molecule comprising one ac-C(Acm)Ttds-CCS17N17 ligated via one thioether bond to one Br-acetyl-GGGS17N17 peptide chain. The dimeric species reacts overnight to form the trimeric product ac-C(Acm)(thioS17N17)$_3$. The overall yield of the trimerization reaction is more than 90%. To the solution was added 100 µL of TFA, and the solution was directly purified was purified by gel permeation chromatography (GPC) on TSK-gel Toyopearl HW-50S resin (700×26 mm column), using 30% acetonitrile in water as eluent, 0.1% TFA, flow rate 1 mL/min. The eluted fractions were analyzed by HPLC with a Phenomenex, Jupiter C$_4$ column (150×4.6 mm, 5 µm) using as eluents: (A) 0.1% TFA in water and (B) 0.1% TFA in acetonitrile. The following gradient of eluent B was used: 45%-60% B (in 20 min)-80% (in 3 min), flow rate 1 mL/min on the LC-MS Waters-Micromass LCZ Platform in a positive mode (ES$^+$). The expected MW is 13222 Da; while the found MW was 13221 Da.

Deprotection of NH$_2$-terminal cysteine of ac-C(Acnt)(thioS17N17)$_3$ to form ac-C(thioS17N17)$_3$—The purified peptide precursor, ac-C(Acm)(thioS17N17)$_3$ (15 mg), was dissolved at a concentration 20 mg/mL with glacial acetic acid, anisole 2% and 50 eq. AgOTf (silver trifluoromethanesulfonate) at 4° C. for 10 minutes. 600 µl of H$_2$O/acetonitrile (50/50) was added to the reaction mixture and the solution directly loaded on gel permeation chromatography (GPC) on TSK-gel Toyopearl HW-50S resin (700×26 mm column), using 30% acetonitrile in water as eluent, 0.1% TFA, flow rate 2 mL/min. The eluted fractions were analyzed by HPLC with a Phenomenex, Jupiter C$_4$ column (150×4.6 mm, 5 µm) using as eluents: (A) 0.1% TFA in water and (B) 0.1% TFA in acetonitrile. The following gradient of eluent B was used: 45%-65% B (in 20 min)-80% (in 3 min), flow rate 1 mL/min on the LC-MS Waters-Micromass LCZ Platform in a positive mode (ES$^+$). The theoretical average MW is 13150 Da, and the found MW was 13150 Da.

Covalent immobilization of ac-C-(thioS17N17)$_3$ to SulfoLink Gel—A 2 mL SulfoLink Coupling Gel column (Pierce, Cat. No.: 44895) washed with 8 mL of 100 mM HEPES, 2 mM EDTA, pH adjusted to 8.2. 12 mg of ac-C-(thioS17N17)$_3$, covalent trimer via thioether linkages, was dissolved in 1.668 mL of 100 mM BEPES, 2 mM EDTA, pH adjusted to 8.2, at 7.2 mg/mL peptide concentration. The peptide solution was loaded on the resin, the column gently mixed for 15 min and incubated overnight at room temperature. The solution, containing the unbound peptide, was drained from the column which washed with 7 mL of buffer. The drained peptide solution and column wash solution were collected together for determination of peptide content after coupling. Determination of coupling efficiency was assessed by HPLC/absorbance analysis of the peptide solution before and after the coupling step, taking into consideration the column washing dilution. A 50% reduction of peptide amount was observed, indicating that 6 mg of peptide had been covalently linked to the column. The column was further washed with 2 ml of buffer: no HPLC visible trace of peptide was detected in this eluate. The un-reacted binding sites on gel were blocked by incubation with 2 mL of a 0.05 M solution of cysteine in buffer for 30 minutes at room temperature. Then the column washed with 15 mL of 20 mM HEPES pH 7.2 and stored at 4° C.

Synthesis of Br-acetyl-GGGE10N17 (peptide 6 in Table 7)—GGGE10N17 (SEQ ID NO:110) was synthesized following the same protocol as previously described for IZN17. The bromoacetylation reaction was performed at the end of the peptide assembly by reaction with a 10-fold excess of bromoacetic anhydride in DMF. The crude peptide, Br-acetyl-GGGE10N17, was purified by reverse-phase HPLC on semi-preparative Waters RCM Delta-Pak™ C$_{-4}$ cartridges (40×200 mm, 15 µm) using as eluents (A) 0.1% TFA in water and (B) 0.1% TFA in acetonitrile. The following gradient of eluent B was used: 45%-60% over 20 min, flow rate 80 µL/min. Analysis of the crude peptide, the eluted fractions and the purified pool was carried out by analytical HPLC on Jupiter C$_4$ column (150×4.6 mm, 5 µm, 300 A, Phenomenex), flow rate 1 mL/min, using as eluents: (A) 0.1 TFA in water and (B) 0.1% TFA in acetonitrile. The following gradient of eluent B was used: 55%-70% over 15 min-80% over 3 minutes. The purified peptide was characterized by electrospray mass spectrometry on a Micromass LCZ platform. The theoretical average MW is 3527 Da, and the found MW was 3527 Da.

Synthesis of ac-C(Acm)Ttds-CCE10N17 (peptide 7 in Table 7)—CCCE10N17 (SEQ ID NO:109) was synthesized following the same protocol as previously described for IZN17. The N-terminal residue C(Acm) was acylated as Fmoc-Cys(Acm)-OH. After deprotection of the Fmoc-group, the peptide was acetylated by reaction with a 10-fold excess of acetic anhydride in DMF. The crude peptide, ac-C(Acm)Ttds-CCE10N17, was purified by reverse-phase HPLC on semi-preparative Waters RCM Delta-Pak™ C$_{-4}$ cartridges (40×200 mm, 15 µm) using as eluents (A) 0.1% TFA in water and (B) 0.1% TFA in acetonitrile. The following gradient of eluent B was used: 45%-60% over 20 min, flow rate 80 mL/min. Analysis of the crude peptide, the eluted fractions and the purified pool was carried out by analytical HPLC on Jupiter C$_4$ column (150×4.6 mm, 5 µm, 300 A, Phenomenex), flow rate 1 mL/min, using as eluents: (A) 0.1% TFA in water and (B) 0.1% TFA in acetonitrile. The following gradient of eluent B was used: 50%-70% over 20 min-80% over 3 minutes. The purified peptide was characterized by electrospray mass spectrometry on a Micromass LCZ platform. The theoretical average MW is 4073 Da, and the found MW was 4073 Da.

Synthesis of ac-C(Acm)(thioE10N17)$_3$—covalent trimerization by formation of thioether bonds—The purified peptide precursor, Br-acetyl-GGGE10N17 (peptide 6 in Table 7) (57 mg), was dissolved in 6.0 mL of 6 M guanidinium chloride, 0.25M Tris HCl, pH 8.5, 2 mM EDTA. To this solution was added the other peptide precursor, ac-C(Acm)Ttds-CCE10N17 (peptide 7 in table 7) (30 mg). The molar ratio of the two peptide precursors was 2.2:1, Br-acetyl-GGGE10N17:ac-C(Acm)Ttds-CCE10N17. The trimerization reaction was monitored by LC-MS analysis using a Waters-Micromass LCZ Platform with a Phenomenex, Jupiter $C_4$ column (150×4.6 mm, 5 µm) using as eluents (A) 0.1% TFA in water and (B) 0.1% TFA in acetonitrile. The following gradient of eluent B was used: 50%-80% B (in 23 min), flow rate 1 mL/min. The thioether formation reaction proceeded smoothly. After two hours, we observed quantitative formation of a main product corresponding to the trimer, ac-C(Acm)Ttds-(thioE10N17)$_3$ (with two thioether bonds formed) eluting at $t_R$=19.8' whose mass corresponds to that of one molecule comprising one ac-C(Acm)Ttds-CCE10N17 ligated via two thioether bonds to two Br-acetyl-GGGE10N17 peptide chains. The overall yield of the trimerization reaction is more than 90%. To the solution was added 100 µL of TFA. In these conditions we observed precipitation of the trimeric product which was separated by centrifugation After removing the supernatant, the precipitate was washed twice with an aqueous solution containing O, S % TFA. The peptide pellet was dissolved in water and acetonitrile 50/50 and analyzed by LC-MS Waters-Micromass LCZ Platform in a positive mode (ES$^+$). The expected MW is 13222 Da; while the found MW was 13221 Da freeze-dried.

Deprotection of ac-C(Acm)(thioE10N17)$_3$ to form ac-C(thioE10N17)$_3$—The purified peptide precursor, ac-C(Acm)(thioE10N17)$_3$ (20 mg), was dissolved at a concentration 20 mg/mL with glacial acetic acid, anisole 2% and 50 eq. AgOTf (silver trifluoromethanesulfonate) at 4° C. for 10 minutes. 600 µl of $H_2O$/acetonitrile, 40/60 was added to the reaction mixture and the solution directly loaded on gel permeation chromatography (GPC) on TSK-gel Toyopearl HW-50S resin (700×26 mm column), using 60% acetonitrile in water as eluent, 0.1% TFA, flow rate 1 mL/min. The eluted fractions were analyzed by HPLC with a Phenomenex, Jupiter $C_4$ column (150×4.6 mm, 5 µm) using as eluents: (A) 0.1% TFA in water and (B) 0.1% TFA in acetonitrile. The following gradient of eluent B was used: 60%-80% B (in 23 min), flow rate 1 mL/min on the LC-MS Waters-Micromass LCZ Platform in a positive mode (ES$^+$). The theoretical average MW is 10894 Da, and the found MW was 10894 Da.

Conjugation of ac-C(thioE10N17)$_3$ to OMPC—Various methods of purifying OMPC from the gram-negative bacteria have been devised (Frasch et al., 1997, *J Exp. Med.* 140:87; Frasch et al., 1978, *J. Exp. Med.* 147:629; U.S. Pat. No. 4,707,543; Helting et al., 1981. *Acta Path. Microbiol. Scand. Sect. C.* 89:69; and, U.S. Pat. No. 4,271,147). *N. meningitidis* B improved Outer Membrane Protein Complex (iOMPC) can be obtained using techniques well known in the art such as those described by Fu, U.S. Pat. No. 5,494,808.

To 1.0 mL of *Neisseria meningitidis* improved Outer Membrane Protein Complex (iOMPC) solution (7.13 mg/ml), 0.5 M $NaHCO_3$ (0.114 mL) was added to a final concentration of 50 mM, pH 8.5. To this was added, drop-wise, 0.308 mL of a 20 µM solution of the heterobifunctional crosslinker sulfosuccinimidyl 4-(N-maleimidomethyl)cyclohexane-1-carboxylate (sSMCC, Pierce Chemical Co.) with a 2-fold excess (with respect to lysine residues of OMPC, 0.42 µmol lysine/mg OMPC protein). The pH was readjusted by further addition of 0.034 mL 0.5 M $NaHCO_3$. After aging the solution for 1 hour in the dark at 4° C., the pH was lowered to neutrality by adding a 1 M $NaH_2PO_4$ solution (14.8 µl). The solution was dialyzed at 4° C. using 300K MWCO DispoDialyser (Spectrum Laboratories Inc., CA) with 6-buffer changes (every 2 h) of 2 L 20 mM HEPES pH 7.3 (4-(2-Hydroxyethyl)piperazine-1-ethanesulfonic acid), 2 mM EDTA (Ethylenediaminetetracetic acid) to remove excess reagents. A total of 1.57 mL of activated OMPC (aOMPC) was recovered after dialysis.

A 1.9 mg/ml stock solution of the Cys-containing peptide ac-C(thioE10N17)$_3$ was prepared in degassed solution of 0.1 M HEPES, 2 mM EDTA pH 7.3. To define the maximum amount of peptide ligand that could be safely incorporated on aOMPC without causing precipitation, the conjugation reaction was first followed in small-scale trials where the aOMPC was incubated with increasing amounts of peptide ligand. The maximum number of maleimide groups that can be incorporated on the OMPC is limited by the total lysine residues on the OMPC, namely 0.42 µmoles lysine/mg OMPC. If one considers an average MW of $40 \times 10^6$ Da for OMPC, this corresponds to 16,000 lysine moles/OMPCmol. Of these, only a portion can be activated with sSMCC (up to 35%), which corresponds to a maximum peptide load attainable of about 5000 moles. Therefore, aOMPC was incubated with the following molar excesses of peptide ligand per OMPC mol: 500, 1000, 2000, 3000, 4000. After one hour, the samples were compared with an aOMPC sample to check for the presence of any precipitation or enhancement of turbidity. In the case of ac-C(thioE10N17)$_3$, which has a favorable pI of 4.25, no precipitation or increase of turbidity was visible up to the highest molar excess of ligand used, 4000 moles/OMPC mol.

On the basis of these observations a large-scale reaction was performed: to 1 mL (4.65 mg) of aOMPC in 20 mM HEPES, 2 mM EDTA pH 7.3, was added 2.64 mL of the peptide stock solution, drop-wise while gently vortexing, which corresponds to 4000 molar excess of peptide moles/OMPC mol. A sample of maleimide-activated OMPC solution was retained as blank for the determination of the peptide loading of the final conjugate. The conjugation reaction mixture was allowed to age for 17 h at 4° C. in the dark. Any residual maleimide groups on the OMPC were then quenched with µ-mercaptoethanol to a final concentration of 15 mM (3.8 µL total volume added) for 1 h at 4° C. in the dark. The solution was dialyzed 4×, 4 hour/change, with 1 L of 20 mM HEPES pH 7.3 at 4° C. with 300K MWCO DispoDialyser to remove unconjugated peptide and β-mercaptoethanol. The concentration was determined by Lowry assay (Lowry et al., 1951, *J. Biol. Chem.* 193:265), revealing 0.98 mg/mL for the OMPC-(thioE10N17)$_3$. The conjugate and aOMPC samples were hydrolyzed in evacuated, sealed glass tubes with azeotropic HCl for 70 h at 110° C. The amino acid composition was determined by amino acid analysis. The conjugation load of peptide to OMPC protein was determined by comparing the conjugate amino acid composition with both that of the OMPC carrier and that of peptide ligand and by multiple regression, least squares analysis of the data (Shuler et al., 1992, *J. Immunol. Methods* 156:137-149). For the conjugate OMPC-(thioE10N17)$_3$, a molar ratio of peptide versus OMPC mole of 2264 was obtained.

Synthesis of Br-acetyl-GGGE17GluN17. (peptide 8 in Table 7)—The peptide is synthesized by solid phase on a Pioneer Peptide Synthesizer (Applied Biosystems). The resin used is the Fmoc-Linker AM-Champion, 1% cross-linked (Biosearch Technologies, Inc.), a PEG-PS based resin derivatized with a modified Rink linker p-[(R,S)-α-[9H-Fluoren-9-yl-methoxyformamido]-2,4-dimethoxybenzyl]-phenoxyacetic acid (Rink, H., 1987, *Tetrahedron Lett.* 28:3787-3789;

Bernatowicz, M. S. et al., 1989, *Tetrahedron Lett.* 30:4645-4667). All the acylation reactions are performed for 90 minutes with 4-fold excess of activated amino acid over the resin free amino groups. Amino acids were activated with equimolar amounts of HBTU (2-(1H-benzotriazole-1-yl)-1,1,3,3-tetramethyluronium hexafluorophosphate) and a 2-fold molar excess of DIEA (N,N-diisopropylethylamine). A standard Fmoc/t-Bu chemistry is used. The side chain protecting groups are as follows: tert-butyl for glutamic acid (Glu) and threonine (Thr); trityl for cysteine (Cys) and glutamine (Gln); tert-butoxy-carbonyl for lysine (Lys) and tryptophan (Trp); and, 2,2,4,6,7-pentamethyldihydrobenzofuran-5-sulfonyl for arginine (Arg). At the end of the amino acid assembly, the N-terminal group is bromoacetylated by reaction with a 10-fold excess of bromoacetic anhydride in DMF. At the end of the synthesis of Bracetyl-E17GluN17, the dry peptide-resin is treated with 88% trifluoroacetic acid (TFA), 5% phenol, 2% triisopropylsilane and 5% water (Sole, N. A. and G. Barany, 1992, *J. Org. Chem.* 57:5399-5403) for 1.5 hours at room temperature. The resin is filtered and the solution is added to cold methyl-t-butyl ether in order to precipitate the peptide. After centrifugation, the peptide pellets are washed with fresh, cold methyl-t-butyl ether to remove the organic scavengers. The process is repeated twice. The final pellets are dried, resuspended in $H_2O$, 20% acetonitrile and lyophilized.

The crude peptide Br-acetyl GGGE17GluN17 (SEQ ID NO:123) is purified by gel permeation chromatography (GPC) on a 700×26 mm column packed with a Toyopearl HW-50S resin, using 60% acetonitrile in water, 0.1% TFA as eluent. In a typical run, 900 mg of crude peptide is dissolved in 25 mL of eluent and directly loaded on the column, flow rate 1 mL/min. Analytical HPLC of eluted fractions is performed on a Beckman HPLC with a Phenomenex, Jupiter $C_4$ column (150×4.6 mm, 5 µm). On the basis of the purity, the fractions are pooled and further purified by reverse phase HPLC using semi-preparative Waters RCM Delta-Pak™ $C_{-4}$ cartridges (40×200 mm, 15 µm) and using as eluents (A) 0.1% TFA in water and (B) 0.1% TFA in acetonitrile. The purified peptide is characterized by electrospray mass spectrometry on a Micromass LCZ platform spectrometer.

Synthesis of Ac-C(Acm)Ttds-CCE17GluN17 (peptide 9 in Table 7)—The peptide is assembled on solid phase as described for Br-acetyl GGGE17GluN17. The reaction with Ttds (1-amino-4,7,10-trioxa-13-tridecamine succinic acid (—NH—$(CH_2)_3$—O—$(CH_2)_2$—O—$(CH_2)_2$—O—$(CH_2)_3$—NH—CO—$CH_2)_2$—CO—) is performed by reaction with a 4-fold excess of Ttds activated with an equimolar amount of HBTU and a 2-fold molar excess of DIEA for two hours. The N-terminal residue C(Acm) is acylated in the same condition as above as Fmoc-Cys(Acm)-OH and then after Fmoc deprotection the peptide is acetylated by reaction with a 10-fold excess of acetic anhydride in DMF. After cleavage from resin as described for previous example, the crude peptide, acetyl-C(Acm)Ttds-CCE17GluN17 (peptide 9 in Table 7), is purified by gel permeation chromatography (GPC) on TSK-gel Toyopearl HW-50S resin (700×26 mm column), using 60% acetonitrile in water as eluent, 0.1% TFA, flow rate 1 mL/min. The pooled fractions obtained by GPC are further purified to >95% purity by reverse-phase HPLC on semi-preparative Waters RCM Delta-Pak™ $C_{-4}$ cartridges (40×200 mm, 15 µm) using as eluents (A) 0.1% TFA in water and (B) 0.1% TFA in acetonitrile. Analysis of the crude peptide, the eluted fractions and the purified pool was carried out by analytical HPLC on Jupiter $C_4$ column (150×4.6 mm, 5 µm, 300 A, Phenomenex), flow rate 1 mL/min, using as eluents: (A) 0.1% TFA in water and (B) 0.1% TFA in acetonitrile. The purified peptide is characterized by electrospray mass spectrometry on a Micromass LCZ platform.

Synthesis of Acetyl-C(Acm)(thioE17GluN17)$_3$—covalent trimerization by formation of thioether bonds—The purified peptide precursor, Br-acetyl-GGGE17GluN17 (peptide 8 in Table 7), is dissolved in 6 M guanidinium chloride, 0.25M Tris HCl, pH 8.5, 2 mM EDTA at a concentration of 5 mg/mL. To this solution is added the other peptide precursor, Acetyl-C(Acm)Ttds-CCE17GluN17 (peptide 9 in Table 7). The actual molar ratio of the two peptide precursors is 2.2:1, Br-acetyl-GGGE17GluN17: Acetyl-C(Acm)Ttds-CCE17GluN17. The trimerization reaction is monitored by LC-MS analysis using a Waters-Micromass LCZ Platform with a Phenomenex, Jupiter $C_4$ column (150×4.6 mm, 5 µm) using as eluents (A) 0.1% TFA in water and (B) 0.1% TFA in acetonitrile. After two hours, one product is formed, whose mass corresponds to one molecule comprising one Acetyl-C(Acm)Ttds-CCE17GluN17 peptide chain ligated via two thioether bonds to two acetyl-GGGE17GluN17 peptide chains. To the solution is added 20 µL of TFA, and the solution is directly purified by gel permeation chromatography (GPC) on TSK-gel Toyopearl HW-50S resin (700×26 mm column), using 60% acetonitrile in water as eluent, 0.1% TFA, flow rate 1 mL/min. The eluted fractions are analyzed by HPLC with a Phenomenex, Jupiter $C_4$ column (150×4.6 mm, 5 µm) using as eluents: (A) 0.1% TFA in water and (B) 0.1% TFA in acetonitrile on the LC-MS Waters-Micromass LCZ Platform in a positive mode (ES$^+$).

Deprotection of the acetylated-cysteine of ac-C(Acm)(thioE17GluN17)$_3$ to form ac-C(thioE17GluN17)$_3$—The purified coiled-coil precursor ac-C(Acm)(thioE17GluN17)$_3$ is dissolved at a concentration of 20 mg/ml with TFA, anisole 2% and 50 eq. AgOTf (silver trifluoromethanesulfonate) at 4° C. for 3 hours. Ice-cold, dry ether is added to the reaction mixture and the precipitate is isolated by centrifugation. The precipitate is washed twice with ice-cold, dry ether. The peptide is redissolved in $H_2O$/acetonitrile, 0.1% TFA and purified by gel permeation chromatography (GPC) on TSK-gel Toyopearl HW-50S resin (700×26 mm column), using 60% acetonitrile in water as eluent, 0.1% TFA, flow rate 1 mL/min. The purified peptide is characterized by electrospray mass spectrometry on a Micromass LCZ platform.

Synthesis of Br-acetyl-GGGEZN17 (peptide 10 in Table 7)—The peptide is synthesized by solid phase on a Pioneer Peptide Synthesizer (Applied Biosystems) as previously described for Br-acetyl-GGGE17GluN17 (peptide 8 µl Table 7). The crude peptide Br-acetyl-GGGEZN17 (SEQ ID NO:121) is purified by gel permeation chromatography (GPC) on a 700×26 mm column packed with a Toyopearl HW-50S resin, using 60% acetonitrile in water, 0.1% TFA as eluent. In a typical run, 900 mg of crude peptide is dissolved in 25 mL of eluent and directly loaded on the column, flow rate 1 mL/min. Analytical HPLC of eluted fractions is performed on a Beckman HPLC with a Phenomenex, Jupiter $C_4$ column (150×4.6 mm, 5 µm). On the basis of the purity, the fractions are pooled and further purified by reverse phase HPLC using semi-preparative Waters RCM Delta-Pak™ $C_{-4}$ cartridges (40×200 mm, 15 µm) and using as eluents (A) 0.1% TFA in water and (B) 0.1% TFA in acetonitrile. The purified peptide is characterized by electrospray mass spectrometry on a Micromass LCZ platform spectrometer.

Synthesis of Ac-C(Acm)Ttds-CCEZN17 (peptide 11 in Table 7)—The peptide is assembled on solid phase as described for Ac-C(Acm)Ttds-CCE17GluN17 (peptide 9 in Table 7). After cleavage from resin as described for previous example, the crude peptide, acetyl-C(Acm)Ttds-CCEZN17 (peptide 11 in Table 7), is purified by gel permeation chromatography (GPC) on TSK-gel Toyopearl HW-50S resin (700×26 mm column), using 60% acetonitrile in water as eluent, 0.1% TFA, flow rate 1 mL/min. The pooled fractions obtained by GPC are further purified to >95% purity by reverse-phase HPLC on semi-preparative Waters RCM Delta-Pak™ $C_{1-4}$ cartridges (40×200 mm, 15 µm) using as eluents (A) 0.1% TFA in water and (B) 0.1% TFA in acetonitrile. Analysis of the crude peptide, the eluted fractions and the purified pool was carried out by analytical HPLC on Jupiter $C_4$ column (150×4.6 mm, 5 µm, 300 A, Phenomenex), flow rate 1 mL/min, using as eluents: (A) 0.1% TFA in water and (B) 0.1% TFA in acetonitrile. The purified peptide is characterized by electrospray mass spectrometry on a Micromass LCZ platform.

Synthesis of Acetyl-C(Acm)(thioEZN17)$_3$—covalent trimerization by formation of thioether bonds—The purified peptide precursor, Br-acetyl-GGGE2N17 (peptide 10 in Table 7), is dissolved in 6 M guanidinium chloride, 0.25M Tris HCl, pH 8.5, 2 mM EDTA at a concentration of 5 mg/mL. To this solution is added the other peptide precursor, Acetyl-C(Acm)Ttds-CCEZN17 (peptide 11 in Table 7). The actual molar ratio of the two-peptide precursors is 2.2:1, Br-acetyl-GGGEZN17: Acetyl-C(Acm)Ttds-CCEZN17. The trimerization reaction is monitored by LC-MS analysis using a Waters-Micromass LCZ Platform with a Phenomenex, Jupiter $C_4$ column (150×4.6 mm, 5 µm) using as eluents (A) 0.1% TFA in water and (B) 0.1% TFA in acetonitrile. After two hours, one product is formed, whose mass corresponds to one molecule comprising one Acetyl-C(Acm)Ttds-CCEZN17 peptide chain ligated via two thioether bonds to two acetyl-GGGEZN17 peptide chains. To the solution is added 20 µL of TFA, and the solution is directly purified by gel permeation chromatography (GPC) on TSK-gel Toyopearl HW-50S resin (700×26 mm column), using 60% acetonitrile in water as eluent, 0.1% TFA, flow rate 1 mL/min. The eluted fractions are analyzed by HPLC with a Phenomenex, Jupiter $C_4$ column (150×4.6 mm, 5 µm) using as eluents: (A) 0.1% TFA in water and (B) 0.1% TFA in acetonitrile on the LC-MS Waters-Micromass LCZ Platform in a positive mode (ES$^+$).

Deprotection of the acetylated-cysteine of ac-C(Acm)(thioEZN17)$_3$ to form ac-C(thioEZN17)$_3$—The purified coiled-coil precursor ac-C(Acm)(thioEZN17)$_3$ is dissolved at a concentration of 20 mg/ml with TFA, anisole 2% and 50 eq. AgOTf (silver trifluoromethanesulfonate) at 4° C. for 3 hours. Ice-cold, dry ether is added to the reaction mixture and the precipitate is isolated by centrifugation. The precipitate is washed twice with ice-cold, dry ether. The peptide is redissolved in H$_2$O/acetonitrile, 0.1% TFA and purified by gel permeation chromatography (GPC) on TSK-gel Toyopearl HW-50S resin (700×26 mm column), using 60% acetonitrile in water as eluent, 0.1% TFA, flow rate 1 mL/min. The purified peptide is characterized by electrospray mass spectrometry on a Micromass LCZ platform.

Conjugation of ac-C(thioE17GluN17)$_3$ and ac-C(thioEZN17)$_3$ to OMPC—Various methods of purifying OMPC from the gram-negative bacteria have been devised (Frasch et al., 1997, supra; Frasch et al., 1978, supra; U.S. Pat. No. 4,707,543; Helting et al., 1981, supra; and, U.S. Pat. No. 4,271,147). *N. meningitidis* B improved Outer Membrane Protein Complex (iOMPC) can be obtained using techniques well known in the art such as those described by Fu, U.S. Pat. No. 5,494,808.

To 1.36 mL of *Neisseria meningitidis* improved Outer Membrane Protein Complex (iOMPC) solution (7.13 mg/ml), 0.5 M NaHCO$_3$ (0.151 mL) is added to a final concentration of 50 nM, pH 8.5. To this is added, drop-wise, 0.407 mL of a 20 µM solution of the heterobifunctional crosslinker sulfosuccinimidyl 4-(N-maleimidomethyl)cyclohexane-1-carboxylate (sSMCC, Pierce Chemical Co.) with a 2-fold excess (with respect to lysine residues of OMPC, 0.42 µmol lysine/mg OMPC protein). The pH is readjusted by further addition of 0.045 mL 0.5 M NaHCO$_3$. After aging the solution for 1 hour in the dark at 4° C., the pH is lowered to neutrality by adding a 1 M NaH$_2$PO$_4$ solution (16 µl). The solution is dialyzed at 4° C. using 300K MWCO DispoDialyser (Spectrum Laboratories Inc., CA) with 6-buffer changes (every 2 h) of 2 L 20 mM HEPES pH 7.3 (4-(2-Hydroxyethyl)piperazine-1-ethanesulfonic acid), 2 mM EDTA (Ethylenediaminetetracetic acid) to remove excess reagents. A total of 1.9 mL of activated OMPC (aOMPC) is recovered after dialysis.

A 0.5 mg/ml stock solutions of the two Cys-containing peptides ac-C(thioE17GluN17)$_3$ and ac-C(thioEZN17)$_3$ are prepared in degassed solution of 0.1 M HEPES, 2 mM EDTA pH 7.3. To define the maximum amount of peptide ligand that can be safely incorporated on aOMPC without causing precipitation, the conjugation reaction is first followed in small-scale trials where the aOMPC is incubated with increasing amounts of peptide ligand. The maximum number of maleimide groups that can be incorporated on the OMPC is limited by the total lysine residues on the OMPC, namely 0.42 µmoles lysine/mg OMPC. If one considers an average MW of 40×10$^6$ Da for OMPC, this corresponds to 16,000 lysine moles/OMPCmol. Of these, only a portion can be activated with sSMCC (up to 35%), which corresponds to a maximum peptide load attainable of about 5000 moles. In this case, aOMPC is incubated with the following molar excesses of peptide ligand per OMPC mol: 1000, 2000, 3000. After one hour, the samples are compared with an aOMPC sample to check for the presence of any precipitation or enhancement of turbidity. Large scale conjugation reactions are performed at the highest molar excesses of peptide/OMPC mol by adding peptide stock solutions, drop-wise while gently vortexing.

A sample of maleimide-activated OMPC solution is retained as blank for the determination of the peptide loading of the final conjugate. The conjugation reaction mixture is allowed to age for 17 h at 4° C. in the dark. Any residual maleimide groups on the OMPC are then quenched with β-mercaptoethanol to a final concentration of 15 mM for 1 h at 4° C. in the dark. The solutions are dialyzed 4×, 4 hour/change, with 1 L of 20 mM HEPES pH 7.3 at 4° C. with 300K MWCO DispoDialyser to remove unconjugated peptides and β-mercaptoethanol. The concentrations are determined by Lowry assay (Lowry et al., 1951, supra). The conjugate and aOMPC samples are hydrolyzed in evacuated, sealed glass tubes with azeotropic HCl for 70 h at 110° C. The amino acid composition is determined by amino acid analysis. The conjugation load of peptide to OMPC protein is determined by comparing the conjugate amino acid composition with both that of the OMPC carrier and that of peptide ligand and by multiple regression, least squares analysis of the data (Shuler et al., 1992, supra).

Results—Several chemoselective ligation reactions have been proposed for the synthesis of complex biomolecules. Generally chemoselectivity of the ligation is imposed by incorporating unique, mutually reactive groups—one within each peptide segment to be joined (reviewed in Lemieux G. A. and Bertozzi C. R., 1998, *Trends Biotechnol.* 16: 506-513; and Borgia, J. A. and Fields G. B., 2000, *Trends Biotechnol.* 15:243-251). One of these chemoselective approaches involves the formation of thioether bonds. The formation of a thioether bond can be accomplished by including a unique cysteine residue with its nucleophilic sulfhydryl on one peptide/biomolecule and an electrophilic bromoacetyl unit on the other peptide/biomolecule to be joined (see Muir, T. W. et al., 1994, *Biochemistry* 33:7701-7708; Zeng, W. et al., 2001, *Vaccine* 19:3843-3852; and Schelte, P. et al., 2000, *Bioconjugate Chem.* 11:118).

A strategy is described herein for the covalent stabilization of trimeric coiled-coil mimetics of the present invention. The strategy is based on chemoselective formation of two thioether bonds between one CC-chimeric N-peptide chain containing a pair of unprotected cysteine residues and two derivatized-chimeric N-peptides, each further comprising an electrophilic bromoacetyl moiety. In the current example, the cysteine-containing peptide has an additional, suitably-protected cysteine residue which can be deprotected after trimerization is completed.

This strategy is exemplified with the production of $NH_2$—C(Fm)(thioIZN17)$_3$. First, two peptide precursors were synthesized:

1) $NH_2$—C(Fm)Ttds-CCIZN17 (peptide 1 in Table 7): a peptide having two cysteine residues separated from the scaffold domain through a flexible spacer (-GG-; other flexible spacers are suitable) and a third cysteine residue with a protected thiol group for conjugation (a fluorenylmethoxy (Fm) protecting group is used, but other protecting groups are suitable); and, 2) bromoacetyl-GGGIZN17 (peptide 2 in Table 7): a peptide having a bromoacetyl moiety separated from the scaffold domain through a flexible linker (-GGG-; other flexible spacers are suitable, provided they are compatible with the formation of two thioether bonds between two derivatized-chimeric N-peptide chains and one CC-chimeric N-peptide).

TABLE 7

Examples of IZN17-, S17-, E10-, EZ-, E17-, and E17Glu-based chimeric peptides for participation in chemoselective ligation reactions generating thioether bonds between said peptides.

| Peptide No.[1] | Peptide Name | Peptide characteristics[2] |
|---|---|---|
| 1 | $NH_2$-C(Fm)Ttds-CCIZN17 | $NH_2$-*C*(Fm) <u>Ttds-</u> <u><u>CCGG</u></u>IKKEIEAIKKEQEA IKKKIEAIEKLLQLTVWGIKQLQARIL (SEQ ID NO:103) |
| 2 | Br-acetyl-GGGIZN17 | Br-acetyl-<u><u>GGG</u></u>IKKEIEAIKKEQEAIKKKI EAIEKLLQLTVWGIKQLQARIL (SEQ ID NO:104) |
| 3 | ac-C(Acm)Ttds-CCIZN17 | Acetyl-*C*(Acm) <u>Ttds-</u> <u><u>CCGG</u></u>IKKEIEAIKK EQEAIKKKIEAIEKLLQLTVWGTKQLQARIL (SEQ ID NO:103) |
| 4 | ac-C(Acm)Ttds-CCS17N17 | Acetyl-*C*(Acm) <u>Ttds-</u> <u><u>CCGG</u></u>IEKKIEAIEK KIEAIEKLLQLTVWGIKQLQARIL (SEQ ID NO:105) |
| 5 | Br-acetyl-GGGS17N17 | Br-acetyl-<u><u>GGG</u></u>IEKKIEAIEKKIEAIEKLL QLTVWGIKQLQARIL (SEQ ID NO:106) |
| 6 | Br-acetyl-GGGE10N17 | Br-acetyl-<u><u>GGG</u></u>IEEKIEEIEELLQLTVWGI KQLQARIL (SEQ ID NO:110) |

TABLE 7-continued

Examples of IZN17-, S17-, E10-, EZ-, E17-, and E17Glu-based chimeric peptides for participation in chemoselective ligation reactions generating thioether bonds between said peptides.

| Peptide No.[1] | Peptide Name | Peptide characteristics[2] |
|---|---|---|
| 7 | ac-C(Acm)Ttds-CCE10N17 | Acetyl-*C*(Acm) <u>Ttds-</u> <u><u>CCGG</u></u>IEEKIEEIEE LLQLTVWGIKQLQARIL (SEQ ID NO:111) |
| 8 | Br-acetyl-GGGE17GluN17 | Br-acetyl-<u><u>GGG</u></u>IEKKIEEIEEKIEEIEKLL QLTVWGIKQLQARIL (SEQ ID NO:123) |
| 9 | ac-C(Acm)Ttds-CCE17GluN17 | Acetyl-*C*(Acm) <u>Ttds-</u> <u><u>CCGG</u></u>IEKKIEEIEE KIEEIEKLLQLTVWGIKQLQARIL (SEQ ID NO:124) |
| 10 | Br-acetyl-GGGEZN17 | Br-acetyl-<u><u>GGG</u></u>IEKKIEEIEKKIEEIEKKI EEIEKLLQLTVWGIKQLQARIL (SEQ ID NO:121) |
| 11 | ac-C(Acm)Ttds-CCEZN17 | Acetyl-*C*(Acm) <u>Ttds-</u> <u><u>CCGG</u></u>IEKKIEEIEK KIEEIEKKIEEIEKLLQLTVWGIKQLQARIL (SEQ ID NO:122) |
| 12 | Br-acetyl-GGGE17N17 | Br-acetyl-<u><u>GGG</u></u>IEKKIEEIEKKIEEIEKLL QLTVWGIKQLQARIL (SEQ ID NO:125) |
| 13 | ac-C(Acm)Tds-CCE17N17 | Acetyl-*C*(Acm) <u>Ttds-</u> <u><u>CCGG</u></u>IEKKIEEIEK KIEEIEKLLQLTVWGIKQLQARIL (SEQ ID NO:126) |

[1] Peptide sequence 1 has a free amino group on the $NH_2$-terminal cysteine.
[2] in italics, non-HIV residues; single-underlined, "cysteine-" portion of CC-chimeric N-peptides (including cysteine residues and glycine linker); double-underlined, linker region of derivatized-chimeric N-peptides (glycine residues) or CC-chimeric N-peptides (synthetic Ttds linker).

The two peptide precursors, $NH_2$—C(Fm)Ttds-CCIZN17 (peptide 1 in Table 7) and Br-acetyl-GGGIZN17 (peptide 2 in Table 7), were dissolved in a degassed solution of 25 mM TRIS-HCl buffer, pH 8-8.5, GuHCl 6M, EDTA 2 mM, with a concentration ratio of 1:2.6, respectively. The chemoselective ligation reaction proceeded with formation of two thioether bonds, wherein each bromoderivative of the Br-acetyl-GGGIZN17 peptides reacts with one of the two cysteine residues of the $NH_2$—C(Fm)Ttds-CCIZN17 peptide. This chemoselective ligation reaction forms the covalently-stabilized trimer named $NH_2$—C(Fm)(thioIZN17)$_3$. $NH_2$—C(Fm)(thioIZN17)$_3$ was tested for antiviral activity against HIV-1 HXB2 (single cell infectivity assay, as described in Example 3) and was found to have an $IC_{50}$ of 1.1 nM, comparable to that of covalently-stabilized, homotrimeric coiled-coil (CCIZN17)$_3$.

In order to have a suitable precursor for conjugation reactions, it is necessary to remove the Fm-protecting group of the $NH_2$-terminal cysteine residue of the $NH_2$—C(Fm)(thioIZN17)$_3$ trimer. The deprotection reaction was performed by incubating the trimer at 5 mg/ml in 10% piperidine in DMF. Under these conditions, a relatively low yield of the final product, $NH_2$—C(thioIZN17)$_3$, was purified. Therefore, a new trimer, ac-C(Acm)(thioIZN17)$_3$, was designed having Acm (acetamidomethyl group) as the protecting group for the NH$_2$-terminal cysteine residue. A new peptide precursor, ac-C(Acm)Ttds-CCIZN17 (peptide 3 in Table 7), was first produced, and the chemoselective reaction with two Br-acetyl-GGGIZN17 molecules was accomplished following the same protocol as described for NH$_2$—C(Fm)(thioIZN17)$_3$, generating ac-C(Acm)(thioIZN17)$_3$. The stabilized coiled-coil, ac-C(thioIZN17)$_3$, was synthesized by deprotection of the Acm-group within the ac-C(Acm)Ttds-CCIZN17 peptide of the heterotrimer and shows an IC$_{50}$ of 0.24 nM against HIV-HXB2 in anti-viral activity assays.

A covalent trimer based on the S17N17 (SEQ ID NO:99) sequence stabilized by thioether bonds was also produced, ac-C(Acm)(thioS17N17)$_3$. Two peptide precursors, Br-acetyl-GGGS17N17 (peptide 5 in Table 7) and ac-C(Acm)Ttds-CCS17N17 (peptide 4 in Table 7), were synthesized to enable the formation of the trimeric construct stabilized by thioether bonds. The covalent trimer ac-C(Acm)(thioS17N17)$_3$ was tested for antiviral activity against HIV-1 HXB2 (single cell infectivity assay, as described in Example 3) and was found to have an IC$_{50}$ of 0.27 nM, comparable to that of covalently-stabilized, trimeric coiled-coils (CCS17N17)$_3$ and (CCIZN17)$_3$.

Deprotection of the acetamidomethyl group from the NH$_2$-terminal cysteine residue generated the trimeric construct, ac-C(thioS17N17)$_3$, having a free thiol group for conjugation to either a carrier protein or a resin to produce a suitable affinity resin for the purification of antigen specific antibodies. The trimeric peptide mimetic, ac-C(thioS17N17)$_3$, was successfully used in the preparation of a SulphoLink-(thioS17N17)$_3$ resin.

A covalent trimer based on the E10N17 (SEQ ID NO:108) sequence stabilized by thioether bonds was also produced, ac-C(Acm)(thioE10N17)$_3$. Two peptide precursors, Br-acetyl-GGGE10N17 (peptide 6 in Table 7) and ac-C(Acm)Ttds-CCE10N17 (peptide 7 in Table 7), were synthesized to enable the formation of the trimeric construct stabilized by thioether bonds. The E10 (SEQ ID NO:107) scaffold was generated by mutating three amino acid residues of the S10 (SEQ ID NO:113) scaffold. The resulting E10N17 (SEQ ID NO:108) peptide, with a pI of 4.2, is a good candidate for OMPC conjugation. The trimer, ac-C(Acm)(thioE10N17)$_3$, showed even increased stability to thermal denaturation with respect to (CCS10N17)$_3$, showing a melting temperature above 90° C. in the presence of 2M guanidinium chloride. The trimeric peptide precursor, ac-C(Acm)(thioE10N17)$_3$, was treated with a solution of silver trifluoromethansulfonate in acetic acid to remove the acetamidomethyl protecting group from the NH$_2$-terminal cysteine residue. The reactivity of the free thiol was assessed by reaction with a maleimidyl-biotin product (Pierce), which also enabled the preparation of the biotinylated(thioE10N17)$_3$ peptide useful for antisera screening by ELISA. The trimer ac-C(thioE10N17)$_3$ was then incubated with the maleimidated OMPC carrier, previously activated with SMCC (Pierce). Various molar excesses of peptide moles/OMPC mole were tested (e.g., 1000, 2000, 3000, and 4000); and no precipitation was observed, even at the highest ratio. Thus, a large-scale conjugation reaction was set at the 4000 molar ratio. The conjugation molar ratio achieved was determined by Lowry assay and amino acid analysis, demonstrating an excellent value of 2260 moles of peptide/OMPC mole.

The two trimeric peptides (CCS10N17)$_3$ and ac-C(Acm)(thioE10N17)$_3$ were tested for antiviral activity against HIV-1 HXB2 (single cell infectivity assay, as described in Example 3) and were found to have much lower potencies with respect to trimers having longer scaffold as peptides (CCS17N17)$_3$ and (CCIZN17)$_3$, as shown in FIG. 13.

Thioether bond-stabilized, trimeric structures can also be generated using EZ- or EZ-like-scaffolded chimeric peptides (see Example 6, supra). For example, two peptide precursors, Br-acetyl-GGGEZN17 (peptide 10 in Table 7) and ac-C(Acm)Ttds-CCEZN17 (peptide 11 in Table 7), can be synthesized to enable the formation of a trimeric peptide precursor, ac-C(Acm)(thioEZN17)$_3$, stabilized by thioether bonds. The scaffold domain of this trimeric coiled-coil is comprised of the EZ scaffold domain (SEQ ID NO:32). Similarly, two peptide precursors, Br-acetyl-GGGE17N17 (peptide 12 in Table 7) and ac-C(Acm)Ttds-CCE17N17 (peptide 13 in Table 7), can be synthesized to enable the formation of a trimeric peptide precursor, ac-C(Acm)(thioE17N17)$_3$, stabilized by thioether bonds and having the shortened EZ scaffold, E17 (SEQ ID NO: 114). Furthermore, two peptide precursors, Br-acetyl-GGGE17GluN17 (peptide 8 in Table 7) and ac-C(Acm)Ttds-CCE17GluN17 (peptide 9 in Table 7), can be synthesized to enable the formation of a trimeric peptide precursor, ac-C(Acm)(thioE17GluN17)$_3$, stabilized by thioether bonds and having the shortened and mutated (i.e., a single Lys to Glu mutation) E17-like scaffold, E17Glu (SEQ ID NO:119). The EZ and EZ-like scaffolds of these coiled-coils facilitate conjugation of the trimeric structures to OMPC because, as demonstrated, e.g., in Table 8 with the EZ and E17Glu scaffold domains, said scaffold proteins help to reduce the overall pI of the coiled-coil. Each of these trimeric precursor can be treated with a solution of silver trifluoromethansulfonate in acetic acid to remove the acetamidomethyl protecting group from the NH$_2$-terminal cysteine residue, forming the thiolated peptides, e.g., C(thioEZN17)$_3$ and C(thioE17GluN17)$_3$, peptides 5 and 3, respectively; each acetylated at the NH$_2$-terminus. These thiolated peptides can be used to prepare peptide conjugates to the maleiamide activated OMPC carrier.

TABLE 8

Comparison of the isoelectric point ("pI") of various mimetics of HIV gp41 fusion intermediates described as part of the present invention.

| Coiled-Coil No. | Gp41 Mimetics[1] | pI |
| --- | --- | --- |
| 1 | (CCEZN17)$_3$ | 5.30 |
| 2 | Ac—C(Acm)-(thioE17GluN17)$_3$ | 4.73 |
| 3 | Ac—C-(thioE17GluN17)$_3$ | 4.73 |
| 4 | Ac—C(Acm)-(thioEZN17)$_3$ | 5.30 |
| 5 | Ac—C-(thioEZN17)$_3$ | 5.30 |

[1]"Acm," acetamidomethyl protection group; "Ac," acetylated NH$_2$-terminus

EXAMPLE 12

Generation of D5-Competitive Antibodies by Immunization with (CCIZN17)$_3$

Sera from (CCIZN17)$_3$-immunized rabbits contain D5-competitive antibodies—Six rabbits were immunized intramuscularly with (CCIZN17)$_3$ mixed with either QS21 adjuvant or a combination of Alum and QS21 adjuvants. At approximately 8 weeks post-immunization, serum samples from these animals were tested for the presence of D5 IgG-competitive antibodies. Such antibodies were detected in crude serum and in protein-A purified antibody fractions (data not shown). Neither crude serum nor purified antibodies produced antiviral activity.

To enrich for antibodies capable of interacting with the hydrophobic pocket located within the heptad repeat 1 (HR1)

region of the gp41 ectodomain, immuno-affinity purification was performed using 5-Helix (Root, M. J. et al., 2001, supra), a distinct peptide that also contains the hydrophobic pocket. Pooled rabbit serum from several post-8 week bleeds was subjected to protein-A chromatography which yielded approximately 800 mg of purified IgG. This material was percolated over a 5-Helix column. The column washed with PBS and the bound antibodies were eluted using an acidic buffer. All column fractions, including washes, flow-through, and eluants were tested for presence of D5-competing antibodies using a 5-Helix/D5-FITC interaction assay. The washes did not contain significant amounts of D5-competitive antibodies but several flow-though and eluant fractions did contain detectable D5-competitive antibodies (see FIG. 15A). In fact, the concentration of D5-competitive antibodies in eluant fractions 5 and 6 corresponded to 10 times the $IC_{50}$ of the D5 IgG against the HIV-HXB2 isolate.

Antibodies elicited by $(CCIZ17)_3$ immunization and immunoaffinity purified on 5-Helix possess specific inhibitory activity against HIV-1—Fractions 5 and 6 were concentrated 10-fold and tested for antiviral activity in the HIV single cycle infectivity assay (see Example 3). Both eluants S and 6 displayed a concentration-dependent inhibitory effect on HIV-HXB2 infection (see FIG. 15B, left panel). These fractions which produced $IC_{50}$s of 4-5 µM (Eluant 5—4.1 µM; Eluant 6—5.0 µM) were approximately 3-4-fold less potent than the D5 IgG in this viral assay (D5 IgG—1.35 µM; FIG. 15B, left panel). Neither fraction produced inhibitory activity when tested against HIV particles pseudotyped with a heterologous viral envelope derived from the Rhabdovirus VSV (FIG. 15B, right panel).

Polyclonal rabbit antibodies elicited by $(CCIZN17)_3$ immunization bind the hydrophobic pocket formed in the heptad-repeat 1 region—An AlphaScreen-based (Perkin Elmer) assay (see Example 4) was devised to formally demonstrate that $(CCIZN17)_3$ elicited rabbit polyclonal antibodies interacted with the HR1 hydrophobic pocket. The 5-Helix immunoaffinity purified rabbit antibodies corresponding to eluant fractions 5 and 6 were pooled and titrated against biotinylated 5-Helix in the presence of streptavidin coated donor beads and protein-A coated acceptor beads. These latter beads specifically capture antibodies. Peak signals were generated when 1-10 mM 5-Helix was combined with 250 µg/ml of antibody (FIG. 16A). These results demonstrate the presence of antibodies capable of interacting with 5-Helix. Since the immunogen, $(CCIZN17)_3$, used to elicit these antibodies only has the hydrophobic pocket in common with 5-Helix, these findings suggest that a subset of antibodies in these fractions interact with the HR1 hydrophobic pocket.

To test this hypothesis directly, peptides C34 (Chan et al., 1997, supra), which binds the entire HR1 groove, and D10-p5-2K (Eckert et al., 1999, supra), which specifically interacts with the hydrophobic pocket, were evaluated for ability to interfere with the binding of these rabbit polyclonal antibodies with 5-Helix. When increasing concentrations of C34 peptide were incubated with 5-Helix prior to the addition of the rabbit antibodies, a profound inhibition of the attachment of antibody to 5-Helix was observed (FIG. 16B). Although less potent, the peptide D10-p5-2K (L-472 in FIG. 16B) also produced concentration-dependent suppression of the binding of antibody to 5-Helix. A negative control peptide (C8) had only a mild effect in this interaction assay at the highest concentration tested. These results further demonstrate that a subset of rabbit polyclonal antibodies elicited by $(CCIZN17)_3$ immunization specifically interact with the HR1 hydrophobic pocket which contains the epitope of the HIV-neutralizing mAb D5.

Antibodies elicited by $(CCIZN17)_3$ immunization that are purified using protein-A—Immunoglobulin-G (IgG) from the sera of rabbits immunized with $(CCIZN17)_3$ was purified using protein-A chromatography. To assess whether these IgG preparations have antiviral activity, they were titrated in an HIV-1 single-cycle infectivity assay (see Example 3). Clear concentration-dependent antiviral activity was observed in this assay when the IgG preparation was titrated against the HIV-1 strain HXB2 (see FIG. 17A). The antiviral activity (IC50=9511 ug/ml) of this IgG preparation was significantly less potent than that observed with the human monoclonal antibody D5 (IC50=144.1 ug/ml). These rabbit IgGs were also capable of inhibiting infection by the CCR5-utilizing HIV-1 strain BaL but the activity appeared less potent when compared to the activity observed against HIV-HXB2 (see FIG. 17B). These results indicate that $(CCIZN17)_3$-immunization elicits polyclonal antibodies that inhibit HIV-1 infection in vitro.

Finally, to determine whether the rabbit IgG-associated antiviral activity was specific for the HIV-1 envelope, the IgG preparation was tested against an isogenic HIV-1 clone carrying a heterologous viral envelope (VSV-G) derived from the Vesicular Stomatitis Virus (FIG. 17C). No inhibitory activity was observed against this virus pseudotype indicating that the antiviral activity associated with these IgGs derived from $(CCIZN17)_3$ immunized rabbits is specific for HIV-1.

---

What is claimed is:

1. A soluble chimeric peptide which comprises:
   (a) a scaffold portion comprising a soluble, α-helical region capable of forming a trimeric coiled-coil;
   (b) a N-peptide portion comprising all or a portion of the HIV gp41 NH$_2$-terminal heptad repeat domain; and,
   (c) a cysteine portion comprising at least two cysteine residues;
   wherein said scaffold portion in (a) is fused in helical phase to said N-peptide portion in (b), forming an α-helical domain, and said cysteine portion in (c) is located outside of said α-helical domain at either the NH$_2$- or COOH-terminus.

2. The chimeric peptide of claim 1, wherein said N-peptide portion is fused to the COOH-terminus of the scaffold portion of said peptide.

3. The chimeric peptide of claim 2, wherein said N-peptide portion comprises a sufficient portion of the HIV gp41NH$_2$-terminal heptad repeat domain to include amino acid residues which form the N-helix coiled-coil hydrophobic pocket.

4. The chimeric peptide of claim 3, wherein said N-peptide portion comprises N17 (LLQLTVWGIKQLQARIL (SEQ ID NO:44)).

5. The chimeric peptide of claim 2, wherein the scaffold portion of said peptide comprises all or a portion of a coiled-coil motif selected from the group consisting of:
   (a) the Suzuki-IZ coiled-coil motif (YGGIEKKIEAIEK-KIEAIEKKIEAIEKKIEA (SEQ ID NO:29)), or a modified form thereof;
   (b) the IZ coiled-coil motif (IKKEIEAIKKEQEAIKK-KIEAIEK (SEQ ID NO:31)), or a modified form thereof;

(c) the EZ coiled-coil motif (IEKKIEEIEKKIEEIEK-KIEEIEK (SEQ ID NO:32)), or a modified form thereof; and;
(d) the SZ coiled-coil motif (IEKKIEAIEKKIEAIEK-KIEAIEK SEQ ID NO: 112), or a modified form thereof.

6. The chimeric peptide of claim 5, wherein the scaffold portion of said peptide comprises the IZ coiled-coil motif.

7. The chimeric peptide of claim 2, wherein the cysteine portion of said peptide is located at the $NH_2$-terminus of the α-helical domain of said peptide.

8. The chimeric peptide of claim 7, wherein said cysteine portion is separated from said α-helical domain by a spacer region.

9. The chimeric peptide of claim 2, wherein the cysteine portion is located at the COOH-terminus of the α-helical domain of said peptide.

10. The chimeric peptide of claim 7, wherein the cysteine portion comprises three consecutive cysteine residues.

11. The chimeric peptide of claim 10, wherein said cysteine portion is separated from said α-helical domain by a spacer region.

12. The chimeric peptide of claim 10, wherein the $NH_2$-terminal cysteine residue has a protected thiol group.

13. A soluble chimeric peptide comprising an amino acid sequence selected from the group consisting of
  (a) SEQ ID NO:2, designated as CCIZN17;
  (b) SEQ ID NO:7, designated as CCEZN17;
  (c) SEQ ID NO:5, designated as CCIZN17Ala4;
  (d) SEQ ID NO:9, designated as CCEZN17Ala4;
  (e) SEQ ID NO:13, designated as CCIZN23;
  (f) SEQ ID NO:15, designated as CCEZN23;
  (g) SEQ ID NO:12, designated as Biotin-CCIZN23;
  (h) SEQ ID NO:21, designated as SCCIZN17;
  (i) SEQ ID NO:98, designated as CCSZN17;
  (j) SEQ ID NO:100, designated as CCS17N17;
  (k) SEQ ID NO:109, designated as CCE10N17;
  (l) SEQ ID NO:116, designated as CCE17N17;
  (m) SEQ ID NO:120, designated as CCE17GluN17; and,
  (n) SEQ ID NO:18, designated as CCIZN36.

14. A covalently-stabilized, trimeric coiled-coil that mimics all or a portion of the internal, trimeric coiled-coil motif of HIV gp41 comprising three chimeric peptides, wherein each chimeric peptide comprises:
  (a) a soluble α-helical domain fused in helical phase to all or a portion of the HIV gp41 $NH_2$-terminal heptad repeat domain; and,
  (b) a cysteine portion comprising at least two cysteine residues located outside of said α-helical domain at the $NH_2$-terminus of said α-helical domain;
  wherein said chimeric peptides are covalently-stabilized as a coiled-coil via disulfide bonds between said cysteine residues of individual peptides.

15. A covalently-stabilized, trimeric coiled-coil that mimics all or a portion of the internal, trimeric coiled-coil motif of HIV gp41 which comprises:
  (a) one chimeric peptide comprising:
    a soluble α-helical domain fused in helical phase to all or a portion of the HIV gp41 $NH_2$-terminal heptad repeat domain; and,
    (ii) a cysteine portion comprising at least two cysteine residues located outside of the α-helical domain of said peptide at the $NH_2$-terminus of said α-helical domain; and,
  (b) two chimeric peptides comprising a soluble α-helical domain fused in helical phase to all or a portion of the HIV gp41 $NH_2$-terminal heptad repeat domain, each derivatized with an electrophilic moiety at the $NH_2$-terminus of said α-helical domain present in said two chimeric peptides;
  wherein a nucleophilic sulfhydryl of each cysteine residue in the chimeric peptide in (a) forms a thioether bond with the electrophilic moiety of each derivatized chimeric peptide in (b).

16. A covalently-stabilized, trimeric coiled-coil that mimics all or a portion of the internal, trimeric coiled-coil motif of HIV-1 gp41 selected from the group consisting of:
  (a) $(CCIZN17)_3$ ([SEQ ID NO:2]$_3$);
  (b) $(CCEZN17)_3$ ([SEQ ID NO:7]$_3$);
  (c) $(CCIZN17Ala4)_3$ ([SEQ ID NO:5]$_3$);
  (d) $(CCEZN17Ala4)_3$ ([SEQ ID NO:9]$_3$);
  (e) $(CCIZN23)_3$ ([SEQ ID NO:13]$_3$);
  (f) $(CCEZN23)_3$ ([SEQ ID NO:15]$_3$);
  (g) $(Biotin-CCIZN23)_3$ ([SEQ ID NO:12]$_3$);
  (h) $(SCCIZN17)_3$ ([SEQ ID NO:21]$_3$);
  (i) $C(thiolZN17)_3$;
  (j) $C(thioS17N17)_3$;
  (k) $C(thioE10N17)_3$;
  (l) $C(thioEZN17)_3$;
  (m) $C(thioE17N17)_3$;
  (n) $C(thioE17GluN17)_3$; and,
  (o) $(CCIZN36)_3$ ([SEQ ID NO:18]$_3$).

17. A soluble chimeric peptide which comprises:
  (a) a scaffold portion comprising a soluble, α-helical region capable of forming a trimeric coiled-coil; and,
  (b) a N-peptide portion comprising all or a portion of the HIV gp41 $NH_2$-terminal heptad repeat domain;
  wherein said chimeric peptide is derivatized to incorporate an electrophilic moiety capable of forming a thioether bond,
  wherein said scaffold portion in (a) is fused in helical phase to said N-peptide portion in (b), forming an α-helical domain, and said electrophilic moiety is located outside of said α-helical domain.

18. The chimeric peptide of claim 17, wherein said electrophilic moiety is selected from the group consisting of an alkyl halide moiety and a Michael acceptor.

19. The chimeric peptide of claim 18, wherein said alkyl halide moiety is a bromoacetyl moiety.

20. The covalently-stabilized trimeric coiled-coil of claim 16 that is (SEQ ID NO:18)$_3$.

21. The chimeric peptide of claim 7, wherein said scaffold portion comprises a sequence selected from the group consisting of:
  SEQ ID NO: 29;
  SEQ ID NO: 30;
  SEQ ID NO: 31;
  SEQ ID NO: 32;
  SEQ ID NO: 35;
  SEQ ID NO: 36;
  SEQ ID NO: 37;
  SEQ ID NO: 38;
  SEQ ID NO: 39;
  SEQ ID NO: 40;
  SEQ ID NO: 112;
  SEQ ID NO: 114; and
  SEQ ID NO: 119.

22. The chimeric peptide of claim 21, wherein said N-peptide portion comprises a sequence selected from the group consisting of:
  SEQ ID NO: 44;
  SEQ ID NO: 46;
  SEQ ID NO: 48;
  SEQ ID NO: 50;

SEQ ID NO: 51;
SEQ ID NO: 52; and
SEQ ID NO: 53.

23. The chimeric peptide of claim 22, wherein said N-peptide portion consists of a sequence selected from the group consisting of:
SEQ ID NO: 44;
SEQ ID NO: 46;
SEQ ID NO: 48;
SEQ ID NO: 50;
SEQ ID NO: 51;
SEQ ID NO: 52; and
SEQ ID NO: 53.

24. The chimeric peptide of claim 23, wherein said cysteine portion consists of the sequence of SEQ ID NO: 28.

25. The chimeric peptide of claim 7, wherein said chimeric peptide consists of SEQ ID NO: 18.

26. A covalently-stabilized, trimeric coiled-coil that mimics all or a portion of a HIV gp41 N-peptide coiled-coil comprising three chimeric peptides, wherein each chimeric peptide is as described in claim 7, wherein said three chimeric peptides are covalently-stabilized as a coiled-coil via disulfide bonds between cysteine residues present in said cysteine portion of each of said three chimeric peptides.

27. The trimeric coiled-coil of claim 26, wherein said trimeric coiled-coil is homotrimeric.

28. The trimeric coiled-coil of claim 27, wherein said scaffold portion of each chimeric peptide comprises a sequence selected from the group consisting of:
SEQ ID NO: 29;
SEQ ID NO: 30;
SEQ ID NO: 31;
SEQ ID NO: 32;
SEQ ID NO: 35;
SEQ ID NO: 36;
SEQ ID NO: 37;
SEQ ID NO: 38;
SEQ ID NO: 39;
SEQ ID NO: 40;
SEQ ID NO: 112;
SEQ ID NO: 114; and
SEQ ID NO: 119.

29. The trimeric coiled-coil of claim 28, wherein said N-peptide portion of each chimeric peptide comprises a sequence selected from the group consisting of:
SEQ ID NO: 44;
SEQ ID NO: 46;
SEQ ID NO: 48;
SEQ ID NO: 50;
SEQ ID NO: 51;
SEQ ID NO: 52; and
SEQ ID NO: 53.

30. The trimeric coiled-coil of claim 29, wherein said N-peptide portion of each chimeric peptide consists of a sequence selected from the group consisting of:
SEQ ID NO: 44;
SEQ ID NO: 46;
SEQ ID NO: 48;
SEQ ID NO: 50;
SEQ ID NO: 51;
SEQ ID NO: 52; and
SEQ ID NO: 53.

31. The trimeric coiled-coil of claim 30, wherein said cysteine portion of each chimeric peptide consists of the sequence of SEQ ID NO: 28.

* * * * *

SEQUENCE LISTING

<160> NUMBER OF SEQ ID NOS: 126

<210> SEQ ID NO 1
<211> LENGTH: 41
<212> TYPE: PRT
<213> ORGANISM: Artificial Sequence
<220> FEATURE:
<223> OTHER INFORMATION: Synthetic peptide

<400> SEQUENCE: 1

Ile Lys Lys Glu Ile Glu Ala Ile Lys Lys Glu Gln Glu Ala Ile Lys
 1               5                   10                  15

Lys Lys Ile Glu Ala Ile Glu Lys Leu Leu Gln Leu Thr Val Trp Gly
             20                  25                  30

```
Ile Lys Gln Leu Gln Ala Arg Ile Leu
        35                  40

<210> SEQ ID NO 2
<211> LENGTH: 45
<212> TYPE: PRT
<213> ORGANISM: Artificial Sequence
<220> FEATURE:
<223> OTHER INFORMATION: Synthetic peptide

<400> SEQUENCE: 2

Cys Cys Gly Gly Ile Lys Lys Glu Ile Glu Ala Ile Lys Lys Glu Gln
1               5                   10                  15

Glu Ala Ile Lys Lys Lys Ile Glu Ala Ile Glu Lys Leu Leu Gln Leu
            20                  25                  30

Thr Val Trp Gly Ile Lys Gln Leu Gln Ala Arg Ile Leu
        35                  40                  45

<210> SEQ ID NO 3
<211> LENGTH: 44
<212> TYPE: PRT
<213> ORGANISM: Artificial Sequence
<220> FEATURE:
<223> OTHER INFORMATION: Synthetic peptide

<400> SEQUENCE: 3

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Leu Leu Gln Leu Thr
            20                  25                  30

Val Trp Gly Ile Lys Gln Leu Gln Ala Arg Ile Leu
        35                  40

<210> SEQ ID NO 4
<211> LENGTH: 41
<212> TYPE: PRT
<213> ORGANISM: Artificial Sequence
<220> FEATURE:
<223> OTHER INFORMATION: Synthetic peptide

<400> SEQUENCE: 4

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Lys Ala Leu Ala Ala Ala Ile Ala
        35                  40

<210> SEQ ID NO 5
<211> LENGTH: 45
<212> TYPE: PRT
<213> ORGANISM: Artificial Sequence
<220> FEATURE:
<223> OTHER INFORMATION: Synthetic peptide

<400> SEQUENCE: 5

Cys Cys Gly Gly Ile Lys Lys Glu Ile Glu Ala Ile Lys Lys Glu Gln
1               5                   10                  15

Glu Ala Ile Lys Lys Lys Ile Glu Ala Ile Glu Lys Leu Leu Gln Leu
            20                  25                  30

Thr Val Trp Gly Ile Lys Ala Leu Ala Ala Ala Ile Ala
        35                  40                  45
```

```
<210> SEQ ID NO 6
<211> LENGTH: 41
<212> TYPE: PRT
<213> ORGANISM: Artificial Sequence
<220> FEATURE:
<223> OTHER INFORMATION: Synthetic peptide

<400> SEQUENCE: 6

Ile Glu Lys Lys Ile Glu Glu Ile Glu Lys Lys Ile Glu Glu Ile Glu
 1               5                  10                  15

Lys Lys Ile Glu Glu Ile Glu Lys Leu Leu Gln Leu Thr Val Trp Gly
            20                  25                  30

Ile Lys Gln Leu Gln Ala Arg Ile Leu
        35                  40

<210> SEQ ID NO 7
<211> LENGTH: 45
<212> TYPE: PRT
<213> ORGANISM: Artificial Sequence
<220> FEATURE:
<223> OTHER INFORMATION: Synthetic peptide

<400> SEQUENCE: 7

Cys Cys Gly Gly Ile Glu Lys Lys Ile Glu Glu Ile Glu Lys Lys Ile
 1               5                  10                  15

Glu Glu Ile Glu Lys Lys Ile Glu Glu Ile Glu Lys Leu Leu Gln Leu
            20                  25                  30

Thr Val Trp Gly Ile Lys Gln Leu Gln Ala Arg Ile Leu
            35                  40                  45

<210> SEQ ID NO 8
<211> LENGTH: 41
<212> TYPE: PRT
<213> ORGANISM: Artificial Sequence
<220> FEATURE:
<223> OTHER INFORMATION: Synthetic peptide

<400> SEQUENCE: 8

Ile Glu Lys Lys Ile Glu Glu Ile Glu Lys Lys Ile Glu Glu Ile Glu
 1               5                  10                  15

Lys Lys Ile Glu Glu Ile Glu Lys Leu Leu Gln Leu Thr Val Trp Gly
            20                  25                  30

Ile Lys Ala Leu Ala Ala Ala Ile Ala
        35                  40

<210> SEQ ID NO 9
<211> LENGTH: 45
<212> TYPE: PRT
<213> ORGANISM: Artificial Sequence
<220> FEATURE:
<223> OTHER INFORMATION: Synthetic peptide

<400> SEQUENCE: 9

Cys Cys Gly Gly Ile Glu Lys Lys Ile Glu Glu Ile Glu Lys Lys Ile
 1               5                  10                  15

Glu Glu Ile Glu Lys Lys Ile Glu Glu Ile Glu Lys Leu Leu Gln Leu
            20                  25                  30

Thr Val Trp Gly Ile Lys Ala Leu Ala Ala Ala Ile Ala
            35                  40                  45

<210> SEQ ID NO 10
```

```
<211> LENGTH: 48
<212> TYPE: PRT
<213> ORGANISM: Artificial Sequence
<220> FEATURE:
<223> OTHER INFORMATION: Synthetic peptide

<400> SEQUENCE: 10

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Ala Gln Gln His Leu
            20                  25                  30

Leu Gln Leu Thr Val Trp Gly Ile Lys Gln Leu Gln Ala Arg Ile Leu
        35                  40                  45

<210> SEQ ID NO 11
<211> LENGTH: 50
<212> TYPE: PRT
<213> ORGANISM: Artificial Sequence
<220> FEATURE:
<223> OTHER INFORMATION: Synthetic peptide

<400> SEQUENCE: 11

Gly Gly Ile Lys Lys Glu Ile Glu Ala Ile Lys Lys Glu Gln Glu Ala
1               5                   10                  15

Ile Lys Lys Lys Ile Glu Ala Ile Glu Lys Glu Ile Glu Ala Gln Gln
            20                  25                  30

His Leu Leu Gln Leu Thr Val Trp Gly Ile Lys Gln Leu Gln Ala Arg
        35                  40                  45

Ile Leu
    50

<210> SEQ ID NO 12
<211> LENGTH: 53
<212> TYPE: PRT
<213> ORGANISM: Artificial Sequence
<220> FEATURE:
<223> OTHER INFORMATION: Synthetic peptide

<400> SEQUENCE: 12

Gly Cys Cys Gly Gly Ile Lys Lys Glu Ile Glu Ala Ile Lys Lys Glu
1               5                   10                  15

Gln Glu Ala Ile Lys Lys Lys Ile Glu Ala Ile Glu Lys Glu Ile Glu
            20                  25                  30

Ala Gln Gln His Leu Leu Gln Leu Thr Val Trp Gly Ile Lys Gln Leu
        35                  40                  45

Gln Ala Arg Ile Leu
    50

<210> SEQ ID NO 13
<211> LENGTH: 52
<212> TYPE: PRT
<213> ORGANISM: Artificial Sequence
<220> FEATURE:
<223> OTHER INFORMATION: Synthetic peptide

<400> SEQUENCE: 13

Cys Cys Gly Gly Ile Lys Lys Glu Ile Glu Ala Ile Lys Lys Glu Gln
1               5                   10                  15

Glu Ala Ile Lys Lys Lys Ile Glu Ala Ile Glu Lys Glu Ile Glu Ala
            20                  25                  30

Gln Gln His Leu Leu Gln Leu Thr Val Trp Gly Ile Lys Gln Leu Gln
        35                  40                  45
```

Ala Arg Ile Leu
    50

<210> SEQ ID NO 14
<211> LENGTH: 48
<212> TYPE: PRT
<213> ORGANISM: Artificial Sequence
<220> FEATURE:
<223> OTHER INFORMATION: Synthetic peptide

<400> SEQUENCE: 14

Ile Glu Lys Lys Ile Glu Glu Ile Glu Lys Lys Ile Glu Glu Ile Glu
1               5                   10                  15

Lys Lys Ile Glu Glu Ile Glu Glu Lys Ile Glu Ala Gln Gln His Leu
            20                  25                  30

Leu Gln Leu Thr Val Trp Gly Ile Lys Gln Leu Gln Ala Arg Ile Leu
        35                  40                  45

<210> SEQ ID NO 15
<211> LENGTH: 52
<212> TYPE: PRT
<213> ORGANISM: Artificial Sequence
<220> FEATURE:
<223> OTHER INFORMATION: Synthetic peptide

<400> SEQUENCE: 15

Cys Cys Gly Gly Ile Glu Lys Lys Ile Glu Glu Ile Glu Lys Lys Ile
1               5                   10                  15

Glu Glu Ile Glu Lys Lys Ile Glu Glu Ile Glu Glu Lys Ile Glu Ala
            20                  25                  30

Gln Gln His Leu Leu Gln Leu Thr Val Trp Gly Ile Lys Gln Leu Gln
        35                  40                  45

Ala Arg Ile Leu
    50

<210> SEQ ID NO 16
<211> LENGTH: 62
<212> TYPE: PRT
<213> ORGANISM: Artificial Sequence
<220> FEATURE:
<223> OTHER INFORMATION: Synthetic peptide

<400> SEQUENCE: 16

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Ser Gly Ile Val Gln Gln
            20                  25                  30

Gln Asn Asn Leu Leu Arg Ala Ile Glu Ala Gln Gln His Leu Leu Gln
        35                  40                  45

Leu Thr Val Trp Gly Ile Lys Gln Leu Gln Ala Arg Ile Leu
        50                  55                  60

<210> SEQ ID NO 17
<211> LENGTH: 65
<212> TYPE: PRT
<213> ORGANISM: Artificial Sequence
<220> FEATURE:
<223> OTHER INFORMATION: Synthetic peptide

<400> SEQUENCE: 17

Gly Lys Gly Ile Lys Lys Glu Ile Glu Ala Ile Lys Lys Glu Gln Glu
1               5                   10                  15

```
Ala Ile Lys Lys Lys Ile Glu Ala Ile Glu Lys Glu Ile Ser Gly Ile
            20                  25                  30

Val Gln Gln Gln Asn Asn Leu Leu Arg Ala Ile Glu Ala Gln Gln His
        35                  40                  45

Leu Leu Gln Leu Thr Val Trp Gly Ile Lys Gln Leu Gln Ala Arg Ile
    50                  55                  60

Leu
65

<210> SEQ ID NO 18
<211> LENGTH: 66
<212> TYPE: PRT
<213> ORGANISM: Artificial Sequence
<220> FEATURE:
<223> OTHER INFORMATION: Synthetic peptide

<400> SEQUENCE: 18

Cys Cys Gly Gly Ile Lys Lys Glu Ile Glu Ala Ile Lys Lys Glu Gln
 1               5                  10                  15

Glu Ala Ile Lys Lys Lys Ile Glu Ala Ile Glu Lys Glu Ile Ser Gly
            20                  25                  30

Ile Val Gln Gln Gln Asn Asn Leu Leu Arg Ala Ile Glu Ala Gln Gln
        35                  40                  45

His Leu Leu Gln Leu Thr Val Trp Gly Ile Lys Gln Leu Gln Ala Arg
    50                  55                  60

Ile Leu
65

<210> SEQ ID NO 19
<211> LENGTH: 62
<212> TYPE: PRT
<213> ORGANISM: Artificial Sequence
<220> FEATURE:
<223> OTHER INFORMATION: Synthetic peptide

<400> SEQUENCE: 19

Ile Glu Lys Lys Ile Glu Glu Ile Glu Lys Lys Ile Glu Glu Ile Glu
 1               5                  10                  15

Lys Lys Ile Glu Glu Ile Glu Glu Lys Ile Ser Gly Ile Val Gln Gln
            20                  25                  30

Gln Asn Asn Leu Leu Arg Ala Ile Glu Ala Gln Gln His Leu Leu Gln
        35                  40                  45

Leu Thr Val Trp Gly Ile Lys Gln Leu Gln Ala Arg Ile Leu
    50                  55                  60

<210> SEQ ID NO 20
<211> LENGTH: 31
<212> TYPE: PRT
<213> ORGANISM: Artificial Sequence
<220> FEATURE:
<223> OTHER INFORMATION: Synthetic peptide

<400> SEQUENCE: 20

Cys Cys Gly Gly Ile Lys Lys Lys Ile Glu Ala Ile Glu Lys Leu Leu
 1               5                  10                  15

Gln Leu Thr Val Trp Gly Ile Lys Gln Leu Gln Ala Arg Ile Leu
            20                  25                  30

<210> SEQ ID NO 21
<211> LENGTH: 48
```

<212> TYPE: PRT
<213> ORGANISM: Artificial Sequence
<220> FEATURE:
<223> OTHER INFORMATION: Synthetic peptide

<400> SEQUENCE: 21

Ser Gly Gly Cys Cys Gly Gly Ile Lys Lys Glu Ile Glu Ala Ile Lys
1               5                   10                  15

Lys Glu Gln Glu Ala Ile Lys Lys Ile Glu Ala Ile Glu Lys Leu
            20                  25                  30

Leu Gln Leu Thr Val Trp Gly Ile Lys Gln Leu Gln Ala Arg Ile Leu
        35                  40                  45

<210> SEQ ID NO 22
<211> LENGTH: 41
<212> TYPE: PRT
<213> ORGANISM: Artificial Sequence
<220> FEATURE:
<223> OTHER INFORMATION: Synthetic peptide

<400> SEQUENCE: 22

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Asp
            20                  25                  30

Ile Lys Gln Leu Gln Ala Arg Ile Leu
        35                  40

<210> SEQ ID NO 23
<211> LENGTH: 45
<212> TYPE: PRT
<213> ORGANISM: Artificial Sequence
<220> FEATURE:
<223> OTHER INFORMATION: Synthetic peptide

<400> SEQUENCE: 23

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Leu Gln Leu
            20                  25                  30

Thr Val Trp Gly Ile Lys Gln Leu Gln Ala Arg Ile Leu
        35                  40                  45

<210> SEQ ID NO 24
<211> LENGTH: 52
<212> TYPE: PRT
<213> ORGANISM: Artificial Sequence
<220> FEATURE:
<223> OTHER INFORMATION: Synthetic peptide

<400> SEQUENCE: 24

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Ile Glu Ala
            20                  25                  30

Gln Gln His Leu Leu Gln Leu Thr Val Trp Gly Ile Lys Gln Leu Gln
        35                  40                  45

Ala Arg Ile Leu
    50

<210> SEQ ID NO 25
<211> LENGTH: 66

```
<212> TYPE: PRT
<213> ORGANISM: Artificial Sequence
<220> FEATURE:
<223> OTHER INFORMATION: Synthetic peptide

<400> SEQUENCE: 25

Arg Met Lys Gln Ile Glu Asp Lys Ile Glu Glu Ile Glu Ser Lys Gln
 1               5                  10                  15

Lys Lys Ile Glu Asn Glu Ile Ala Arg Ile Lys Lys Leu Ile Ser Gly
             20                  25                  30

Ile Val Gln Gln Gln Asn Asn Leu Leu Arg Ala Ile Glu Ala Gln Gln
         35                  40                  45

His Leu Leu Gln Leu Thr Val Trp Gly Ile Lys Gln Leu Gln Ala Arg
     50                  55                  60

Ile Leu
65

<210> SEQ ID NO 26
<211> LENGTH: 49
<212> TYPE: PRT
<213> ORGANISM: Artificial Sequence
<220> FEATURE:
<223> OTHER INFORMATION: Synthetic peptide

<400> SEQUENCE: 26

Cys Cys Gly Gly Arg Met Lys Gln Ile Glu Asp Lys Ile Glu Glu Ile
 1               5                  10                  15

Glu Ser Lys Gln Lys Lys Ile Glu Asn Glu Ile Ala Arg Ile Lys Lys
             20                  25                  30

Leu Leu Gln Leu Thr Val Trp Gly Ile Lys Gln Leu Gln Ala Arg Ile
         35                  40                  45

Leu

<210> SEQ ID NO 27
<211> LENGTH: 49
<212> TYPE: PRT
<213> ORGANISM: Artificial Sequence
<220> FEATURE:
<223> OTHER INFORMATION: Synthetic peptide

<400> SEQUENCE: 27

Cys Cys Gly Gly Arg Met Lys Gln Ile Glu Asp Lys Ile Glu Glu Ile
 1               5                  10                  15

Glu Ser Lys Gln Lys Lys Ile Glu Asn Glu Ile Ala Arg Ile Lys Lys
             20                  25                  30

Leu Leu Gln Leu Thr Val Trp Gly Ile Lys Ala Leu Ala Ala Ala Ile
         35                  40                  45

Ala

<210> SEQ ID NO 28
<211> LENGTH: 4
<212> TYPE: PRT
<213> ORGANISM: Artificial Sequence
<220> FEATURE:
<223> OTHER INFORMATION: Synthetic sequence

<400> SEQUENCE: 28

Cys Cys Gly Gly
 1

<210> SEQ ID NO 29
```

```
<211> LENGTH: 31
<212> TYPE: PRT
<213> ORGANISM: Artificial Sequence
<220> FEATURE:
<223> OTHER INFORMATION: Synthetic sequence

<400> SEQUENCE: 29

Tyr Gly Gly Ile Glu Lys Lys Ile Glu Ala Ile Glu Lys Lys Ile Glu
1               5                   10                  15

Ala Ile Glu Lys Lys Ile Glu Ala Ile Glu Lys Lys Ile Glu Ala
            20                  25                  30

<210> SEQ ID NO 30
<211> LENGTH: 33
<212> TYPE: PRT
<213> ORGANISM: Artificial Sequence
<220> FEATURE:
<223> OTHER INFORMATION: Synthetic sequence

<400> SEQUENCE: 30

Arg Met Lys Gln Ile Glu Asp Lys Ile Glu Glu Ile Leu Ser Lys Gln
1               5                   10                  15

Tyr His Ile Glu Asn Glu Ile Ala Arg Ile Lys Lys Leu Ile Gly Glu
            20                  25                  30

Arg

<210> SEQ ID NO 31
<211> LENGTH: 24
<212> TYPE: PRT
<213> ORGANISM: Artificial Sequence
<220> FEATURE:
<223> OTHER INFORMATION: Synthetic sequence

<400> SEQUENCE: 31

Ile Lys Lys Glu Ile Glu Ala Ile Lys Lys Glu Gln Glu Ala Ile Lys
1               5                   10                  15

Lys Lys Ile Glu Ala Ile Glu Lys
            20

<210> SEQ ID NO 32
<211> LENGTH: 24
<212> TYPE: PRT
<213> ORGANISM: Artificial Sequence
<220> FEATURE:
<223> OTHER INFORMATION: Synthetic sequence

<400> SEQUENCE: 32

Ile Glu Lys Lys Ile Glu Glu Ile Glu Lys Lys Ile Glu Glu Ile Glu
1               5                   10                  15

Lys Lys Ile Glu Glu Ile Glu Lys
            20

<210> SEQ ID NO 33
<211> LENGTH: 7
<212> TYPE: PRT
<213> ORGANISM: Artificial Sequence
<220> FEATURE:
<223> OTHER INFORMATION: Synthetic sequence

<400> SEQUENCE: 33

Ile Glu Lys Lys Ile Glu Ala
1               5

<210> SEQ ID NO 34
```

```
<211> LENGTH: 7
<212> TYPE: PRT
<213> ORGANISM: Artificial Sequence
<220> FEATURE:
<223> OTHER INFORMATION: Synthetic sequence

<400> SEQUENCE: 34

Ile Glu Lys Lys Ile Glu Glu
1               5

<210> SEQ ID NO 35
<211> LENGTH: 29
<212> TYPE: PRT
<213> ORGANISM: Artificial Sequence
<220> FEATURE:
<223> OTHER INFORMATION: Synthetic sequence

<400> SEQUENCE: 35

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu
            20                  25

<210> SEQ ID NO 36
<211> LENGTH: 15
<212> TYPE: PRT
<213> ORGANISM: Artificial Sequence
<220> FEATURE:
<223> OTHER INFORMATION: Synthetic sequence

<400> SEQUENCE: 36

Lys Gln Lys Lys Ile Glu Asn Glu Ile Ala Ala Ile Lys Lys Leu
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic sequence

<400> SEQUENCE: 37

Lys Ile Lys Lys Ile Glu Asn Glu Ile Ala Arg Ile Lys Lys Leu
1               5                   10                  15

<210> SEQ ID NO 38
<211> LENGTH: 22
<212> TYPE: PRT
<213> ORGANISM: Artificial Sequence
<220> FEATURE:
<223> OTHER INFORMATION: Synthetic sequence

<400> SEQUENCE: 38

Lys Ile Glu Glu Ile Glu Ser Lys Gln Lys Lys Ile Glu Asn Glu Ile
1               5                   10                  15

Ala Arg Ile Lys Lys Leu
            20

<210> SEQ ID NO 39
<211> LENGTH: 21
<212> TYPE: PRT
<213> ORGANISM: Artificial Sequence
<220> FEATURE:
<223> OTHER INFORMATION: Synthetic sequence

<400> SEQUENCE: 39
```

```
Lys Ile Glu Glu Ile Glu Ser Lys Ile Lys Lys Ile Glu Asn Glu Ile
1               5                   10                  15

Ala Arg Ile Lys Lys
            20
```

<210> SEQ ID NO 40
<211> LENGTH: 17
<212> TYPE: PRT
<213> ORGANISM: Artificial Sequence
<220> FEATURE:
<223> OTHER INFORMATION: Synthetic sequence

<400> SEQUENCE: 40

```
Ile Lys Lys Glu Ile Glu Ala Ile Lys Lys Glu Gln Glu Ala Ile Lys
1               5                   10                  15

Lys
```

<210> SEQ ID NO 41
<211> LENGTH: 34
<212> TYPE: PRT
<213> ORGANISM: Artificial Sequence
<220> FEATURE:
<223> OTHER INFORMATION: Synthetic peptide

<400> SEQUENCE: 41

```
Ile Lys Lys Glu Ile Glu Ala Ile Lys Lys Glu Gln Glu Ala Ile Lys
1               5                   10                  15

Lys Leu Leu Gln Leu Thr Val Trp Gly Ile Lys Gln Leu Gln Ala Arg
            20                  25                  30

Ile Leu
```

<210> SEQ ID NO 42
<211> LENGTH: 38
<212> TYPE: PRT
<213> ORGANISM: Artificial Sequence
<220> FEATURE:
<223> OTHER INFORMATION: Synthetic peptide

<400> SEQUENCE: 42

```
Cys Cys Gly Gly Ile Lys Lys Glu Ile Glu Ala Ile Lys Lys Glu Gln
1               5                   10                  15

Glu Ala Ile Lys Lys Leu Leu Gln Leu Thr Val Trp Gly Ile Lys Gln
            20                  25                  30

Leu Gln Ala Arg Ile Leu
            35
```

<210> SEQ ID NO 43
<211> LENGTH: 38
<212> TYPE: PRT
<213> ORGANISM: Artificial Sequence
<220> FEATURE:
<223> OTHER INFORMATION: Synthetic peptide

<400> SEQUENCE: 43

```
Ile Lys Lys Glu Ile Glu Ala Ile Lys Lys Glu Gln Glu Ala Ile Lys
1               5                   10                  15

Lys Leu Leu Gln Leu Thr Val Trp Gly Ile Lys Gln Leu Gln Ala Arg
            20                  25                  30

Ile Leu Gly Gly Cys Cys
            35
```

<210> SEQ ID NO 44

```
<211> LENGTH: 17
<212> TYPE: PRT
<213> ORGANISM: Artificial Sequence
<220> FEATURE:
<223> OTHER INFORMATION: Synthetic sequence

<400> SEQUENCE: 44

Leu Leu Gln Leu Thr Val Trp Gly Ile Lys Gln Leu Gln Ala Arg Ile
1               5                   10                  15

Leu

<210> SEQ ID NO 45
<211> LENGTH: 10
<212> TYPE: PRT
<213> ORGANISM: Artificial Sequence
<220> FEATURE:
<223> OTHER INFORMATION: Synthetic sequence

<400> SEQUENCE: 45

Ile Lys Lys Lys Ile Glu Ala Ile Glu Lys
1               5                   10

<210> SEQ ID NO 46
<211> LENGTH: 36
<212> TYPE: PRT
<213> ORGANISM: Artificial Sequence
<220> FEATURE:
<223> OTHER INFORMATION: HIV-1 peptide

<400> SEQUENCE: 46

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 47
<211> LENGTH: 34
<212> TYPE: PRT
<213> ORGANISM: Artificial Sequence
<220> FEATURE:
<223> OTHER INFORMATION: HIV-1 peptide

<400> SEQUENCE: 47

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 48
<211> LENGTH: 23
<212> TYPE: PRT
<213> ORGANISM: Artificial Sequence
<220> FEATURE:
<223> OTHER INFORMATION: HIV-1 peptide

<400> SEQUENCE: 48

Ile Glu Ala Gln Gln His Leu Leu Gln Leu Thr Val Trp Gly Ile Lys
1               5                   10                  15

Gln Leu Gln Ala Arg Ile Leu
            20
```

```
<210> SEQ ID NO 49
<211> LENGTH: 7
<212> TYPE: PRT
<213> ORGANISM: Artificial Sequence
<220> FEATURE:
<223> OTHER INFORMATION: HIV-1 peptide

<400> SEQUENCE: 49

Ala Val Glu Arg Tyr Leu Lys
 1               5

<210> SEQ ID NO 50
<211> LENGTH: 24
<212> TYPE: PRT
<213> ORGANISM: Artificial Sequence
<220> FEATURE:
<223> OTHER INFORMATION: HIV-1 peptide

<400> SEQUENCE: 50

Leu Leu Gln Leu Thr Val Trp Gly Ile Lys Gln Leu Gln Ala Arg Ile
 1               5                  10                  15

Leu Ala Val Glu Arg Tyr Leu Lys
            20

<210> SEQ ID NO 51
<211> LENGTH: 30
<212> TYPE: PRT
<213> ORGANISM: Artificial Sequence
<220> FEATURE:
<223> OTHER INFORMATION: HIV-1 peptide

<400> SEQUENCE: 51

Ile Glu Ala Gln Gln His Leu Leu Gln Leu Thr Val Trp Gly Ile Lys
 1               5                  10                  15

Gln Leu Gln Ala Arg Ile Leu Ala Val Glu Arg Tyr Leu Lys
            20                  25                  30

<210> SEQ ID NO 52
<211> LENGTH: 43
<212> TYPE: PRT
<213> ORGANISM: Artificial Sequence
<220> FEATURE:
<223> OTHER INFORMATION: HIV-1 peptide

<400> SEQUENCE: 52

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ile Leu Ala Val Glu Arg Tyr Leu Lys
            35                  40

<210> SEQ ID NO 53
<211> LENGTH: 48
<212> TYPE: PRT
<213> ORGANISM: Artificial Sequence
<220> FEATURE:
<223> OTHER INFORMATION: HIV-1 peptide

<400> SEQUENCE: 53

Ala Arg Gln Leu Leu Ser Gly Ile Val Gln Gln Gln Asn Asn Leu Leu
 1               5                  10                  15

Arg Ala Ile Glu Ala Gln Gln His Leu Leu Gln Leu Thr Val Trp Gly
            20                  25                  30
```

```
Ile Lys Gln Leu Gln Ala Arg Ile Leu Ala Val Glu Arg Tyr Leu Lys
        35                  40                  45
```

<210> SEQ ID NO 54
<211> LENGTH: 48
<212> TYPE: PRT
<213> ORGANISM: Artificial Sequence
<220> FEATURE:
<223> OTHER INFORMATION: Synthetic peptide

<400> SEQUENCE: 54

```
Ile Lys Lys Glu Ile Glu Ala Ile Lys Lys Glu Gln Glu Ala Ile Lys
  1               5                  10                  15

Lys Lys Ile Glu Ala Ile Glu Lys Leu Leu Gln Leu Thr Val Trp Gly
            20                  25                  30

Ile Lys Gln Leu Gln Ala Arg Ile Leu Ala Val Glu Arg Tyr Leu Lys
        35                  40                  45
```

<210> SEQ ID NO 55
<211> LENGTH: 49
<212> TYPE: PRT
<213> ORGANISM: Artificial Sequence
<220> FEATURE:
<223> OTHER INFORMATION: Synthetic peptide

<400> SEQUENCE: 55

```
Ile Glu Lys Lys Ile Glu Glu Ile Lys Lys Ile Glu Glu Ile Glu
  1               5                  10                  15

Lys Lys Ile Glu Glu Ile Glu Glu Lys Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys
```

<210> SEQ ID NO 56
<211> LENGTH: 52
<212> TYPE: PRT
<213> ORGANISM: Artificial Sequence
<220> FEATURE:
<223> OTHER INFORMATION: Synthetic peptide

<400> SEQUENCE: 56

```
Arg Met Lys Gln Ile Glu Asp Lys Ile Glu Glu Ile Glu Ser Lys Gln
  1               5                  10                  15

Lys Lys Ile Glu Asn Glu Ile Ala Arg Ile Lys Lys Leu Leu Gln Leu
            20                  25                  30

Thr Val Trp Gly Ile Lys Gln Leu Gln Ala Arg Ile Leu Ala Val Glu
        35                  40                  45

Arg Tyr Leu Lys
    50
```

<210> SEQ ID NO 57
<211> LENGTH: 41
<212> TYPE: PRT
<213> ORGANISM: Artificial Sequence
<220> FEATURE:
<223> OTHER INFORMATION: Synthetic peptide

<400> SEQUENCE: 57

```
Ile Lys Lys Glu Ile Glu Ala Ile Lys Lys Glu Gln Glu Ala Ile Lys
  1               5                  10                  15
```

-continued

```
Lys Glu Ile Glu Ala Gln Gln His Leu Leu Gln Leu Thr Val Trp Gly
         20                  25                  30

Ile Lys Gln Leu Gln Ala Arg Ile Leu
         35                  40

<210> SEQ ID NO 58
<211> LENGTH: 55
<212> TYPE: PRT
<213> ORGANISM: Artificial Sequence
<220> FEATURE:
<223> OTHER INFORMATION: Synthetic peptide

<400> SEQUENCE: 58

Ile Lys Lys Glu Ile Glu Ala Ile Lys Lys Glu Gln Glu Ala Ile Lys
1               5                   10                  15

Lys Glu Ile Ser Gly Ile Val Gln Gln Gln Asn Asn Leu Leu Arg Ala
         20                  25                  30

Ile Glu Ala Gln Gln His Leu Leu Gln Leu Thr Val Trp Gly Ile Lys
         35                  40                  45

Gln Leu Gln Ala Arg Ile Leu
         50              55

<210> SEQ ID NO 59
<211> LENGTH: 41
<212> TYPE: PRT
<213> ORGANISM: Artificial Sequence
<220> FEATURE:
<223> OTHER INFORMATION: Synthetic peptide

<400> SEQUENCE: 59

Ile Lys Lys Glu Ile Glu Ala Ile Lys Lys Glu Gln Glu Ala Ile Lys
1               5                   10                  15

Lys Leu Leu Gln Leu Thr Val Trp Gly Ile Lys Gln Leu Gln Ala Arg
         20                  25                  30

Ile Leu Ala Val Glu Arg Tyr Leu Lys
         35                  40

<210> SEQ ID NO 60
<211> LENGTH: 17
<212> TYPE: PRT
<213> ORGANISM: Artificial Sequence
<220> FEATURE:
<223> OTHER INFORMATION: Synthetic sequence

<400> SEQUENCE: 60

Leu Leu Gln Leu Thr Val Trp Gly Ile Lys Ala Leu Ala Ala Ala Ile
1               5                   10                  15

Ala

<210> SEQ ID NO 61
<211> LENGTH: 38
<212> TYPE: PRT
<213> ORGANISM: Artificial Sequence
<220> FEATURE:
<223> OTHER INFORMATION: Synthetic peptide

<400> SEQUENCE: 61

Cys Cys Gly Gly Ile Lys Lys Glu Ile Glu Ala Ile Lys Lys Glu Gln
1               5                   10                  15

Glu Ala Ile Lys Lys Leu Leu Gln Leu Thr Val Trp Gly Ile Lys Ala
         20                  25                  30

Leu Ala Ala Ala Ile Ala
```

```
<210> SEQ ID NO 62
<211> LENGTH: 36
<212> TYPE: PRT
<213> ORGANISM: Artificial Sequence
<220> FEATURE:
<223> OTHER INFORMATION: SIV peptide

<400> SEQUENCE: 62

Ala Gly Ile Val Gln Gln Gln Gln Leu Leu Asp Val Val Lys Arg
  1               5                  10                  15

Gln Gln Glu Leu Leu Arg Leu Thr Val Trp Gly Thr Lys Asn Leu Gln
             20                  25                  30

Thr Arg Val Ser
         35

<210> SEQ ID NO 63
<211> LENGTH: 36
<212> TYPE: PRT
<213> ORGANISM: Artificial Sequence
<220> FEATURE:
<223> OTHER INFORMATION: Visna virus peptide

<400> SEQUENCE: 63

Gln Ser Leu Ala Asn Ala Thr Ala Ala Gln Gln Asn Val Leu Glu Ala
  1               5                  10                  15

Thr Tyr Ala Met Val Gln His Val Ala Lys Gly Val Arg Ile Leu Glu
             20                  25                  30

Ala Arg Val Ala
         35

<210> SEQ ID NO 64
<211> LENGTH: 36
<212> TYPE: PRT
<213> ORGANISM: Artificial Sequence
<220> FEATURE:
<223> OTHER INFORMATION: CAEV peptide

<400> SEQUENCE: 64

Gln Thr Leu Ala Asn Ala Thr Ala Ala Gln Gln Asp Ala Leu Glu Ala
  1               5                  10                  15

Thr Tyr Ala Met Val Gln His Val Ala Lys Gly Val Arg Ile Leu Glu
             20                  25                  30

Ala Arg Val Ala
         35

<210> SEQ ID NO 65
<211> LENGTH: 36
<212> TYPE: PRT
<213> ORGANISM: Artificial Sequence
<220> FEATURE:
<223> OTHER INFORMATION: FIV peptide

<400> SEQUENCE: 65

Ala Thr His Gln Glu Thr Ile Glu Lys Val Thr Glu Ala Leu Lys Ile
  1               5                  10                  15

Asn Asn Leu Arg Leu Val Thr Leu Glu His Gln Val Leu Val Ile Gly
             20                  25                  30

Leu Lys Val Glu
         35
```

-continued

<210> SEQ ID NO 66
<211> LENGTH: 36
<212> TYPE: PRT
<213> ORGANISM: Artificial Sequence
<220> FEATURE:
<223> OTHER INFORMATION: EIAV peptide

<400> SEQUENCE: 66

Asn His Thr Phe Glu Val Glu Asn Ser Thr Leu Asn Gly Met Asp Leu
1               5                   10                  15

Ile Glu Arg Gln Ile Lys Ile Leu Tyr Ala Met Ile Leu Gln Thr His
            20                  25                  30

Ala Asp Val Gln
        35

<210> SEQ ID NO 67
<211> LENGTH: 36
<212> TYPE: PRT
<213> ORGANISM: Artificial Sequence
<220> FEATURE:
<223> OTHER INFORMATION: BIV peptide

<400> SEQUENCE: 67

Glu Arg Val Val Gln Asn Val Ser Tyr Ile Ala Gln Thr Gln Asp Gln
1               5                   10                  15

Phe Thr His Leu Phe Arg Asn Ile Asn Asn Arg Leu Asn Val Leu His
            20                  25                  30

Arg Arg Val Ser
        35

<210> SEQ ID NO 68
<211> LENGTH: 46
<212> TYPE: PRT
<213> ORGANISM: Artificial Sequence
<220> FEATURE:
<223> OTHER INFORMATION: Synthetic peptide

<400> SEQUENCE: 68

Gly Cys Cys Gly Gly Ile Lys Lys Glu Ile Glu Ala Ile Lys Lys Glu
1               5                   10                  15

Gln Glu Ala Ile Lys Lys Lys Ile Glu Ala Ile Glu Lys Leu Leu Gln
            20                  25                  30

Leu Thr Val Trp Gly Ile Lys Gln Leu Gln Ala Arg Ile Leu
        35                  40                  45

<210> SEQ ID NO 69
<211> LENGTH: 46
<212> TYPE: PRT
<213> ORGANISM: Artificial Sequence
<220> FEATURE:
<223> OTHER INFORMATION: Synthetic peptide

<400> SEQUENCE: 69

Gly Cys Cys Gly Gly Ile Glu Lys Lys Ile Glu Glu Ile Glu Lys Lys
1               5                   10                  15

Ile Glu Glu Ile Glu Lys Lys Ile Glu Glu Ile Glu Lys Leu Leu Gln
            20                  25                  30

Leu Thr Val Trp Gly Ile Lys Gln Leu Gln Ala Arg Ile Leu
        35                  40                  45

<210> SEQ ID NO 70
<211> LENGTH: 46
<212> TYPE: PRT

<213> ORGANISM: Artificial Sequence
<220> FEATURE:
<223> OTHER INFORMATION: Synthetic peptide

<400> SEQUENCE: 70

Gly Cys Cys Gly Gly Ile Lys Lys Glu Ile Glu Ala Ile Lys Lys Glu
1               5                   10                  15

Gln Glu Ala Ile Lys Lys Lys Ile Glu Ala Ile Glu Lys Leu Leu Gln
            20                  25                  30

Leu Thr Val Trp Gly Ile Lys Ala Leu Ala Ala Ala Ile Ala
        35                  40                  45

<210> SEQ ID NO 71
<211> LENGTH: 46
<212> TYPE: PRT
<213> ORGANISM: Artificial Sequence
<220> FEATURE:
<223> OTHER INFORMATION: Synthetic peptide

<400> SEQUENCE: 71

Gly Cys Cys Gly Gly Ile Glu Lys Lys Ile Glu Ala Ile Glu Lys Lys
1               5                   10                  15

Ile Glu Glu Ile Glu Lys Lys Ile Glu Glu Ile Glu Lys Leu Leu Gln
            20                  25                  30

Leu Thr Val Trp Gly Ile Lys Ala Leu Ala Ala Ala Ile Ala
        35                  40                  45

<210> SEQ ID NO 72
<211> LENGTH: 41
<212> TYPE: PRT
<213> ORGANISM: Artificial Sequence
<220> FEATURE:
<223> OTHER INFORMATION: Synthetic peptide

<400> SEQUENCE: 72

Ile Lys Lys Glu Ile Glu Ala Ile Lys Lys Glu Gln Glu Ala Ile Lys
1               5                   10                  15

Lys Lys Ile Glu Ala Ile Glu Lys Ala Leu Gln Leu Thr Val Trp Gly
            20                  25                  30

Ile Lys Gln Leu Gln Ala Arg Ile Leu
        35                  40

<210> SEQ ID NO 73
<211> LENGTH: 41
<212> TYPE: PRT
<213> ORGANISM: Artificial Sequence
<220> FEATURE:
<223> OTHER INFORMATION: Synthetic peptide

<400> SEQUENCE: 73

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Ala Leu Thr Val Trp Gly
            20                  25                  30

Ile Lys Gln Leu Gln Ala Arg Ile Leu
        35                  40

<210> SEQ ID NO 74
<211> LENGTH: 41
<212> TYPE: PRT
<213> ORGANISM: Artificial Sequence
<220> FEATURE:
<223> OTHER INFORMATION: Synthetic peptide

```
<400> SEQUENCE: 74

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Ala Thr Val Trp Gly
            20                  25                  30

Ile Lys Gln Leu Gln Ala Arg Ile Leu
        35                  40

<210> SEQ ID NO 75
<211> LENGTH: 41
<212> TYPE: PRT
<213> ORGANISM: Artificial Sequence
<220> FEATURE:
<223> OTHER INFORMATION: Synthetic peptide

<400> SEQUENCE: 75

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Ala Trp Gly
            20                  25                  30

Ile Lys Gln Leu Gln Ala Arg Ile Leu
        35                  40

<210> SEQ ID NO 76
<211> LENGTH: 41
<212> TYPE: PRT
<213> ORGANISM: Artificial Sequence
<220> FEATURE:
<223> OTHER INFORMATION: Synthetic peptide

<400> SEQUENCE: 76

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Ala Gly
            20                  25                  30

Ile Lys Gln Leu Gln Ala Arg Ile Leu
        35                  40

<210> SEQ ID NO 77
<211> LENGTH: 41
<212> TYPE: PRT
<213> ORGANISM: Artificial Sequence
<220> FEATURE:
<223> OTHER INFORMATION: Synthetic peptide

<400> SEQUENCE: 77

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Ala Gln Leu Gln Ala Arg Ile Leu
        35                  40

<210> SEQ ID NO 78
<211> LENGTH: 41
<212> TYPE: PRT
<213> ORGANISM: Artificial Sequence
<220> FEATURE:
<223> OTHER INFORMATION: Synthetic peptide

<400> SEQUENCE: 78
```

```
Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Lys Ala Leu Gln Ala Arg Ile Leu
        35                  40
```

<210> SEQ ID NO 79
<211> LENGTH: 41
<212> TYPE: PRT
<213> ORGANISM: Artificial Sequence
<220> FEATURE:
<223> OTHER INFORMATION: Synthetic peptide

<400> SEQUENCE: 79

```
Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Lys Gln Leu Ala Ala Arg Ile Leu
        35                  40
```

<210> SEQ ID NO 80
<211> LENGTH: 41
<212> TYPE: PRT
<213> ORGANISM: Artificial Sequence
<220> FEATURE:
<223> OTHER INFORMATION: Synthetic peptide

<400> SEQUENCE: 80

```
Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Lys Gln Leu Gln Ala Ala Ile Leu
        35                  40
```

<210> SEQ ID NO 81
<211> LENGTH: 41
<212> TYPE: PRT
<213> ORGANISM: Artificial Sequence
<220> FEATURE:
<223> OTHER INFORMATION: Synthetic peptide

<400> SEQUENCE: 81

```
Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Lys Gln Leu Gln Ala Arg Ile Ala
        35                  40
```

<210> SEQ ID NO 82
<211> LENGTH: 4
<212> TYPE: PRT
<213> ORGANISM: Artificial Sequence
<220> FEATURE:
<223> OTHER INFORMATION: Synthetic sequence

<400> SEQUENCE: 82

```
Gly Gly Cys Cys
1
```

<210> SEQ ID NO 83
<211> LENGTH: 31
<212> TYPE: PRT
<213> ORGANISM: Artificial Sequence
<220> FEATURE:
<223> OTHER INFORMATION: Synthetic peptide

<400> SEQUENCE: 83

Ile Lys Lys Lys Ile Glu Ala Ile Glu Lys Leu Leu Gln Leu Thr Val
1               5                   10                  15

Trp Gly Ile Lys Gln Leu Gln Ala Arg Ile Leu Gly Gly Cys Cys
            20                  25                  30

<210> SEQ ID NO 84
<211> LENGTH: 5
<212> TYPE: PRT
<213> ORGANISM: Artificial Sequence
<220> FEATURE:
<223> OTHER INFORMATION: HIV-1 peptide

<400> SEQUENCE: 84

Ala Ser Gln Leu Leu
1               5

<210> SEQ ID NO 85
<211> LENGTH: 17
<212> TYPE: PRT
<213> ORGANISM: Artificial Sequence
<220> FEATURE:
<223> OTHER INFORMATION: Synthetic sequence

<400> SEQUENCE: 85

Leu Ile Gln Leu Ile Val Trp Gly Ile Lys Gln Ile Gln Ala Arg Ile
1               5                   10                  15

Leu

<210> SEQ ID NO 86
<211> LENGTH: 27
<212> TYPE: PRT
<213> ORGANISM: Artificial Sequence
<220> FEATURE:
<223> OTHER INFORMATION: Synthetic peptide

<400> SEQUENCE: 86

Ile Lys Lys Lys Ile Glu Ala Ile Glu Lys Leu Ile Gln Leu Ile Val
1               5                   10                  15

Trp Gly Ile Lys Gln Ile Gln Ala Arg Ile Leu
            20                  25

<210> SEQ ID NO 87
<211> LENGTH: 31
<212> TYPE: PRT
<213> ORGANISM: Artificial Sequence
<220> FEATURE:
<223> OTHER INFORMATION: Synthetic peptide

<400> SEQUENCE: 87

Cys Cys Gly Gly Ile Lys Lys Lys Ile Glu Ala Ile Glu Lys Leu Ile
1               5                   10                  15

Gln Leu Ile Val Trp Gly Ile Lys Gln Ile Gln Ala Arg Ile Leu
            20                  25                  30

<210> SEQ ID NO 88
<211> LENGTH: 31

```
<212> TYPE: PRT
<213> ORGANISM: Artificial Sequence
<220> FEATURE:
<223> OTHER INFORMATION: Synthetic peptide

<400> SEQUENCE: 88

Ile Lys Lys Lys Ile Glu Ala Ile Glu Lys Leu Ile Gln Leu Ile Val
1               5                   10                  15

Trp Gly Ile Lys Gln Ile Gln Ala Arg Ile Leu Gly Gly Cys Cys
            20                  25                  30

<210> SEQ ID NO 89
<211> LENGTH: 34
<212> TYPE: PRT
<213> ORGANISM: Artificial Sequence
<220> FEATURE:
<223> OTHER INFORMATION: Synthetic peptide

<400> SEQUENCE: 89

Ile Lys Lys Glu Ile Glu Ala Ile Lys Lys Glu Gln Glu Ala Ile Lys
1               5                   10                  15

Lys Leu Ile Gln Leu Ile Val Trp Gly Ile Lys Gln Ile Gln Ala Arg
            20                  25                  30

Ile Leu

<210> SEQ ID NO 90
<211> LENGTH: 38
<212> TYPE: PRT
<213> ORGANISM: Artificial Sequence
<220> FEATURE:
<223> OTHER INFORMATION: Synthetic peptide

<400> SEQUENCE: 90

Cys Cys Gly Gly Ile Lys Lys Glu Ile Glu Ala Ile Lys Lys Glu Gln
1               5                   10                  15

Glu Ala Ile Lys Lys Leu Ile Gln Leu Ile Val Trp Gly Ile Lys Gln
            20                  25                  30

Ile Gln Ala Arg Ile Leu
        35

<210> SEQ ID NO 91
<211> LENGTH: 38
<212> TYPE: PRT
<213> ORGANISM: Artificial Sequence
<220> FEATURE:
<223> OTHER INFORMATION: Synthetic peptide

<400> SEQUENCE: 91

Ile Lys Lys Glu Ile Glu Ala Ile Lys Lys Glu Gln Glu Ala Ile Lys
1               5                   10                  15

Lys Leu Ile Gln Leu Ile Val Trp Gly Ile Lys Gln Ile Gln Ala Arg
            20                  25                  30

Ile Leu Gly Gly Cys Cys
        35

<210> SEQ ID NO 92
<211> LENGTH: 34
<212> TYPE: PRT
<213> ORGANISM: Artificial Sequence
<220> FEATURE:
<223> OTHER INFORMATION: Synthetic peptide

<400> SEQUENCE: 92
```

-continued

Ile Lys Lys Lys Ile Glu Ala Ile Glu Lys Leu Leu Gln Leu Thr Val
1               5                   10                  15

Trp Gly Ile Lys Gln Leu Gln Ala Arg Ile Leu Ala Val Glu Arg Tyr
            20                  25                  30

Leu Lys

<210> SEQ ID NO 93
<211> LENGTH: 44
<212> TYPE: PRT
<213> ORGANISM: Artificial Sequence
<220> FEATURE:
<223> OTHER INFORMATION: Synthetic peptide

<400> SEQUENCE: 93

Cys Cys Gly Gly Leu Leu Gln Leu Thr Val Trp Gly Ile Lys Gln Leu
1               5                   10                  15

Gln Ala Arg Ile Leu Ala Ile Lys Lys Glu Ile Glu Ala Ile Lys Lys
            20                  25                  30

Glu Gln Glu Ala Ile Lys Lys Lys Ile Glu Ala Ile
        35                  40

<210> SEQ ID NO 94
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 94

Leu Leu Gln Leu Thr Val Trp Gly Ile Lys Gln Leu Gln Ala Arg Ile
1               5                   10                  15

Leu Ala Ile Lys Lys Glu Ile Glu Ala Ile Lys Lys Glu Gln Glu Ala
            20                  25                  30

Ile Lys Lys Lys Ile Glu Ala Ile
        35                  40

<210> SEQ ID NO 95
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 95

Cys Cys Gly Gly Ile Lys Lys Glu Ile Glu Ala Ile Lys Lys Glu Gln
1               5                   10                  15

Glu Ala Ile Lys Lys Lys Ile Glu Ala Ile Glu Lys Leu Leu Gln Leu
            20                  25                  30

Thr Val Trp Gly Ile Lys Gln Leu Gln
        35                  40

<210> SEQ ID NO 96
<211> LENGTH: 47
<212> TYPE: PRT
<213> ORGANISM: Artificial Sequence
<220> FEATURE:
<223> OTHER INFORMATION: Synthetic Peptide

<400> SEQUENCE: 96

Cys Cys Gly Gly Ile Lys Lys Glu Ile Glu Ala Ile Lys Lys Glu Gln
1               5                   10                  15

Glu Ala Ile Lys Lys Lys Ile Glu Ala Ile Glu Lys Leu Leu Gln Leu

Thr Val Trp Gly Ile Lys Gln Ile Lys Lys Glu Ile Glu Ala Ile
        35                  40                  45

<210> SEQ ID NO 97
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 97

Ile Glu Lys Lys Ile Glu Ala Ile Glu Lys Lys Ile Glu Ala Ile Glu
1               5                   10                  15

Lys Lys Ile Glu Ala Ile Glu Lys Leu Leu Gln Leu Thr Val Trp Gly
            20                  25                  30

Ile Lys Gln Leu Gln Ala Arg Ile Leu
        35                  40

<210> SEQ ID NO 98
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 98

Cys Cys Gly Gly Ile Glu Lys Lys Ile Glu Ala Ile Glu Lys Lys Ile
1               5                   10                  15

Glu Ala Ile Glu Lys Lys Ile Glu Ala Ile Glu Lys Leu Leu Gln Leu
            20                  25                  30

Thr Val Trp Gly Ile Lys Gln Leu Gln Ala Arg Ile Leu
        35                  40                  45

<210> SEQ ID NO 99
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 99

Ile Glu Lys Lys Ile Glu Ala Ile Glu Lys Lys Ile Glu Ala Ile Glu
1               5                   10                  15

Lys Leu Leu Gln Leu Thr Val Trp Gly Ile Lys Gln Leu Gln Ala Arg
            20                  25                  30

Ile Leu

<210> SEQ ID NO 100
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 100

Cys Cys Gly Gly Ile Glu Lys Lys Ile Glu Ala Ile Glu Lys Lys Ile
1               5                   10                  15

Glu Ala Ile Glu Lys Leu Leu Gln Leu Thr Val Trp Gly Ile Lys Gln
            20                  25                  30

Leu Gln Ala Arg Ile Leu
        35

<210> SEQ ID NO 101
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 101

Ile Glu Lys Lys Ile Glu Ala Ile Glu Lys Leu Leu Gln Leu Thr Val
1               5                   10                  15

Trp Gly Ile Lys Gln Leu Gln Ala Arg Ile Leu
            20                  25

<210> SEQ ID NO 102
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 102

Cys Cys Gly Gly Ile Glu Lys Lys Ile Glu Ala Ile Glu Lys Leu Leu
1               5                   10                  15

Gln Leu Thr Val Trp Gly Ile Lys Gln Leu Gln Ala Arg Ile Leu
            20                  25                  30

<210> SEQ ID NO 103
<211> LENGTH: 46
<212> TYPE: PRT
<213> ORGANISM: Artificial Sequence
<220> FEATURE:
<223> OTHER INFORMATION: Synthetic Peptide

<400> SEQUENCE: 103

Cys Cys Cys Gly Gly Ile Lys Lys Glu Ile Glu Ala Ile Lys Lys Glu
1               5                   10                  15

Gln Glu Ala Ile Lys Lys Lys Ile Glu Ala Ile Glu Lys Leu Leu Gln
            20                  25                  30

Leu Thr Val Trp Gly Ile Lys Gln Leu Gln Ala Arg Ile Leu
        35                  40                  45

<210> SEQ ID NO 104
<211> LENGTH: 44
<212> TYPE: PRT
<213> ORGANISM: Artificial Sequence
<220> FEATURE:
<223> OTHER INFORMATION: Synthetic Peptide

<400> SEQUENCE: 104

Gly Gly Gly Ile Lys Lys Glu Ile Glu Ala Ile Lys Lys Glu Gln Glu
1               5                   10                  15

Ala Ile Lys Lys Lys Ile Glu Ala Ile Glu Lys Leu Leu Gln Leu Thr
            20                  25                  30

Val Trp Gly Ile Lys Gln Leu Gln Ala Arg Ile Leu
        35                  40

<210> SEQ ID NO 105
<211> LENGTH: 39
<212> TYPE: PRT
<213> ORGANISM: Artificial Sequence
<220> FEATURE:
<223> OTHER INFORMATION: Synthetic Peptide -continued

```
<400> SEQUENCE: 105

Cys Cys Cys Gly Gly Ile Glu Lys Lys Ile Glu Ala Ile Glu Lys Lys
 1               5                  10                  15

Ile Glu Ala Ile Glu Lys Leu Leu Gln Leu Thr Val Trp Gly Ile Lys
            20                  25                  30

Gln Leu Gln Ala Arg Ile Leu
        35

<210> SEQ ID NO 106
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 106

Gly Gly Gly Ile Glu Lys Lys Ile Glu Ala Ile Glu Lys Lys Ile Glu
 1               5                  10                  15

Ala Ile Glu Lys Leu Leu Gln Leu Thr Val Trp Gly Ile Lys Gln Leu
            20                  25                  30

Gln Ala Arg Ile Leu
        35

<210> SEQ ID NO 107
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 107

Ile Glu Glu Lys Ile Glu Glu Ile Glu Glu
 1               5                  10

<210> SEQ ID NO 108
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 108

Ile Glu Glu Lys Ile Glu Glu Ile Glu Glu Leu Leu Gln Leu Thr Val
 1               5                  10                  15

Trp Gly Ile Lys Gln Leu Gln Ala Arg Ile Leu
            20                  25

<210> SEQ ID NO 109
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 109

Cys Cys Gly Gly Ile Glu Glu Lys Ile Glu Glu Ile Glu Glu Leu Leu
 1               5                  10                  15

Gln Leu Thr Val Trp Gly Ile Lys Gln Leu Gln Ala Arg Ile Leu
            20                  25                  30

<210> SEQ ID NO 110
<211> LENGTH: 30
<212> TYPE: PRT
```

```
<213> ORGANISM: Artificial Sequence
<220> FEATURE:
<223> OTHER INFORMATION: Synthetic Peptide

<400> SEQUENCE: 110

Gly Gly Gly Ile Glu Glu Lys Ile Glu Glu Ile Glu Glu Leu Leu Gln
1               5                   10                  15

Leu Thr Val Trp Gly Ile Lys Gln Leu Gln Ala Arg Ile Leu
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 111

Cys Cys Cys Gly Gly Ile Glu Glu Lys Ile Glu Glu Ile Glu Glu Leu
1               5                   10                  15

Leu Gln Leu Thr Val Trp Gly Ile Lys Gln Leu Gln Ala Arg Ile Leu
            20                  25                  30

<210> SEQ ID NO 112
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 112

Ile Glu Lys Lys Ile Glu Ala Ile Glu Lys Lys Ile Glu Ala Ile Glu
1               5                   10                  15

Lys Lys Ile Glu Ala Ile Glu Lys
            20

<210> SEQ ID NO 113
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 113

Ile Glu Lys Lys Ile Glu Ala Ile Glu Lys
1               5                   10

<210> SEQ ID NO 114
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 114

Ile Glu Lys Lys Ile Glu Glu Ile Glu Lys Lys Ile Glu Glu Ile Glu
1               5                   10                  15

Lys

<210> SEQ ID NO 115
<211> LENGTH: 34
<212> TYPE: PRT
<213> ORGANISM: Artificial Sequence
<220> FEATURE:
<223> OTHER INFORMATION: Synthetic Peptide
```

<400> SEQUENCE: 115

Ile Glu Lys Lys Ile Glu Glu Ile Glu Lys Lys Ile Glu Glu Ile Glu
1               5                   10                  15
Lys Leu Leu Gln Leu Thr Val Trp Gly Ile Lys Gln Leu Gln Ala Arg
            20                  25                  30
Ile Leu

<210> SEQ ID NO 116
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 116

Cys Cys Gly Gly Ile Glu Lys Lys Ile Glu Glu Ile Glu Lys Lys Ile
1               5                   10                  15
Glu Glu Ile Glu Lys Leu Leu Gln Leu Thr Val Trp Gly Ile Lys Gln
            20                  25                  30
Leu Gln Ala Arg Ile Leu
            35

<210> SEQ ID NO 117
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 117

Ile Glu Lys Lys Ile Glu Glu Ile Glu Lys Lys Ile Glu Glu Ile Glu
1               5                   10                  15
Lys Leu Leu Gln Leu Thr Val Trp Gly Ile Lys Gln Leu Gln Ala Arg
            20                  25                  30
Ile Leu Gly Gly Cys Cys
            35

<210> SEQ ID NO 118
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 118

Ile Glu Lys Lys Ile Glu Glu Ile Glu Glu Lys Ile Glu Glu Ile Glu
1               5                   10                  15
Lys Leu Leu Gln Leu Thr Val Trp Gly Ile Lys Gln Leu Gln Ala Arg
            20                  25                  30
Ile Leu

<210> SEQ ID NO 119
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 119

Ile Glu Lys Lys Ile Glu Glu Ile Glu Glu Lys Ile Glu Glu Ile Glu
1               5                   10                  15

Lys

<210> SEQ ID NO 120
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 120

Cys Cys Gly Gly Ile Glu Lys Lys Ile Glu Glu Ile Glu Lys Ile
1               5                   10                  15

Glu Glu Ile Glu Lys Leu Leu Gln Leu Thr Val Trp Gly Ile Lys Gln
            20                  25                  30

Leu Gln Ala Arg Ile Leu
        35

<210> SEQ ID NO 121
<211> LENGTH: 44
<212> TYPE: PRT
<213> ORGANISM: Artificial Sequence
<220> FEATURE:
<223> OTHER INFORMATION: Synthetic Peptide

<400> SEQUENCE: 121

Gly Gly Gly Ile Glu Lys Lys Ile Glu Glu Ile Glu Lys Lys Ile Glu
1               5                   10                  15

Glu Ile Glu Lys Lys Ile Glu Glu Ile Glu Lys Leu Leu Gln Leu Thr
            20                  25                  30

Val Trp Gly Ile Lys Gln Leu Gln Ala Arg Ile Leu
        35                  40

<210> SEQ ID NO 122
<211> LENGTH: 46
<212> TYPE: PRT
<213> ORGANISM: Artificial Sequence
<220> FEATURE:
<223> OTHER INFORMATION: Synthetic Peptide

<400> SEQUENCE: 122

Cys Cys Cys Gly Gly Ile Glu Lys Lys Ile Glu Glu Ile Glu Lys Lys
1               5                   10                  15

Ile Glu Glu Ile Glu Lys Lys Ile Glu Glu Ile Glu Lys Leu Leu Gln
            20                  25                  30

Leu Thr Val Trp Gly Ile Lys Gln Leu Gln Ala Arg Ile Leu
        35                  40                  45

<210> SEQ ID NO 123
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 123

Gly Gly Gly Ile Glu Lys Lys Ile Glu Glu Ile Glu Glu Lys Ile Glu
1               5                   10                  15

Glu Ile Glu Lys Leu Leu Gln Leu Thr Val Trp Gly Ile Lys Gln Leu
            20                  25                  30

Gln Ala Arg Ile Leu
        35

```
<210> SEQ ID NO 124
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 124

Cys Cys Cys Gly Gly Ile Glu Lys Lys Ile Glu Glu Ile Glu Lys
 1               5                  10                  15

Ile Glu Glu Ile Glu Lys Leu Leu Gln Leu Thr Val Trp Gly Ile Lys
            20                  25                  30

Gln Leu Gln Ala Arg Ile Leu
        35

<210> SEQ ID NO 125
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 125

Gly Gly Gly Ile Glu Lys Lys Ile Glu Glu Ile Glu Lys Lys Ile Glu
 1               5                  10                  15

Glu Ile Glu Lys Leu Leu Gln Leu Thr Val Trp Gly Ile Lys Gln Leu
            20                  25                  30

Gln Ala Arg Ile Leu
        35

<210> SEQ ID NO 126
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 126

Cys Cys Cys Gly Gly Ile Glu Lys Lys Ile Glu Glu Ile Glu Lys Lys
 1               5                  10                  15

Ile Glu Glu Ile Glu Lys Leu Leu Gln Leu Thr Val Trp Gly Ile Lys
            20                  25                  30

Gln Leu Gln Ala Arg Ile Leu
        35
```